US010252913B2

(12) United States Patent
Bonnet et al.

(10) Patent No.: US 10,252,913 B2
(45) **Date of Patent: *Apr. 9, 2019**

(54) COMPOSITION COMPRISING HF AND 2,3,3,3-TETRAFLUOROPROPENE

(71) Applicant: ARKEMA FRANCE, Colombes (FR)

(72) Inventors: Philippe Bonnet, Lyons (FR); Bertrand Collier, Saint-genis-laval (FR); Dominique Deur-Bert, Charly (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 149 days.

This patent is subject to a terminal disclaimer.

(21) Appl. No.: 14/772,950

(22) PCT Filed: Feb. 21, 2014

(86) PCT No.: PCT/FR2014/050357

§ 371 (c)(1),
(2) Date: Sep. 4, 2015

(87) PCT Pub. No.: WO2014/147310

PCT Pub. Date: Sep. 25, 2014

(65) Prior Publication Data

US 2016/0009555 A1 Jan. 14, 2016

(30) Foreign Application Priority Data

Mar. 20, 2013 (FR) ..................................... 13 52482

(51) Int. Cl.
*C01B 7/19* (2006.01)
*C07C 19/08* (2006.01)
*C07C 21/18* (2006.01)

(52) U.S. Cl.
CPC .............. *C01B 7/191* (2013.01); *C07C 19/08* (2013.01); *C07C 21/18* (2013.01)

(58) Field of Classification Search
None
See application file for complete search history.

(56) References Cited

U.S. PATENT DOCUMENTS 6,013,846 A * 1/2000 Wismer .................. C07C 17/00 570/164
8,070,977 B2 12/2011 Rached
8,075,798 B2 12/2011 Rached
8,246,850 B2 8/2012 Rached
8,252,198 B2 8/2012 Rached
8,450,537 B2 * 5/2013 Rao ......................... C07C 17/10 570/156
8,557,135 B2 10/2013 Rached
8,808,569 B2 8/2014 Rached
8,858,824 B2 10/2014 Boussand
8,858,825 B2 10/2014 Guerin et al.
9,011,711 B2 4/2015 Rached
9,028,706 B2 5/2015 Rached et al.
9,039,922 B2 5/2015 Rached
9,127,191 B2 9/2015 Rached
9,133,379 B2 9/2015 Rached
9,175,203 B2 11/2015 Rached
9,267,064 B2 2/2016 Rached
9,315,708 B2 4/2016 Guerin et al.
9,399,726 B2 7/2016 Rached
9,505,968 B2 11/2016 Rached
9,512,343 B2 12/2016 Rached et al.
9,599,381 B2 3/2017 Rached
9,650,551 B2 5/2017 Collier et al.
9,650,553 B2 5/2017 Deur-Bert et al.
9,663,697 B2 5/2017 Rached
9,676,984 B2 6/2017 Guerin et al.
9,683,155 B2 6/2017 Deur-Bert et al.
9,683,157 B2 6/2017 Rached (Continued)

FOREIGN PATENT DOCUMENTS

WO WO 2007/053736 A2 5/2007
WO WO 2008/002500 A1 1/2008

(Continued)

OTHER PUBLICATIONS

**Rached, Wissam, et al., U.S. Appl. No. 15/368,347 entitled "Vehicle Heating and/or Air Conditioning Method", filed Dec. 2, 2016.
**Rached, Wissam, U.S. Appl. No. 15/396,855 entitled "Heat Transfer Fluid," filed Jan. 3, 2017.
**Rached, Wissam, U.S. Appl. No. 15/238,883 entitled "Heat Transfer Fluid Replacing R-134a," filed Aug. 17, 2016.
**Rached, Wissam, et al., U.S. Appl. No. 15/297,569 entitled "Composition Based on 2,3,3,3-Tetrafluoropropene," filed Oct. 19, 2016.
**Guérin, Sophie, et al., U.S. Appl. No. 14/903,461, entitled, "2,3,3,3-Tetrafluoropropene Compositions Having Improved Miscibility," filed Jan. 7, 2016.

(Continued)

*Primary Examiner* — Joseph D Anthony

(74) *Attorney, Agent, or Firm* — Buchanan Ingersoll & Rooney P.C.

(57) ABSTRACT

An azeotropic or quasi-azeotropic composition including hydrogen fluoride, 2,3,3,3-tetrafluoropropene and one or more (hydro)halogen-carbon compounds including between 1 and 3 carbon atoms. Also a azeotropic or quasi-azeotropic composition including hydrogen fluoride, 2,3,3,3-tetrafluoropropene, and one or more organic compounds selected from among 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, Z-1,1,1,2,3-pentafluoropropene and 2-chloro,1,1,1,2-tetrafluoropropane.

16 Claims, No Drawings

(56) References Cited

U.S. PATENT DOCUMENTS 9,884,984 B2 2/2018 Rached
9,908,828 B2 3/2018 Rached et al.
9,969,918 B2 5/2018 Deur-Bert et al.
10,023,780 B2 7/2018 Guerin et al.
10,035,938 B2 7/2018 Rached
10,119,055 B2 11/2018 Boussand
10,125,296 B2 11/2018 Rached
2007/0100173 A1* 5/2007 Miller .................... C01B 7/191 570/178
2007/0100175 A1* 5/2007 Miller .................... C01B 7/196 570/178
2008/0051612 A1* 2/2008 Knapp .................... C07C 17/25 570/178
2009/0127496 A1* 5/2009 Rao .................... B01J 27/125 252/67
2009/0224207 A1 9/2009 Pham et al.
2010/0072415 A1* 3/2010 Rao .................... B01J 23/26 252/67
2010/0187088 A1* 7/2010 Merkel .................... B01D 3/36 203/50
2010/0237279 A1* 9/2010 Hulse .................... C07C 17/206 252/182.12
2011/0084228 A1 4/2011 Rached
2011/0095224 A1 4/2011 Rached
2011/0112340 A1* 5/2011 Smith .................... C07C 17/04 570/169
2011/0186772 A1 8/2011 Rached
2011/0218369 A1* 9/2011 Elsheikh .............. C07C 17/206 570/151
2011/0219791 A1 9/2011 Rached
2011/0219792 A1 9/2011 Rached
2011/0240254 A1 10/2011 Rached
2011/0284181 A1 11/2011 Rached
2012/0041239 A1* 2/2012 Suzuki .................. C07C 17/206 570/160
2012/0049104 A1 3/2012 Rached
2012/0053369 A1* 3/2012 Hulse .................... C07C 17/206 570/135
2012/0056122 A1* 3/2012 Hulse .................... C01B 7/191 252/67
2012/0056123 A1 3/2012 Rached
2012/0068105 A1 3/2012 Rached et al.
2012/0138841 A1* 6/2012 Hulse .................. A62D 1/0057 252/2
2012/0144857 A1 6/2012 Rached
2012/0151958 A1 6/2012 Rached
2012/0151959 A1 6/2012 Rached
2012/0153213 A1 6/2012 Rached
2012/0159982 A1 6/2012 Rached
2012/0161064 A1 6/2012 Rached
2012/0167615 A1 7/2012 Rached
2012/0205574 A1 8/2012 Rached et al.
2012/0222448 A1* 9/2012 Chaki .................. C07C 17/383 62/617
2013/0092869 A1 4/2013 Boussand
2013/0102814 A1 4/2013 Rao et al.
2013/0105296 A1* 5/2013 Chaki .................... C01B 7/196 203/60
2013/0105724 A1 5/2013 Boussand
2013/0186114 A1 7/2013 Guerin et al.
2014/0008565 A1 1/2014 Rached et al.
2014/0012052 A1* 1/2014 Pham .................... C07C 17/38 570/160
2014/0075969 A1 3/2014 Guerin et al.
2014/0318160 A1 10/2014 Rached
2014/0326017 A1 11/2014 Rached
2015/0027146 A1 1/2015 Boussand
2015/0152306 A1 6/2015 Rached
2015/0152307 A1 6/2015 Rached
2015/0322317 A1 11/2015 Collier et al.
2015/0322321 A1 11/2015 Deur-Bert et al.
2015/0344761 A1 12/2015 Rached
2015/0353799 A1 12/2015 Deur-Bert et al.
2015/0353802 A1 12/2015 Rached
2016/0009555 A1* 1/2016 Bonnet .................. C07C 21/18 252/182.12
2016/0023176 A1* 1/2016 Bonnet .................. C01B 7/191 51/307
2016/0023974 A1* 1/2016 Bonnet .................. C07C 21/18 252/182.12
2016/0024363 A1 1/2016 Rached
2016/0025394 A1 1/2016 Rached
2016/0031773 A1* 2/2016 Bonnet .................. C01B 7/195 252/182.12
2016/0046548 A1* 2/2016 Bonnet .................... C01B 7/19 252/182.12
2016/0115361 A1 4/2016 Boussand
2016/0122609 A1 5/2016 Rached
2016/0194541 A1 7/2016 Guerin et al.
2016/0244652 A1 8/2016 Rached
2016/0272561 A1 9/2016 Rached et al.
2016/0298014 A1 10/2016 Rached
2016/0355718 A1 12/2016 Rached
2016/0376484 A1 12/2016 Guerin et al.
2017/0037291 A1 2/2017 Rached et al.
2017/0080773 A1 3/2017 Rached
2017/0145276 A1 5/2017 Rached
2017/0210960 A1 7/2017 Deur-Bert et al.
2017/0210962 A1 7/2017 Collier et al.
2017/0218241 A1 8/2017 Deur-Bert et al.
2017/0218242 A1 8/2017 Rached
2018/0086173 A1 3/2018 Rached
2018/0134936 A1 5/2018 Rached
2018/0148395 A1 5/2018 Rached et al.
2018/0244970 A1 8/2018 Rached
2018/0282603 A1 10/2018 Guerin et al.
2018/0327645 A1 11/2018 Boussand

FOREIGN PATENT DOCUMENTS

WO WO 2008/054781 A1 5/2008
WO WO 2009/105512 A1 8/2009
WO WO 2009/105517 A2 8/2009
WO WO 2010/059493 A1 5/2010
WO WO 2012/075283 A2 6/2012

OTHER PUBLICATIONS

**Boussand, Beatrice, et al., U.S. Appl. No. 14/990,159, entitled "Stable 2,3,3,3-Tetrafluoropropene Composition," filed Jan 7, 2016.

**Rached, Wissam, U.S. Appl. No. 14/992,387 entitled, "Ternary Compositions for High-Capacity Refrigeration," filed Jan. 11, 2016.

**Guerin, Sophie, et al., U.S. Appl. No. 15/070,955, entitled "Heat-Transfer Compositions Exhbiting Impoved Miscibility with the Lubricating Oil," filed Mar. 15, 2016.

**Rached, Wissam, et al., U.S. Appl. No, 15/073,108 entitled "Stabilization of 1-Chloro-3,3,3-Trifluoropropene," filed Mar. 17, 2016.

**Collier, Bertrand, et al., U.S. Appl. No. 14/651,855 entitled "Composition Including 2,3,3,3-Tetrafluoropropene," filed Jun. 12, 2015.

**Deur-Bert, Dominique, el al., U.S. Appl. No. 14/651,925 entitled "Composition Containing 2,3,3,3-Tetrafluoropropene and 1,2-Difluoroethylene," filed Jun. 12, 2015.

**Deur-Bert, Dominique, el al., U.S. Appl. No. 14/655,500 entitled "Azeotropic or Quasi-Azeotropic Composition of Chloromethane," filed Jun. 25, 2015.

**Rached, Wissam, U.S. Appl. No. 14/823,430 entitled "Use of Ternary Compositions," filed Aug. 11, 2015.

**Rached, Wissam, U.S. Appl. No. 14/830,130 entitled "Binary Refrigerating Fluid," filed on Aug. 19, 2015.

**Rached, Wissam, U.S. Appl. No. 14/873,855 entitled "Heat Transfer Fluid," filed Oct. 2, 2015.

**Rached, Wissam, U.S. Appl. No. 14/873,891 entitled "Ternary Compositions for Low-Capacity Refrigeration," filed Oct. 2, 2015.

International Search Report (PCT/ISA/210) dated Jul. 6, 2014, by the European Patent Office as the International Searching Authority for International Application No. PCT/FR2014/050357.

(56) References Cited

OTHER PUBLICATIONS

**Collier, Bertrand, et al., U.S. Appl. No. 15/481,815 entitled "Composition including 2,3,3,3-Tetrafluoropropene," filed Apr. 7, 2017
**Deur-Bert, Dominque, et al. , U.S. Appl. No. 15/481,873 entitled "Azeotropic or Quasi-Azeotropic Composition of Chloromethane," filed Apr. 7, 2017
**Deur-Bert, Dominique, el al., U.S. Appl. No. 15/490,541 entitled "Composition Containing 2,3,3,3-Tetrafluoropropene and 1,2-Difluoroethylene," filed Apr. 18, 2017
**Rached, Wissam, U.S. Appl. No. 15/491,717 entitled "Heat Transfer Method," filed Apr. 19, 2017.
**Rached, Wissam, U.S. Appl. No. 15/809,164 entitled "Vehicle Heating and/or Air Conditioning Method," filed Nov. 10, 2017.
**Rached. Wissam, U.S. Appl. No. 15/820,996 entitled "Method for Heating and/or Air Conditioning a Vehicle," filed Nov. 22, 2017.
**Rached, Wissam, U.S. Appl. No. 15/856,703 entitled "Binary Refrigerating Fluid," filed Dec. 28, 2017.
**Rached, Wissam, et al., U.S. Appl. No. 15/878,794 entitled "Stabilization of 1-Chloro-3,3,3-Trifluoropropene," filed Jan. 24, 2018.
**Guerin, Sophie, et al., U.S. Appl No. 15/997,077 entitled "2,3,3,3-Tetrafluoropropene Compositions Having Improved Miscibility," filed Jun. 4, 2018.
**Boussand, Beatrice, U.S. Appl. No. 16/034,539 entitled "Stable 2,3,3,3-Tetrafluoropropene Composition," filed Jul. 13, 2018.
**Rached, Wissam, U.S. Appl. No. 16/142,492 entitled "Heat Transfer Fluid," filed in the U.S. Patent and Trademark Office dated Sep. 26, 2018.
**Rached, Wissam, U.S. Appl. No. 16/143,518 entitled "Binary Refrigerating Fluid," filed in the U.S. Patent and Trademark Office dated Sep. 27, 2018.

* cited by examiner

COMPOSITION COMPRISING HF AND 2,3,3,3-TETRAFLUOROPROPENE

The present invention relates to azeotropic or quasi-azeotropic compositions comprising 2,3,3,3-tetrafluoropropene and hydrogen fluoride. These compositions may originate from intermediate compositions in the production of 2,3,3,3-tetrafluoropropene and are generally useful in processes for recycling hydrogen fluoride.

The manufacture of 2,3,3,3-tetrafluoropropene accompanied by a multitude of by-products, having a boiling point close to HFO-1234yf, leads to relatively complex and expensive purification steps. The difficulty encountered during the purification of HFO-1234yf generally implies an appreciable loss of desired product. Furthermore, these by-products may form azeotropic compositions with 2,3,3,3-tetrafluoropropene, making separation by distillation simple, very difficult, or even impossible.

The binary azeotropes HF-HFO-1234yf (WO2007/053736), HF-HFO-1234zeE (US2007/0100173), HF-HFO-1234zeZ (WO2008/002500), HF-HCFO-1233xf (WO2008/054781, US2009/0224207), HF-HFO-1243zf (WO2009/105517), HF-HFCFO-1233zdZ (WO2012/075283) and HF-HFC-245cb (WO2008/054781) are not homogeneous but heterogeneous, and are thus all heteroazeotropes.

The subject of the present invention is an azeotropic or quasi-azeotropic composition comprising hydrogen fluoride, 2,3,3,3-tetrafluoropropene and one or more (hydro)halocarbon compounds comprising between 1 and 3 carbon atoms.

According to one embodiment of the invention, the composition is heteroazeotropic or quasi-heteroazeotropic.

A heteroazeotropic or quasi-heteroazeotropic mixture is an azeotropic or quasi-azeotropic mixture in which the condensed liquid forms two immiscible solutions that can be readily separated, for example by decantation. This property is a considerable advantage for the recovery of HF.

The term “quasi-azeotropic” or “quasi-heteroazeotropic” has a broad meaning and is intended to include compositions that are strictly azeotropic or strictly heteroazeotropic and those that behave like an azeotropic or heteroazeotropic mixture.

A mixture is azeotropic when the pressure at the dew point is equal to that at the bubble formation point, which means that the vapor composition is equal to that of the condensed liquid.

A mixture is considered as quasi-azeotropic when the pressure at the dew point is substantially equal to that at the bubble formation point, which means that the vapor composition is substantially equal to that of the condensed liquid.

Another way of characterizing a mixture as quasi-azeotropic when the pressure difference between the pressure at the dew point and the pressure at the bubble formation point is low, preferentially less than or equal to 5%, on the basis of the pressure at the bubble formation point.

Compositions according to the invention especially concern the following compounds, the acronyms of which represent:

HF: hydrogen fluoride
HCC-40: chloromethane, or $CH_3Cl$
HCFC-115: chloropentafluoroethane, or $C_2F_5Cl$
HCFC-124: chlorotetrafluoroethane, or $C_2HF_4Cl$
HFC-125: pentafluoroethane, or $C_2HF_5$
HCFC-133a: 1-chloro-2,2,2-trifluoroethane, or $C_2H_2F_3Cl$
HFC-134a: 1,1,1,2-tetrafluoroethane, or $C_2H_2F_4$
HCFC-142b: 1-chloro-1,1-difluoroethane, or $C_2H_3F_2Cl$
HFC-143a: 1,1,1-trifluoroethane, or $C_2H_3F_3$
HFC-152a: 1,1-difluoroethane, or $C_2H_4F_2$
HFO-1132: 1,2-difluoroethylene, or $C_2H_2F_2$
HFO-1141: fluoroethylene, or $C_2H_3F$
HFO-1234yf: 2,3,3,3-tetrafluoropropene or $CH_2{=}CF{-}CF_3$
HFC-245cb: 1,1,1,2,2-pentafluoropropane or $CF_3{-}CF_2{-}CH_3$
HFO-1234zeE: E-1,3,3,3-tetrafluoropropene or E-$CF_3{-}CH{=}CHF$
HFO-1234zeZ: Z-1,3,3,3-tetrafluoropropene or Z—$CF_3{-}CH{=}CHF$
HFO-1243zf: 3,3,3-trifluoropropene or $CF_3{-}CH{=}CH_2$
HCFO-1233xf: 3,3,3-trifluoro-2-chloropropene or $CF_3{-}CCl{=}CH_2$
HCFO-1233zdE: E-3,3,3-trifluoro-1-chloropropene or E-$CF_3{-}CH{=}CHCl$
HCFO-1233zdZ: Z-3,3,3-trifluoro-1-chloropropene or Z—$CF_3{-}CH{=}CHCl$
HFO-1225yeZ: Z-1,1,1,2,3-pentafluoropropene or Z—$CHF{=}CF{-}CF_3$
HFO-1225yeE: E-1,1,1,2,3-pentafluoropropene or E-$CHF{=}CF{-}CF_3$
HFO-1225zc: 1,1,3,3,3-pentafluoropropene or $CF_2{=}CH{-}CF_3$
HFO-1225yc: 1,1,2,3,3-pentafluoropropene or $CF_2{=}CF{-}CF_2$
HCFC-1214: dichlorotetrafluoropropene, or $C_3F_4Cl_2$
HCFO-1215: chloropentafluoropropene, or $C_3F_5Cl$
HFO-1216: hexafluoropropene, or $C_3F_6$
HCFO-1223: dichlorotrifluoropropene, or $C_3HF_3Cl_2$
HCFO-1224: chlorotetrafluoropropene, or $C_3HF_4Cl$
HCFO-1232: dichlorodifluoropropene, or $C_3H_2F_2Cl_2$
HCFO-1233xc: 1,1,3-trifluoro-2-chloropropene or $CH_2F{-}CCl{=}CF_2$
HCFO-1233xe: 1,3,3-trifluoro-2-chloropropene or $CHF_2{-}CCl{=}CHF$
HCFO-1233yb: 1,2,3-trifluoro-1-chloropropene or $CH_2F{-}CF{=}CFCl$
HCFO-1233yc: 1,1,2-trifluoro-3-chloropropene or $CH_2Cl{-}CF{=}CF_2$
HCFO-1233yd: 2,3,3-trifluoro-1-chloropropene or $CHF_2{-}CF{=}CHCl$
HCFO-1233ye: 1,2,3-trifluoro-3-chloropropene or $CHClF{-}CF{=}CHF$
HCFO-1233yf: 2,3,3-trifluoro-3-chloropropene or $CClF_2{-}CF{=}CH_2$
HCFO-1233zb: 1,3,3-trifluoro-1-chloropropene or $CHF_2{-}CH{=}CFCl$
HCFO-1233zc: 1,1,3-trifluoro-3-chloropropene or $CHClF{-}CH{=}CF_2$
HCFO-1233ze: 1,3,3-trifluoro-3-chloropropene or $CClF_2{-}CH{=}CHF$
HFO-1234yc: 1,1,2,3-tetrafluoropropene or $CF_2{=}CF{-}CH_2F$
HFO-1234ye: 1,2,3,3-tetrafluoropropene or $CHF{=}CF{-}CHF_2$
HFO-1234zc: 1,1,3,3-tetrafluoropropene or $CF_2{=}CH{-}CHF_2$
HCFO-1242: chlorodifluoropropene, or $C_3H_3F_2Cl$
HFO-1243yc: 1,1,2-trifluoropropene or $CH_3{-}CF{=}CF_2$
HFO-1243ye: 1,2,3-trifluoropropene or $CH_2F{-}CF{=}CHF$
HFO-1243yf: 2,3,3-trifluoropropene or $CHF_2{-}CF{=}CH_2$
HFO-1243zc: 1,1,3-trifluoropropene or $CH_2F{-}CH{=}CF_2$ HFO-1243ze: 1,3,3-trifluoropropene or $CHF_2$—CH═CHF
HCFO-1251: chlorofluoropropene, or $C_3H_4FCl$
HFO-1252: difluoropropene, or $C_3H_4F_2$
HFO-216: hexafluoropropene, or $C_3F_6Cl_2$
HCFO-217: chloroheptafluoropropane, or $C_3F_7Cl$
HFC-218: octafluoropropane, or $C_3F_8$
HCFC-225: dichloropentafluoropropane, or $C_3HF_5Cl_2$
HCFC-226: chlorohexafluoropropane, or $C_3HF_6Cl$
HFC-227: heptafluoropropane, or $C_3HF_7$
HCFC-234: dichlorotetrafluoropropane, or $C_3H_2F_4Cl_2$
HCFC-235: chloropentafluoropropane, or $C_3H_2F_5Cl$
HFC-236: hexafluoropropane, or $C_3H_2F_6$
HCFC-243: dichlorotrifluoropropane, or $C_3H_3F_3Cl_2$
HCFC-244: chlorotetrafluoropropane, or $C_3H_3F_4Cl$
HCFC-244bb: 2-chloro,1,1,1,2-tetrafluoropropane or $CF_3$—CFCl—$CH_3$
HFC-245fa: 1,1,1,3,3-pentafluoropropane or $CF_3$—$CH_2$—$CHF_2$
HFC-245ea: 1,1,2,3,3-pentafluoropropane or $CHF_2$—CHF—$CHF_2$
HFC-245eb: 1,1,1,2,3-pentafluoropropane or $CF_3$—CHF—$CH_2F$
HFC-245ca: 1,1,2,2,3-pentafluoropropane or $CHF_2$—$CF_2$—$CH_2F$
HCFC-253: chlorotrifluoropropane, or $C_3H_4F_3Cl$
HFC-254: tetrafluoropropane, or $C_3H_4F_4$
HCFC-262: Chlorodifluoropropane, or $C_3H_5F_2Cl$
HFC-263: trifluoropropane, or $C_3H_5F_3$
Trifluoropropyne: $CF_3$—C≡CH The composition according to the invention may optionally be a mixture of one or more azeotropes and/or heteroazeotropes of ternary, quaternary, penternary systems, systems with six compounds, systems with seven compounds, systems with eight or more compounds.

The compound 1,3,3,3-tetrafluoropropene comprises either the compound E-1,3,3,3-tetrafluoropropene or the compound Z-1,3,3,3-tetrafluoropropene or a mixture of the compounds E-1,3,3,3-tetrafluoropropene and Z-1,3,3,3-tetrafluoropropene.

The compound 1,1,1,2,3-pentafluoropropene comprises either the compound E-1,1,1,2,3-pentafluoropropene or the compound Z-1,1,1,2,3-pentafluoropropene or a mixture of the compounds E-1,1,1,2,3-pentafluoropropene and Z-1,1,1,2,3-pentafluoropropene.

The compound(s) containing 1 and/or 2 carbon atoms may be chosen especially from chloromethane, chloropentafluoroethane, 1-chloro-1,2,2,2-tetrafluoroethane, 1-chloro-1,1,2,2-tetrafluoroethane, pentafluoroethane, 1-chloro-1,2,2-trifluoroethane, 1-chloro-2,2,2-trifluoroethane, 1,1,2,2-tetrafluoroethane, 1,1,1,2-tetrafluoroethane, 1-chloro-1,2-difluoroethane, 1-chloro-1,1-difluoroethane, 1,1,2-trifluoroethane, 1,1,1-trifluoroethane, 1,1,2-trifluoroethane, 1,1-difluoroethane, 1,2-difluoroethylene and fluoroethylene.

The compound(s) containing 3 carbon atoms may be chosen especially from 1,2-dichloro-1,1,2,3,3,3-hexafluoropropane, 1,3-dichloro-1,1,2,2,3,3-hexafluoropropane, 1,1-dichloro-1,2,2,3,3,3-hexafluoropropane, 2,2-dichloro-1,1,1,3,3,3-hexafluoropropane, 1-chloro-1,1,2,2,3,3,3-heptafluoropropane, 2-chloro-1,1,1,2,3,3,3-heptafluoropropane, octafluoropropane, dichloropentafluoropropane, 2,2-dichloro-1,1,1,3,3-pentafluoropropane, 2,3-dichloro-1,1,1,2,3-pentafluoropropane, 1,2-dichloro-1,1,2,3,3-pentafluoropropane, 3,3-dichloro-1,1,1,2,2-pentafluoropropane, 1,3-dichloro-1,1,2,2,3-pentafluoropropane, 1,1-dichloro-1,2,2,3,3-pentafluoropropane, 1,2-dichloro-1,1,3,3,3-pentafluoropropane, 1,3-dichloro-1,1,2,3,3-pentafluoropropane, 1,1-dichloro-1,2,3,3,3-pentafluoropropane, chlorohexafluoropropane, 2-chloro-1,1,1,2,3,3-hexafluoropropane, 3-chloro-1,1,1,2,2,3-hexafluoropropane, 1-chloro-1,1,2,2,3,3-hexafluoropropane, 2-chloro-1,1,1,3,3,3-hexafluoropropane, 1-chloro-1,1,2,3,3,3-hexafluoropropane, 1,1,2,2,3,3,3-heptafluoropropane, 1,1,1,2,3,3,3-Heptafluoropropane, dichlorotetrafluoropropane, 2,2-dichloro-1,1,3,3-tetrafluoropropane, 2,2-dichloro-1,1,1,3-tetrafluoropropane, 1,2-dichloro-1,2,3,3-tetrafluoropropane, 2,3-dichloro-1,1,1,2-tetrafluoropropane, 1,2-dichloro-1,1,2,3-tetrafluoropropane, 1,3-dichloro-1,2,2,3-tetrafluoropropane, 1,1-dichloro-2,2,3,3-tetrafluoropropane, 1,3-dichloro-1,1,2,2-tetrafluoropropane, 1,1-dichloro-1,2,2,3-tetrafluoropropane, 2,3-dichloro-1,1,1,3-tetrafluoropropane, 1,3-dichloro-1,1,3,3-tetrafluoropropane, 1,3-dichloro-1,1,3,3-tetrafluoropropane, 1,1-dichloro-1,3,3,3-tetrafluoropropane, 1,1-dichloro-2,3,3,3-tetrafluoropropane, 1,3-dichloro-1,1,2,3-tetrafluoropropane, 1,1-dichloro-1,2,3,3-tetrafluoropropane, chloropentafluoropropane, 1-chloro-1,2,2,3,3-pentafluoropropane, 3-chloro-1,1,1,2,3-pentafluoropropane, 1-chloro-1,1,2,2,3-pentafluoropropane, 2-chloro-1,1,1,3,3-pentafluoropropane, 1-chloro-1,1,3,3,3-pentafluoropropane, 1-chloro-1,1,2,3,3-pentafluoropropane, 3-chloro-1,1,1,2,2-pentafluoropropane, 2-chloro-1,1,2,3,3-pentafluoropropane, 2-chloro-1,1,1,2,3-pentafluoropropane, 1,1,1,2,2,3-hexafluoropropane, 1,1,1,2,3,3-hexafluoropropane, 1,1,1,3,3,3-hexafluoropropane, 1,1,2,2,3,3-hexafluoropropane, dichlorotrifluoropropane, 1,1-dichloro-3,3,3-trifluoropropane, 1,3-dichloro-1,1,3-trifluoropropane, 1,1-dichloro-1,3,3-trifluoropropane, 1,3-dichloro-1,2,3-trifluoropropane, 1,1-dichloro-2,3,3-trifluoropropane, 1,3-dichloro-1,1,2-trifluoropropane, 1,1-dichloro-1,2,3-trifluoropropane, 1,2-dichloro-1,3,3-trifluoropropane, 2,3-dichloro-1,1,1-trifluoropropane, 1,2-dichloro-1,1,3-trifluoropropane, 1,3-dichloro-1,2,2-trifluoropropane, 1,1-dichloro-2,2,3-trifluoropropane, 1,1-dichloro-1,2,2-trifluoropropane, 2,3-dichloro-1,1,2-trifluoropropane, 1,2-dichloro-1,2,3-trifluoropropane, 1,2-dichloro-1,1,2-trifluoropropane, 2,2-dichloro-1,1,3-trifluoropropane, 2,2-dichloro-3,3,3-trifluoropropane, chlorotetrafluoropropane, 2-chloro-1,2,3,3-tetrafluoropropane, 2-chloro-1,1,1,2-tetrafluoropropane, 3-chloro-1,1,2,2-tetrafluoropropane, 1-chloro-1,2,2,3-tetrafluoropropane, 1-chloro-1,1,2,2-tetrafluoropropane, 2-chloro-1,1,3,3-tetrafluoropropane, 2-chloro-1,1,1,3-tetrafluoropropane, 3-chloro-1,1,2,3-tetrafluoropropane, 3-chloro-1,1,1,2-tetrafluoropropane, 1-chloro-1,1,2,3-tetrafluoropropane, 3-chloro-1,1,1,3-tetrafluoropropane, 1-chloro-1,1,3,3-tetrafluoropropane, pentafluoropropane, 1,1,2,2,3-pentafluoropropane, 1,1,2,3,3-pentafluoropropane, 1,1,1,2,3-pentafluoropropane, 1,1,1,3,3-pentafluoropropane, chlorotrifluoropropane, 2-chloro-1,2,3-trifluoropropane, 2-chloro-1,1,2-trifluoropropane, 1-chloro-2,2,3-trifluoropropane, 1-chloro-1,2,2-trifluoropropane, 3-chloro-1,1,2-trifluoropropane, 1-chloro-1,2,3-trifluoropropane, 1-chloro-1,1,2-trifluoropropane, 3-chloro-1,3,3-trifluoropropane, 3-chloro-1,1,1-trifluoropropane, 1-chloro-1,1,3-trifluoropropane, 2-chloro-1,1,3-trifluoropropane, 2-chloro-1,1,1-trifluoropropane, 1,1,2,2-tetrafluoropropane, 1,1,1,3-tetrafluoropropane, 1,1,2,3-tetrafluoropropane, 1,1,1,2-tetrafluoropropane, 1,2,2,3-tetrafluoropropane, 1,1,3,3-tetrafluoropropane, chlorodifluoropropane, 1-chloro-2,2-difluoropropane, 3-chloro-1,1-difluoropropane, 1-chloro-1,3-difluoropropane, 1-chloro-1,1-difluoropropane, 1-chloro-2,3-difluoropropane, 1-chloro-1,2-difluoropropane, 2-chloro-1,3-difluoropropane, 2-chloro-1,1-difluoropropane, 2-chloro-1,2-difluoropropane, trifluoropropane, 1,1,1-trifluoropropane, 1,1,3-trifluoropropane, 1,2,3-trifluoropropane, 1,1,2-trifluoropropane, 1,2,2-trifluoropropane, dichlorotetrafluoropropene, 1,2-dichloro-1,3,3,3-tetrafluoropropene, 1,1-dichloro-2,3,3,3-tetrafluoropropene, 1,3-dichloro-1,2,3,3-tetrafluoropropene, 2,3-dichloro-1,1,3,3-tetrafluoropropene, 3,3-dichloro-1,1,2,3-tetrafluoropropene, chloropentafluoropropene, 1-chloropentafluoropropene, 2-chloropentafluoropropene, 3-chloropentafluoropropene, hexafluoropropene, dichlorotrifluoropropene, 1,1-dichloro-3,3,3-trifluoropropene, 1,2-dichloro-3,3,3-trifluoropropene, 2,3-dichloro-1,3,3-trifluoropropene, 1,3-dichloro-2,3,3-trifluoropropene, 1,2-dichloro-1,3,3-trifluoropropene, 2,3-dichloro-1,1,3-trifluoropropene, 1,1-dichloro-2,3,3-trifluoropropene, 1,3-dichloro-1,2,3-trifluoropropene, 3,3-dichloro-1,1,2-trifluoropropene, 3,3-dichloro-1,2,3-trifluoropropene, 1,3-dichloro-1,3,3-trifluoropropene, 3,3-dichloro-1,1,3-trifluoropropene, 1-chloro-2,3,3,3-tetrafluoropropene, 1-chloro-1,3,3,3-tetrafluoropropene, 2-chloro-1,3,3,3-tetrafluoropropene, 3-chloro-1,2,3,3-tetrafluoropropene, 3-chloro-1,1,3,3-tetrafluoropropene, 2-chloro-1,1,3,3-tetrafluoropropene, 1-chloro-1,2,3,3-tetrafluoropropene, 3-chloro-1,1,2,3-tetrafluoropropene, 1,2,3,3,3-pentafluoropropene, 1,1,3,3,3-pentafluoropropene, 1,1,2,3,3-pentafluoropropene, dichlorodifluoropropene, 2,3-dichloro-3,3-difluoropropene, 1,2-dichloro-1,3-difluoropropene, 2,3-dichloro-1,1-difluoropropene, 1,2-dichloro-3,3-difluoropropene, 2,3-dichloro-1,3-difluoropropene, 1,1-dichloro-2,3-difluoropropene, 1,3-dichloro-1,2-difluoropropene, 1,3-dichloro-2,3-difluoropropene, 3,3-dichloro-1,2-difluoropropene, 3,3-dichloro-2,3-difluoropropene, 1,1-dichloro-3,3-difluoropropene, 1,3-dichloro-1,3-difluoropropene, 3,3-dichloro-1,1-difluoropropene, 1,3-dichloro-3,3-difluoropropene, 3,3-dichloro-1,3-difluoropropene, chlorotrifluoropropene, 2-chloro-1,1,3-trifluoropropene, 2-chloro-1,3,3-trifluoropropene, 1-chloro-1,2,3-trifluoropropene, 3-chloro-1,1,2-trifluoropropene, 1-chloro-2,3,3-trifluoropropene, 3-chloro-1,2,3-trifluoropropene, 3-chloro-2,3,3-trifluoropropene, 1-chloro-1,3,3-trifluoropropene, 3-chloro-1,1,3-trifluoropropene, 3-chloro-1,3,3-trifluoropropene, 1,1,2,3-tetrafluoropropene, 1,2,3,3-tetrafluoropropene, 1,1,3,3-tetrafluoropropene, chlorodifluoropropene, 3-chloro-3,3-difluoropropene, 3-chloro-1,3-difluoropropene, 2-chloro-1,1-difluoropropene, 2-chloro-1,3-difluoropropene, 2-chloro-3,3-difluoropropene, 1-chloro-1,2-difluoropropene, 1-chloro-2,3-difluoropropene, 3-chloro-1,2-difluoropropene, 3-chloro-2,3-difluoropropene, 1-chloro-1,3-difluoropropene, 3-chloro-1,1-difluoropropene, 1-chloro-3,3-difluoropropene, trifluoropropene, 1,1,2-trifluoropropene, 1,2,3-trifluoropropene, 2,3,3-trifluoropropene, 1,1,3-trifluoropropene, 1,3,3-trifluoropropene, chlorofluoropropene, 1-chloro-3-fluoropropene, 1-chloro-1-fluoropropene, 1-chloro-2-fluoropropene, 2-chloro-1-fluoropropene, 2-chloro-3-fluoropropene, 3-chloro-2-fluoropropene, 3-chloro-1-fluoropropene, 3-chloro-3-fluoropropene, difluoropropene, 1,2-difluoropropene, 2,3-difluoropropene, 1,1-difluoropropene, 1,3-difluoropropene, 3,3-difluoropropene, 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, Z-3,3,3-trifluoro-1-chloropropene and trifluoropropyne.

A subject of the present invention is also an azeotropic or quasi-azeotropic composition comprising hydrogen fluoride, 2,3,3,3-tetrafluoropropene and one or more compounds chosen from 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro-1,1,1,2-tetrafluoropropane.

A subject of the present invention is also an azeotropic or quasi-azeotropic composition comprising hydrogen fluoride, 2,3,3,3-tetrafluoropropene and one or more compounds chosen from 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene and E-3,3,3-trifluoro-1-chloropropene.

A subject of the present invention is an azeotropic or quasi-azeotropic composition comprising hydrogen fluoride, 2,3,3,3-tetrafluoropropene and one or more compounds chosen from E-1,3,3,3-tetrafluoropropene, Z-1,3,3,3-tetrafluoropropene, 3,3,3-trifluoropropene, 3,3,3-trifluoro-2-chloropropene and E-3,3,3-trifluoro-1-chloropropene.

According to one embodiment of the invention, the composition comprises hydrogen fluoride, 2,3,3,3-tetrafluoropropene, 1,1,1,2,2-pentafluoropropane and optionally one or more compounds chosen from E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro,1,1,1,2-tetrafluoropropane.

According to another embodiment of the invention, the composition comprises hydrogen fluoride, 2,3,3,3-tetrafluoropropene, E-1,3,3,3-tetrafluoropropene and optionally one or more compounds chosen from Z-1,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro,1,1,1,2-tetrafluoropropane.

According to another embodiment of the invention, the composition comprises hydrogen fluoride, 2,3,3,3-tetrafluoropropene, 2-chloro,1,1,1,2-tetrafluoropropane and optionally one or more compounds chosen from Z-1,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene and 1,1,1,2,3-pentafluoropropene.

In one embodiment, the composition comprises hydrogen fluoride, 2,3,3,3-tetrafluoropropene, Z-1,3,3,3-tetrafluoropropene and optionally one or more compounds chosen from 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene and 1,1,1,2,3-pentafluoropropene.

In another embodiment, the composition comprises hydrogen fluoride, 2,3,3,3-tetrafluoropropene, 3,3,3-trifluoropropene and optionally one or more compounds chosen from 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene and 1,1,1,2,3-pentafluoropropene.

According to one embodiment of the invention, the composition comprises hydrogen fluoride, 2,3,3,3-tetrafluoropropene, 3,3,3-trifluoro-2-chloropropene and optionally one or more compounds chosen from E-3,3,3-trifluoro-1-chloropropene, trifluoropropyne, 1,1,1,3,3-pentafluoropropane, 1,1,1,3,3-pentafluoropropene and 1,1,1,2,3-pentafluoropropene.

According to another embodiment of the invention, the composition comprises hydrogen fluoride, 2,3,3,3-tetrafluoropropene, E-3,3,3-trifluoro-1-chloropropene and optionally one or more compounds chosen from trifluoropropyne, 1,1,1,3,3-pentafluoropropane, 1,1,1,3,3-pentafluoropropene and 1,1,1,2,3-pentafluoropropene.

According to another embodiment of the invention, the composition comprises hydrogen fluoride, 2,3,3,3-tetrafluoropropene, trifluoropropyne and optionally one or more compounds chosen from 1,1,1,3,3-pentafluoropropane, 1,1,1,3,3-pentafluoropropene and 1,1,1,2,3-pentafluoropropene.

According to another embodiment of the invention, the composition comprises hydrogen fluoride, 2,3,3,3-tetrafluoropropene, 1,1,1,3,3-pentafluoropropane and optionally one or more compounds chosen from 1,1,1,3,3-pentafluoropropene and 1,1,1,2,3-pentafluoropropene.

According to another embodiment of the invention, the composition comprises hydrogen fluoride, 2,3,3,3-tetrafluoropropene, 1,1,1,3,3-pentafluoropropene and optionally 1,1,1,2,3-pentafluoropropene.

According to another embodiment of the invention, the composition comprises hydrogen fluoride, 2,3,3,3-tetrafluoropropene and 1,1,1,2,3-pentafluoropropene.

Irrespective of the embodiment, the composition preferably comprises from 1% to 85% and advantageously from 5% to 80% by weight of hydrogen fluoride and from 99% to 15% and advantageously from 20% to 95% by weight of the sum of the organic compounds; more particularly, the composition comprises from 1% to 85% by weight of hydrogen fluoride and from 99% to 15% by weight of the sum of the organic compounds (HFO-1234yf and the (hydro)halocarbon compounds).

Irrespective of the embodiment, the boiling point of the composition according to the invention is between −20° C. and 80° C. and at a pressure between 0.1 and 44 bar absolute, preferentially between 0° C. and 40° C. and preferentially at a pressure of between 0.7 and 18 bar absolute, advantageously between 0.9 and 12.5 bar absolute.

When the compound HFC-245cb or HCFO-1232xf is present, quaternary compositions and higher are preferred.

The Applicant has discovered that the compositions according to the invention have advantageous properties in particular for the recycling of HF in the reaction step. Thus, the condensed phase of these compositions, optionally when they are subjected to a distillation step and/or a liquid/liquid separation step, such as by decantation, form two immiscible liquid phases.

By way of example, for the ternary compounds containing hydrogen fluoride, 2,3,3,3-tetrafluoropropene and a compound chosen from 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene and E-3,3,3-trifluoro-1-chloropropene, the appearance of a heteroazeotrope characterized by two liquid phases, one rich in HF and the other depleted in HF, depends on the amount of HF in the composition. These decantation ranges as a function of the HF content in the compositions were characterized for at least isotherms at 0° C., 25° C. and 40° C.

Similarly, the decantation ranges for the ternary compounds containing hydrogen fluoride, 2,3,3,3-tetrafluoropropene and a compound chosen from trifluoropropyne, 1,1,1,3,3-pentafluoropropane, 1,1,1,3,3-pentafluoropropene, Z-1,1,1,2,3-pentafluoropropene and 2-chloro,1,1,1,2-tetrafluoropropane are characterized by a phase depleted in HF and a phase enriched in HF for at least isotherms at 0° C., 25° C. and 40° C.

The Applicant has observed the same phenomenon for compositions of hydrogen fluoride and 2,3,3,3-tetrafluoropropene comprising several compounds chosen from 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, trifluoropropyne, 1,1,1,3,3-pentafluoropropane, 1,1,1,3,3-pentafluoropropene, 1,1,1,2,3-pentafluoropropene and 2-chloro,1,1,1,2-tetrafluoropropane.

An azeotropic or quasi-azeotropic composition that is preferred according to the invention comprises from 1% to 85% by weight of hydrogen fluoride and from 99% to 15% by weight of the sum of HFO-1234yf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 1% to 80% by weight of hydrogen fluoride and from 99% to 20% by weight of the sum of HFO-1234yf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf and of HFO-1225yeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of HFO-1225yeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf and of HFO-1225zc, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of HFO-1225zc, the boiling point of this preferred composition is between 0 and 40° C. at a pressure of between 0.9 and 11.6 bar absolute.

An azeotropic or quasi-azeotropic composition that is preferred according to the invention preferably comprises from 1% to 80% by weight of hydrogen fluoride and from 99% to 20% by weight of the sum of HFO-1234yf and of trifluoropropyne, the boiling point of this preferred composition is between 0 and 40° C. at a pressure of between 0.9 and 18.0 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of trifluoropropyne, the boiling point of this preferred composition is between 0 and 40° C. at a pressure of between 0.9 and 18.0 bar absolute.

An azeotropic or quasi-azeotropic composition that is preferred according to the invention preferably comprises from 1% to 80% by weight of hydrogen fluoride and from 99% to 20% by weight of the sum of HFO-1234yf and of HFC-245fa, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of HFC-245fa, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf and of HCFC-244bb, the boiling point of this preferred composition is between 0 and 40° C. at a pressure of between 0.7 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf and of HCFC-244bb, the boiling point of this preferred composition is between 0 and 40° C. at a pressure of between 0.7 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HFO-1225yeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HFO-1225yeZ, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HFO-1225zc, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HFO-1225zc, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HFC-245fa, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HFC-245fa, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of HCFC-244bb, the boiling point of this preferred composition is between 0 and 40° C. at a pressure of between 0.7 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of HCFC-244bb, the boiling point of this preferred composition is between 0 and 40° C. at a pressure of between 0.7 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFC-245cb and of trifluoropropyne, the boiling point of this preferred composition is between 0 and 40° C. at a pressure of between 0.9 and 18.0 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFC-245cb and of trifluoropropyne, the boiling point of this preferred composition is between 0 and 40° C. at a pressure of between 0.9 and 18.0 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233xf and of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233xf and of HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233xf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233xf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233xf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233xf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233xf and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233xf and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeZ and of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeZ and of HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE and of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE and of HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE and of HFO-1225yeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE and of HFO-1225yeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE and of HFO-1225zc, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE and of HFO-1225zc, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE and of HFC-245fa, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE and of HFC-245fa, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE and of HCFC-244bb, the boiling point of this preferred composition is between 0 and 40° C. at a pressure of between 0.7 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE and of HCFC-244bb, the boiling point of this preferred composition is between 0 and 40° C. at a pressure of between 0.7 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE and of trifluoropropyne, the boiling point of this preferred composition is between 0 and 40° C. at a pressure of between 0.9 and 18.0 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE and of trifluoropropyne, the boiling point of this preferred composition is between 0 and 40° C. at a pressure of between 0.9 and 18.0 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1225yeZ and of trifluoropropyne, the boiling point of this preferred composition is between 0 and 40° C. at a pressure of between 0.9 and 18.0 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1225yeZ and of trifluoropropyne, the boiling point of this preferred composition is between 0 and 40° C. at a pressure of between 0.9 and 18.0 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFC-244bb and of trifluoropropyne, the boiling point of this preferred composition is between 0 and 40° C. at a pressure of between 0.7 and 18.0 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFC-244bb and of trifluoropropyne, the boiling point of this preferred composition is between 0 and 40° C. at a pressure of between 0.7 and 18.0 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFC-244bb and of HFC-245fa, the boiling point of this preferred composition is between 0 and 40° C. at a pressure of between 0.7 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFC-244bb and of HFC-245fa, the boiling point of this preferred composition is between 0 and 40° C. at a pressure of between 0.7 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeZ and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeZ and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1243zf and of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1243zf and of HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1233xf and of HCFC-244bb, the boiling point of this preferred composition is between 0 and 40° C. at a pressure of between 0.7 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1243zf and of HCFO-1233zdE, the boiling point of this preferred composition is between 0 and 40° C. at a pressure of between 0.7 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HCFO-1233xf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HCFO-1233xf and of HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeE, of HCFO-1233xf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeE, of HCFO-1233xf and of HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HCFO-1233xf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HCFO-1233xf and of HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1243zf, of HCFO-1233xf and of HFC-245cb, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1243zf, of HCFO-1233xf and of HFC-245cb, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeZ, of HCFO-1233xf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeZ, of HCFO-1233xf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1243zf, of HCFO-1233xf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1243zf, of HCFO-1233xf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233zdE, of HCFO-1233xf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233zdE, of HCFO-1233xf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1243zf, of HCFO-1233xf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1243zf, of HCFO-1233xf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233zdE, of HCFO-1233xf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233zdE, of HCFO-1233xf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233zdE, of HCFO-1233xf and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233zdE, of HCFO-1233xf and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233zdE, of HFO-1234zeZ and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233zdE, of HFO-1234zeZ and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeZ, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeZ, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233zdE, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233zdE, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233zdE, of HFO-1243zf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233zdE, of HFO-1243zf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1243zf, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1243zf, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb and of HCFO-1233zdE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb and of HCFO-1233zdE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HFC-245cb and of HFO-1243zf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HFC-245cb and of HFO-1243zf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233xf, of HFC-245cb and of HCFC-244bb, the boiling point of this preferred composition is between 0 and 40° C. at a pressure of between 0.7 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233xf, of HFC-245cb and of HCFC-244bb, the boiling point of this preferred composition is between 0 and 40° C. at a pressure of between 0.7 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeE, of HFO-1234zeZ, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeE, of HFO-1234zeZ, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeE, of HCFO-1233zdE, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeE, of HCFO-1233zdE, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeE, of HFO-1243zf, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeE, of HFO-1243zf, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HFO-1234zeZ, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HFO-1234zeZ, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1243zf, of HFO-1234zeZ, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1243zf, of HFO-1234zeZ, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1243zf, of HCFO-1233zdE, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1243zf, of HCFO-1233zdE, of HFC-245cb and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE, of HFO-1234zeZ, of HCFO-1233zdE and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE, of HFO-1234zeZ, of HCFO-1233zdE and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE, of HFO-1234zeZ, of HFO-1243zf and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE, of HFO-1234zeZ, of HFO-1243zf and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeE, of HCFO-1233zdE, of HFO-1243zf and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeE, of HCFO-1233zdE, of HFO-1243zf and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeZ, of HCFO-1233zdE, of HFO-1243zf and of HCFO-1233xf, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeZ, of HCFO-1233zdE, of HFO-1243zf and of HCFO-1233xf, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HCFO-1233zdE, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HCFO-1233zdE, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFO-1243zf, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFO-1243zf, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HFO-1243zf, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HFO-1243zf, of HFC-245cb and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HFO-1243zf, of HFC-245cb and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HFO-1243zf, of HFC-245cb and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HCFO-1233zdE, of HFO-1243zf, of HFO-1234zeZ and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HCFO-1233zdE, of HFO-1243zf, of HFO-1234zeZ and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HCFO-1233xf, of HFC-245cb, of HFO-1234zeZ and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HCFO-1233xf, of HFC-245cb, of HFO-1234zeZ and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HCFO-1233xf, of HFC-245cb, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HCFO-1233xf, of HFC-245cb, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HCFO-1233zdE, of HCFO-1233xf, of HFC-245cb, of HFO-1243zf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HCFO-1233zdE, of HCFO-1233xf, of HFC-245cb, of HFO-1243zf and of HFO-1234zeZ, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HCFO-1233xf, of HFC-245cb, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HCFO-1233xf, of HFC-245cb, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFO-1234zeZ, of HCFO-1233xf, of HCFO-1233zdE, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFO-1234zeZ, of HCFO-1233xf, of HCFO-1233zdE, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb, of HCFO-1233zdE, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb, of HCFO-1233zdE, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 80% by weight of hydrogen fluoride and from 99% to 20% by weight of the sum of HFO-1234yf, of HFC-245fa, of HCFC-244bb, of trifluoropropyne, of HFO-1225yeZ and of HFO-1225zc, the boiling point of this preferred composition is between 0 and 40° C. at a pressure of between 0.7 and 18.0 bar absolute.

An azeotropic or quasi-azeotropic composition that is preferred according to the invention preferably comprises from 5% to 75% by weight of hydrogen fluoride and from 95% to 25% by weight of the sum of HFO-1234yf, of HFC-245fa, of HCFC-244bb, of trifluoropropyne, of HFO-1225yeZ and of HFO-1225zc, the boiling point of this preferred composition is between 0 and 40° C. at a pressure of between 0.7 and 18.0 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb, of HCFO-1233zdE, of HCFO-1233xf, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb, of HCFO-1233zdE, of HCFO-1233xf, of HFO-1243zf and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb, of HCFO-1233zdE, of HCFO-1233xf, of HCFC-244bb and of HFO-1234zeE, the boiling point of this preferred composition is between 0 and 40° C. at a pressure of between 0.7 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb, of HCFO-1233zdE, of HCFO-1233xf, of HCFC-244bb and of HFO-1234zeE, the boiling point of this preferred composition is between 0 and 40° C. at a pressure of between 0.7 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb, of HCFO-1233zdE, of HCFO-1233xf, of trifluoropropyne and of HFO-1234zeE, the boiling point of this preferred composition is between 0 and 40° C. at a pressure of between 0.9 and 18 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb, of HCFO-1233zdE, of HCFO-1233xf, of trifluoropropyne and of HFO-1234zeE, the boiling point of this preferred composition is between 0 and 40° C. at a pressure of between 0.9 and 18 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb, of HCFO-1233zdE, of HCFO-1233xf, of HFC-245fa and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb, of HCFO-1233zdE, of HCFO-1233xf, of HFC-245fa and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb, of HCFO-1233zdE, of HCFO-1233xf, of HFO-1225yeZ and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb, of HCFO-1233zdE, of HCFO-1233xf, of HFO-1225yeZ and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb, of HCFO-1233zdE, of HCFO-1233xf, of HFO-1225zc and of HFO-1234zeE, the boiling point of this preferred composition is between 0 and 40° C. at a pressure of between 0.9 and 11.6 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb, of HCFO-1233zdE, of HCFO-1233xf, of HFO-1225zc and of HFO-1234zeE, the boiling point of this preferred composition is between 0 and 40° C. at a pressure of between 0.9 and 11.6 bar absolute.

An azeotropic or quasi-azeotropic composition that is preferred according to the invention comprises from 1% to 85% by weight of hydrogen fluoride and from 99% to 15% by weight of the sum of HFO-1234yf, of HFO-1234zeZ, of HFC-245cb, of HCFO-1233zdE, of HCFO-1233xf, of HFO-1225zc, of trifluoropropyne, of HCFC-244bb, of HFC-245fa, of HFO-1225yeZ, of HFO-1243zf and of HFO-1234zeE, the boiling point of this preferred composition is between 0 and 40° C. at a pressure of between 0.7 and 18 bar absolute.

An azeotropic or quasi-azeotropic composition that is preferred according to the invention preferably comprises from 5% to 80% by weight of hydrogen fluoride and from 95% to 20% by weight of the sum of HFO-1234yf, of HFO-1234zeZ, of HFC-245cb, of HCFO-1233zdE, of HCFO-1233xf, of HFO-1225zc, of trifluoropropyne, of HCFC-244bb, of HFC-245fa, of HFO-1225yeZ, of HFO-1243zf and of HFO-1234zeE, the boiling point of this preferred composition is between 0 and 40° C. at a pressure of between 0.7 and 18 bar absolute.

An azeotropic or quasi-azeotropic composition according to the invention comprises from 1% to 80% by weight of hydrogen fluoride and from 99% to 20% by weight of trifluoropropyne, the boiling point of this composition is between 0 and 40° C. at a pressure of between 6 and 18 bar absolute.

An azeotropic or quasi-azeotropic composition according to the invention preferably comprises from 5% to 75% by weight of hydrogen fluoride and from 95% to 25% by weight of trifluoropropyne, the boiling point of this composition is between 0 and 40° C. at a pressure of between 6 and 18 bar absolute.

An azeotropic or quasi-azeotropic composition according to the invention comprises from 1% to 90% by weight of hydrogen fluoride and from 99% to 10% by weight of 2-chloro,1,1,1,2-tetrafluoropropane, the boiling point of this composition is between 0 and 40° C. at a pressure of between 0.7 and 3 bar absolute.

An azeotropic or quasi-azeotropic composition according to the invention preferably comprises from 5% to 85% by weight of hydrogen fluoride and from 95% to 15% by weight of 2-chloro,1,1,1,2-tetrafluoropropane, the boiling point of this composition is between 0 and 40° C. at a pressure of between 0.7 and 3 bar absolute.

An azeotropic or quasi-azeotropic composition according to the invention comprises from 1% to 90% by weight of hydrogen fluoride and from 99% to 10% by weight of 1,1,1,3,3-pentafluoropropane, the boiling point of this composition is between 0 and 40° C. at a pressure of between 1 and 4.4 bar absolute.

An azeotropic or quasi-azeotropic composition according to the invention preferably comprises from 5% to 85% by weight of hydrogen fluoride and from 95% to 15% by weight of 1,1,1,3,3-pentafluoropropane, the boiling point of this composition is between 0 and 40° C. at a pressure of between 1 and 4.4 bar absolute.

The pressure characteristics of the mixtures of Examples 1 to 7 were calculated for an isotherm at 25° C.

Examples 8 to 14 represent the boiling point and pressure ranges of the mixtures corresponding to those of Examples 1 to 7.

Examples 15 to 21 represent the decantation ranges of the mixtures of Examples 1 to 7 as a function of the mass percentage of HF characterized for isotherms at 0° C., 25° C. and 40° C.

Example 22 represents the pressure characteristics of the binary mixtures HF-trifluoropropyne, HF-HCFC-244bb and HF-HFC-245fa, calculated for an isotherm at 25° C.

Example 23 represents the boiling point and pressure ranges of the mixtures corresponding to those of Example 22.

Example 24 represents the decantation ranges of the mixtures of Example 22 as a function of the mass percentage of HF characterized for isotherms at 0° C., 25° C. and 40° C.

The decantation ranges of Examples 15 to 21 and 24 are calculated for mixtures of organic compounds having equivalent mass contents. By way of example, for a ternary mixture, a mixture containing 50% by weight of each of the two organic compounds is considered; for a penternary mixture, a mixture containing 25% by weight of each of the four organic compounds is considered, the mass fraction of HF ranging from 0 to 1. These calculations are performed at liquid-vapour equilibrium, under azeotropic conditions.

EXAMPLE 1

Ternary Mixtures

| HF-HFO-1234yf-HFC-245cb | | | | | |
|---|---|---|---|---|---|
| Organics 0.95 F1234yf + 0.05 F245cb | | Organics 0.05 F1234yf + 0.95 F245cb | | Organics 0.05 F1234yf + 0.95 F245cb | |
| MASSFRAC HF | TOTAL PRESSURE bar | MASSFRAC HF | TOTAL PRESSURE bar | MASSFRAC HF | TOTAL PRESSURE bar |
| 0 | 6.7 | 0 | 5.8 | 0 | 4.8 |
| 0.05 | 7.7 | 0.05 | 6.9 | 0.05 | 5.9 |
| 0.1 | 7.7 | 0.1 | 6.9 | 0.1 | 5.9 |
| 0.15 | 7.7 | 0.15 | 6.9 | 0.15 | 5.9 |
| 0.2 | 7.7 | 0.2 | 6.9 | 0.2 | 5.9 |
| 0.25 | 7.7 | 0.25 | 6.9 | 0.25 | 5.9 |

-continued

| HF-HFO-1234yf-HFC-245cb | | | | | |
|---|---|---|---|---|---|
| Organics 0.95 F1234yf + 0.05 F245cb | | Organics 0.05 F1234yf + 0.95 F245cb | | Organics 0.05 F1234yf + 0.95 F245cb | |
| MASSFRAC HF | TOTAL PRESSURE bar | MASSFRAC HF | TOTAL PRESSURE bar | MASSFRAC HF | TOTAL PRESSURE bar |
| 0.3 | 7.7 | 0.3 | 6.9 | 0.3 | 5.9 |
| 0.35 | 7.7 | 0.35 | 6.9 | 0.35 | 5.9 |
| 0.4 | 7.7 | 0.4 | 6.9 | 0.4 | 5.9 |
| 0.45 | 7.7 | 0.45 | 6.9 | 0.45 | 5.9 |
| 0.5 | 7.7 | 0.5 | 6.8 | 0.5 | 5.9 |
| 0.55 | 7.7 | 0.55 | 6.8 | 0.55 | 5.9 |
| 0.6 | 7.7 | 0.6 | 6.8 | 0.6 | 5.9 |
| 0.65 | 7.7 | 0.65 | 6.8 | 0.65 | 5.9 |
| 0.7 | 7.6 | 0.7 | 6.8 | 0.7 | 5.9 |
| 0.75 | 7.5 | 0.75 | 6.8 | 0.75 | 5.9 |
| 0.8 | 7.2 | 0.8 | 6.8 | 0.8 | 5.9 |
| 0.85 | 6.6 | 0.85 | 6.3 | 0.85 | 5.9 |
| 0.9 | 5.6 | 0.9 | 5.3 | 0.9 | 5.1 |
| 0.95 | 3.9 | 0.95 | 3.7 | 0.95 | 3.6 |
| 1 | 1.2 | 1 | 1.2 | 1 | 1.2 |

| HF-HFO-1234yf-HFO-1234zeE | | | | | |
|---|---|---|---|---|---|
| Organics 0.95 F1234zeE + 0.05 F1234yf | | Organics 0.5 F1234zeE + 0.5 F1234yf | | Organics 0.05 F1234zeE + 0.95 F1234yf | |
| MASSFRAC HF | TOTAL PRESSURE bar | MASSFRAC HF | TOTAL PRESSURE bar | MASSFRAC HF | TOTAL PRESSURE bar |
| 0 | 5.0 | 0 | 5.9 | 0 | 6.7 |
| 0.05 | 5.9 | 0.05 | 6.8 | 0.05 | 7.7 |
| 0.1 | 5.9 | 0.1 | 6.8 | 0.1 | 7.7 |
| 0.15 | 5.9 | 0.15 | 6.8 | 0.15 | 7.7 |
| 0.2 | 5.9 | 0.2 | 6.8 | 0.2 | 7.7 |
| 0.25 | 5.9 | 0.25 | 6.8 | 0.25 | 7.6 |
| 0.3 | 5.9 | 0.3 | 6.8 | 0.3 | 7.7 |
| 0.35 | 5.9 | 0.35 | 6.8 | 0.35 | 7.7 |
| 0.4 | 5.9 | 0.4 | 6.8 | 0.4 | 7.7 |
| 0.45 | 5.9 | 0.45 | 6.8 | 0.45 | 7.7 |
| 0.5 | 5.9 | 0.5 | 6.8 | 0.5 | 7.7 |
| 0.55 | 5.8 | 0.55 | 6.8 | 0.55 | 7.7 |
| 0.6 | 5.8 | 0.6 | 6.8 | 0.6 | 7.7 |
| 0.65 | 5.7 | 0.65 | 6.7 | 0.65 | 7.7 |
| 0.7 | 5.5 | 0.7 | 6.6 | 0.7 | 7.6 |
| 0.75 | 5.3 | 0.75 | 6.4 | 0.75 | 7.5 |
| 0.8 | 4.9 | 0.8 | 6.1 | 0.8 | 7.1 |
| 0.85 | 4.4 | 0.85 | 5.5 | 0.85 | 6.5 |
| 0.9 | 3.7 | 0.9 | 4.6 | 0.9 | 5.5 |
| 0.95 | 2.6 | 0.95 | 3.2 | 0.95 | 3.8 |
| 1 | 1.2 | 1 | 1.2 | 1 | 1.2 |

| HF-HFO-1234yf-HFO-1234zeZ | | | | | |
|---|---|---|---|---|---|
| Organics 0.95 F1234zeZ + 0.05 F1234yf | | Organics 0.5 F1234zeZ + 0.5 F1234yf | | Organics 0.05 F1234zeZ + 0.95 F1234yf | |
| MASS-FRAC HF | TOTAL PRESSURE bar | MASS-FRAC HF | TOTAL PRESSURE bar | MASS-FRAC HF | TOTAL PRESSURE bar |
| 0 | 2.1 | 0 | 4.3 | 0 | 6.5 |
| 0.05 | 3.2 | 0.05 | 5.4 | 0.05 | 7.5 |
| 0.1 | 3.2 | 0.1 | 5.4 | 0.1 | 7.5 |

-continued

| HF-HFO-1234yf-HFO-1234zeZ | | | | | |
|---|---|---|---|---|---|
| Organics 0.95 F1234zeZ + 0.05 F1234yf | | Organics 0.5 F1234zeZ + 0.5 F1234yf | | Organics 0.05 F1234zeZ + 0.95 F1234yf | |
| MASS-FRAC HF | TOTAL PRESSURE bar | MASS-FRAC HF | TOTAL PRESSURE bar | MASS-FRAC HF | TOTAL PRESSURE bar |
| 0.15 | 3.2 | 0.15 | 5.4 | 0.15 | 7.5 |
| 0.2 | 3.2 | 0.2 | 5.4 | 0.2 | 7.5 |

-continued

| HF-HFO-1234yf-HFO-1234zeZ | | | | | |
|---|---|---|---|---|---|
| Organics 0.95 F1234zeZ + 0.05 F1234yf | | Organics 0.5 F1234zeZ + 0.5 F1234yf | | Organics 0.05 F1234zeZ + 0.95 F1234yf | |
| MASS-FRAC HF | TOTAL PRESSURE bar | MASS-FRAC HF | TOTAL PRESSURE bar | MASS-FRAC HF | TOTAL PRESSURE bar |
| 0.25 | 3.2 | 0.25 | 5.4 | 0.25 | 7.5 |
| 0.3 | 3.2 | 0.3 | 5.4 | 0.3 | 7.5 |
| 0.35 | 3.2 | 0.35 | 5.4 | 0.35 | 7.5 |
| 0.4 | 3.2 | 0.4 | 5.4 | 0.4 | 7.5 |
| 0.45 | 3.2 | 0.45 | 5.4 | 0.45 | 7.5 |
| 0.5 | 3.2 | 0.5 | 5.4 | 0.5 | 7.5 |
| 0.55 | 3.2 | 0.55 | 5.4 | 0.55 | 7.5 |
| 0.6 | 3.2 | 0.6 | 5.4 | 0.6 | 7.5 |
| 0.65 | 3.2 | 0.65 | 5.4 | 0.65 | 7.5 |
| 0.7 | 3.2 | 0.7 | 5.4 | 0.7 | 7.5 |
| 0.75 | 3.2 | 0.75 | 5.3 | 0.75 | 7.3 |
| 0.8 | 3.0 | 0.8 | 5.0 | 0.8 | 7.0 |
| 0.85 | 2.8 | 0.85 | 4.6 | 0.85 | 6.5 |
| 0.9 | 2.5 | 0.9 | 3.9 | 0.9 | 5.4 |
| 0.95 | 1.9 | 0.95 | 2.8 | 0.95 | 3.8 |
| 1 | 1.2 | 1 | 1.2 | 1 | 1.2 |

| HF-HFO-1234yf-HFO-1243zf | | | | | |
|---|---|---|---|---|---|
| Organics 0.95 F1243zf + 0.05 F1234yf | | Organics 0.5 F1243zf + 0.5 F1234yf | | Organics 0.05 F1243zf + 0.95 F1234yf | |
| MASS-FRAC HF | TOTAL PRESSURE bar | MASS-FRAC HF | TOTAL PRESSURE bar | MASS-FRAC HF | TOTAL PRESSURE bar |
| 0 | 5.9 | 0 | 6.3 | 0 | 6.7 |
| 0.05 | 6.8 | 0.05 | 7.2 | 0.05 | 7.7 |
| 0.1 | 6.9 | 0.1 | 7.3 | 0.1 | 7.7 |
| 0.15 | 6.9 | 0.15 | 7.3 | 0.15 | 7.7 |
| 0.2 | 6.8 | 0.2 | 7.2 | 0.2 | 7.7 |
| 0.25 | 6.8 | 0.25 | 7.2 | 0.25 | 7.7 |
| 0.3 | 6.8 | 0.3 | 7.2 | 0.3 | 7.7 |
| 0.35 | 6.8 | 0.35 | 7.2 | 0.35 | 7.7 |
| 0.4 | 6.8 | 0.4 | 7.2 | 0.4 | 7.7 |
| 0.45 | 6.8 | 0.45 | 7.2 | 0.45 | 7.7 |
| 0.5 | 6.8 | 0.5 | 7.2 | 0.5 | 7.7 |
| 0.55 | 6.8 | 0.55 | 7.2 | 0.55 | 7.7 |
| 0.6 | 6.8 | 0.6 | 7.2 | 0.6 | 7.7 |
| 0.65 | 6.7 | 0.65 | 7.2 | 0.65 | 7.7 |
| 0.7 | 6.6 | 0.7 | 7.1 | 0.7 | 7.7 |
| 0.75 | 6.5 | 0.75 | 7.0 | 0.75 | 7.5 |
| 0.8 | 6.2 | 0.8 | 6.7 | 0.8 | 7.2 |
| 0.85 | 5.7 | 0.85 | 6.1 | 0.85 | 6.6 |
| 0.9 | 4.8 | 0.9 | 5.2 | 0.9 | 5.6 |
| 0.95 | 3.4 | 0.95 | 3.6 | 0.95 | 3.8 |
| 1 | 1.2 | 1 | 1.2 | 1 | 1.2 |

| HF-HFO-1234yf-HCFO-1233xf | | | | | |
|---|---|---|---|---|---|
| Organics 0.95 F1233xf + 0.05 F1234yf | | Organics 0.5 F1233xf + 0.5 F1234yf | | Organics 0.05 F1233xf + 0.95 F1234yf | |
| MASS-FRAC HF | TOTAL PRESSURE bar | MASS-FRAC HF | TOTAL PRESSURE bar | MASS-FRAC HF | TOTAL PRESSURE bar |
| 0 | 1.9 | 0 | 4.3 | 0 | 6.6 |
| 0.05 | 3.0 | 0.05 | 5.4 | 0.05 | 7.5 |
| 0.1 | 3.0 | 0.1 | 5.4 | 0.1 | 7.5 |
| 0.15 | 3.0 | 0.15 | 5.4 | 0.15 | 7.5 |

-continued

| HF-HFO-1234yf-HCFO-1233xf | | | | | |
|---|---|---|---|---|---|
| Organics 0.95 F1233xf + 0.05 F1234yf | | Organics 0.5 F1233xf + 0.5 F1234yf | | Organics 0.05 F1233xf + 0.95 F1234yf | |
| MASS-FRAC HF | TOTAL PRESSURE bar | MASS-FRAC HF | TOTAL PRESSURE bar | MASS-FRAC HF | TOTAL PRESSURE bar |
| 0.2 | 3.0 | 0.2 | 5.4 | 0.2 | 7.5 |
| 0.25 | 3.0 | 0.25 | 5.4 | 0.25 | 7.5 |
| 0.3 | 3.0 | 0.3 | 5.4 | 0.3 | 7.5 |
| 0.35 | 3.0 | 0.35 | 5.4 | 0.35 | 7.5 |
| 0.4 | 3.0 | 0.4 | 5.4 | 0.4 | 7.5 |
| 0.45 | 3.0 | 0.45 | 5.4 | 0.45 | 7.5 |
| 0.5 | 3.0 | 0.5 | 5.4 | 0.5 | 7.5 |
| 0.55 | 3.0 | 0.55 | 5.4 | 0.55 | 7.5 |
| 0.6 | 3.0 | 0.6 | 5.4 | 0.6 | 7.5 |
| 0.65 | 2.9 | 0.65 | 5.4 | 0.65 | 7.5 |
| 0.7 | 2.9 | 0.7 | 5.4 | 0.7 | 7.5 |
| 0.75 | 2.9 | 0.75 | 5.3 | 0.75 | 7.4 |
| 0.8 | 2.8 | 0.8 | 5.0 | 0.8 | 7.0 |
| 0.85 | 2.6 | 0.85 | 4.6 | 0.85 | 6.5 |
| 0.9 | 2.3 | 0.9 | 3.9 | 0.9 | 5.4 |
| 0.95 | 1.8 | 0.95 | 2.8 | 0.95 | 3.8 |
| 1 | 1.2 | 1 | 1.2 | 1 | 1.2 |

| HF-HFO-1234yf-HCFO-1233zdE | | | | | |
|---|---|---|---|---|---|
| Organics 0.95 F1233zdE + 0.05 F1234yf | | Organics 0.5 F1233zdE + 0.5 F1234yf | | Organics 0.05 F1233zdE + 0.95 F1234yf | |
| MASS-FRAC HF | TOTAL PRESSURE bar | MASS-FRAC HF | TOTAL PRESSURE bar | MASS-FRAC HF | TOTAL PRESSURE bar |
| 0 | 1.6 | 0 | 4.2 | 0 | 6.5 |
| 0.05 | 2.7 | 0.05 | 5.3 | 0.05 | 7.5 |
| 0.1 | 2.7 | 0.1 | 5.3 | 0.1 | 7.5 |
| 0.15 | 2.7 | 0.15 | 5.3 | 0.15 | 7.5 |
| 0.2 | 2.7 | 0.2 | 5.3 | 0.2 | 7.5 |
| 0.25 | 2.7 | 0.25 | 5.3 | 0.25 | 7.5 |
| 0.3 | 2.7 | 0.3 | 5.3 | 0.3 | 7.5 |
| 0.35 | 2.7 | 0.35 | 5.3 | 0.35 | 7.5 |
| 0.4 | 2.7 | 0.4 | 5.3 | 0.4 | 7.5 |
| 0.45 | 2.7 | 0.45 | 5.3 | 0.45 | 7.5 |
| 0.5 | 2.7 | 0.5 | 5.3 | 0.5 | 7.5 |
| 0.55 | 2.7 | 0.55 | 5.3 | 0.55 | 7.5 |
| 0.6 | 2.7 | 0.6 | 5.3 | 0.6 | 7.5 |
| 0.65 | 2.7 | 0.65 | 5.3 | 0.65 | 7.5 |
| 0.7 | 2.7 | 0.7 | 5.3 | 0.7 | 7.5 |
| 0.75 | 2.7 | 0.75 | 5.2 | 0.75 | 7.4 |
| 0.8 | 2.6 | 0.8 | 4.9 | 0.8 | 7.0 |
| 0.85 | 2.4 | 0.85 | 4.5 | 0.85 | 6.5 |
| 0.9 | 2.1 | 0.9 | 3.8 | 0.9 | 5.4 |
| 0.95 | 1.7 | 0.95 | 2.8 | 0.95 | 3.8 |
| 1 | 1.2 | 1 | 1.2 | 1 | 1.2 |

| HF-HFO-1234yf-Trifluoropropyne | | | | | |
|---|---|---|---|---|---|
| Organics 0.5 F1234yf + 0.5 TFP | | Organics 0.95 F1234yf + 0.05 TFP | | Organics 0.05 F1234yf + 0.95 TFP | |
| MASS-FRAC HF | TOTAL PRESSURE bar | MASS-FRAC HF | TOTAL PRESSURE bar | MASS-FRAC HF | TOTAL PRESSURE bar |
| 0 | 9.4 | 0 | 7.1 | 0 | 11.4 |
| 0.05 | 10.2 | 0.05 | 8.0 | 0.05 | 12.2 |
| 0.1 | 10.2 | 0.1 | 8.0 | 0.1 | 12.1 |

-continued

HF-HFO-1234yf-Trifluoropropyne

| Organics 0.5 F1234yf + 0.5 TFP | | Organics 0.95 F1234yf + 0.05 TFP | | Organics 0.05 F1234yf + 0.95 TFP | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0.15 | 10.1 | 0.15 | 8.0 | 0.15 | 12.0 |
| 0.2 | 10.1 | 0.2 | 8.0 | 0.2 | 11.9 |
| 0.25 | 10.0 | 0.25 | 8.0 | 0.25 | 11.8 |
| 0.3 | 9.9 | 0.3 | 8.0 | 0.3 | 11.7 |
| 0.35 | 9.9 | 0.35 | 8.0 | 0.35 | 11.6 |
| 0.4 | 9.9 | 0.4 | 8.0 | 0.4 | 11.6 |
| 0.45 | 9.9 | 0.45 | 8.0 | 0.45 | 11.6 |
| 0.5 | 9.9 | 0.5 | 8.0 | 0.5 | 11.6 |
| 0.55 | 9.9 | 0.55 | 8.0 | 0.55 | 11.6 |
| 0.6 | 9.9 | 0.6 | 8.0 | 0.6 | 11.6 |
| 0.65 | 9.9 | 0.65 | 8.0 | 0.65 | 11.6 |
| 0.7 | 9.9 | 0.7 | 8.0 | 0.7 | 11.6 |
| 0.75 | 9.9 | 0.75 | 7.8 | 0.75 | 11.6 |
| 0.8 | 9.5 | 0.8 | 7.5 | 0.8 | 11.4 |
| 0.85 | 8.8 | 0.85 | 6.9 | 0.85 | 10.6 |
| 0.9 | 7.4 | 0.9 | 5.8 | 0.9 | 9.0 |
| 0.95 | 5.0 | 0.95 | 4.0 | 0.95 | 6.0 |
| 1 | 1.2 | 1 | 1.2 | 1 | 1.2 |

HF-HFO-1234yf-HCFC-244bb

| Organics 0.5 F1234yf + 0.5 F244bb | | Organics 0.95 F1234yf + 0.05 F244bb | | Organics 0.05 F1234yf + 0.95 F244bb | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0 | 4.1 | 0 | 6.5 | 0 | 1.0 |
| 0.05 | 5.2 | 0.05 | 7.5 | 0.05 | 2.2 |
| 0.1 | 5.2 | 0.1 | 7.5 | 0.1 | 2.2 |
| 0.15 | 5.2 | 0.15 | 7.5 | 0.15 | 2.2 |
| 0.2 | 5.2 | 0.2 | 7.5 | 0.2 | 2.2 |
| 0.25 | 5.1 | 0.25 | 7.5 | 0.25 | 2.2 |
| 0.3 | 5.1 | 0.3 | 7.5 | 0.3 | 2.2 |
| 0.35 | 5.1 | 0.35 | 7.5 | 0.35 | 2.2 |
| 0.4 | 5.1 | 0.4 | 7.5 | 0.4 | 2.2 |
| 0.45 | 5.1 | 0.45 | 7.5 | 0.45 | 2.2 |
| 0.5 | 5.1 | 0.5 | 7.5 | 0.5 | 2.1 |
| 0.55 | 5.0 | 0.55 | 7.5 | 0.55 | 2.1 |
| 0.6 | 5.0 | 0.6 | 7.5 | 0.6 | 2.1 |
| 0.65 | 4.9 | 0.65 | 7.5 | 0.65 | 2.1 |
| 0.7 | 4.9 | 0.7 | 7.5 | 0.7 | 2.1 |
| 0.75 | 4.8 | 0.75 | 7.3 | 0.75 | 2.1 |
| 0.8 | 4.6 | 0.8 | 7.0 | 0.8 | 2.1 |
| 0.85 | 4.3 | 0.85 | 6.4 | 0.85 | 2.0 |
| 0.9 | 3.7 | 0.9 | 5.4 | 0.9 | 1.9 |
| 0.95 | 2.7 | 0.95 | 3.8 | 0.95 | 1.6 |
| 1 | 1.2 | 1 | 1.2 | 1 | 1.2 |

HF-HFO-1234yf-HFC-245fa

| Organics 0.5 F1234yf + 0.5 F245fa | | Organics 0.95 F1234yf + 0.05 F245fa | | Organics 0.05 F1234yf + 0.95 F245fa | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0 | 4.3 | 0 | 6.6 | 0 | 1.8 |
| 0.05 | 5.4 | 0.05 | 7.5 | 0.05 | 2.9 |

-continued

HF-HFO-1234yf-HFC-245fa

| Organics 0.5 F1234yf + 0.5 F245fa | | Organics 0.95 F1234yf + 0.05 F245fa | | Organics 0.05 F1234yf + 0.95 F245fa | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0.1 | 5.4 | 0.1 | 7.5 | 0.1 | 2.9 |
| 0.15 | 5.4 | 0.15 | 7.5 | 0.15 | 2.9 |
| 0.2 | 5.4 | 0.2 | 7.5 | 0.2 | 2.9 |
| 0.25 | 5.4 | 0.25 | 7.5 | 0.25 | 2.9 |
| 0.3 | 5.4 | 0.3 | 7.5 | 0.3 | 2.9 |
| 0.35 | 5.4 | 0.35 | 7.5 | 0.35 | 2.9 |
| 0.4 | 5.4 | 0.4 | 7.5 | 0.4 | 2.9 |
| 0.45 | 5.4 | 0.45 | 7.5 | 0.45 | 2.9 |
| 0.5 | 5.4 | 0.5 | 7.5 | 0.5 | 2.9 |
| 0.55 | 5.4 | 0.55 | 7.5 | 0.55 | 2.9 |
| 0.6 | 5.4 | 0.6 | 7.5 | 0.6 | 2.9 |
| 0.65 | 5.4 | 0.65 | 7.5 | 0.65 | 2.9 |
| 0.7 | 5.4 | 0.7 | 7.5 | 0.7 | 2.9 |
| 0.75 | 5.3 | 0.75 | 7.4 | 0.75 | 2.9 |
| 0.8 | 5.0 | 0.8 | 7.0 | 0.8 | 2.8 |
| 0.85 | 4.6 | 0.85 | 6.5 | 0.85 | 2.6 |
| 0.9 | 3.9 | 0.9 | 5.4 | 0.9 | 2.3 |
| 0.95 | 2.8 | 0.95 | 3.8 | 0.95 | 1.8 |
| 1 | 1.2 | 1 | 1.2 | 1 | 1.2 |

HF-HFO-1234yf -HFO-1225yeZ

| Organics 0.5 F1234yf + 0.5 F1225yeZ | | Organics 0.95 F1234yf + 0.05 F1225yeZ | | Organics 0.05 F1234yf + 0.95 F1225yeZ | |
|---|---|---|---|---|---|
| MASS-FRAC HF | TOTAL PRESSURE bar | MASS-FRAC HF | TOTAL PRESSURE bar | MASS-FRAC HF | TOTAL PRESSURE bar |
| 0 | 6.0 | 0 | 6.7 | 0 | 5.3 |
| 0.05 | 7.0 | 0.05 | 7.7 | 0.05 | 6.3 |
| 0.1 | 7.1 | 0.1 | 7.7 | 0.1 | 6.3 |
| 0.15 | 7.0 | 0.15 | 7.7 | 0.15 | 6.3 |
| 0.2 | 7.0 | 0.2 | 7.7 | 0.2 | 6.3 |
| 0.25 | 7.0 | 0.25 | 7.7 | 0.25 | 6.3 |
| 0.3 | 7.0 | 0.3 | 7.7 | 0.3 | 6.3 |
| 0.35 | 7.0 | 0.35 | 7.7 | 0.35 | 6.3 |
| 0.4 | 7.0 | 0.4 | 7.7 | 0.4 | 6.3 |
| 0.45 | 7.0 | 0.45 | 7.7 | 0.45 | 6.3 |
| 0.5 | 7.0 | 0.5 | 7.7 | 0.5 | 6.3 |
| 0.55 | 7.1 | 0.55 | 7.7 | 0.55 | 6.3 |
| 0.6 | 7.1 | 0.6 | 7.7 | 0.6 | 6.3 |
| 0.65 | 7.1 | 0.65 | 7.7 | 0.65 | 6.3 |
| 0.7 | 7.0 | 0.7 | 7.7 | 0.7 | 6.2 |
| 0.75 | 6.8 | 0.75 | 7.5 | 0.75 | 6.0 |
| 0.8 | 6.5 | 0.8 | 7.2 | 0.8 | 5.7 |
| 0.85 | 5.9 | 0.85 | 6.6 | 0.85 | 5.2 |
| 0.9 | 4.9 | 0.9 | 5.5 | 0.9 | 4.3 |
| 0.95 | 3.4 | 0.95 | 3.8 | 0.95 | 3.0 |
| 1 | 1.2 | 1 | 1.2 | 1 | 1.2 |

| HF-HFO-1234vf -HFO-1225zc | | | | | |
|---|---|---|---|---|---|
| Organics 0.5 F1234yf + 0.5 F1225zc | | Organics 0.95 F1234yf + 0.05 F1225zc | | Organics 0.05 F1234yf + 0.95 F1225zc | |
| MASS-FRAC HF | TOTAL PRESSURE bar | MASS-FRAC HF | TOTAL PRESSURE bar | MASS-FRAC HF | TOTAL PRESSURE bar |
| 0 | 6.1 | 0 | 6.7 | 0 | 5.4 |
| 0.05 | 7.1 | 0.05 | 7.7 | 0.05 | 6.4 |
| 0.1 | 7.1 | 0.1 | 7.7 | 0.1 | 6.4 |
| 0.15 | 7.1 | 0.15 | 7.7 | 0.15 | 6.4 |
| 0.2 | 7.1 | 0.2 | 7.7 | 0.2 | 6.4 |
| 0.25 | 7.1 | 0.25 | 7.7 | 0.25 | 6.4 |
| 0.3 | 7.1 | 0.3 | 7.7 | 0.3 | 6.4 |
| 0.35 | 7.1 | 0.35 | 7.7 | 0.35 | 6.4 |
| 0.4 | 7.1 | 0.4 | 7.7 | 0.4 | 6.4 |
| 0.45 | 7.1 | 0.45 | 7.7 | 0.45 | 6.4 |
| 0.5 | 7.1 | 0.5 | 7.7 | 0.5 | 6.3 |
| 0.55 | 7.1 | 0.55 | 7.7 | 0.55 | 6.3 |
| 0.6 | 7.1 | 0.6 | 7.7 | 0.6 | 6.2 |
| 0.65 | 7.0 | 0.65 | 7.7 | 0.65 | 6.1 |

-continued

| HF-HFO-1234vf -HFO-1225zc | | | | | |
|---|---|---|---|---|---|
| Organics 0.5 F1234yf + 0.5 F1225zc | | Organics 0.95 F1234yf + 0.05 F1225zc | | Organics 0.05 F1234yf + 0.95 F1225zc | |
| MASS-FRAC HF | TOTAL PRESSURE bar | MASS-FRAC HF | TOTAL PRESSURE bar | MASS-FRAC HF | TOTAL PRESSURE bar |
| 0.7 | 6.9 | 0.7 | 7.7 | 0.7 | 6.0 |
| 0.75 | 6.7 | 0.75 | 7.5 | 0.75 | 5.7 |
| 0.8 | 6.3 | 0.8 | 7.2 | 0.8 | 5.3 |
| 0.85 | 5.7 | 0.85 | 6.6 | 0.85 | 4.7 |
| 0.9 | 4.8 | 0.9 | 5.5 | 0.9 | 3.9 |
| 0.95 | 3.3 | 0.95 | 3.8 | 0.95 | 2.8 |
| 1 | 1.2 | 1 | 1.2 | 1 | 1.2 |

EXAMPLE 2

Quaternary Mixtures

| HF-HCFO-1233xf-HFO-1234yf-HFC-245cb | | | | | | | |
|---|---|---|---|---|---|---|---|
| Organics 0.9 F1233xf + 0.05 F1234yf + 0.05 F245cb | | Organics 0.4 F1233xf + 0.3 F1234yf + 0.3 F245cb | | Organics 0.05 F1233xf + 0.9 F1234yf + 0.05 F245cb | | Organics 0.05 F1233xf + 0.05 F1234yf + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.2 | 0 | 6.5 | 0 | 4.6 |
| 0.05 | 3.1 | 0.05 | 5.3 | 0.05 | 7.4 | 0.05 | 5.8 |
| 0.1 | 3.1 | 0.1 | 5.3 | 0.1 | 7.4 | 0.1 | 5.8 |
| 0.15 | 3.1 | 0.15 | 5.3 | 0.15 | 7.4 | 0.15 | 5.8 |
| 0.2 | 3.1 | 0.2 | 5.3 | 0.2 | 7.4 | 0.2 | 5.8 |
| 0.25 | 3.1 | 0.25 | 5.3 | 0.25 | 7.4 | 0.25 | 5.8 |
| 0.3 | 3.1 | 0.3 | 5.3 | 0.3 | 7.4 | 0.3 | 5.8 |
| 0.35 | 3.1 | 0.35 | 5.3 | 0.35 | 7.4 | 0.35 | 5.8 |
| 0.4 | 3.1 | 0.4 | 5.3 | 0.4 | 7.4 | 0.4 | 5.8 |
| 0.45 | 3.1 | 0.45 | 5.3 | 0.45 | 7.4 | 0.45 | 5.8 |
| 0.5 | 3.1 | 0.5 | 5.3 | 0.5 | 7.4 | 0.5 | 5.8 |
| 0.55 | 3.1 | 0.55 | 5.3 | 0.55 | 7.4 | 0.55 | 5.8 |
| 0.6 | 3.1 | 0.6 | 5.3 | 0.6 | 7.4 | 0.6 | 5.8 |
| 0.65 | 3.1 | 0.65 | 5.3 | 0.65 | 7.4 | 0.65 | 5.8 |
| 0.7 | 3.1 | 0.7 | 5.3 | 0.7 | 7.4 | 0.7 | 5.8 |
| 0.75 | 3.1 | 0.75 | 5.4 | 0.75 | 7.3 | 0.75 | 5.8 |
| 0.8 | 3.0 | 0.8 | 5.2 | 0.8 | 7.0 | 0.8 | 5.8 |
| 0.85 | 2.8 | 0.85 | 4.8 | 0.85 | 6.4 | 0.85 | 5.7 |
| 0.9 | 2.4 | 0.9 | 4.1 | 0.9 | 5.4 | 0.9 | 4.9 |
| 0.95 | 1.9 | 0.95 | 2.9 | 0.95 | 3.7 | 0.95 | 3.5 |
| 1 | 1.2 | 1 | 1.2 | 1 | 1.2 | 1 | 1.2 |

| HF-HFO-1234yf-HCFO-1233zdE-HFC-245cb | | | | | | | |
|---|---|---|---|---|---|---|---|
| Organics 0.9 F1234yf + 0.05 F1233zdE + 0.05 F245cb | | Organics 0.4 F1234yf + 0.3 F1233zdE + 0.3 F245cb | | Organics 0.05 F1234yf + 0.9 F1233zdE + 0.05 F245cb | | Organics 0.05 F1234yf + 0.05 F1233zdE + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.6 | 0 | 1.8 | 0 | 4.6 |
| 0.05 | 7.4 | 0.05 | 5.7 | 0.05 | 2.9 | 0.05 | 5.8 |
| 0.1 | 7.4 | 0.1 | 5.7 | 0.1 | 2.9 | 0.1 | 5.8 |
| 0.15 | 7.4 | 0.15 | 5.7 | 0.15 | 2.9 | 0.15 | 5.8 |
| 0.2 | 7.4 | 0.2 | 5.7 | 0.2 | 2.9 | 0.2 | 5.8 |
| 0.25 | 7.4 | 0.25 | 5.7 | 0.25 | 2.9 | 0.25 | 5.8 |

-continued

| HF-HFO-1234yf-HCFO-1233zdE-HFC-245cb | | | | | | | |
|---|---|---|---|---|---|---|---|
| Organics 0.9 F1234yf + 0.05 F1233zdE + 0.05 F245cb | | Organics 0.4 F1234yf + 0.3 F1233zdE + 0.3 F245cb | | Organics 0.05 F1234yf + 0.9 F1233zdE + 0.05 F245cb | | Organics 0.05 F1234yf + 0.05 F1233zdE + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0.3 | 7.4 | 0.3 | 5.7 | 0.3 | 2.9 | 0.3 | 5.8 |
| 0.35 | 7.4 | 0.35 | 5.7 | 0.35 | 2.9 | 0.35 | 5.8 |
| 0.4 | 7.4 | 0.4 | 5.7 | 0.4 | 2.9 | 0.4 | 5.8 |
| 0.45 | 7.4 | 0.45 | 5.7 | 0.45 | 2.9 | 0.45 | 5.8 |
| 0.5 | 7.4 | 0.5 | 5.7 | 0.5 | 2.9 | 0.5 | 5.8 |
| 0.55 | 7.4 | 0.55 | 5.7 | 0.55 | 2.9 | 0.55 | 5.8 |
| 0.6 | 7.4 | 0.6 | 5.7 | 0.6 | 2.9 | 0.6 | 5.8 |
| 0.65 | 7.4 | 0.65 | 5.8 | 0.65 | 2.9 | 0.65 | 5.8 |
| 0.7 | 7.4 | 0.7 | 5.8 | 0.7 | 2.9 | 0.7 | 5.8 |
| 0.75 | 7.3 | 0.75 | 5.8 | 0.75 | 2.9 | 0.75 | 5.8 |
| 0.8 | 7.0 | 0.8 | 5.6 | 0.8 | 2.8 | 0.8 | 5.8 |
| 0.85 | 6.4 | 0.85 | 5.1 | 0.85 | 2.6 | 0.85 | 5.7 |
| 0.9 | 5.4 | 0.9 | 4.4 | 0.9 | 2.3 | 0.9 | 4.9 |
| 0.95 | 3.7 | 0.95 | 3.1 | 0.95 | 1.8 | 0.95 | 3.5 |
| 1 | 1.2 | 1 | 1.2 | 1 | 1.2 | 1 | 1.2 |

| HF-HFO-1234yf-HFO-1234zeE-HFC-245cb | | | | | | | |
|---|---|---|---|---|---|---|---|
| Organics 0.9 F1234yf + 0.05 F1234zeE + 0.05 F245cb | | Organics 0.4 F1234yf + 0.3 F1234zeE + 0.3 F245cb | | Organics 0.05 F1234yf + 0.9 F1234zeE + 0.05 F245cb | | Organics 0.05 F1234yf + 0.05 F1234zeE + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 5.6 | 0 | 5.0 | 0 | 4.8 |
| 0.05 | 7.6 | 0.05 | 6.7 | 0.05 | 5.9 | 0.05 | 6.0 |
| 0.1 | 7.6 | 0.1 | 6.7 | 0.1 | 6.0 | 0.1 | 6.0 |
| 0.15 | 7.6 | 0.15 | 6.7 | 0.15 | 6.0 | 0.15 | 6.0 |
| 0.2 | 7.6 | 0.2 | 6.7 | 0.2 | 6.0 | 0.2 | 6.0 |
| 0.25 | 7.6 | 0.25 | 6.7 | 0.25 | 6.0 | 0.25 | 6.0 |
| 0.3 | 7.6 | 0.3 | 6.7 | 0.3 | 6.0 | 0.3 | 6.0 |
| 0.35 | 7.6 | 0.35 | 6.7 | 0.35 | 6.0 | 0.35 | 6.0 |
| 0.4 | 7.6 | 0.4 | 6.7 | 0.4 | 6.0 | 0.4 | 6.0 |
| 0.45 | 7.6 | 0.45 | 6.7 | 0.45 | 5.9 | 0.45 | 6.0 |
| 0.5 | 7.6 | 0.5 | 6.7 | 0.5 | 5.9 | 0.5 | 6.0 |
| 0.55 | 7.6 | 0.55 | 6.7 | 0.55 | 5.9 | 0.55 | 5.9 |
| 0.6 | 7.6 | 0.6 | 6.7 | 0.6 | 5.8 | 0.6 | 5.9 |
| 0.65 | 7.6 | 0.65 | 6.7 | 0.65 | 5.7 | 0.65 | 5.9 |
| 0.7 | 7.6 | 0.7 | 6.7 | 0.7 | 5.6 | 0.7 | 5.9 |
| 0.75 | 7.4 | 0.75 | 6.6 | 0.75 | 5.3 | 0.75 | 5.9 |
| 0.8 | 7.1 | 0.8 | 6.3 | 0.8 | 5.0 | 0.8 | 5.9 |
| 0.85 | 6.5 | 0.85 | 5.7 | 0.85 | 4.5 | 0.85 | 5.8 |
| 0.9 | 5.5 | 0.9 | 4.8 | 0.9 | 3.8 | 0.9 | 5.0 |
| 0.95 | 3.8 | 0.95 | 3.4 | 0.95 | 2.7 | 0.95 | 3.5 |
| 1 | 1.2 | 1 | 1.2 | 1 | 1.2 | 1 | 1.2 |

| HF-HFO-1234yf-HFO-1234zeZ-FC-245cb | | | | | | | |
|---|---|---|---|---|---|---|---|
| Organics 0.9 F1234yf + 0.05 F1234zeZ + 0.05 F245cb | | Organics 0.4 F1234yf + 0.3 F1234zeZ + 0.3 F245cb | | Organics 0.05 F1234yf + 0.9 F1234zeZ + 0.05 F245cb | | Organics 0.05 F1234yf + 0.05 F1234zeZ + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.6 | 0 | 2.2 | 0 | 4.6 |
| 0.05 | 7.4 | 0.05 | 5.7 | 0.05 | 3.3 | 0.05 | 5.8 |

-continued

| HF-HFO-1234yf-HFO-1234zeZ-FC-245cb | | | | | | | |
|---|---|---|---|---|---|---|---|
| Organics 0.9 F1234yf + 0.05 F1234zeZ + 0.05 F245cb | | Organics 0.4 F1234yf + 0.3 F1234zeZ + 0.3 F245cb | | Organics 0.05 F1234yf + 0.9 F1234zeZ + 0.05 F245cb | | Organics 0.05 F1234yf + 0.05 F1234zeZ + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0.1 | 7.4 | 0.1 | 5.7 | 0.1 | 3.3 | 0.1 | 5.8 |
| 0.15 | 7.4 | 0.15 | 5.7 | 0.15 | 3.3 | 0.15 | 5.8 |
| 0.2 | 7.4 | 0.2 | 5.7 | 0.2 | 3.3 | 0.2 | 5.8 |
| 0.25 | 7.4 | 0.25 | 5.7 | 0.25 | 3.3 | 0.25 | 5.8 |
| 0.3 | 7.4 | 0.3 | 5.7 | 0.3 | 3.3 | 0.3 | 5.8 |
| 0.35 | 7.4 | 0.35 | 5.7 | 0.35 | 3.3 | 0.35 | 5.8 |
| 0.4 | 7.4 | 0.4 | 5.8 | 0.4 | 3.3 | 0.4 | 5.8 |
| 0.45 | 7.4 | 0.45 | 5.8 | 0.45 | 3.3 | 0.45 | 5.8 |
| 0.5 | 7.4 | 0.5 | 5.8 | 0.5 | 3.3 | 0.5 | 5.8 |
| 0.55 | 7.4 | 0.55 | 5.8 | 0.55 | 3.3 | 0.55 | 5.8 |
| 0.6 | 7.4 | 0.6 | 5.8 | 0.6 | 3.3 | 0.6 | 5.8 |
| 0.65 | 7.4 | 0.65 | 5.8 | 0.65 | 3.3 | 0.65 | 5.8 |
| 0.7 | 7.4 | 0.7 | 5.8 | 0.7 | 3.3 | 0.7 | 5.8 |
| 0.75 | 7.3 | 0.75 | 5.8 | 0.75 | 3.3 | 0.75 | 5.8 |
| 0.8 | 7.0 | 0.8 | 5.6 | 0.8 | 3.2 | 0.8 | 5.8 |
| 0.85 | 6.4 | 0.85 | 5.2 | 0.85 | 3.0 | 0.85 | 5.7 |
| 0.9 | 5.4 | 0.9 | 4.4 | 0.9 | 2.6 | 0.9 | 4.9 |
| 0.95 | 3.8 | 0.95 | 3.2 | 0.95 | 2.0 | 0.95 | 3.5 |
| 1 | 1.2 | 1 | 1.2 | 1 | 1.2 | 1 | 1.2 |

| HF-HFO-1234yf-HFO-1243zf-HFC-245cb | | | | | | | |
|---|---|---|---|---|---|---|---|
| Organics 0.9 F1234yf + 0.05 F1243zf + 0.05 F245cb | | Organics 0.4 F1234yf + 0.3 F1243zf + 0.3 F245cb | | Organics 0.05 F1234yf + 0.9 F1243zf + 0.05 F245cb | | Organics 0.05 F1234yf + 0.05 F1243zf + 0.9 F245cb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.7 | 0 | 5.9 | 0 | 5.8 | 0 | 4.9 |
| 0.05 | 7.6 | 0.05 | 6.9 | 0.05 | 6.8 | 0.05 | 6.0 |
| 0.1 | 7.6 | 0.1 | 7.0 | 0.1 | 6.8 | 0.1 | 6.0 |
| 0.15 | 7.6 | 0.15 | 6.9 | 0.15 | 6.8 | 0.15 | 6.0 |
| 0.2 | 7.6 | 0.2 | 6.9 | 0.2 | 6.8 | 0.2 | 6.0 |
| 0.25 | 7.6 | 0.25 | 6.9 | 0.25 | 6.8 | 0.25 | 6.0 |
| 0.3 | 7.6 | 0.3 | 6.9 | 0.3 | 6.8 | 0.3 | 6.0 |
| 0.35 | 7.6 | 0.35 | 6.9 | 0.35 | 6.8 | 0.35 | 6.0 |
| 0.4 | 7.6 | 0.4 | 6.9 | 0.4 | 6.8 | 0.4 | 6.0 |
| 0.45 | 7.6 | 0.45 | 6.9 | 0.45 | 6.8 | 0.45 | 6.0 |
| 0.5 | 7.6 | 0.5 | 6.9 | 0.5 | 6.8 | 0.5 | 6.0 |
| 0.55 | 7.6 | 0.55 | 6.9 | 0.55 | 6.8 | 0.55 | 6.0 |
| 0.6 | 7.6 | 0.6 | 6.9 | 0.6 | 6.8 | 0.6 | 6.0 |
| 0.65 | 7.6 | 0.65 | 6.9 | 0.65 | 6.7 | 0.65 | 6.0 |
| 0.7 | 7.6 | 0.7 | 6.9 | 0.7 | 6.6 | 0.7 | 6.0 |
| 0.75 | 7.5 | 0.75 | 6.9 | 0.75 | 6.5 | 0.75 | 6.0 |
| 0.8 | 7.2 | 0.8 | 6.6 | 0.8 | 6.2 | 0.8 | 6.0 |
| 0.85 | 6.6 | 0.85 | 6.1 | 0.85 | 5.7 | 0.85 | 5.9 |
| 0.9 | 5.5 | 0.9 | 5.2 | 0.9 | 4.8 | 0.9 | 5.1 |
| 0.95 | 3.8 | 0.95 | 3.6 | 0.95 | 3.4 | 0.95 | 3.6 |
| 1 | 1.2 | 1 | 1.2 | 1 | 1.2 | 1 | 1.2 |

| HF-HCFO-1233xf-HFO-1234yf-HCFO-1233zdE | | | | | | | |
|---|---|---|---|---|---|---|---|
| Organics 0.9 F1233xf + 0.05 F1234yf + 0.05 F1233zdE | | Organics 0.05 F1233xf + 0.9 F1234yf + 0.05 F1233zdE | | Organics 0.05 F1233xf + 0.05 F1234yf + 0.9 F1233zdE | | Organics 0.4 F1233xf + 0.3 F1234yf + 0.3 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 6.3 | 0 | 1.7 | 0 | 3.2 |
| 0.05 | 3.0 | 0.05 | 7.3 | 0.05 | 2.8 | 0.05 | 4.3 |
| 0.1 | 3.0 | 0.1 | 7.3 | 0.1 | 2.8 | 0.1 | 4.3 |
| 0.15 | 3.0 | 0.15 | 7.3 | 0.15 | 2.8 | 0.15 | 4.3 |
| 0.2 | 2.9 | 0.2 | 7.3 | 0.2 | 2.8 | 0.2 | 4.3 |
| 0.25 | 2.9 | 0.25 | 7.3 | 0.25 | 2.8 | 0.25 | 4.3 |
| 0.3 | 2.9 | 0.3 | 7.3 | 0.3 | 2.8 | 0.3 | 4.3 |
| 0.35 | 2.9 | 0.35 | 7.3 | 0.35 | 2.8 | 0.35 | 4.3 |
| 0.4 | 2.9 | 0.4 | 7.3 | 0.4 | 2.8 | 0.4 | 4.3 |
| 0.45 | 2.9 | 0.45 | 7.3 | 0.45 | 2.7 | 0.45 | 4.3 |
| 0.5 | 2.9 | 0.5 | 7.3 | 0.5 | 2.7 | 0.5 | 4.3 |
| 0.55 | 2.9 | 0.55 | 7.3 | 0.55 | 2.7 | 0.55 | 4.3 |
| 0.6 | 2.9 | 0.6 | 7.3 | 0.6 | 2.7 | 0.6 | 4.3 |
| 0.65 | 2.9 | 0.65 | 7.3 | 0.65 | 2.7 | 0.65 | 4.3 |
| 0.7 | 2.9 | 0.7 | 7.3 | 0.7 | 2.7 | 0.7 | 4.3 |
| 0.75 | 2.9 | 0.75 | 7.1 | 0.75 | 2.7 | 0.75 | 4.2 |
| 0.8 | 2.8 | 0.8 | 6.8 | 0.8 | 2.6 | 0.8 | 4.0 |
| 0.85 | 2.6 | 0.85 | 6.2 | 0.85 | 2.4 | 0.85 | 3.7 |
| 0.9 | 2.3 | 0.9 | 5.3 | 0.9 | 2.1 | 0.9 | 3.1 |
| 0.95 | 1.8 | 0.95 | 3.7 | 0.95 | 1.7 | 0.95 | 2.3 |
| 1 | 1.2 | 1 | 1.2 | 1 | 1.2 | 1 | 1.2 |

| HF-HCFO-1233xf-HFO-1234yf-HFO-1234zeE | | | | | | | |
|---|---|---|---|---|---|---|---|
| Organics 0.9 F1233xf + 0.05 F1234yf + 0.05 F1234zeE | | Organics 0.05 F1233xf + 0.9 F1234yf + 0.05 F1234zeE | | Organics 0.05 F1233xf + 0.05 F1234yf + 0.9 F1234zeE | | Organics 0.4 F1233xf + 0.3 F1234yf + 0.3 F1234zeE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 6.5 | 0 | 4.8 | 0 | 4.2 |
| 0.05 | 3.1 | 0.05 | 7.4 | 0.05 | 5.8 | 0.05 | 5.3 |
| 0.1 | 3.1 | 0.1 | 7.4 | 0.1 | 5.8 | 0.1 | 5.3 |
| 0.15 | 3.1 | 0.15 | 7.4 | 0.15 | 5.8 | 0.15 | 5.3 |
| 0.2 | 3.1 | 0.2 | 7.4 | 0.2 | 5.8 | 0.2 | 5.3 |
| 0.25 | 3.1 | 0.25 | 7.4 | 0.25 | 5.8 | 0.25 | 5.3 |
| 0.3 | 3.1 | 0.3 | 7.4 | 0.3 | 5.8 | 0.3 | 5.3 |
| 0.35 | 3.1 | 0.35 | 7.4 | 0.35 | 5.8 | 0.35 | 5.3 |
| 0.4 | 3.1 | 0.4 | 7.4 | 0.4 | 5.8 | 0.4 | 5.3 |
| 0.45 | 3.1 | 0.45 | 7.4 | 0.45 | 5.8 | 0.45 | 5.3 |
| 0.5 | 3.1 | 0.5 | 7.4 | 0.5 | 5.8 | 0.5 | 5.3 |
| 0.55 | 3.1 | 0.55 | 7.4 | 0.55 | 5.7 | 0.55 | 5.3 |
| 0.6 | 3.1 | 0.6 | 7.4 | 0.6 | 5.6 | 0.6 | 5.3 |
| 0.65 | 3.1 | 0.65 | 7.5 | 0.65 | 5.5 | 0.65 | 5.3 |
| 0.7 | 3.1 | 0.7 | 7.4 | 0.7 | 5.4 | 0.7 | 5.2 |
| 0.75 | 3.1 | 0.75 | 7.2 | 0.75 | 5.2 | 0.75 | 5.0 |
| 0.8 | 2.9 | 0.8 | 6.9 | 0.8 | 4.8 | 0.8 | 4.7 |
| 0.85 | 2.7 | 0.85 | 6.3 | 0.85 | 4.3 | 0.85 | 4.3 |
| 0.9 | 2.3 | 0.9 | 5.3 | 0.9 | 3.6 | 0.9 | 3.6 |
| 0.95 | 1.9 | 0.95 | 3.7 | 0.95 | 2.6 | 0.95 | 2.6 |
| 1 | 1.2 | 1 | 1.2 | 1 | 1.2 | 1 | 1.2 |

| HF-HCFO-1233xf-HFO-1234yf-HFO-1234zeZ | | | | | | | |
|---|---|---|---|---|---|---|---|
| Organics 0.9 F1233xf + 0.05 F1234yf + 0.05 F1234zeZ | | Organics 0.05 F1233xf + 0.9 F1234yf + 0.05 F1234zeZ | | Organics 0.05 F1233xf + 0.05 F1234yf + 0.9 F1234zeZ | | Organics 0.4 F1233xf + 0.3 F1234yf + 0.3 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 6.3 | 0 | 2.1 | 0 | 3.3 |
| 0.05 | 3.0 | 0.05 | 7.3 | 0.05 | 3.2 | 0.05 | 4.4 |
| 0.1 | 3.0 | 0.1 | 7.3 | 0.1 | 3.2 | 0.1 | 4.4 |
| 0.15 | 3.0 | 0.15 | 7.3 | 0.15 | 3.2 | 0.15 | 4.4 |
| 0.2 | 3.0 | 0.2 | 7.3 | 0.2 | 3.2 | 0.2 | 4.4 |
| 0.25 | 3.0 | 0.25 | 7.3 | 0.25 | 3.2 | 0.25 | 4.4 |
| 0.3 | 3.0 | 0.3 | 7.3 | 0.3 | 3.2 | 0.3 | 4.4 |
| 0.35 | 3.0 | 0.35 | 7.3 | 0.35 | 3.2 | 0.35 | 4.4 |
| 0.4 | 3.0 | 0.4 | 7.3 | 0.4 | 3.2 | 0.4 | 4.4 |
| 0.45 | 3.0 | 0.45 | 7.3 | 0.45 | 3.2 | 0.45 | 4.4 |
| 0.5 | 3.0 | 0.5 | 7.3 | 0.5 | 3.2 | 0.5 | 4.4 |
| 0.55 | 3.0 | 0.55 | 7.3 | 0.55 | 3.2 | 0.55 | 4.4 |
| 0.6 | 3.0 | 0.6 | 7.3 | 0.6 | 3.2 | 0.6 | 4.4 |
| 0.65 | 3.0 | 0.65 | 7.3 | 0.65 | 3.2 | 0.65 | 4.4 |
| 0.7 | 3.0 | 0.7 | 7.3 | 0.7 | 3.2 | 0.7 | 4.4 |
| 0.75 | 2.9 | 0.75 | 7.1 | 0.75 | 3.1 | 0.75 | 4.3 |
| 0.8 | 2.8 | 0.8 | 6.8 | 0.8 | 3.0 | 0.8 | 4.1 |
| 0.85 | 2.6 | 0.85 | 6.3 | 0.85 | 2.8 | 0.85 | 3.7 |
| 0.9 | 2.3 | 0.9 | 5.3 | 0.9 | 2.4 | 0.9 | 3.2 |
| 0.95 | 1.8 | 0.95 | 3.7 | 0.95 | 1.9 | 0.95 | 2.4 |
| 1 | 1.2 | 1 | 1.2 | 1 | 1.2 | 1 | 1.2 |

| HF-HCFO-1233xf-HFO-1234yf-HFO-1243zf | | | | | | | |
|---|---|---|---|---|---|---|---|
| Organics 0.9 F1233xf + 0.05 F1234yf + 0.05 F1243zf | | Organics 0.05 F1233xf + 0.9 F1234yf + 0.05 F1243zf | | Organics 0.05 F1233xf + 0.05 F1234yf + 0.9 F1243zf | | Organics 0.4 F1233xf + 0.3 F1234yf + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.1 | 0 | 6.5 | 0 | 5.8 | 0 | 4.6 |
| 0.05 | 3.2 | 0.05 | 7.5 | 0.05 | 6.8 | 0.05 | 5.6 |
| 0.1 | 3.2 | 0.1 | 7.5 | 0.1 | 6.8 | 0.1 | 5.7 |
| 0.15 | 3.2 | 0.15 | 7.5 | 0.15 | 6.8 | 0.15 | 5.6 |
| 0.2 | 3.2 | 0.2 | 7.5 | 0.2 | 6.8 | 0.2 | 5.6 |
| 0.25 | 3.2 | 0.25 | 7.5 | 0.25 | 6.8 | 0.25 | 5.6 |
| 0.3 | 3.2 | 0.3 | 7.5 | 0.3 | 6.8 | 0.3 | 5.6 |
| 0.35 | 3.2 | 0.35 | 7.5 | 0.35 | 6.8 | 0.35 | 5.6 |
| 0.4 | 3.2 | 0.4 | 7.5 | 0.4 | 6.8 | 0.4 | 5.6 |
| 0.45 | 3.2 | 0.45 | 7.5 | 0.45 | 6.8 | 0.45 | 5.6 |
| 0.5 | 3.2 | 0.5 | 7.5 | 0.5 | 6.8 | 0.5 | 5.6 |
| 0.55 | 3.2 | 0.55 | 7.5 | 0.55 | 6.7 | 0.55 | 5.6 |
| 0.6 | 3.2 | 0.6 | 7.5 | 0.6 | 6.7 | 0.6 | 5.6 |
| 0.65 | 3.2 | 0.65 | 7.5 | 0.65 | 6.7 | 0.65 | 5.6 |
| 0.7 | 3.2 | 0.7 | 7.4 | 0.7 | 6.6 | 0.7 | 5.6 |
| 0.75 | 3.2 | 0.75 | 7.3 | 0.75 | 6.4 | 0.75 | 5.4 |
| 0.8 | 3.0 | 0.8 | 7.0 | 0.8 | 6.1 | 0.8 | 5.1 |
| 0.85 | 2.8 | 0.85 | 6.4 | 0.85 | 5.6 | 0.85 | 4.7 |
| 0.9 | 2.4 | 0.9 | 5.4 | 0.9 | 4.8 | 0.9 | 4.0 |
| 0.95 | 1.9 | 0.95 | 3.7 | 0.95 | 3.4 | 0.95 | 2.9 |
| 1 | 1.2 | 1 | 1.2 | 1 | 1.2 | 1 | 1.2 |

| HF-HFO-1234yf-HFO-1234zeE-HFO-1234zeZ | | | | | | | |
|---|---|---|---|---|---|---|---|
| Organics 0.9 F1234yf + 0.05 F1234zeE + 0.05 F1234zeZ | | Organics 0.05 F1234yf + 0.9 F1234zeE + 0.05 F1234zeZ | | Organics 0.05 F1234yf + 0.05 F1234zeE + 0.9 F1234zeZ | | Organics 0.4 F1234yf + 0.3 F1234zeE + 0.3 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.8 | 0 | 2.2 | 0 | 4.7 |
| 0.05 | 7.4 | 0.05 | 5.8 | 0.05 | 3.3 | 0.05 | 5.7 |
| 0.1 | 7.4 | 0.1 | 5.8 | 0.1 | 3.3 | 0.1 | 5.7 |
| 0.15 | 7.4 | 0.15 | 5.8 | 0.15 | 3.3 | 0.15 | 5.7 |
| 0.2 | 7.4 | 0.2 | 5.8 | 0.2 | 3.3 | 0.2 | 5.7 |
| 0.25 | 7.4 | 0.25 | 5.8 | 0.25 | 3.3 | 0.25 | 5.8 |
| 0.3 | 7.4 | 0.3 | 5.8 | 0.3 | 3.3 | 0.3 | 5.8 |
| 0.35 | 7.4 | 0.35 | 5.8 | 0.35 | 3.3 | 0.35 | 5.8 |
| 0.4 | 7.4 | 0.4 | 5.8 | 0.4 | 3.3 | 0.4 | 5.8 |
| 0.45 | 7.4 | 0.45 | 5.8 | 0.45 | 3.3 | 0.45 | 5.8 |
| 0.5 | 7.4 | 0.5 | 5.7 | 0.5 | 3.3 | 0.5 | 5.8 |
| 0.55 | 7.4 | 0.55 | 5.7 | 0.55 | 3.3 | 0.55 | 5.8 |
| 0.6 | 7.4 | 0.6 | 5.6 | 0.6 | 3.3 | 0.6 | 5.8 |
| 0.65 | 7.4 | 0.65 | 5.5 | 0.65 | 3.3 | 0.65 | 5.7 |
| 0.7 | 7.4 | 0.7 | 5.4 | 0.7 | 3.3 | 0.7 | 5.6 |
| 0.75 | 7.2 | 0.75 | 5.2 | 0.75 | 3.3 | 0.75 | 5.5 |
| 0.8 | 6.9 | 0.8 | 4.8 | 0.8 | 3.1 | 0.8 | 5.2 |
| 0.85 | 6.3 | 0.85 | 4.3 | 0.85 | 2.9 | 0.85 | 4.7 |
| 0.9 | 5.3 | 0.9 | 3.6 | 0.9 | 2.5 | 0.9 | 4.0 |
| 0.95 | 3.7 | 0.95 | 2.6 | 0.95 | 2.0 | 0.95 | 2.9 |
| 1 | 1.2 | 1 | 1.2 | 1 | 1.2 | 1 | 1.2 |

| HF-HFO-1234yf-HFO-1234zeE-HCFO-1233zdE | | | | | | | |
|---|---|---|---|---|---|---|---|
| Organics 0.9 F1234yf + 0.05 F1234zeE + 0.05 F1233zdE | | Organics 0.05 F1234yf + 0.9 F1234zeE + 0.05 F1233zdE | | Organics 0.05 F1234yf + 0.05 F1234zeE + 0.9 F1233zdE | | Organics 0.4 F1234yf + 0.3 F1234zeE + 0.3 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 4.8 | 0 | 1.8 | 0 | 4.7 |
| 0.05 | 7.4 | 0.05 | 5.8 | 0.05 | 2.9 | 0.05 | 5.7 |
| 0.1 | 7.4 | 0.1 | 5.8 | 0.1 | 2.9 | 0.1 | 5.7 |
| 0.15 | 7.4 | 0.15 | 5.8 | 0.15 | 2.9 | 0.15 | 5.7 |
| 0.2 | 7.4 | 0.2 | 5.8 | 0.2 | 2.9 | 0.2 | 5.7 |
| 0.25 | 7.4 | 0.25 | 5.8 | 0.25 | 2.9 | 0.25 | 5.7 |
| 0.3 | 7.4 | 0.3 | 5.8 | 0.3 | 2.9 | 0.3 | 5.7 |
| 0.35 | 7.4 | 0.35 | 5.8 | 0.35 | 2.9 | 0.35 | 5.7 |
| 0.4 | 7.4 | 0.4 | 5.8 | 0.4 | 2.9 | 0.4 | 5.7 |
| 0.45 | 7.4 | 0.45 | 5.8 | 0.45 | 2.9 | 0.45 | 5.7 |
| 0.5 | 7.4 | 0.5 | 5.7 | 0.5 | 2.9 | 0.5 | 5.7 |
| 0.55 | 7.4 | 0.55 | 5.7 | 0.55 | 2.9 | 0.55 | 5.7 |
| 0.6 | 7.4 | 0.6 | 5.6 | 0.6 | 2.9 | 0.6 | 5.7 |
| 0.65 | 7.4 | 0.65 | 5.5 | 0.65 | 2.9 | 0.65 | 5.7 |
| 0.7 | 7.4 | 0.7 | 5.4 | 0.7 | 2.9 | 0.7 | 5.6 |
| 0.75 | 7.2 | 0.75 | 5.1 | 0.75 | 2.9 | 0.75 | 5.4 |
| 0.8 | 6.9 | 0.8 | 4.8 | 0.8 | 2.7 | 0.8 | 5.1 |
| 0.85 | 6.3 | 0.85 | 4.3 | 0.85 | 2.5 | 0.85 | 4.7 |
| 0.9 | 5.3 | 0.9 | 3.6 | 0.9 | 2.2 | 0.9 | 3.9 |
| 0.95 | 3.7 | 0.95 | 2.6 | 0.95 | 1.8 | 0.95 | 2.8 |
| 1 | 1.2 | 1 | 1.2 | 1 | 1.2 | 1 | 1.2 |

| HF-HFO-1234yf-HFO-1234zeE-HFO-1243zf | | | | | | | |
|---|---|---|---|---|---|---|---|
| Organics 0.9 F1234yf + 0.05 F1234zeE + 0.05 F1243zf | | Organics 0.05 F1234yf + 0.9 F1234zeE + 0.05 F1243zf | | Organics 0.05 F1234yf + 0.05 F1234zeE + 0.9 F1243zf | | Organics 0.4 F1234yf + 0.3 F1234zeE + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.7 | 0 | 5.0 | 0 | 5.8 | 0 | 5.9 |
| 0.05 | 7.6 | 0.05 | 6.0 | 0.05 | 6.8 | 0.05 | 6.9 |
| 0.1 | 7.6 | 0.1 | 6.0 | 0.1 | 6.8 | 0.1 | 6.9 |
| 0.15 | 7.6 | 0.15 | 6.0 | 0.15 | 6.8 | 0.15 | 6.9 |
| 0.2 | 7.6 | 0.2 | 6.0 | 0.2 | 6.8 | 0.2 | 6.9 |
| 0.25 | 7.6 | 0.25 | 6.0 | 0.25 | 6.8 | 0.25 | 6.9 |
| 0.3 | 7.6 | 0.3 | 6.0 | 0.3 | 6.8 | 0.3 | 6.9 |
| 0.35 | 7.6 | 0.35 | 6.0 | 0.35 | 6.8 | 0.35 | 6.9 |
| 0.4 | 7.6 | 0.4 | 6.0 | 0.4 | 6.8 | 0.4 | 6.9 |
| 0.45 | 7.6 | 0.45 | 6.0 | 0.45 | 6.8 | 0.45 | 6.9 |
| 0.5 | 7.6 | 0.5 | 6.0 | 0.5 | 6.8 | 0.5 | 6.9 |
| 0.55 | 7.6 | 0.55 | 5.9 | 0.55 | 6.8 | 0.55 | 6.9 |
| 0.6 | 7.6 | 0.6 | 5.8 | 0.6 | 6.7 | 0.6 | 6.9 |
| 0.65 | 7.6 | 0.65 | 5.7 | 0.65 | 6.7 | 0.65 | 6.8 |
| 0.7 | 7.6 | 0.7 | 5.6 | 0.7 | 6.6 | 0.7 | 6.7 |
| 0.75 | 7.4 | 0.75 | 5.4 | 0.75 | 6.4 | 0.75 | 6.5 |
| 0.8 | 7.1 | 0.8 | 5.0 | 0.8 | 6.1 | 0.8 | 6.2 |
| 0.85 | 6.5 | 0.85 | 4.5 | 0.85 | 5.6 | 0.85 | 5.7 |
| 0.9 | 5.5 | 0.9 | 3.8 | 0.9 | 4.8 | 0.9 | 4.8 |
| 0.95 | 3.8 | 0.95 | 2.7 | 0.95 | 3.4 | 0.95 | 3.3 |
| 1 | 1.2 | 1 | 1.2 | 1 | 1.2 | 1 | 1.2 |

| HF-HFO-1234yf-HFO-1234zeZ-HCFO-1233zdE | | | | | | | |
|---|---|---|---|---|---|---|---|
| Organics 0.9 F1234yf + 0.05 F1234zeZ + 0.05 F1233zdE | | Organics 0.05 F1234yf + 0.9 F1234zeZ + 0.05 F1233zdE | | Organics 0.05 F1234yf + 0.05 F1234zeZ + 0.9 F1233zdE | | Organics 0.4 F1234yf + 0.3 F1234zeZ + 0.3 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.3 | 0 | 2.0 | 0 | 1.7 | 0 | 3.8 |
| 0.05 | 7.3 | 0.05 | 3.2 | 0.05 | 2.8 | 0.05 | 4.8 |
| 0.1 | 7.3 | 0.1 | 3.2 | 0.1 | 2.8 | 0.1 | 4.8 |
| 0.15 | 7.3 | 0.15 | 3.2 | 0.15 | 2.8 | 0.15 | 4.8 |
| 0.2 | 7.3 | 0.2 | 3.2 | 0.2 | 2.8 | 0.2 | 4.8 |
| 0.25 | 7.3 | 0.25 | 3.2 | 0.25 | 2.8 | 0.25 | 4.8 |
| 0.3 | 7.3 | 0.3 | 3.2 | 0.3 | 2.8 | 0.3 | 4.8 |
| 0.35 | 7.3 | 0.35 | 3.1 | 0.35 | 2.8 | 0.35 | 4.8 |
| 0.4 | 7.3 | 0.4 | 3.1 | 0.4 | 2.8 | 0.4 | 4.8 |
| 0.45 | 7.3 | 0.45 | 3.1 | 0.45 | 2.8 | 0.45 | 4.8 |
| 0.5 | 7.3 | 0.5 | 3.1 | 0.5 | 2.8 | 0.5 | 4.8 |
| 0.55 | 7.3 | 0.55 | 3.1 | 0.55 | 2.8 | 0.55 | 4.8 |
| 0.6 | 7.3 | 0.6 | 3.1 | 0.6 | 2.8 | 0.6 | 4.8 |
| 0.65 | 7.3 | 0.65 | 3.1 | 0.65 | 2.8 | 0.65 | 4.8 |
| 0.7 | 7.3 | 0.7 | 3.1 | 0.7 | 2.7 | 0.7 | 4.8 |
| 0.75 | 7.1 | 0.75 | 3.1 | 0.75 | 2.7 | 0.75 | 4.7 |
| 0.8 | 6.8 | 0.8 | 3.0 | 0.8 | 2.6 | 0.8 | 4.5 |
| 0.85 | 6.2 | 0.85 | 2.8 | 0.85 | 2.4 | 0.85 | 4.1 |
| 0.9 | 5.3 | 0.9 | 2.4 | 0.9 | 2.2 | 0.9 | 3.5 |
| 0.95 | 3.7 | 0.95 | 1.9 | 0.95 | 1.7 | 0.95 | 2.6 |
| 1 | 1.2 | 1 | 1.2 | 1 | 1.2 | 1 | 1.2 |

| HF-HFO-1234yf-HFO-1234zeZ-HFO-1243zf | | | | | | | |
|---|---|---|---|---|---|---|---|
| Organics 0.9 F1234yf + 0.05 F1234zeZ + 0.05 F1243zf | | Organics 0.05 F1234yf + 0.9 F1234zeZ + 0.05 F1243zf | | Organics 0.05 F1234yf + 0.05 F1234zeZ + 0.9 F1243zf | | Organics 0.4 F1234yf + 0.3 F1234zeZ + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 2.3 | 0 | 5.7 | 0 | 5.0 |
| 0.05 | 7.5 | 0.05 | 3.4 | 0.05 | 6.7 | 0.05 | 6.0 |
| 0.1 | 7.5 | 0.1 | 3.4 | 0.1 | 6.7 | 0.1 | 6.1 |
| 0.15 | 7.5 | 0.15 | 3.4 | 0.15 | 6.7 | 0.15 | 6.1 |
| 0.2 | 7.4 | 0.2 | 3.4 | 0.2 | 6.7 | 0.2 | 6.1 |
| 0.25 | 7.4 | 0.25 | 3.4 | 0.25 | 6.7 | 0.25 | 6.1 |
| 0.3 | 7.4 | 0.3 | 3.4 | 0.3 | 6.7 | 0.3 | 6.1 |
| 0.35 | 7.5 | 0.35 | 3.4 | 0.35 | 6.7 | 0.35 | 6.1 |
| 0.4 | 7.5 | 0.4 | 3.4 | 0.4 | 6.7 | 0.4 | 6.1 |
| 0.45 | 7.5 | 0.45 | 3.4 | 0.45 | 6.7 | 0.45 | 6.1 |
| 0.5 | 7.5 | 0.5 | 3.4 | 0.5 | 6.7 | 0.5 | 6.1 |
| 0.55 | 7.5 | 0.55 | 3.4 | 0.55 | 6.6 | 0.55 | 6.1 |
| 0.6 | 7.5 | 0.6 | 3.4 | 0.6 | 6.6 | 0.6 | 6.1 |
| 0.65 | 7.5 | 0.65 | 3.4 | 0.65 | 6.6 | 0.65 | 6.1 |
| 0.7 | 7.4 | 0.7 | 3.4 | 0.7 | 6.5 | 0.7 | 6.0 |
| 0.75 | 7.3 | 0.75 | 3.3 | 0.75 | 6.3 | 0.75 | 5.9 |
| 0.8 | 7.0 | 0.8 | 3.2 | 0.8 | 6.0 | 0.8 | 5.6 |
| 0.85 | 6.4 | 0.85 | 3.0 | 0.85 | 5.5 | 0.85 | 5.1 |
| 0.9 | 5.4 | 0.9 | 2.6 | 0.9 | 4.7 | 0.9 | 4.4 |
| 0.95 | 3.7 | 0.95 | 2.0 | 0.95 | 3.3 | 0.95 | 3.1 |
| 1 | 1.2 | 1 | 1.2 | 1 | 1.2 | 1 | 1.2 |

| HF-HFO-1234yf-HCFO-1233zdE-HFO-1243zf | | | | | | | |
|---|---|---|---|---|---|---|---|
| Organics 0.9 F1234yf + 0.05 F1233zdE + 0.05 F1243zf | | Organics 0.05 F1234yf + 0.9 F1233zdE + 0.05 F1243zf | | Organics 0.05 F1234yf + 0.05 F1233zdE + 0.9 F1243zf | | Organics 0.4 F1234yf + 0.3 F1233zdE + 0.3 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.9 | 0 | 5.7 | 0 | 5.0 |
| 0.05 | 7.5 | 0.05 | 3.0 | 0.05 | 6.7 | 0.05 | 6.0 |
| 0.1 | 7.5 | 0.1 | 3.0 | 0.1 | 6.7 | 0.1 | 6.0 |
| 0.15 | 7.5 | 0.15 | 3.0 | 0.15 | 6.7 | 0.15 | 6.0 |
| 0.2 | 7.4 | 0.2 | 3.0 | 0.2 | 6.7 | 0.2 | 6.0 |
| 0.25 | 7.4 | 0.25 | 3.0 | 0.25 | 6.7 | 0.25 | 6.0 |
| 0.3 | 7.5 | 0.3 | 3.0 | 0.3 | 6.7 | 0.3 | 6.0 |
| 0.35 | 7.5 | 0.35 | 3.0 | 0.35 | 6.7 | 0.35 | 6.0 |
| 0.4 | 7.5 | 0.4 | 3.0 | 0.4 | 6.7 | 0.4 | 6.0 |
| 0.45 | 7.5 | 0.45 | 3.0 | 0.45 | 6.7 | 0.45 | 6.0 |
| 0.5 | 7.5 | 0.5 | 3.0 | 0.5 | 6.6 | 0.5 | 6.0 |
| 0.55 | 7.5 | 0.55 | 3.0 | 0.55 | 6.6 | 0.55 | 6.0 |
| 0.6 | 7.5 | 0.6 | 3.0 | 0.6 | 6.6 | 0.6 | 6.0 |
| 0.65 | 7.5 | 0.65 | 3.0 | 0.65 | 6.6 | 0.65 | 6.0 |
| 0.7 | 7.4 | 0.7 | 3.0 | 0.7 | 6.5 | 0.7 | 6.0 |
| 0.75 | 7.3 | 0.75 | 3.0 | 0.75 | 6.3 | 0.75 | 5.8 |
| 0.8 | 7.0 | 0.8 | 2.8 | 0.8 | 6.0 | 0.8 | 5.5 |
| 0.85 | 6.4 | 0.85 | 2.6 | 0.85 | 5.5 | 0.85 | 5.1 |
| 0.9 | 5.4 | 0.9 | 2.3 | 0.9 | 4.7 | 0.9 | 4.3 |
| 0.95 | 3.7 | 0.95 | 1.8 | 0.95 | 3.3 | 0.95 | 3.1 |
| 1 | 1.2 | 1 | 1.2 | 1 | 1.2 | 1 | 1.2 |

| HF-HFO-1234yf-HFC-245cb-Trifluoropropyne | | | | | | | |
|---|---|---|---|---|---|---|---|
| Organics 0.34 F1234yf + 0.33 F245cb + 0.33 TFP | | Organics 0.99 F1234yf + 0.005 F245cb + 0.005 TFP | | Organics 0.005 F1234yf + 0.99 F245cb + 0.005 TFP | | Organics 0.005 F1234yf + 0.005 F245cb + 0.99 TFP | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 8.0 | 0 | 6.8 | 0 | 4.7 | 0 | 11.6 |
| 0.05 | 8.9 | 0.05 | 7.8 | 0.05 | 5.9 | 0.05 | 12.4 |
| 0.1 | 8.9 | 0.1 | 7.8 | 0.1 | 5.9 | 0.1 | 12.3 |
| 0.15 | 8.8 | 0.15 | 7.8 | 0.15 | 5.9 | 0.15 | 12.2 |
| 0.2 | 8.8 | 0.2 | 7.8 | 0.2 | 5.9 | 0.2 | 12.1 |
| 0.25 | 8.7 | 0.25 | 7.8 | 0.25 | 5.9 | 0.25 | 12.0 |
| 0.3 | 8.8 | 0.3 | 7.7 | 0.3 | 5.9 | 0.3 | 11.9 |
| 0.35 | 8.8 | 0.35 | 7.8 | 0.35 | 5.9 | 0.35 | 11.8 |
| 0.4 | 8.8 | 0.4 | 7.8 | 0.4 | 5.9 | 0.4 | 11.7 |
| 0.45 | 8.8 | 0.45 | 7.8 | 0.45 | 5.9 | 0.45 | 11.8 |
| 0.5 | 8.7 | 0.5 | 7.8 | 0.5 | 5.9 | 0.5 | 11.8 |
| 0.55 | 8.7 | 0.55 | 7.8 | 0.55 | 5.9 | 0.55 | 11.8 |
| 0.6 | 8.7 | 0.6 | 7.8 | 0.6 | 5.9 | 0.6 | 11.8 |
| 0.65 | 8.7 | 0.65 | 7.8 | 0.65 | 5.9 | 0.65 | 11.8 |
| 0.7 | 8.7 | 0.7 | 7.7 | 0.7 | 5.9 | 0.7 | 11.8 |
| 0.75 | 8.7 | 0.75 | 7.6 | 0.75 | 5.9 | 0.75 | 11.8 |
| 0.8 | 8.5 | 0.8 | 7.3 | 0.8 | 5.9 | 0.8 | 11.6 |
| 0.85 | 7.9 | 0.85 | 6.7 | 0.85 | 5.9 | 0.85 | 10.8 |
| 0.9 | 6.6 | 0.9 | 5.6 | 0.9 | 5.1 | 0.9 | 9.1 |
| 0.95 | 4.5 | 0.95 | 3.9 | 0.95 | 3.6 | 0.95 | 6.1 |
| 1 | 1.2 | 1 | 1.2 | 1 | 1.2 | 1 | 1.2 |

| HF-HFO-1234yf-HFC-245cb-HCFC-244bb | | | | | | | |
|---|---|---|---|---|---|---|---|
| Organics 0.34 F1234yf + 0.33 F245cb + 0.33 F244bb | | Organics 0.99 F1234yf + 0.005 F245cb + 0.005 F244bb | | Organics 0.005 F1234yf + 0.99 F245cb + 0.005 F244bb | | Organics 0.005 F1234yf + 0.005 F245cb + 0.99 F244bb | |
| MASSFRAC HF | TOTAL PRESSURE bar | MASSFRAC HF | TOTAL PRES bar | MASSFRAC HF | TOTAL PRES bar | MASSFRAC HF | TOTAL PRES bar |
| 0 | 4.3 | 0 | 6.8 | 0 | 4.6 | 0 | 0.7 |
| 0.05 | 5.4 | 0.05 | 7.7 | 0.05 | 5.8 | 0.05 | 1.8 |
| 0.1 | 5.4 | 0.1 | 7.7 | 0.1 | 5.8 | 0.1 | 1.8 |
| 0.15 | 5.4 | 0.15 | 7.7 | 0.15 | 5.8 | 0.15 | 1.8 |
| 0.2 | 5.4 | 0.2 | 7.7 | 0.2 | 5.8 | 0.2 | 1.8 |
| 0.25 | 5.4 | 0.25 | 7.7 | 0.25 | 5.8 | 0.25 | 1.8 |
| 0.3 | 5.4 | 0.3 | 7.7 | 0.3 | 5.8 | 0.3 | 1.8 |
| 0.35 | 5.4 | 0.35 | 7.7 | 0.35 | 5.8 | 0.35 | 1.8 |
| 0.4 | 5.4 | 0.4 | 7.7 | 0.4 | 5.8 | 0.4 | 1.8 |
| 0.45 | 5.3 | 0.45 | 7.7 | 0.45 | 5.8 | 0.45 | 1.8 |
| 0.5 | 5.3 | 0.5 | 7.7 | 0.5 | 5.8 | 0.5 | 1.8 |
| 0.55 | 5.3 | 0.55 | 7.7 | 0.55 | 5.8 | 0.55 | 1.8 |
| 0.6 | 5.3 | 0.6 | 7.7 | 0.6 | 5.8 | 0.6 | 1.8 |
| 0.65 | 5.3 | 0.65 | 7.7 | 0.65 | 5.8 | 0.65 | 1.8 |
| 0.7 | 5.2 | 0.7 | 7.7 | 0.7 | 5.8 | 0.7 | 1.8 |
| 0.75 | 5.2 | 0.75 | 7.5 | 0.75 | 5.8 | 0.75 | 1.8 |
| 0.8 | 5.1 | 0.8 | 7.2 | 0.8 | 5.8 | 0.8 | 1.8 |
| 0.85 | 4.8 | 0.85 | 6.6 | 0.85 | 5.8 | 0.85 | 1.8 |
| 0.9 | 4.2 | 0.9 | 5.6 | 0.9 | 5.0 | 0.9 | 1.8 |
| 0.95 | 3.0 | 0.95 | 3.9 | 0.95 | 3.6 | 0.95 | 1.5 |
| 1 | 1.2 | 1 | 1.2 | 1 | 1.2 | 1 | 1.2 |

| HF-HFO-1234yf-HFC-245cb-HFC-245fa | | | | | | | |
|---|---|---|---|---|---|---|---|
| Organics 0.34 F1234yf + 0.33 F245cb + 0.33 F245fa | | Organics 0.99 F1234yf + 0.005 F245cb + 0.005 F245fa | | Organics 0.005 F1234yf + 0.99 F245cb + 0.005 F245fa | | Organics 0.005 F1234yf + 0.005 F245cb + 0.99 F245fa | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.8 | 0 | 4.6 | 0 | 1.6 |
| 0.05 | 5.6 | 0.05 | 7.7 | 0.05 | 5.8 | 0.05 | 2.7 |
| 0.1 | 5.6 | 0.1 | 7.7 | 0.1 | 5.8 | 0.1 | 2.7 |
| 0.15 | 5.6 | 0.15 | 7.7 | 0.15 | 5.8 | 0.15 | 2.7 |
| 0.2 | 5.6 | 0.2 | 7.7 | 0.2 | 5.8 | 0.2 | 2.7 |
| 0.25 | 5.6 | 0.25 | 7.7 | 0.25 | 5.8 | 0.25 | 2.7 |
| 0.3 | 5.6 | 0.3 | 7.7 | 0.3 | 5.8 | 0.3 | 2.7 |
| 0.35 | 5.6 | 0.35 | 7.7 | 0.35 | 5.8 | 0.35 | 2.7 |
| 0.4 | 5.6 | 0.4 | 7.7 | 0.4 | 5.8 | 0.4 | 2.7 |
| 0.45 | 5.6 | 0.45 | 7.7 | 0.45 | 5.8 | 0.45 | 2.7 |
| 0.5 | 5.6 | 0.5 | 7.7 | 0.5 | 5.8 | 0.5 | 2.7 |
| 0.55 | 5.6 | 0.55 | 7.7 | 0.55 | 5.8 | 0.55 | 2.7 |
| 0.6 | 5.6 | 0.6 | 7.7 | 0.6 | 5.8 | 0.6 | 2.7 |
| 0.65 | 5.6 | 0.65 | 7.7 | 0.65 | 5.8 | 0.65 | 2.7 |
| 0.7 | 5.6 | 0.7 | 7.7 | 0.7 | 5.8 | 0.7 | 2.7 |
| 0.75 | 5.6 | 0.75 | 7.5 | 0.75 | 5.8 | 0.75 | 2.7 |
| 0.8 | 5.5 | 0.8 | 7.2 | 0.8 | 5.8 | 0.8 | 2.6 |
| 0.85 | 5.0 | 0.85 | 6.6 | 0.85 | 5.8 | 0.85 | 2.4 |
| 0.9 | 4.3 | 0.9 | 5.6 | 0.9 | 5.0 | 0.9 | 2.1 |
| 0.95 | 3.1 | 0.95 | 3.9 | 0.95 | 3.6 | 0.95 | 1.7 |
| 1 | 1.2 | 1 | 1.2 | 1 | 1.2 | 1 | 1.2 |

| HF-HFO-1234yf-HFC-245cb-HFO-1225yeZ | | | | | | | |
|---|---|---|---|---|---|---|---|
| Organics 0.34 F1234yf + 0.33 F245cb + 0.33 F1225yeZ | | Organics 0.99 F1234yf + 0.005 F245cb + 0.005 F1225yeZ | | Organics 0.005 F1234yf + 0.99 F245cb + 0.005 F1225yeZ | | Organics 0.005 F1234yf + 0.005 F245cb + 0.99 F1225yeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 5.6 | 0 | 6.8 | 0 | 4.7 | 0 | 5.2 |
| 0.05 | 6.7 | 0.05 | 7.7 | 0.05 | 5.8 | 0.05 | 6.2 |
| 0.1 | 6.7 | 0.1 | 7.8 | 0.1 | 5.8 | 0.1 | 6.2 |
| 0.15 | 6.7 | 0.15 | 7.7 | 0.15 | 5.8 | 0.15 | 6.2 |
| 0.2 | 6.7 | 0.2 | 7.7 | 0.2 | 5.8 | 0.2 | 6.2 |
| 0.25 | 6.7 | 0.25 | 7.7 | 0.25 | 5.8 | 0.25 | 6.2 |
| 0.3 | 6.7 | 0.3 | 7.7 | 0.3 | 5.8 | 0.3 | 6.2 |
| 0.35 | 6.7 | 0.35 | 7.7 | 0.35 | 5.8 | 0.35 | 6.2 |
| 0.4 | 6.7 | 0.4 | 7.7 | 0.4 | 5.8 | 0.4 | 6.2 |
| 0.45 | 6.7 | 0.45 | 7.7 | 0.45 | 5.8 | 0.45 | 6.2 |
| 0.5 | 6.7 | 0.5 | 7.7 | 0.5 | 5.8 | 0.5 | 6.2 |
| 0.55 | 6.7 | 0.55 | 7.7 | 0.55 | 5.8 | 0.55 | 6.2 |
| 0.6 | 6.7 | 0.6 | 7.7 | 0.6 | 5.8 | 0.6 | 6.2 |
| 0.65 | 6.7 | 0.65 | 7.7 | 0.65 | 5.8 | 0.65 | 6.2 |
| 0.7 | 6.6 | 0.7 | 7.7 | 0.7 | 5.8 | 0.7 | 6.1 |
| 0.75 | 6.6 | 0.75 | 7.6 | 0.75 | 5.8 | 0.75 | 5.9 |
| 0.8 | 6.4 | 0.8 | 7.3 | 0.8 | 5.8 | 0.8 | 5.6 |
| 0.85 | 5.9 | 0.85 | 6.6 | 0.85 | 5.8 | 0.85 | 5.1 |
| 0.9 | 5.0 | 0.9 | 5.6 | 0.9 | 5.0 | 0.9 | 4.2 |
| 0.95 | 3.5 | 0.95 | 3.9 | 0.95 | 3.6 | 0.95 | 3.0 |
| 1 | 1.2 | 1 | 1.2 | 1 | 1.2 | 1 | 1.2 |

HF-HFO-1234yf-HFC-245cb-HFO-1225zc

| Organics 0.34 F1234yf + 0.33 F245cb + 0.33 F1225zc | | Organics 0.99 F1234yf + 0.005 F245cb + 0.005 F1225zc | | Organics 0.005 F1234yf + 0.99 F245cb + 0.005 F1225zc | | Organics 0.005 F1234yf + 0.005 F245cb + 0.99 F1225zc | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 5.7 | 0 | 6.8 | 0 | 4.7 | 0 | 5.3 |
| 0.05 | 6.7 | 0.05 | 7.7 | 0.05 | 5.8 | 0.05 | 6.3 |
| 0.1 | 6.7 | 0.1 | 7.8 | 0.1 | 5.8 | 0.1 | 6.3 |
| 0.15 | 6.7 | 0.15 | 7.7 | 0.15 | 5.8 | 0.15 | 6.3 |
| 0.2 | 6.7 | 0.2 | 7.7 | 0.2 | 5.8 | 0.2 | 6.3 |
| 0.25 | 6.7 | 0.25 | 7.7 | 0.25 | 5.8 | 0.25 | 6.3 |
| 0.3 | 6.7 | 0.3 | 7.7 | 0.3 | 5.8 | 0.3 | 6.3 |
| 0.35 | 6.7 | 0.35 | 7.7 | 0.35 | 5.8 | 0.35 | 6.3 |
| 0.4 | 6.7 | 0.4 | 7.7 | 0.4 | 5.8 | 0.4 | 6.3 |
| 0.45 | 6.7 | 0.45 | 7.7 | 0.45 | 5.8 | 0.45 | 6.3 |
| 0.5 | 6.7 | 0.5 | 7.7 | 0.5 | 5.8 | 0.5 | 6.3 |
| 0.55 | 6.7 | 0.55 | 7.7 | 0.55 | 5.8 | 0.55 | 6.2 |
| 0.6 | 6.7 | 0.6 | 7.7 | 0.6 | 5.8 | 0.6 | 6.1 |
| 0.65 | 6.7 | 0.65 | 7.7 | 0.65 | 5.8 | 0.65 | 6.0 |
| 0.7 | 6.7 | 0.7 | 7.7 | 0.7 | 5.8 | 0.7 | 5.9 |
| 0.75 | 6.6 | 0.75 | 7.6 | 0.75 | 5.8 | 0.75 | 5.6 |
| 0.8 | 6.3 | 0.8 | 7.2 | 0.8 | 5.8 | 0.8 | 5.2 |
| 0.85 | 5.8 | 0.85 | 6.6 | 0.85 | 5.8 | 0.85 | 4.6 |
| 0.9 | 4.9 | 0.9 | 5.6 | 0.9 | 5.0 | 0.9 | 3.8 |
| 0.95 | 3.4 | 0.95 | 3.9 | 0.95 | 3.6 | 0.95 | 2.7 |
| 1 | 1.2 | 1 | 1.2 | 1 | 1.2 | 1 | 1.2 |

HF-HFO-1234yf-HFO-1234zeE-Trifluoropropyne

| Organics 0.34 F1234yf + 0.33 F1234zeE + 0.33 TFP | | Organics 0.99 F1234yf + 0.005 F1234zeE + 0.005 TFP | | Organics 0.005 F1234yf + 0.99 F1234zeE + 0.005 TFP | | Organics 0.005 F1234yf + 0.005 F1234zeE + 0.99 TFP | |
|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 8.0 | 0 | 6.8 | 0 | 4.9 | 0 | 11.6 |
| 0.05 | 8.8 | 0.05 | 7.8 | 0.05 | 5.9 | 0.05 | 12.4 |
| 0.1 | 8.8 | 0.1 | 7.8 | 0.1 | 5.9 | 0.1 | 12.3 |
| 0.15 | 8.8 | 0.15 | 7.8 | 0.15 | 5.9 | 0.15 | 12.2 |
| 0.2 | 8.8 | 0.2 | 7.8 | 0.2 | 5.9 | 0.2 | 12.1 |
| 0.25 | 8.7 | 0.25 | 7.8 | 0.25 | 5.9 | 0.25 | 12.0 |
| 0.3 | 8.7 | 0.3 | 7.7 | 0.3 | 5.9 | 0.3 | 11.9 |
| 0.35 | 8.7 | 0.35 | 7.8 | 0.35 | 5.9 | 0.35 | 11.8 |
| 0.4 | 8.7 | 0.4 | 7.8 | 0.4 | 5.9 | 0.4 | 11.8 |
| 0.45 | 8.7 | 0.45 | 7.8 | 0.45 | 5.9 | 0.45 | 11.8 |
| 0.5 | 8.7 | 0.5 | 7.8 | 0.5 | 5.8 | 0.5 | 11.8 |
| 0.55 | 8.7 | 0.55 | 7.8 | 0.55 | 5.8 | 0.55 | 11.8 |
| 0.6 | 8.7 | 0.6 | 7.8 | 0.6 | 5.7 | 0.6 | 11.8 |
| 0.65 | 8.7 | 0.65 | 7.8 | 0.65 | 5.6 | 0.65 | 11.8 |
| 0.7 | 8.6 | 0.7 | 7.7 | 0.7 | 5.4 | 0.7 | 11.8 |
| 0.75 | 8.5 | 0.75 | 7.6 | 0.75 | 5.2 | 0.75 | 11.8 |
| 0.8 | 8.1 | 0.8 | 7.3 | 0.8 | 4.8 | 0.8 | 11.6 |
| 0.85 | 7.4 | 0.85 | 6.7 | 0.85 | 4.3 | 0.85 | 10.8 |
| 0.9 | 6.2 | 0.9 | 5.6 | 0.9 | 3.6 | 0.9 | 9.1 |
| 0.95 | 4.2 | 0.95 | 3.9 | 0.95 | 2.6 | 0.95 | 6.1 |
| 1 | 1.2 | 1 | 1.2 | 1 | 1.2 | 1 | 1.2 |

| HF-HFO-1234yf-HFO-1234zeE-HCFC-244bb | | | | | | | |
|---|---|---|---|---|---|---|---|
| Organics 0.34 F1234yf + 0.33 F1234zeE + 0.33 F244bb | | Organics 0.99 F1234yf + 0.005 F1234zeE + 0.005 F244bb | | Organics 0.005 F1234yf + 0.99 F1234zeE + 0.005 F244bb | | Organics 0.005 F1234yf + 0.005 F1234zeE + 0.99 F244bb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.4 | 0 | 6.8 | 0 | 4.9 | 0 | 0.7 |
| 0.05 | 5.4 | 0.05 | 7.7 | 0.05 | 5.8 | 0.05 | 1.8 |
| 0.1 | 5.4 | 0.1 | 7.7 | 0.1 | 5.8 | 0.1 | 1.8 |
| 0.15 | 5.4 | 0.15 | 7.7 | 0.15 | 5.8 | 0.15 | 1.8 |
| 0.2 | 5.4 | 0.2 | 7.7 | 0.2 | 5.8 | 0.2 | 1.8 |
| 0.25 | 5.4 | 0.25 | 7.7 | 0.25 | 5.8 | 0.25 | 1.8 |
| 0.3 | 5.4 | 0.3 | 7.7 | 0.3 | 5.8 | 0.3 | 1.8 |
| 0.35 | 5.4 | 0.35 | 7.7 | 0.35 | 5.8 | 0.35 | 1.8 |
| 0.4 | 5.4 | 0.4 | 7.7 | 0.4 | 5.8 | 0.4 | 1.8 |
| 0.45 | 5.3 | 0.45 | 7.7 | 0.45 | 5.8 | 0.45 | 1.8 |
| 0.5 | 5.3 | 0.5 | 7.7 | 0.5 | 5.8 | 0.5 | 1.8 |
| 0.55 | 5.3 | 0.55 | 7.7 | 0.55 | 5.7 | 0.55 | 1.8 |
| 0.6 | 5.2 | 0.6 | 7.7 | 0.6 | 5.6 | 0.6 | 1.8 |
| 0.65 | 5.2 | 0.65 | 7.7 | 0.65 | 5.5 | 0.65 | 1.8 |
| 0.7 | 5.1 | 0.7 | 7.7 | 0.7 | 5.4 | 0.7 | 1.8 |
| 0.75 | 5.0 | 0.75 | 7.5 | 0.75 | 5.1 | 0.75 | 1.8 |
| 0.8 | 4.8 | 0.8 | 7.2 | 0.8 | 4.8 | 0.8 | 1.8 |
| 0.85 | 4.3 | 0.85 | 6.6 | 0.85 | 4.3 | 0.85 | 1.8 |
| 0.9 | 3.7 | 0.9 | 5.6 | 0.9 | 3.6 | 0.9 | 1.7 |
| 0.95 | 2.7 | 0.95 | 3.8 | 0.95 | 2.6 | 0.95 | 1.5 |
| 1 | 1.2 | 1 | 1.2 | 1 | 1.2 | 1 | 1.2 |

| HF-HFO-1234yf-HFO-1234zeE-HFC-245fa | | | | | | | |
|---|---|---|---|---|---|---|---|
| Organics 0.34 F1234yf + 0.33 F1234zeE + 0.33 F245fa | | Organics 0.99 F1234yf + 0.005 F1234zeE + 0.005 F245fa | | Organics 0.005 F1234yf + 0.99 F1234zeE + 0.005 F245fa | | Organics 0.005 F1234yf + 0.005 F1234zeE + 0.99 F245fa | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 4.5 | 0 | 6.8 | 0 | 4.9 | 0 | 1.6 |
| 0.05 | 5.6 | 0.05 | 7.7 | 0.05 | 5.8 | 0.05 | 2.7 |
| 0.1 | 5.6 | 0.1 | 7.7 | 0.1 | 5.8 | 0.1 | 2.7 |
| 0.15 | 5.6 | 0.15 | 7.7 | 0.15 | 5.8 | 0.15 | 2.7 |
| 0.2 | 5.6 | 0.2 | 7.7 | 0.2 | 5.8 | 0.2 | 2.7 |
| 0.25 | 5.6 | 0.25 | 7.7 | 0.25 | 5.8 | 0.25 | 2.7 |
| 0.3 | 5.6 | 0.3 | 7.7 | 0.3 | 5.8 | 0.3 | 2.7 |
| 0.35 | 5.6 | 0.35 | 7.7 | 0.35 | 5.8 | 0.35 | 2.7 |
| 0.4 | 5.6 | 0.4 | 7.7 | 0.4 | 5.8 | 0.4 | 2.7 |
| 0.45 | 5.6 | 0.45 | 7.7 | 0.45 | 5.8 | 0.45 | 2.7 |
| 0.5 | 5.6 | 0.5 | 7.7 | 0.5 | 5.8 | 0.5 | 2.7 |
| 0.55 | 5.5 | 0.55 | 7.7 | 0.55 | 5.7 | 0.55 | 2.7 |
| 0.6 | 5.5 | 0.6 | 7.7 | 0.6 | 5.6 | 0.6 | 2.7 |
| 0.65 | 5.5 | 0.65 | 7.7 | 0.65 | 5.5 | 0.65 | 2.7 |
| 0.7 | 5.4 | 0.7 | 7.7 | 0.7 | 5.4 | 0.7 | 2.7 |
| 0.75 | 5.3 | 0.75 | 7.5 | 0.75 | 5.1 | 0.75 | 2.7 |
| 0.8 | 5.0 | 0.8 | 7.2 | 0.8 | 4.8 | 0.8 | 2.6 |
| 0.85 | 4.5 | 0.85 | 6.6 | 0.85 | 4.3 | 0.85 | 2.4 |
| 0.9 | 3.8 | 0.9 | 5.6 | 0.9 | 3.6 | 0.9 | 2.1 |
| 0.95 | 2.7 | 0.95 | 3.9 | 0.95 | 2.6 | 0.95 | 1.7 |
| 1 | 1.2 | 1 | 1.2 | 1 | 1.2 | 1 | 1.2 |

| HF-HFO-1234yf-HFO-1234zeE-HFO-1225yeZ | | | | | | | |
|---|---|---|---|---|---|---|---|
| Organics 0.34 F1234yf + 0.33 F1234zeE + 0.33 | | Organics 0.99 F1234yf + 0.005 F1234zeE + 0.005 | | Organics 0.005 F1234yf + 0.99 F1234zeE + 0.005 | | Organics 0.005 F1234yf + 0.005 F1234zeE + 0.99 | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 5.7 | 0 | 6.8 | 0 | 4.9 | 0 | 5.2 |
| 0.05 | 6.6 | 0.05 | 7.7 | 0.05 | 5.8 | 0.05 | 6.2 |
| 0.1 | 6.7 | 0.1 | 7.8 | 0.1 | 5.9 | 0.1 | 6.2 |
| 0.15 | 6.7 | 0.15 | 7.7 | 0.15 | 5.9 | 0.15 | 6.2 |
| 0.2 | 6.7 | 0.2 | 7.7 | 0.2 | 5.9 | 0.2 | 6.2 |
| 0.25 | 6.7 | 0.25 | 7.7 | 0.25 | 5.9 | 0.25 | 6.2 |
| 0.3 | 6.7 | 0.3 | 7.7 | 0.3 | 5.9 | 0.3 | 6.2 |
| 0.35 | 6.7 | 0.35 | 7.7 | 0.35 | 5.9 | 0.35 | 6.2 |
| 0.4 | 6.7 | 0.4 | 7.7 | 0.4 | 5.8 | 0.4 | 6.2 |
| 0.45 | 6.7 | 0.45 | 7.7 | 0.45 | 5.8 | 0.45 | 6.2 |
| 0.5 | 6.7 | 0.5 | 7.7 | 0.5 | 5.8 | 0.5 | 6.2 |
| 0.55 | 6.7 | 0.55 | 7.7 | 0.55 | 5.7 | 0.55 | 6.2 |
| 0.6 | 6.6 | 0.6 | 7.7 | 0.6 | 5.7 | 0.6 | 6.2 |
| 0.65 | 6.6 | 0.65 | 7.7 | 0.65 | 5.6 | 0.65 | 6.2 |
| 0.7 | 6.5 | 0.7 | 7.7 | 0.7 | 5.4 | 0.7 | 6.1 |
| 0.75 | 6.3 | 0.75 | 7.6 | 0.75 | 5.2 | 0.75 | 5.9 |
| 0.8 | 5.9 | 0.8 | 7.2 | 0.8 | 4.8 | 0.8 | 5.6 |
| 0.85 | 5.4 | 0.85 | 6.6 | 0.85 | 4.3 | 0.85 | 5.1 |
| 0.9 | 4.5 | 0.9 | 5.6 | 0.9 | 3.6 | 0.9 | 4.2 |
| 0.95 | 3.1 | 0.95 | 3.9 | 0.95 | 2.6 | 0.95 | 3.0 |
| 1 | 1.2 | 1 | 1.2 | 1 | 1.2 | 1 | 1.2 |

| HF-HFO-1234yf-HFO-1234zeE-HFO-1225zc | | | | | | | |
|---|---|---|---|---|---|---|---|
| Organics 0.34 F1234yf + 0.33 F1234zeE + 0.33 F1225zc | | Organics 0.99 F1234yf + 0.005 F1234zeE + 0.005 F1225zc | | Organics 0.005 F1234yf + 0.99 F1234zeE + 0.005 F1225zc | | Organics 0.005 F1234yf + 0.005 F1234zeE + 0.99 F1225zc | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 5.7 | 0 | 6.8 | 0 | 4.9 | 0 | 5.3 |
| 0.05 | 6.7 | 0.05 | 7.7 | 0.05 | 5.8 | 0.05 | 6.3 |
| 0.1 | 6.7 | 0.1 | 7.8 | 0.1 | 5.9 | 0.1 | 6.3 |
| 0.15 | 6.7 | 0.15 | 7.7 | 0.15 | 5.9 | 0.15 | 6.3 |
| 0.2 | 6.7 | 0.2 | 7.7 | 0.2 | 5.9 | 0.2 | 6.3 |
| 0.25 | 6.7 | 0.25 | 7.7 | 0.25 | 5.9 | 0.25 | 6.3 |
| 0.3 | 6.7 | 0.3 | 7.7 | 0.3 | 5.9 | 0.3 | 6.3 |
| 0.35 | 6.7 | 0.35 | 7.7 | 0.35 | 5.9 | 0.35 | 6.3 |
| 0.4 | 6.7 | 0.4 | 7.7 | 0.4 | 5.8 | 0.4 | 6.3 |
| 0.45 | 6.7 | 0.45 | 7.7 | 0.45 | 5.8 | 0.45 | 6.3 |
| 0.5 | 6.7 | 0.5 | 7.7 | 0.5 | 5.8 | 0.5 | 6.2 |
| 0.55 | 6.7 | 0.55 | 7.7 | 0.55 | 5.7 | 0.55 | 6.2 |
| 0.6 | 6.6 | 0.6 | 7.7 | 0.6 | 5.7 | 0.6 | 6.1 |
| 0.65 | 6.5 | 0.65 | 7.7 | 0.65 | 5.6 | 0.65 | 6.0 |
| 0.7 | 6.4 | 0.7 | 7.7 | 0.7 | 5.4 | 0.7 | 5.9 |
| 0.75 | 6.2 | 0.75 | 7.6 | 0.75 | 5.2 | 0.75 | 5.6 |
| 0.8 | 5.8 | 0.8 | 7.2 | 0.8 | 4.8 | 0.8 | 5.2 |
| 0.85 | 5.3 | 0.85 | 6.6 | 0.85 | 4.3 | 0.85 | 4.6 |
| 0.9 | 4.4 | 0.9 | 5.6 | 0.9 | 3.6 | 0.9 | 3.8 |
| 0.95 | 3.1 | 0.95 | 3.9 | 0.95 | 2.6 | 0.95 | 2.7 |
| 1 | 1.2 | 1 | 1.2 | 1 | 1.2 | 1 | 1.2 |

| HF-HFO-1234yf-HFO-1225yeZ-Trifluoropropyne | | | | | | | |
|---|---|---|---|---|---|---|---|
| Organics 0.34 F1234yf + 0.33 F1225yeZ + 0.33 TFP | | Organics 0.99 F1234yf + 0.005 F1225yeZ + 0.005 TFP | | Organics 0.005 F1234yf + 0.99 F1225yeZ + 0.005 TFP | | Organics 0.005 F1234yf + 0.005 F1225yeZ + 0.99 TFP | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 8.2 | 0 | 6.8 | 0 | 5.2 | 0 | 11.6 |
| 0.05 | 9.0 | 0.05 | 7.8 | 0.05 | 6.3 | 0.05 | 12.4 |
| 0.1 | 9.0 | 0.1 | 7.8 | 0.1 | 6.3 | 0.1 | 12.3 |
| 0.15 | 9.0 | 0.15 | 7.8 | 0.15 | 6.3 | 0.15 | 12.2 |
| 0.2 | 8.9 | 0.2 | 7.8 | 0.2 | 6.3 | 0.2 | 12.1 |
| 0.25 | 8.9 | 0.25 | 7.8 | 0.25 | 6.3 | 0.25 | 12.0 |
| 0.3 | 8.9 | 0.3 | 7.7 | 0.3 | 6.3 | 0.3 | 11.9 |
| 0.35 | 8.8 | 0.35 | 7.8 | 0.35 | 6.3 | 0.35 | 11.8 |
| 0.4 | 8.8 | 0.4 | 7.8 | 0.4 | 6.3 | 0.4 | 11.7 |
| 0.45 | 8.8 | 0.45 | 7.8 | 0.45 | 6.3 | 0.45 | 11.7 |
| 0.5 | 8.9 | 0.5 | 7.8 | 0.5 | 6.3 | 0.5 | 11.7 |
| 0.55 | 8.9 | 0.55 | 7.8 | 0.55 | 6.3 | 0.55 | 11.8 |
| 0.6 | 8.9 | 0.6 | 7.8 | 0.6 | 6.3 | 0.6 | 11.8 |
| 0.65 | 8.9 | 0.65 | 7.8 | 0.65 | 6.3 | 0.65 | 11.8 |
| 0.7 | 8.9 | 0.7 | 7.7 | 0.7 | 6.2 | 0.7 | 11.8 |
| 0.75 | 8.7 | 0.75 | 7.6 | 0.75 | 6.0 | 0.75 | 11.8 |
| 0.8 | 8.3 | 0.8 | 7.3 | 0.8 | 5.6 | 0.8 | 11.6 |
| 0.85 | 7.6 | 0.85 | 6.7 | 0.85 | 5.1 | 0.85 | 10.8 |
| 0.9 | 6.4 | 0.9 | 5.6 | 0.9 | 4.3 | 0.9 | 9.1 |
| 0.95 | 4.3 | 0.95 | 3.9 | 0.95 | 3.0 | 0.95 | 6.1 |
| 1 | 1.2 | 1 | 1.2 | 1 | 1.2 | 1 | 1.2 |

| HF-HFO-1234yf-HCFC-244bb-Trifluoropropyne | | | | | | | |
|---|---|---|---|---|---|---|---|
| Organics 0.34 F1234yf + 0.33 F244bb + 0.33 TFP | | Organics 0.99 F1234yf + 0.005 F244bb + 0.005 TFP | | Organics 0.005 F1234yf + 0.99 F244bb + 0.005 TFP | | Organics 0.005 F1234yf + 0.005 F244bb + 0.99 TFP | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 7.0 | 0 | 6.8 | 0 | 0.8 | 0 | 11.6 |
| 0.05 | 8.0 | 0.05 | 7.8 | 0.05 | 1.9 | 0.05 | 12.3 |
| 0.1 | 7.9 | 0.1 | 7.8 | 0.1 | 1.9 | 0.1 | 12.3 |
| 0.15 | 7.9 | 0.15 | 7.8 | 0.15 | 1.9 | 0.15 | 12.2 |
| 0.2 | 7.9 | 0.2 | 7.7 | 0.2 | 1.9 | 0.2 | 12.0 |
| 0.25 | 7.9 | 0.25 | 7.7 | 0.25 | 1.9 | 0.25 | 11.9 |
| 0.3 | 7.9 | 0.3 | 7.7 | 0.3 | 1.9 | 0.3 | 11.8 |
| 0.35 | 7.9 | 0.35 | 7.7 | 0.35 | 1.9 | 0.35 | 11.8 |
| 0.4 | 7.8 | 0.4 | 7.7 | 0.4 | 1.9 | 0.4 | 11.7 |
| 0.45 | 7.8 | 0.45 | 7.7 | 0.45 | 1.9 | 0.45 | 11.7 |
| 0.5 | 7.8 | 0.5 | 7.7 | 0.5 | 1.9 | 0.5 | 11.7 |
| 0.55 | 7.8 | 0.55 | 7.7 | 0.55 | 1.9 | 0.55 | 11.7 |
| 0.6 | 7.7 | 0.6 | 7.7 | 0.6 | 1.9 | 0.6 | 11.7 |
| 0.65 | 7.7 | 0.65 | 7.7 | 0.65 | 1.9 | 0.65 | 11.7 |
| 0.7 | 7.6 | 0.7 | 7.7 | 0.7 | 1.9 | 0.7 | 11.7 |
| 0.75 | 7.5 | 0.75 | 7.6 | 0.75 | 1.9 | 0.75 | 11.7 |
| 0.8 | 7.2 | 0.8 | 7.3 | 0.8 | 1.9 | 0.8 | 11.5 |
| 0.85 | 6.6 | 0.85 | 6.7 | 0.85 | 1.9 | 0.85 | 10.8 |
| 0.9 | 5.6 | 0.9 | 5.6 | 0.9 | 1.8 | 0.9 | 9.1 |
| 0.95 | 3.9 | 0.95 | 3.9 | 0.95 | 1.5 | 0.95 | 6.1 |
| 1 | 1.2 | 1 | 1.2 | 1 | 1.2 | 1 | 1.2 |

| HF-HFO-1234yf-HCFC-244bb-HFC-245fa | | | | | | | |
|---|---|---|---|---|---|---|---|
| Organics 0.34 F1234yf + 0.33 F244bb + 0.33 F245fa | | Organics 0.99 F1234yf + 0.005 F244bb + 0.005 F245fa | | Organics 0.005 F1234yf + 0.99 F244bb + 0.005 F245fa | | Organics 0.005 F1234yf + 0.005 F244bb + 0.99 F245fa | |
| MASSFRAC HF | TOTAL PRES bar | MASSFRAC HF | TOTAL PRES bar | MASSFRAC HF | TOTAL PRES bar | MASSFRAC HF | TOTAL PRES bar |
| 0 | 3.3 | 0 | 6.7 | 0 | 0.7 | 0 | 1.5 |
| 0.05 | 4.4 | 0.05 | 7.7 | 0.05 | 1.8 | 0.05 | 2.7 |
| 0.1 | 4.4 | 0.1 | 7.7 | 0.1 | 1.8 | 0.1 | 2.7 |
| 0.15 | 4.4 | 0.15 | 7.7 | 0.15 | 1.8 | 0.15 | 2.7 |
| 0.2 | 4.4 | 0.2 | 7.7 | 0.2 | 1.8 | 0.2 | 2.7 |
| 0.25 | 4.4 | 0.25 | 7.7 | 0.25 | 1.8 | 0.25 | 2.7 |
| 0.3 | 4.4 | 0.3 | 7.7 | 0.3 | 1.8 | 0.3 | 2.7 |
| 0.35 | 4.4 | 0.35 | 7.7 | 0.35 | 1.8 | 0.35 | 2.7 |
| 0.4 | 4.4 | 0.4 | 7.7 | 0.4 | 1.8 | 0.4 | 2.7 |
| 0.45 | 4.3 | 0.45 | 7.7 | 0.45 | 1.8 | 0.45 | 2.7 |
| 0.5 | 4.3 | 0.5 | 7.7 | 0.5 | 1.8 | 0.5 | 2.7 |
| 0.55 | 4.3 | 0.55 | 7.7 | 0.55 | 1.8 | 0.55 | 2.7 |
| 0.6 | 4.3 | 0.6 | 7.7 | 0.6 | 1.8 | 0.6 | 2.7 |
| 0.65 | 4.2 | 0.65 | 7.7 | 0.65 | 1.8 | 0.65 | 2.7 |
| 0.7 | 4.2 | 0.7 | 7.7 | 0.7 | 1.8 | 0.7 | 2.7 |
| 0.75 | 4.1 | 0.75 | 7.5 | 0.75 | 1.8 | 0.75 | 2.6 |
| 0.8 | 4.0 | 0.8 | 7.2 | 0.8 | 1.8 | 0.8 | 2.6 |
| 0.85 | 3.7 | 0.85 | 6.6 | 0.85 | 1.8 | 0.85 | 2.4 |
| 0.9 | 3.2 | 0.9 | 5.6 | 0.9 | 1.7 | 0.9 | 2.1 |
| 0.95 | 2.4 | 0.95 | 3.8 | 0.95 | 1.5 | 0.95 | 1.7 |
| 1 | 1.2 | 1 | 1.2 | 1 | 1.2 | 1 | 1.2 |

| HF-HFO-1234yf-HCFO-1233xf-HCFC-244bb | | | | | | | |
|---|---|---|---|---|---|---|---|
| Organics 0.9 F1233xf + 0.05 F1234yf + 0.05 F244bb | | Organics 0.05 F1233xf + 0.9 F1234yf + 0.05 F244bb | | Organics 0.05 F1233xf + 0.05 F1234yf + 0.9 F244bb | | Organics 0.4 F1233xf + 0.3 F1234yf + 0.3 F244bb | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 6.3 | 0 | 1.1 | 0 | 3.1 |
| 0.05 | 2.9 | 0.05 | 7.3 | 0.05 | 2.2 | 0.05 | 4.2 |
| 0.1 | 2.9 | 0.1 | 7.3 | 0.1 | 2.2 | 0.1 | 4.2 |
| 0.15 | 2.9 | 0.15 | 7.3 | 0.15 | 2.2 | 0.15 | 4.2 |
| 0.2 | 2.9 | 0.2 | 7.3 | 0.2 | 2.2 | 0.2 | 4.2 |
| 0.25 | 2.9 | 0.25 | 7.3 | 0.25 | 2.2 | 0.25 | 4.2 |
| 0.3 | 2.9 | 0.3 | 7.3 | 0.3 | 2.2 | 0.3 | 4.2 |
| 0.35 | 2.9 | 0.35 | 7.3 | 0.35 | 2.2 | 0.35 | 4.2 |
| 0.4 | 2.9 | 0.4 | 7.3 | 0.4 | 2.2 | 0.4 | 4.2 |
| 0.45 | 2.9 | 0.45 | 7.3 | 0.45 | 2.2 | 0.45 | 4.2 |
| 0.5 | 2.9 | 0.5 | 7.3 | 0.5 | 2.2 | 0.5 | 4.1 |
| 0.55 | 2.9 | 0.55 | 7.3 | 0.55 | 2.2 | 0.55 | 4.1 |
| 0.6 | 2.9 | 0.6 | 7.3 | 0.6 | 2.2 | 0.6 | 4.1 |
| 0.65 | 2.9 | 0.65 | 7.3 | 0.65 | 2.2 | 0.65 | 4.1 |
| 0.7 | 2.9 | 0.7 | 7.3 | 0.7 | 2.1 | 0.7 | 4.0 |
| 0.75 | 2.9 | 0.75 | 7.1 | 0.75 | 2.1 | 0.75 | 4.0 |
| 0.8 | 2.8 | 0.8 | 6.8 | 0.8 | 2.1 | 0.8 | 3.9 |
| 0.85 | 2.6 | 0.85 | 6.2 | 0.85 | 2.1 | 0.85 | 3.5 |
| 0.9 | 2.2 | 0.9 | 5.2 | 0.9 | 1.9 | 0.9 | 3.1 |
| 0.95 | 1.8 | 0.95 | 3.6 | 0.95 | 1.6 | 0.95 | 2.3 |
| 1 | 1.2 | 1 | 1.2 | 1 | 1.2 | 1 | 1.2 |

EXAMPLE 3

Penternary Mixtures

| HF-HCFO-1233xf-HFC-245cb-HFO-1234yf-HFO-1243zf | | | | | | | | | |
|---|---|---|---|---|---|---|---|---|---|
| Organics 0.9 F1233xf + 0.033 F1234yf + 0 033 F245cb + 0.034 F1243zf | | Organics 0.033 F1233xf + 0.9 F1234yf + 0.033 F245cb + 0.034 F1243zf | | Organics 0.033 F1233xf + 0.033 F1234yf + 0.9 F245cb + 0.034 F1243zf | | Organics 0.034 F1233xf + 0.033 F1234yf + 0.033 F245cb + 0.9 F1243zf | | Organics 0.25 F1233xf + 0.25 F1234yf + 0.25 F245cb + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 6.5 | 0 | 4.7 | 0 | 5.7 | 0 | 4.8 |
| 0.05 | 3.2 | 0.05 | 7.5 | 0.05 | 5.8 | 0.05 | 6.7 | 0.05 | 5.9 |
| 0.1 | 3.2 | 0.1 | 7.5 | 0.1 | 5.9 | 0.1 | 6.7 | 0.1 | 5.9 |
| 0.15 | 3.2 | 0.15 | 7.5 | 0.15 | 5.9 | 0.15 | 6.7 | 0.15 | 5.9 |
| 0.2 | 3.2 | 0.2 | 7.5 | 0.2 | 5.9 | 0.2 | 6.7 | 0.2 | 5.9 |
| 0.25 | 3.2 | 0.25 | 7.5 | 0.25 | 5.9 | 0.25 | 6.7 | 0.25 | 5.9 |
| 0.3 | 3.2 | 0.3 | 7.5 | 0.3 | 5.9 | 0.3 | 6.7 | 0.3 | 5.9 |
| 0.35 | 3.2 | 0.35 | 7.5 | 0.35 | 5.9 | 0.35 | 6.7 | 0.35 | 5.9 |
| 0.4 | 3.2 | 0.4 | 7.5 | 0.4 | 5.9 | 0.4 | 6.7 | 0.4 | 5.9 |
| 0.45 | 3.2 | 0.45 | 7.5 | 0.45 | 5.9 | 0.45 | 6.7 | 0.45 | 5.9 |
| 0.5 | 3.1 | 0.5 | 7.5 | 0.5 | 5.9 | 0.5 | 6.7 | 0.5 | 5.9 |
| 0.55 | 3.1 | 0.55 | 7.5 | 0.55 | 5.9 | 0.55 | 6.7 | 0.55 | 5.9 |
| 0.6 | 3.1 | 0.6 | 7.5 | 0.6 | 5.9 | 0.6 | 6.6 | 0.6 | 5.9 |
| 0.65 | 3.1 | 0.65 | 7.5 | 0.65 | 5.9 | 0.65 | 6.6 | 0.65 | 5.9 |
| 0.7 | 3.1 | 0.7 | 7.5 | 0.7 | 5.9 | 0.7 | 6.5 | 0.7 | 5.9 |
| 0.75 | 3.1 | 0.75 | 7.4 | 0.75 | 5.9 | 0.75 | 6.3 | 0.75 | 5.9 |
| 0.8 | 3.0 | 0.8 | 7.0 | 0.8 | 5.9 | 0.8 | 6.1 | 0.8 | 5.6 |
| 0.85 | 2.7 | 0.85 | 6.5 | 0.85 | 5.8 | 0.85 | 5.6 | 0.85 | 5.2 |
| 0.9 | 2.4 | 0.9 | 5.4 | 0.9 | 5.0 | 0.9 | 4.7 | 0.9 | 4.4 |
| 0.95 | 1.9 | 0.95 | 3.8 | 0.95 | 3.5 | 0.95 | 3.4 | 0.95 | 3.1 |
| 1 | 1.2 | 1 | 1.2 | 1 | 1.2 | 1 | 1.2 | 1 | 1.2 |

| HF-HCFO-1233xf -HFO-1234yf-HFO-1234zeE-HFO-1234zeZ | | | | | | | | | |
|---|---|---|---|---|---|---|---|---|---|
| Organics 0.9 F1233xf + 0.033 F1234zeE + 0.033 F1234zeZ + 0.034 F1234yf | | Organics 0.033 F1233xf + 0.9 F1234zeE + 0.033 F1234zeZ + 0.034 F1234yf | | Organics 0.033 F1233xf + 0.033 F1234zeE + 0.9 F1234zeZ + 0.034 F1234yf | | Organics 0.034 F1233xf + 0.033 F1234zeE + 0.033 F1234zeZ + 0.9 F1234yf | | Organics 0.25 F1233xf + 0.25 F1234zeE + 0.25 F1234zeZ + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 2.1 | 0 | 6.4 | 0 | 3.8 |
| 0.05 | 3.0 | 0.05 | 5.7 | 0.05 | 3.2 | 0.05 | 7.4 | 0.05 | 4.9 |
| 0.1 | 3.0 | 0.1 | 5.7 | 0.1 | 3.2 | 0.1 | 7.4 | 0.1 | 4.9 |
| 0.15 | 3.0 | 0.15 | 5.7 | 0.15 | 3.2 | 0.15 | 7.4 | 0.15 | 4.9 |
| 0.2 | 3.0 | 0.2 | 5.7 | 0.2 | 3.2 | 0.2 | 7.4 | 0.2 | 4.9 |
| 0.25 | 3.0 | 0.25 | 5.7 | 0.25 | 3.2 | 0.25 | 7.4 | 0.25 | 4.9 |
| 0.3 | 3.0 | 0.3 | 5.7 | 0.3 | 3.2 | 0.3 | 7.4 | 0.3 | 4.9 |
| 0.35 | 3.0 | 0.35 | 5.7 | 0.35 | 3.2 | 0.35 | 7.4 | 0.35 | 4.9 |
| 0.4 | 3.0 | 0.4 | 5.7 | 0.4 | 3.2 | 0.4 | 7.4 | 0.4 | 4.9 |
| 0.45 | 3.0 | 0.45 | 5.7 | 0.45 | 3.2 | 0.45 | 7.4 | 0.45 | 4.9 |
| 0.5 | 3.0 | 0.5 | 5.7 | 0.5 | 3.2 | 0.5 | 7.4 | 0.5 | 4.9 |
| 0.55 | 3.0 | 0.55 | 5.6 | 0.55 | 3.2 | 0.55 | 7.4 | 0.55 | 4.9 |
| 0.6 | 3.0 | 0.6 | 5.6 | 0.6 | 3.2 | 0.6 | 7.4 | 0.6 | 4.8 |
| 0.65 | 3.0 | 0.65 | 5.5 | 0.65 | 3.2 | 0.65 | 7.4 | 0.65 | 4.8 |
| 0.7 | 3.0 | 0.7 | 5.3 | 0.7 | 3.2 | 0.7 | 7.4 | 0.7 | 4.8 |
| 0.75 | 2.9 | 0.75 | 5.1 | 0.75 | 3.1 | 0.75 | 7.2 | 0.75 | 4.6 |
| 0.8 | 2.8 | 0.8 | 4.7 | 0.8 | 3.0 | 0.8 | 6.9 | 0.8 | 4.4 |
| 0.85 | 2.6 | 0.85 | 4.3 | 0.85 | 2.8 | 0.85 | 6.3 | 0.85 | 4.0 |
| 0.9 | 2.3 | 0.9 | 3.6 | 0.9 | 2.4 | 0.9 | 5.3 | 0.9 | 3.4 |
| 0.95 | 1.8 | 0.95 | 2.6 | 0.95 | 1.9 | 0.95 | 3.7 | 0.95 | 2.5 |
| 1 | 1.2 | 1 | 1.2 | 1 | 1.2 | 1 | 1.2 | 1 | 1.2 |

| HF-HCFO-1233xf-HFO-1234yf-HFO-1234zeE-HFO-1243zf | | | | | | | | | |
|---|---|---|---|---|---|---|---|---|---|
| Organics 0.9 F1233xf + 0.033 F1234zeE + 0.033 F1243zf + 0.034 F1234yf | | Organics 0.033 F1233xf + 0.9 F1234zeE + 0.033 F1243zf + 0.034 F1234yf | | Organics 0.033 F1233xf + 0.033 F1234zeE + 0.9 F1243zf + 0.034 F1234yf | | Organics 0.034 F1233xf + 0.033 F1234zeE + 0.033 F1243zf + 0.9 F1234yf | | Organics 0.25 F1233xf + 0.25 F1234zeE + 0.25 F1243zf + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.1 | 0 | 4.9 | 0 | 5.7 | 0 | 6.5 | 0 | 4.9 |
| 0.05 | 3.2 | 0.05 | 5.8 | 0.05 | 6.7 | 0.05 | 7.5 | 0.05 | 5.9 |
| 0.1 | 3.2 | 0.1 | 5.9 | 0.1 | 6.7 | 0.1 | 7.5 | 0.1 | 5.9 |
| 0.15 | 3.2 | 0.15 | 5.9 | 0.15 | 6.7 | 0.15 | 7.5 | 0.15 | 5.9 |
| 0.2 | 3.2 | 0.2 | 5.9 | 0.2 | 6.7 | 0.2 | 7.5 | 0.2 | 5.9 |
| 0.25 | 3.2 | 0.25 | 5.9 | 0.25 | 6.7 | 0.25 | 7.5 | 0.25 | 5.9 |
| 0.3 | 3.2 | 0.3 | 5.9 | 0.3 | 6.7 | 0.3 | 7.5 | 0.3 | 5.9 |
| 0.35 | 3.2 | 0.35 | 5.9 | 0.35 | 6.7 | 0.35 | 7.5 | 0.35 | 5.9 |
| 0.4 | 3.1 | 0.4 | 5.8 | 0.4 | 6.7 | 0.4 | 7.5 | 0.4 | 5.9 |
| 0.45 | 3.1 | 0.45 | 5.8 | 0.45 | 6.7 | 0.45 | 7.5 | 0.45 | 5.9 |
| 0.5 | 3.1 | 0.5 | 5.8 | 0.5 | 6.7 | 0.5 | 7.5 | 0.5 | 5.9 |
| 0.55 | 3.1 | 0.55 | 5.8 | 0.55 | 6.7 | 0.55 | 7.5 | 0.55 | 5.9 |
| 0.6 | 3.1 | 0.6 | 5.7 | 0.6 | 6.6 | 0.6 | 7.5 | 0.6 | 5.9 |
| 0.65 | 3.1 | 0.65 | 5.6 | 0.65 | 6.6 | 0.65 | 7.5 | 0.65 | 5.8 |
| 0.7 | 3.1 | 0.7 | 5.4 | 0.7 | 6.5 | 0.7 | 7.5 | 0.7 | 5.7 |
| 0.75 | 3.1 | 0.75 | 5.2 | 0.75 | 6.3 | 0.75 | 7.3 | 0.75 | 5.6 |
| 0.8 | 2.9 | 0.8 | 4.9 | 0.8 | 6.0 | 0.8 | 7.0 | 0.8 | 5.3 |
| 0.85 | 2.7 | 0.85 | 4.4 | 0.85 | 5.5 | 0.85 | 6.4 | 0.85 | 4.8 |
| 0.9 | 2.4 | 0.9 | 3.6 | 0.9 | 4.7 | 0.9 | 5.4 | 0.9 | 4.0 |
| 0.95 | 1.9 | 0.95 | 2.6 | 0.95 | 3.3 | 0.95 | 3.7 | 0.95 | 2.9 |
| 1 | 1.2 | 1 | 1.2 | 1 | 1.2 | 1 | 1.2 | 1 | 1.2 |

| HF-HCFO-1233xf-HFO-1234yf-HFO-1234zeE-HCFO-1233zdE | | | | | | | | | |
|---|---|---|---|---|---|---|---|---|---|
| Organics 0.9 F1233xf + 0.033 F1234zeE + 0.033 F1233zdE + 0.034 F1234yf | | Organics 0.033 F1233xf + 0.9 F1234zeE + 0.033 F1233zdE + 0.034 F1234yf | | Organics 0.033 F1233xf + 0.033 F1234zeE + 0.9 F1233zdE +0.034 F1234yf | | Organics 0.034 F1233xf + 0.033 F1234zeE + 0.033 F1233zdE + 0.9 F1234yf | | Organics 0.25 F1233xf + 0.25 F1234zeE + 0.25 F1233zdE +0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 4.7 | 0 | 1.7 | 0 | 6.4 | 0 | 3.8 |
| 0.05 | 3.0 | 0.05 | 5.7 | 0.05 | 2.8 | 0.05 | 7.4 | 0.05 | 4.8 |
| 0.1 | 3.0 | 0.1 | 5.7 | 0.1 | 2.8 | 0.1 | 7.4 | 0.1 | 4.8 |
| 0.15 | 3.0 | 0.15 | 5.7 | 0.15 | 2.8 | 0.15 | 7.4 | 0.15 | 4.8 |
| 0.2 | 3.0 | 0.2 | 5.7 | 0.2 | 2.8 | 0.2 | 7.4 | 0.2 | 4.8 |
| 0.25 | 3.0 | 0.25 | 5.7 | 0.25 | 2.8 | 0.25 | 7.4 | 0.25 | 4.8 |
| 0.3 | 3.0 | 0.3 | 5.7 | 0.3 | 2.8 | 0.3 | 7.4 | 0.3 | 4.8 |
| 0.35 | 3.0 | 0.35 | 5.7 | 0.35 | 2.8 | 0.35 | 7.4 | 0.35 | 4.8 |
| 0.4 | 3.0 | 0.4 | 5.7 | 0.4 | 2.8 | 0.4 | 7.4 | 0.4 | 4.8 |
| 0.45 | 3.0 | 0.45 | 5.7 | 0.45 | 2.8 | 0.45 | 7.4 | 0.45 | 4.8 |
| 0.5 | 3.0 | 0.5 | 5.7 | 0.5 | 2.8 | 0.5 | 7.4 | 0.5 | 4.8 |
| 0.55 | 3.0 | 0.55 | 5.6 | 0.55 | 2.8 | 0.55 | 7.4 | 0.55 | 4.8 |
| 0.6 | 3.0 | 0.6 | 5.5 | 0.6 | 2.8 | 0.6 | 7.4 | 0.6 | 4.8 |
| 0.65 | 2.9 | 0.65 | 5.4 | 0.65 | 2.7 | 0.65 | 7.4 | 0.65 | 4.8 |
| 0.7 | 2.9 | 0.7 | 5.3 | 0.7 | 2.7 | 0.7 | 7.4 | 0.7 | 4.7 |
| 0.75 | 2.9 | 0.75 | 5.1 | 0.75 | 2.7 | 0.75 | 7.2 | 0.75 | 4.6 |
| 0.8 | 2.8 | 0.8 | 4.7 | 0.8 | 2.6 | 0.8 | 6.9 | 0.8 | 4.3 |
| 0.85 | 2.6 | 0.85 | 4.2 | 0.85 | 2.4 | 0.85 | 6.3 | 0.85 | 3.9 |
| 0.9 | 2.3 | 0.9 | 3.6 | 0.9 | 2.1 | 0.9 | 5.3 | 0.9 | 3.3 |
| 0.95 | 1.8 | 0.95 | 2.6 | 0.95 | 1.7 | 0.95 | 3.7 | 0.95 | 2.4 |
| 1 | 1.2 | 1 | 1.2 | 1 | 1.2 | 1 | 1.2 | 1 | 1.2 |

| HF-HCFO-1233xf-HFO-1234yf-HFO-1234zeZ-HFO-1243zf | | | | | | | | | |
|---|---|---|---|---|---|---|---|---|---|
| Organics 0.9 F1233xf + 0.033 F1234zeZ + 0.033 F1243zf + 0.034 F1234yf | | Organics 0.033 F1233xf + 0.9 F1234zeZ + 0.033 F1243zf + 0.034 F1234yf | | Organics 0.033 F1233xf + 0.033 F1234zeZ + 0.9 F1243zf + 0.034 F1234yf | | Organics 0.034 F1233xf + 0.033 F1234zeZ + 0.033 F1243zf + 0.9 F1234yf | | Organics 0.25 F1233xf + 0.25 F1234zeZ + 0.25 F1243zf + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 5.6 | 0 | 6.4 | 0 | 4.1 |
| 0.05 | 3.1 | 0.05 | 3.2 | 0.05 | 6.6 | 0.05 | 7.4 | 0.05 | 5.2 |
| 0.1 | 3.1 | 0.1 | 3.2 | 0.1 | 6.6 | 0.1 | 7.4 | 0.1 | 5.2 |
| 0.15 | 3.1 | 0.15 | 3.2 | 0.15 | 6.6 | 0.15 | 7.4 | 0.15 | 5.2 |
| 0.2 | 3.1 | 0.2 | 3.2 | 0.2 | 6.6 | 0.2 | 7.4 | 0.2 | 5.2 |
| 0.25 | 3.1 | 0.25 | 3.2 | 0.25 | 6.6 | 0.25 | 7.4 | 0.25 | 5.2 |
| 0.3 | 3.1 | 0.3 | 3.2 | 0.3 | 6.6 | 0.3 | 7.4 | 0.3 | 5.2 |
| 0.35 | 3.0 | 0.35 | 3.2 | 0.35 | 6.6 | 0.35 | 7.4 | 0.35 | 5.2 |
| 0.4 | 3.0 | 0.4 | 3.2 | 0.4 | 6.6 | 0.4 | 7.4 | 0.4 | 5.2 |
| 0.45 | 3.0 | 0.45 | 3.2 | 0.45 | 6.6 | 0.45 | 7.4 | 0.45 | 5.2 |
| 0.5 | 3.0 | 0.5 | 3.2 | 0.5 | 6.6 | 0.5 | 7.4 | 0.5 | 5.2 |
| 0.55 | 3.0 | 0.55 | 3.2 | 0.55 | 6.6 | 0.55 | 7.4 | 0.55 | 5.2 |
| 0.6 | 3.0 | 0.6 | 3.2 | 0.6 | 6.5 | 0.6 | 7.4 | 0.6 | 5.2 |
| 0.65 | 3.0 | 0.65 | 3.2 | 0.65 | 6.5 | 0.65 | 7.4 | 0.65 | 5.2 |
| 0.7 | 3.0 | 0.7 | 3.2 | 0.7 | 6.4 | 0.7 | 7.4 | 0.7 | 5.1 |
| 0.75 | 3.0 | 0.75 | 3.2 | 0.75 | 6.2 | 0.75 | 7.2 | 0.75 | 5.0 |
| 0.8 | 2.9 | 0.8 | 3.1 | 0.8 | 6.0 | 0.8 | 6.9 | 0.8 | 4.8 |
| 0.85 | 2.6 | 0.85 | 2.8 | 0.85 | 5.5 | 0.85 | 6.3 | 0.85 | 4.4 |
| 0.9 | 2.3 | 0.9 | 2.5 | 0.9 | 4.6 | 0.9 | 5.3 | 0.9 | 3.7 |
| 0.95 | 1.8 | 0.95 | 2.0 | 0.95 | 3.3 | 0.95 | 3.7 | 0.95 | 2.7 |
| 1 | 1.2 | 1 | 1.2 | 1 | 1.2 | 1 | 1.2 | 1 | 1.2 |

| HF-HCFO-1233xf-HFO-1234yf-HFO-1234zeZ-HCFO-1233zdE | | | | | | | | | |
|---|---|---|---|---|---|---|---|---|---|
| Organics 0.9 F1233xf + 0.033 F1234zeZ + 0.033 F1233zdE + 0.034 F1234yf | | Organics 0.033 F1233xf + 0.9 F1234zeZ + 0.033 F1233zdE + 0.034 F1234yf | | Organics 0.033 F1233xf + 0.033 F1234zeZ + 0.9 F1233zdE + 0.034 F1234yf | | Organics 0.034 F1233xf + 0.033 F1234zeZ + 0.033 F1233zdE + 0.9 F1234yf | | Organics 0.25 F1233xf + 0.25 F1234zeZ + 0.25 F1233zdE + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.8 | 0 | 2.0 | 0 | 1.6 | 0 | 6.3 | 0 | 3.0 |
| 0.05 | 2.9 | 0.05 | 3.1 | 0.05 | 2.7 | 0.05 | 7.3 | 0.05 | 4.1 |
| 0.1 | 2.9 | 0.1 | 3.1 | 0.1 | 2.7 | 0.1 | 7.3 | 0.1 | 4.1 |
| 0.15 | 2.9 | 0.15 | 3.1 | 0.15 | 2.7 | 0.15 | 7.3 | 0.15 | 4.1 |
| 0.2 | 2.9 | 0.2 | 3.1 | 0.2 | 2.7 | 0.2 | 7.3 | 0.2 | 4.1 |
| 0.25 | 2.9 | 0.25 | 3.1 | 0.25 | 2.7 | 0.25 | 7.3 | 0.25 | 4.1 |
| 0.3 | 2.9 | 0.3 | 3.1 | 0.3 | 2.7 | 0.3 | 7.3 | 0.3 | 4.1 |
| 0.35 | 2.9 | 0.35 | 3.1 | 0.35 | 2.7 | 0.35 | 7.3 | 0.35 | 4.1 |
| 0.4 | 2.9 | 0.4 | 3.1 | 0.4 | 2.7 | 0.4 | 7.3 | 0.4 | 4.1 |
| 0.45 | 2.9 | 0.45 | 3.1 | 0.45 | 2.7 | 0.45 | 7.3 | 0.45 | 4.1 |
| 0.5 | 2.9 | 0.5 | 3.1 | 0.5 | 2.7 | 0.5 | 7.3 | 0.5 | 4.1 |
| 0.55 | 2.9 | 0.55 | 3.1 | 0.55 | 2.7 | 0.55 | 7.3 | 0.55 | 4.1 |
| 0.6 | 2.9 | 0.6 | 3.1 | 0.6 | 2.7 | 0.6 | 7.3 | 0.6 | 4.1 |
| 0.65 | 2.9 | 0.65 | 3.1 | 0.65 | 2.7 | 0.65 | 7.3 | 0.65 | 4.1 |
| 0.7 | 2.9 | 0.7 | 3.1 | 0.7 | 2.7 | 0.7 | 7.3 | 0.7 | 4.0 |
| 0.75 | 2.8 | 0.75 | 3.1 | 0.75 | 2.6 | 0.75 | 7.1 | 0.75 | 4.0 |
| 0.8 | 2.7 | 0.8 | 2.9 | 0.8 | 2.5 | 0.8 | 6.8 | 0.8 | 3.8 |
| 0.85 | 2.5 | 0.85 | 2.7 | 0.85 | 2.4 | 0.85 | 6.2 | 0.85 | 3.5 |
| 0.9 | 2.2 | 0.9 | 2.4 | 0.9 | 2.1 | 0.9 | 5.3 | 0.9 | 3.0 |
| 0.95 | 1.8 | 0.95 | 1.9 | 0.95 | 1.7 | 0.95 | 3.7 | 0.95 | 2.3 |
| 1 | 1.2 | 1 | 1.2 | 1 | 1.2 | 1 | 1.2 | 1 | 1.2 |

| HF-HCFO-1233xf-HFO-1234yf-HCFO-1233zdE-HFO-1243zf | | | | | | | | | |
|---|---|---|---|---|---|---|---|---|---|
| Organics 0.9 F1233xf + 0.033 F1243zf + 0.033 F1233zdE + 0.034 F1234yf | | Organics 0.033 F1233xf + 0.9 F1243zf + 0.033 F1233zdE + 0.034 F1234yf | | Organics 0.033 F1233xf + 0.033 F1243zf + 0.9 F1233zdE + 0.034 F1234yf | | Organics 0.034 F1233xf + 0.033 F1243zf + 0.033 F1233zdE + 0.9 F1234yf | | Organics 0.25 F1233xf + 0.25 F1243zf + 0.25 F1233zdE + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 5.6 | 0 | 1.7 | 0 | 6.4 | 0 | 4.1 |
| 0.05 | 3.0 | 0.05 | 6.6 | 0.05 | 2.8 | 0.05 | 7.4 | 0.05 | 5.2 |
| 0.1 | 3.0 | 0.1 | 6.6 | 0.1 | 2.8 | 0.1 | 7.4 | 0.1 | 5.2 |
| 0.15 | 3.0 | 0.15 | 6.6 | 0.15 | 2.8 | 0.15 | 7.4 | 0.15 | 5.2 |
| 0.2 | 3.0 | 0.2 | 6.6 | 0.2 | 2.8 | 0.2 | 7.4 | 0.2 | 5.2 |
| 0.25 | 3.0 | 0.25 | 6.6 | 0.25 | 2.8 | 0.25 | 7.4 | 0.25 | 5.2 |
| 0.3 | 3.0 | 0.3 | 6.6 | 0.3 | 2.8 | 0.3 | 7.4 | 0.3 | 5.2 |
| 0.35 | 3.0 | 0.35 | 6.6 | 0.35 | 2.8 | 0.35 | 7.4 | 0.35 | 5.2 |
| 0.4 | 3.0 | 0.4 | 6.6 | 0.4 | 2.8 | 0.4 | 7.4 | 0.4 | 5.2 |
| 0.45 | 3.0 | 0.45 | 6.6 | 0.45 | 2.8 | 0.45 | 7.4 | 0.45 | 5.2 |
| 0.5 | 3.0 | 0.5 | 6.6 | 0.5 | 2.8 | 0.5 | 7.4 | 0.5 | 5.1 |
| 0.55 | 3.0 | 0.55 | 6.6 | 0.55 | 2.8 | 0.55 | 7.4 | 0.55 | 5.1 |
| 0.6 | 3.0 | 0.6 | 6.5 | 0.6 | 2.8 | 0.6 | 7.4 | 0.6 | 5.1 |
| 0.65 | 3.0 | 0.65 | 6.5 | 0.65 | 2.8 | 0.65 | 7.4 | 0.65 | 5.1 |
| 0.7 | 3.0 | 0.7 | 6.4 | 0.7 | 2.8 | 0.7 | 7.4 | 0.7 | 5.1 |
| 0.75 | 3.0 | 0.75 | 6.2 | 0.75 | 2.8 | 0.75 | 7.2 | 0.75 | 4.9 |
| 0.8 | 2.8 | 0.8 | 6.0 | 0.8 | 2.7 | 0.8 | 6.9 | 0.8 | 4.7 |
| 0.85 | 2.6 | 0.85 | 5.5 | 0.85 | 2.5 | 0.85 | 6.3 | 0.85 | 4.3 |
| 0.9 | 2.3 | 0.9 | 4.6 | 0.9 | 2.2 | 0.9 | 5.3 | 0.9 | 3.7 |
| 0.95 | 1.8 | 0.95 | 3.3 | 0.95 | 1.8 | 0.95 | 3.7 | 0.95 | 2.7 |
| 1 | 1.2 | 1 | 1.2 | 1 | 1.2 | 1 | 1.2 | 1 | 1.2 |

| HF-HFO-1234yf-HFO-1234zeE-HFO-1234zeZ-HCFO-1233zdE | | | | | | | | | |
|---|---|---|---|---|---|---|---|---|---|
| Organics 0.9 F1234yf + 0.033 F1233zdE + 0.033 F1234zeE + 0.034 F1234zeZ | | Organics 0.033 F1234yf + 0.9 F1233zdE + 0.033 F1234zeE + 0.034 F1234zeZ | | Organics 0.033 F1234yf + 0.033 F1233zdE + 0.9 F1234zeE + 0.034 F1234zeZ | | Organics 0.034 F1234yf + 0.033 F1233zdE + 0.033 F1234zeE + 0.9 F1234zeZ | | Organics 0.25 F1234yf + 0.25 F1233zdE + 0.25 F1234zeE + 0.25 F1234zeZ | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 4.7 | 0 | 2.1 | 0 | 3.8 |
| 0.05 | 7.4 | 0.05 | 2.8 | 0.05 | 5.7 | 0.05 | 3.2 | 0.05 | 4.8 |
| 0.1 | 7.4 | 0.1 | 2.8 | 0.1 | 5.7 | 0.1 | 3.2 | 0.1 | 4.8 |
| 0.15 | 7.4 | 0.15 | 2.8 | 0.15 | 5.7 | 0.15 | 3.2 | 0.15 | 4.8 |
| 0.2 | 7.4 | 0.2 | 2.8 | 0.2 | 5.7 | 0.2 | 3.2 | 0.2 | 4.8 |
| 0.25 | 7.4 | 0.25 | 2.8 | 0.25 | 5.7 | 0.25 | 3.2 | 0.25 | 4.8 |
| 0.3 | 7.4 | 0.3 | 2.8 | 0.3 | 5.7 | 0.3 | 3.2 | 0.3 | 4.8 |
| 0.35 | 7.4 | 0.35 | 2.8 | 0.35 | 5.7 | 0.35 | 3.2 | 0.35 | 4.8 |
| 0.4 | 7.4 | 0.4 | 2.8 | 0.4 | 5.7 | 0.4 | 3.2 | 0.4 | 4.8 |
| 0.45 | 7.4 | 0.45 | 2.8 | 0.45 | 5.7 | 0.45 | 3.2 | 0.45 | 4.8 |
| 0.5 | 7.4 | 0.5 | 2.8 | 0.5 | 5.7 | 0.5 | 3.2 | 0.5 | 4.8 |
| 0.55 | 7.4 | 0.55 | 2.8 | 0.55 | 5.6 | 0.55 | 3.2 | 0.55 | 4.8 |
| 0.6 | 7.4 | 0.6 | 2.8 | 0.6 | 5.5 | 0.6 | 3.2 | 0.6 | 4.8 |
| 0.65 | 7.4 | 0.65 | 2.7 | 0.65 | 5.4 | 0.65 | 3.2 | 0.65 | 4.8 |
| 0.7 | 7.4 | 0.7 | 2.7 | 0.7 | 5.3 | 0.7 | 3.2 | 0.7 | 4.7 |
| 0.75 | 7.2 | 0.75 | 2.7 | 0.75 | 5.1 | 0.75 | 3.1 | 0.75 | 4.6 |
| 0.8 | 6.9 | 0.8 | 2.6 | 0.8 | 4.7 | 0.8 | 3.0 | 0.8 | 4.3 |
| 0.85 | 6.3 | 0.85 | 2.4 | 0.85 | 4.2 | 0.85 | 2.8 | 0.85 | 4.0 |
| 0.9 | 5.3 | 0.9 | 2.1 | 0.9 | 3.6 | 0.9 | 2.4 | 0.9 | 3.4 |
| 0.95 | 3.7 | 0.95 | 1.7 | 0.95 | 2.6 | 0.95 | 1.9 | 0.95 | 2.5 |
| 1 | 1.2 | 1 | 1.2 | 1 | 1.2 | 1 | 1.2 | 1 | 1.2 |

| HF-HFO-1234yf-HFO-1234zeE-HFO-1234zeZ-HFO-1243zf | | | | | | | | | |
|---|---|---|---|---|---|---|---|---|---|
| Organics 0.9 F1234yf + 0.033 F1234zeZ + 0.033 F1234zeE + 0.034 F1243zf | | Organics 0.033 F1234yf + 0.9 F1234zeZ + 0.033 F1234zeE + 0.034 F1243zf | | Organics 0.033 F1234yf + 0.033 F1234zeZ + 0.9 F1234zeE + 0.034 F1243zf | | Organics 0.034 F1234yf + 0.033 F1234zeZ + 0.033 F1234zeE + 0.9 F1243zf | | Organics 0.25 F1234yf + 0.25 F1234zeZ + 0.25 F1234zeE + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 2.2 | 0 | 4.9 | 0 | 5.7 | 0 | 4.9 |
| 0.05 | 7.5 | 0.05 | 3.3 | 0.05 | 5.8 | 0.05 | 6.7 | 0.05 | 5.9 |
| 0.1 | 7.5 | 0.1 | 3.3 | 0.1 | 5.9 | 0.1 | 6.7 | 0.1 | 5.9 |
| 0.15 | 7.5 | 0.15 | 3.3 | 0.15 | 5.8 | 0.15 | 6.7 | 0.15 | 5.9 |
| 0.2 | 7.5 | 0.2 | 3.3 | 0.2 | 5.8 | 0.2 | 6.7 | 0.2 | 5.9 |
| 0.25 | 7.5 | 0.25 | 3.3 | 0.25 | 5.8 | 0.25 | 6.7 | 0.25 | 5.9 |
| 0.3 | 7.5 | 0.3 | 3.3 | 0.3 | 5.8 | 0.3 | 6.7 | 0.3 | 5.9 |
| 0.35 | 7.5 | 0.35 | 3.3 | 0.35 | 5.8 | 0.35 | 6.7 | 0.35 | 5.9 |
| 0.4 | 7.5 | 0.4 | 3.3 | 0.4 | 5.8 | 0.4 | 6.7 | 0.4 | 5.9 |
| 0.45 | 7.5 | 0.45 | 3.3 | 0.45 | 5.8 | 0.45 | 6.7 | 0.45 | 5.9 |
| 0.5 | 7.5 | 0.5 | 3.3 | 0.5 | 5.8 | 0.5 | 6.7 | 0.5 | 5.9 |
| 0.55 | 7.5 | 0.55 | 3.3 | 0.55 | 5.8 | 0.55 | 6.7 | 0.55 | 5.9 |
| 0.6 | 7.5 | 0.6 | 3.3 | 0.6 | 5.7 | 0.6 | 6.6 | 0.6 | 5.9 |
| 0.65 | 7.5 | 0.65 | 3.3 | 0.65 | 5.6 | 0.65 | 6.6 | 0.65 | 5.8 |
| 0.7 | 7.5 | 0.7 | 3.3 | 0.7 | 5.4 | 0.7 | 6.5 | 0.7 | 5.7 |
| 0.75 | 7.3 | 0.75 | 3.3 | 0.75 | 5.2 | 0.75 | 6.3 | 0.75 | 5.6 |
| 0.8 | 7.0 | 0.8 | 3.1 | 0.8 | 4.9 | 0.8 | 6.0 | 0.8 | 5.3 |
| 0.85 | 6.4 | 0.85 | 2.9 | 0.85 | 4.4 | 0.85 | 5.5 | 0.85 | 4.8 |
| 0.9 | 5.4 | 0.9 | 2.5 | 0.9 | 3.7 | 0.9 | 4.7 | 0.9 | 4.1 |
| 0.95 | 3.7 | 0.95 | 2.0 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

| HF-HFO-1234yf-HFO-1234zeE-HCFO-1233zdE-HFO-1243zf | | | | | | | | | |
|---|---|---|---|---|---|---|---|---|---|
| Organics 0.9 F1234yf + 0.033 F1233zdE + 0.033 F1234zeE + 0.034 F1243zf | | Organics 0.033 F1234yf + 0.9 F1233zdE + 0.033 F1234zeE + 0.034 F1243zf | | Organics 0.033 F1234yf + 0.033 F1233zdE + 0.9 F1234zeE + 0.034 F1243zf | | Organics 0.034 F1234yf + 0.033 F1233zdE + 0.033 F1234zeE + 0.9 F1243zf | | Organics 0.25 F1234yf + 0.25 F1233zdE + 0.25 F1234zeE + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.9 | 0 | 4.9 | 0 | 5.7 | 0 | 4.8 |
| 0.05 | 7.5 | 0.05 | 3.0 | 0.05 | 5.8 | 0.05 | 6.7 | 0.05 | 5.8 |
| 0.1 | 7.5 | 0.1 | 3.0 | 0.1 | 5.9 | 0.1 | 6.7 | 0.1 | 5.9 |
| 0.15 | 7.5 | 0.15 | 3.0 | 0.15 | 5.8 | 0.15 | 6.7 | 0.15 | 5.9 |
| 0.2 | 7.5 | 0.2 | 3.0 | 0.2 | 5.8 | 0.2 | 6.7 | 0.2 | 5.9 |
| 0.25 | 7.5 | 0.25 | 3.0 | 0.25 | 5.8 | 0.25 | 6.7 | 0.25 | 5.9 |
| 0.3 | 7.5 | 0.3 | 3.0 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.8 |
| 0.55 | 7.5 | 0.55 | 2.9 | 0.55 | 5.8 | 0.55 | 6.6 | 0.55 | 5.8 |
| 0.6 | 7.5 | 0.6 | 2.9 | 0.6 | 5.7 | 0.6 | 6.6 | 0.6 | 5.8 |
| 0.65 | 7.5 | 0.65 | 2.9 | 0.65 | 5.6 | 0.65 | 6.6 | 0.65 | 5.8 |
| 0.7 | 7.5 | 0.7 | 2.9 | 0.7 | 5.4 | 0.7 | 6.5 | 0.7 | 5.7 |
| 0.75 | 7.3 | 0.75 | 2.9 | 0.75 | 5.2 | 0.75 | 6.3 | 0.75 | 5.5 |
| 0.8 | 7.0 | 0.8 | 2.7 | 0.8 | 4.9 | 0.8 | 6.0 | 0.8 | 5.2 |
| 0.85 | 6.4 | 0.85 | 2.5 | 0.85 | 4.4 | 0.85 | 5.5 | 0.85 | 4.8 |
| 0.9 | 5.4 | 0.9 | 2.2 | 0.9 | 3.6 | 0.9 | 4.7 | 0.9 | 4.0 |
| 0.95 | 3.7 | 0.95 | 1.8 | 0.95 | 2.6 | 0.95 | 3.3 | 0.95 | 2.9 |
| 1 | 1.2 | 1 | 1.2 | 1 | 1.2 | 1 | 1.2 | 1 | 1.2 |

| HF-HFO-1234yf-HFO-1234zeZ-HCFO-1233zdE-HFO-1243zf | | | | | | | | | |
|---|---|---|---|---|---|---|---|---|---|
| Organics 0.9 F1234yf + 0.033 F1233zdE + 0.033 F1234zeZ + 0.034 F1243zf | | Organics 0.033 F1234yf + 0.9 F1233zdE + 0.033 F1234zeZ + 0.034 F1243zf | | Organics 0.033 F1234yf + 0.033 F1233zdE + 0.9 F1234zeZ + 0.034 F1243zf | | Organics 0.034 F1234yf + 0.033 F1233zdE + 0.033 F1234zeZ + 0.9 F1243zf | | Organics 0.25 F1234yf + 0.25 F1233zdE + 0.25 F1234zeZ + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 1.7 | 0 | 2.1 | 0 | 5.6 | 0 | 4.1 |
| 0.05 | 7.4 | 0.05 | 2.9 | 0.05 | 3.2 | 0.05 | 6.6 | 0.05 | 5.2 |
| 0.1 | 7.4 | 0.1 | 2.9 | 0.1 | 3.2 | 0.1 | 6.6 | 0.1 | 5.2 |
| 0.15 | 7.4 | 0.15 | 2.9 | 0.15 | 3.2 | 0.15 | 6.6 | 0.15 | 5.2 |
| 0.2 | 7.4 | 0.2 | 2.9 | 0.2 | 3.2 | 0.2 | 6.6 | 0.2 | 5.2 |
| 0.25 | 7.4 | 0.25 | 2.8 | 0.25 | 3.2 | 0.25 | 6.6 | 0.25 | 5.2 |
| 0.3 | 7.4 | 0.3 | 2.8 | 0.3 | 3.2 | 0.3 | 6.6 | 0.3 | 5.2 |
| 0.35 | 7.4 | 0.35 | 2.8 | 0.35 | 3.2 | 0.35 | 6.6 | 0.35 | 5.1 |
| 0.4 | 7.4 | 0.4 | 2.8 | 0.4 | 3.2 | 0.4 | 6.6 | 0.4 | 5.1 |
| 0.45 | 7.4 | 0.45 | 2.8 | 0.45 | 3.2 | 0.45 | 6.6 | 0.45 | 5.1 |
| 0.5 | 7.4 | 0.5 | 2.8 | 0.5 | 3.2 | 0.5 | 6.6 | 0.5 | 5.1 |
| 0.55 | 7.4 | 0.55 | 2.8 | 0.55 | 3.2 | 0.55 | 6.6 | 0.55 | 5.1 |
| 0.6 | 7.4 | 0.6 | 2.8 | 0.6 | 3.2 | 0.6 | 6.5 | 0.6 | 5.1 |
| 0.65 | 7.4 | 0.65 | 2.8 | 0.65 | 3.2 | 0.65 | 6.5 | 0.65 | 5.1 |
| 0.7 | 7.4 | 0.7 | 2.8 | 0.7 | 3.2 | 0.7 | 6.4 | 0.7 | 5.1 |
| 0.75 | 7.2 | 0.75 | 2.8 | 0.75 | 3.2 | 0.75 | 6.2 | 0.75 | 5.0 |
| 0.8 | 6.9 | 0.8 | 2.7 | 0.8 | 3.0 | 0.8 | 5.9 | 0.8 | 4.7 |
| 0.85 | 6.3 | 0.85 | 2.5 | 0.85 | 2.8 | 0.85 | 5.5 | 0.85 | 4.3 |
| 0.9 | 5.3 | 0.9 | 2.2 | 0.9 | 2.5 | 0.9 | 4.6 | 0.9 | 3.7 |
| 0.95 | 3.7 | 0.95 | 1.8 | 0.95 | 2.0 | 0.95 | 3.3 | 0.95 | 2.7 |
| 1 | 1.2 | 1 | 1.2 | 1 | 1.2 | 1 | 1.2 | 1 | 1.2 |

| HF-HFO-1234yf-HFC-245cb-HFO-1234zeE-HCFO-1233zdE | | | | | | | | | |
|---|---|---|---|---|---|---|---|---|---|
| Organics 0.9 F1234yf + 0.033 F1234zeE + 0.033 F245cb + 0.034 F1233zdE | | Organics 0.033 F1234yf + 0.9 F1234zeE + 0.033 F245cb + 0.034 F1233zdE | | Organics 0.033 F1234yf + 0.033 F1234zeE + 0.9 F245cb + 0.034 F1233zdE | | Organics 0.034 F1234yf + 0.033 F1234zeE + 0.033 F245cb + 0.9 F1233zdE | | Organics 0.25 F1234yf + 0.25 F1234zeE + 0.25 F245cb + 0.25 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 4.8 | 0 | 4.6 | 0 | 1.8 | 0 | 4.5 |
| 0.05 | 7.5 | 0.05 | 5.8 | 0.05 | 5.8 | 0.05 | 2.9 | 0.05 | 5.6 |
| 0.1 | 7.5 | 0.1 | 5.8 | 0.1 | 5.8 | 0.1 | 2.9 | 0.1 | 5.6 |
| 0.15 | 7.5 | 0.15 | 5.8 | 0.15 | 5.8 | 0.15 | 2.9 | 0.15 | 5.6 |
| 0.2 | 7.5 | 0.2 | 5.8 | 0.2 | 5.8 | 0.2 | 2.9 | 0.2 | 5.6 |
| 0.25 | 7.5 | 0.25 | 5.8 | 0.25 | 5.8 | 0.25 | 2.9 | 0.25 | 5.6 |
| 0.3 | 7.5 | 0.3 | 5.8 | 0.3 | 5.8 | 0.3 | 2.9 | 0.3 | 5.6 |
| 0.35 | 7.5 | 0.35 | 5.8 | 0.35 | 5.8 | 0.35 | 2.9 | 0.35 | 5.6 |
| 0.4 | 7.5 | 0.4 | 5.8 | 0.4 | 5.8 | 0.4 | 2.9 | 0.4 | 5.6 |
| 0.45 | 7.5 | 0.45 | 5.8 | 0.45 | 5.8 | 0.45 | 2.9 | 0.45 | 5.6 |
| 0.5 | 7.5 | 0.5 | 5.8 | 0.5 | 5.8 | 0.5 | 2.9 | 0.5 | 5.6 |
| 0.55 | 7.5 | 0.55 | 5.7 | 0.55 | 5.8 | 0.55 | 2.9 | 0.55 | 5.6 |
| 0.6 | 7.5 | 0.6 | 5.7 | 0.6 | 5.8 | 0.6 | 2.9 | 0.6 | 5.6 |
| 0.65 | 7.5 | 0.65 | 5.6 | 0.65 | 5.8 | 0.65 | 2.9 | 0.65 | 5.6 |
| 0.7 | 7.5 | 0.7 | 5.4 | 0.7 | 5.8 | 0.7 | 2.9 | 0.7 | 5.6 |
| 0.75 | 7.3 | 0.75 | 5.2 | 0.75 | 5.8 | 0.75 | 2.9 | 0.75 | 5.5 |
| 0.8 | 7.0 | 0.8 | 4.9 | 0.8 | 5.8 | 0.8 | 2.7 | 0.8 | 5.2 |
| 0.85 | 6.4 | 0.85 | 4.4 | 0.85 | 5.7 | 0.85 | 2.5 | 0.85 | 4.8 |
| 0.9 | 5.4 | 0.9 | 3.6 | 0.9 | 4.9 | 0.9 | 2.2 | 0.9 | 4.1 |
| 0.95 | 3.7 | 0.95 | 2.6 | 0.95 | 3.5 | 0.95 | 1.8 | 0.95 | 2.9 |
| 1 | 1.2 | 1 | 1.2 | 1 | 1.2 | 1 | 1.2 | 1 | 1.2 |

HF-HFO-1234yf-HFC-245cb-HFO-1234zeE-HFO-1234zeZ

| Organics 0.9 F1234yf + 0.033 F1234zeE + 0.033 F245cb + 0.034 F1234zeZ | | Organics 0.033 F1234yf + 0.9 F1234zeE + 0.033 F245cb + 0.034 F1234zeZ | | Organics 0.033 F1234yf + 0.033 F1234zeE + 0.9 F245cb + 0.034 F1234zeZ | | Organics 0.034 F1234yf + 0.033 F1234zeE + 0.033 F245cb + 0.9 F1234zeZ | | Organics 0.25 F1234yf + 0.25 F1234zeE + 0.25 F245cb + 0.25 F1234zeZ | |
|---|---|---|---|---|---|---|---|---|---|
| MASSFRAC HF | TOTAL PRESSURE bar | MASSFRAC HF | TOTAL PRESSURE bar | MASSFRAC | TOTAL PRESSURE bar | MASSFRAC HF | TOTAL PRESSURE bar | MASSFRAC HF | TOTAL PRESSURE bar |
| 0 | 6.5 | 0 | 4.8 | 0 | 4.6 | 0 | 2.2 | 0 | 4.5 |
| 0.05 | 7.5 | 0.05 | 5.8 | 0.05 | 5.8 | 0.05 | 3.3 | 0.05 | 5.6 |
| 0.1 | 7.5 | 0.1 | 5.8 | 0.1 | 5.8 | 0.1 | 3.3 | 0.1 | 5.6 |
| 0.15 | 7.5 | 0.15 | 5.8 | 0.15 | 5.8 | 0.15 | 3.3 | 0.15 | 5.6 |
| 0.2 | 7.5 | 0.2 | 5.8 | 0.2 | 5.8 | 0.2 | 3.3 | 0.2 | 5.6 |
| 0.25 | 7.5 | 0.25 | 5.8 | 0.25 | 5.8 | 0.25 | 3.3 | 0.25 | 5.6 |
| 0.3 | 7.5 | 0.3 | 5.8 | 0.3 | 5.8 | 0.3 | 3.3 | 0.3 | 5.6 |
| 0.35 | 7.5 | 0.35 | 5.8 | 0.35 | 5.8 | 0.35 | 3.3 | 0.35 | 5.6 |
| 0.4 | 7.5 | 0.4 | 5.8 | 0.4 | 5.8 | 0.4 | 3.3 | 0.4 | 5.6 |
| 0.45 | 7.5 | 0.45 | 5.8 | 0.45 | 5.8 | 0.45 | 3.3 | 0.45 | 5.6 |
| 0.5 | 7.5 | 0.5 | 5.8 | 0.5 | 5.8 | 0.5 | 3.3 | 0.5 | 5.6 |
| 0.55 | 7.5 | 0.55 | 5.7 | 0.55 | 5.8 | 0.55 | 3.3 | 0.55 | 5.6 |
| 0.6 | 7.5 | 0.6 | 5.7 | 0.6 | 5.8 | 0.6 | 3.3 | 0.6 | 5.6 |
| 0.65 | 7.5 | 0.65 | 5.6 | 0.65 | 5.8 | 0.65 | 3.3 | 0.65 | 5.6 |
| 0.7 | 7.5 | 0.7 | 5.4 | 0.7 | 5.8 | 0.7 | 3.3 | 0.7 | 5.6 |
| 0.75 | 7.3 | 0.75 | 5.2 | 0.75 | 5.8 | 0.75 | 3.3 | 0.75 | 5.5 |
| 0.8 | 7.0 | 0.8 | 4.9 | 0.8 | 5.8 | 0.8 | 3.1 | 0.8 | 5.3 |
| 0.85 | 6.4 | 0.85 | 4.4 | 0.85 | 5.7 | 0.85 | 2.9 | 0.85 | 4.9 |
| 0.9 | 5.4 | 0.9 | 3.7 | 0.9 | 4.9 | 0.9 | 2.5 | 0.9 | 4.1 |
| 0.95 | 3.7 | 0.95 | 2.6 | 0.95 | 3.5 | 0.95 | 2.0 | 0.95 | 3.0 |
| 1 | 1.2 | 1 | 1.2 | 1 | 1.2 | 1 | 1.2 | 1 | 1.2 |

HF-HFO-1234yf-HFC-245cb-HFO-1234zeE-HFO-1243zf

| Organics 0.9 F1234yf + 0.033 F1234zeE + 0.033 F245cb + 0.034 F1243zf | | Organics 0.033 F1234yf + 0.9 F1234zeE + 0.033 F245cb + 0.034 F1243zf | | Organics 0.033 F1234yf + 0.033 F1234zeE + 0.9 F245cb + 0.034 F1243zf | | Organics 0.034 F1234yf + 0.033 F1234zeE + 0.033 F245cb + 0.9 F1243zf | | Organics 0.25 F1234yf + 0.25 F1234zeE + 0.25 F245cb + 0.25 F1243zf | |
|---|---|---|---|---|---|---|---|---|---|
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.6 | 0 | 5.0 | 0 | 4.8 | 0 | 5.8 | 0 | 5.6 |
| 0.05 | 7.6 | 0.05 | 5.9 | 0.05 | 6.0 | 0.05 | 6.8 | 0.05 | 6.6 |
| 0.1 | 7.6 | 0.1 | 6.0 | 0.1 | 6.0 | 0.1 | 6.8 | 0.1 | 6.6 |
| 0.15 | 7.6 | 0.15 | 6.0 | 0.15 | 6.0 | 0.15 | 6.8 | 0.15 | 6.6 |
| 0.2 | 7.6 | 0.2 | 6.0 | 0.2 | 6.0 | 0.2 | 6.8 | 0.2 | 6.6 |
| 0.25 | 7.6 | 0.25 | 6.0 | 0.25 | 6.0 | 0.25 | 6.8 | 0.25 | 6.6 |
| 0.3 | 7.6 | 0.3 | 6.0 | 0.3 | 6.0 | 0.3 | 6.8 | 0.3 | 6.6 |
| 0.35 | 7.6 | 0.35 | 6.0 | 0.35 | 6.0 | 0.35 | 6.8 | 0.35 | 6.6 |
| 0.4 | 7.6 | 0.4 | 6.0 | 0.4 | 6.0 | 0.4 | 6.8 | 0.4 | 6.6 |
| 0.45 | 7.6 | 0.45 | 5.9 | 0.45 | 6.0 | 0.45 | 6.8 | 0.45 | 6.6 |
| 0.5 | 7.6 | 0.5 | 5.9 | 0.5 | 6.0 | 0.5 | 6.8 | 0.5 | 6.6 |
| 0.55 | 7.6 | 0.55 | 5.9 | 0.55 | 6.0 | 0.55 | 6.7 | 0.55 | 6.6 |
| 0.6 | 7.6 | 0.6 | 5.8 | 0.6 | 6.0 | 0.6 | 6.7 | 0.6 | 6.6 |
| 0.65 | 7.6 | 0.65 | 5.7 | 0.65 | 5.9 | 0.65 | 6.7 | 0.65 | 6.6 |
| 0.7 | 7.6 | 0.7 | 5.6 | 0.7 | 5.9 | 0.7 | 6.6 | 0.7 | 6.6 |
| 0.75 | 7.4 | 0.75 | 5.3 | 0.75 | 5.9 | 0.75 | 6.4 | 0.75 | 6.4 |
| 0.8 | 7.1 | 0.8 | 5.0 | 0.8 | 5.9 | 0.8 | 6.1 | 0.8 | 6.1 |
| 0.85 | 6.5 | 0.85 | 4.5 | 0.85 | 5.8 | 0.85 | 5.6 | 0.85 | 5.6 |
| 0.9 | 5.5 | 0.9 | 3.7 | 0.9 | 5.0 | 0.9 | 4.8 | 0.9 | 4.8 |
| 0.95 | 3.8 | 0.95 | 2.7 | 0.95 | 3.5 | 0.95 | 3.4 | 0.95 | 3.4 |
| 1 | 1.2 | 1 | 1.2 | 1 | 1.2 | 1 | 1.2 | 1 | 1.2 |

| HF-HFO-1234yf-HFC-245cb-HFO-1234zeZ-HCFO-1233zdE | | | | | | | | | |
|---|---|---|---|---|---|---|---|---|---|
| Organics 0.9 F1234yf + 0.033 F1234zeZ + 0.033 F245cb + 0.034 F1233zdE | | Organics 0.033 F1234yf + 0.9 F1234zeZ + 0.033 F245cb + 0.034 F1233zdE | | Organics 0.033 F1234yf + 0.033 F1234zeZ + 0.9 F245cb + 0.034 F1233zdE | | Organics 0.034 F1234yf + 0.033 F1234zeZ + 0.033 F245cb + 0.9 F1233zdE | | Organics 0.25 F1234yf + 0.25 F1234zeZ + 0.25 F245cb + 0.25 F1233zdE | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.4 | 0 | 2.1 | 0 | 4.5 | 0 | 1.7 | 0 | 3.7 |
| 0.05 | 7.4 | 0.05 | 3.2 | 0.05 | 5.7 | 0.05 | 2.8 | 0.05 | 4.8 |
| 0.1 | 7.4 | 0.1 | 3.2 | 0.1 | 5.7 | 0.1 | 2.8 | 0.1 | 4.8 |
| 0.15 | 7.4 | 0.15 | 3.2 | 0.15 | 5.7 | 0.15 | 2.8 | 0.15 | 4.8 |
| 0.2 | 7.4 | 0.2 | 3.2 | 0.2 | 5.7 | 0.2 | 2.8 | 0.2 | 4.8 |
| 0.25 | 7.4 | 0.25 | 3.2 | 0.25 | 5.7 | 0.25 | 2.8 | 0.25 | 4.8 |
| 0.3 | 7.4 | 0.3 | 3.2 | 0.3 | 5.7 | 0.3 | 2.8 | 0.3 | 4.8 |
| 0.35 | 7.4 | 0.35 | 3.2 | 0.35 | 5.7 | 0.35 | 2.8 | 0.35 | 4.8 |
| 0.4 | 7.4 | 0.4 | 3.2 | 0.4 | 5.7 | 0.4 | 2.8 | 0.4 | 4.8 |
| 0.45 | 7.4 | 0.45 | 3.2 | 0.45 | 5.7 | 0.45 | 2.8 | 0.45 | 4.8 |
| 0.5 | 7.4 | 0.5 | 3.2 | 0.5 | 5.7 | 0.5 | 2.8 | 0.5 | 4.8 |
| 0.55 | 7.4 | 0.55 | 3.2 | 0.55 | 5.7 | 0.55 | 2.8 | 0.55 | 4.8 |
| 0.6 | 7.4 | 0.6 | 3.2 | 0.6 | 5.7 | 0.6 | 2.8 | 0.6 | 4.9 |
| 0.65 | 7.4 | 0.65 | 3.2 | 0.65 | 5.7 | 0.65 | 2.8 | 0.65 | 4.9 |
| 0.7 | 7.4 | 0.7 | 3.2 | 0.7 | 5.7 | 0.7 | 2.8 | 0.7 | 4.9 |
| 0.75 | 7.2 | 0.75 | 3.2 | 0.75 | 5.7 | 0.75 | 2.8 | 0.75 | 4.9 |
| 0.8 | 6.9 | 0.8 | 3.0 | 0.8 | 5.7 | 0.8 | 2.7 | 0.8 | 4.7 |
| 0.85 | 6.4 | 0.85 | 2.8 | 0.85 | 5.7 | 0.85 | 2.5 | 0.85 | 4.3 |
| 0.9 | 5.4 | 0.9 | 2.5 | 0.9 | 4.9 | 0.9 | 2.2 | 0.9 | 3.7 |
| 0.95 | 3.7 | 0.95 | 2.0 | 0.95 | 3.5 | 0.95 | 1.8 | 0.95 | 2.7 |
| 1 | 1.2 | 1 | 1.2 | 1 | 1.2 | 1 | 1.2 | 1 | 1.2 |

| HF-HFO-1234yf-HFC-245cb-HFO-1234zeZ-HFO-1243zf | | | | | | | | | |
|---|---|---|---|---|---|---|---|---|---|
| Organics 0.9 F1234yf + 0.033 F1234zeZ + 0.033 F245cb + 0.034 F1243zf | | Organics 0.033 F1234yf + 0.9 F1234zeZ + 0.033 F245cb + 0.034 F1243zf | | Organics 0.033 F1234yf + 0.033 F1234zeZ + 0.9 F245cb + 0.034 F1243zf | | Organics 0.034 F1234yf + 0.033 F1234zeZ + 0.033 F245cb + 0.9 F1243zf | | Organics 0.25 F1234yf + 0.25 F1234zeZ + 0.25 F245cb + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 2.2 | 0 | 4.7 | 0 | 5.7 | 0 | 4.8 |
| 0.05 | 7.5 | 0.05 | 3.3 | 0.05 | 5.8 | 0.05 | 6.7 | 0.05 | 5.9 |
| 0.1 | 7.5 | 0.1 | 3.3 | 0.1 | 5.8 | 0.1 | 6.7 | 0.1 | 5.9 |
| 0.15 | 7.5 | 0.15 | 3.3 | 0.15 | 5.8 | 0.15 | 6.7 | 0.15 | 5.9 |
| 0.2 | 7.5 | 0.2 | 3.3 | 0.2 | 5.8 | 0.2 | 6.7 | 0.2 | 5.9 |
| 0.25 | 7.5 | 0.25 | 3.3 | 0.25 | 5.8 | 0.25 | 6.7 | 0.25 | 5.9 |
| 0.3 | 7.5 | 0.3 | 3.3 | 0.3 | 5.8 | 0.3 | 6.7 | 0.3 | 5.9 |
| 0.35 | 7.5 | 0.35 | 3.3 | 0.35 | 5.8 | 0.35 | 6.7 | 0.35 | 5.9 |
| 0.4 | 7.5 | 0.4 | 3.3 | 0.4 | 5.8 | 0.4 | 6.7 | 0.4 | 5.9 |
| 0.45 | 7.5 | 0.45 | 3.3 | 0.45 | 5.8 | 0.45 | 6.7 | 0.45 | 5.9 |
| 0.5 | 7.5 | 0.5 | 3.3 | 0.5 | 5.8 | 0.5 | 6.7 | 0.5 | 5.9 |
| 0.55 | 7.5 | 0.55 | 3.3 | 0.55 | 5.8 | 0.55 | 6.7 | 0.55 | 5.9 |
| 0.6 | 7.5 | 0.6 | 3.3 | 0.6 | 5.8 | 0.6 | 6.6 | 0.6 | 5.9 |
| 0.65 | 7.5 | 0.65 | 3.3 | 0.65 | 5.8 | 0.65 | 6.6 | 0.65 | 5.9 |
| 0.7 | 7.5 | 0.7 | 3.3 | 0.7 | 5.9 | 0.7 | 6.5 | 0.7 | 5.9 |
| 0.75 | 7.3 | 0.75 | 3.3 | 0.75 | 5.9 | 0.75 | 6.3 | 0.75 | 5.9 |
| 0.8 | 7.0 | 0.8 | 3.2 | 0.8 | 5.9 | 0.8 | 6.1 | 0.8 | 5.6 |
| 0.85 | 6.5 | 0.85 | 2.9 | 0.85 | 5.8 | 0.85 | 5.6 | 0.85 | 5.2 |
| 0.9 | 5.4 | 0.9 | 2.6 | 0.9 | 5.0 | 0.9 | 4.7 | 0.9 | 4.4 |
| 0.95 | 3.8 | 0.95 | 2.0 | 0.95 | 3.5 | 0.95 | 3.4 | 0.95 | 3.2 |
| 1 | 1.2 | 1 | 1.2 | 1 | 1.2 | 1 | 1.2 | 1 | 1.2 |

| HF-HFO-1234yf-HFC-245cb-HCFO-1233zdE-HFO-1243zf | | | | | | | | | |
|---|---|---|---|---|---|---|---|---|---|
| Organics 0.9 F1234yf + 0.033 F1233zdE + 0.033 F245cb + 0.034 F1243zf | | Organics 0.033 F1234yf + 0.9 F1233zdE + 0.033 F245cb + 0.034 F1243zf | | Organics 0.033 F1234yf + 0.033 F1233zdE + 0.9 F245cb + 0.034 F1243zf | | Organics 0.034 F1234yf + 0.033 F1233zdE + 0.033 F245cb + 0.9 F1243zf | | Organics 0.25 F1234yf + 0.25 F1233zdE + 0.25 F245cb + 0.25 F1243zf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 6.5 | 0 | 1.8 | 0 | 4.7 | 0 | 5.7 | 0 | 4.8 |
| 0.05 | 7.5 | 0.05 | 2.9 | 0.05 | 5.8 | 0.05 | 6.7 | 0.05 | 5.9 |
| 0.1 | 7.5 | 0.1 | 2.9 | 0.1 | 5.8 | 0.1 | 6.7 | 0.1 | 5.9 |
| 0.15 | 7.5 | 0.15 | 2.9 | 0.15 | 5.8 | 0.15 | 6.7 | 0.15 | 5.9 |
| 0.2 | 7.5 | 0.2 | 2.9 | 0.2 | 5.8 | 0.2 | 6.7 | 0.2 | 5.9 |
| 0.25 | 7.5 | 0.25 | 2.9 | 0.25 | 5.8 | 0.25 | 6.7 | 0.25 | 5.9 |
| 0.3 | 7.5 | 0.3 | 2.9 | 0.3 | 5.8 | 0.3 | 6.7 | 0.3 | 5.9 |
| 0.35 | 7.5 | 0.35 | 2.9 | 0.35 | 5.8 | 0.35 | 6.7 | 0.35 | 5.9 |
| 0.4 | 7.5 | 0.4 | 2.9 | 0.4 | 5.8 | 0.4 | 6.7 | 0.4 | 5.9 |
| 0.45 | 7.5 | 0.45 | 2.9 | 0.45 | 5.8 | 0.45 | 6.7 | 0.45 | 5.9 |
| 0.5 | 7.5 | 0.5 | 2.9 | 0.5 | 5.8 | 0.5 | 6.7 | 0.5 | 5.9 |
| 0.55 | 7.5 | 0.55 | 2.9 | 0.55 | 5.8 | 0.55 | 6.7 | 0.55 | 5.9 |
| 0.6 | 7.5 | 0.6 | 2.9 | 0.6 | 5.8 | 0.6 | 6.6 | 0.6 | 5.9 |
| 0.65 | 7.5 | 0.65 | 2.9 | 0.65 | 5.8 | 0.65 | 6.6 | 0.65 | 5.9 |
| 0.7 | 7.5 | 0.7 | 2.9 | 0.7 | 5.8 | 0.7 | 6.5 | 0.7 | 5.9 |
| 0.75 | 7.3 | 0.75 | 2.9 | 0.75 | 5.8 | 0.75 | 6.3 | 0.75 | 5.8 |
| 0.8 | 7.0 | 0.8 | 2.8 | 0.8 | 5.8 | 0.8 | 6.1 | 0.8 | 5.6 |
| 0.85 | 6.5 | 0.85 | 2.6 | 0.85 | 5.8 | 0.85 | 5.6 | 0.85 | 5.1 |
| 0.9 | 5.4 | 0.9 | 2.3 | 0.9 | 5.0 | 0.9 | 4.7 | 0.9 | 4.4 |
| 0.95 | 3.8 | 0.95 | 1.8 | 0.95 | 3.5 | 0.95 | 3.4 | 0.95 | 3.1 |
| 1 | 1.2 | 1 | 1.2 | 1 | 1.2 | 1 | 1.2 | 1 | 1.2 |

| HF-HCFO-1233xf-HFC-245cb-HCFO-1233zdE-HFO-1234yf | | | | | | | | | |
|---|---|---|---|---|---|---|---|---|---|
| Organics 0.9 F1233xf + 0.033 F1233zdE + 0.033 F245cb + 0.034 F1234yf | | Organics 0.033 F1233xf + 0.9 F1233zdE + 0.033 F245cb + 0.034 F1234yf | | Organics 0.033 F1233xf + 0.033 F1233zdE + 0.9 F245cb + 0.034 F1234yf | | Organics 0.034 F1233xf + 0.033 F1233zdE + 0.033 F245cb + 0.9 F1234yf | | Organics 0.25 F1233xf + 0.25 F1233zdE + 0.25 F245cb + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 1.7 | 0 | 4.5 | 0 | 6.4 | 0 | 3.7 |
| 0.05 | 3.0 | 0.05 | 2.8 | 0.05 | 5.7 | 0.05 | 7.4 | 0.05 | 4.8 |
| 0.1 | 3.0 | 0.1 | 2.8 | 0.1 | 5.7 | 0.1 | 7.4 | 0.1 | 4.8 |
| 0.15 | 3.0 | 0.15 | 2.8 | 0.15 | 5.7 | 0.15 | 7.4 | 0.15 | 4.8 |
| 0.2 | 3.0 | 0.2 | 2.8 | 0.2 | 5.7 | 0.2 | 7.4 | 0.2 | 4.8 |
| 0.25 | 3.0 | 0.25 | 2.8 | 0.25 | 5.7 | 0.25 | 7.4 | 0.25 | 4.8 |
| 0.3 | 3.0 | 0.3 | 2.8 | 0.3 | 5.7 | 0.3 | 7.4 | 0.3 | 4.8 |
| 0.35 | 3.0 | 0.35 | 2.8 | 0.35 | 5.7 | 0.35 | 7.4 | 0.35 | 4.8 |
| 0.4 | 3.0 | 0.4 | 2.8 | 0.4 | 5.7 | 0.4 | 7.4 | 0.4 | 4.8 |
| 0.45 | 3.0 | 0.45 | 2.8 | 0.45 | 5.7 | 0.45 | 7.4 | 0.45 | 4.8 |
| 0.5 | 3.0 | 0.5 | 2.8 | 0.5 | 5.7 | 0.5 | 7.4 | 0.5 | 4.8 |
| 0.55 | 3.0 | 0.55 | 2.8 | 0.55 | 5.7 | 0.55 | 7.4 | 0.55 | 4.8 |
| 0.6 | 3.0 | 0.6 | 2.8 | 0.6 | 5.7 | 0.6 | 7.4 | 0.6 | 4.8 |
| 0.65 | 3.0 | 0.65 | 2.8 | 0.65 | 5.7 | 0.65 | 7.4 | 0.65 | 4.9 |
| 0.7 | 3.0 | 0.7 | 2.8 | 0.7 | 5.7 | 0.7 | 7.4 | 0.7 | 4.9 |
| 0.75 | 3.0 | 0.75 | 2.8 | 0.75 | 5.7 | 0.75 | 7.2 | 0.75 | 4.9 |
| 0.8 | 2.8 | 0.8 | 2.7 | 0.8 | 5.7 | 0.8 | 6.9 | 0.8 | 4.7 |
| 0.85 | 2.6 | 0.85 | 2.5 | 0.85 | 5.7 | 0.85 | 6.4 | 0.85 | 4.3 |
| 0.9 | 2.3 | 0.9 | 2.2 | 0.9 | 4.9 | 0.9 | 5.4 | 0.9 | 3.7 |
| 0.95 | 1.8 | 0.95 | 1.8 | 0.95 | 3.5 | 0.95 | 3.7 | 0.95 | 2.7 |
| 1 | 1.2 | 1 | 1.2 | 1 | 1.2 | 1 | 1.2 | 1 | 1.2 |

| HF-HCFO-1233xf-HFC-245cb-HFO-1234zeE-HFO-1234yf | | | | | | | | | |
|---|---|---|---|---|---|---|---|---|---|
| Organics 0.9 F1233xf + 0.033 F1234zeE + 0.033 F245cb + 0.034 F1234yf | | Organics 0.033 F1233xf + 0.9 F1234zeE + 0.033 F245cb + 0.034 F1234yf | | Organics 0.033 F1233xf + 0.033 F1234zeE + 0.9 F245cb + 0.034 F1234yf | | Organics 0.034 F1233xf + 0.033 F1234zeE + 0.033 F245cb + 0.9 F1234yf | | Organics 0.25 F1233xf + 0.25 F1234zeE + 0.25 F245cb + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 2.0 | 0 | 4.8 | 0 | 4.6 | 0 | 6.5 | 0 | 4.6 |
| 0.05 | 3.1 | 0.05 | 5.8 | 0.05 | 5.8 | 0.05 | 7.5 | 0.05 | 5.6 |
| 0.1 | 3.1 | 0.1 | 5.8 | 0.1 | 5.8 | 0.1 | 7.5 | 0.1 | 5.6 |
| 0.15 | 3.1 | 0.15 | 5.8 | 0.15 | 5.8 | 0.15 | 7.5 | 0.15 | 5.6 |
| 0.2 | 3.1 | 0.2 | 5.8 | 0.2 | 5.8 | 0.2 | 7.5 | 0.2 | 5.6 |
| 0.25 | 3.1 | 0.25 | 5.8 | 0.25 | 5.8 | 0.25 | 7.5 | 0.25 | 5.6 |
| 0.3 | 3.1 | 0.3 | 5.8 | 0.3 | 5.8 | 0.3 | 7.5 | 0.3 | 5.6 |
| 0.35 | 3.1 | 0.35 | 5.8 | 0.35 | 5.8 | 0.35 | 7.5 | 0.35 | 5.6 |
| 0.4 | 3.1 | 0.4 | 5.8 | 0.4 | 5.8 | 0.4 | 7.5 | 0.4 | 5.6 |
| 0.45 | 3.1 | 0.45 | 5.8 | 0.45 | 5.8 | 0.45 | 7.5 | 0.45 | 5.6 |
| 0.5 | 3.1 | 0.5 | 5.8 | 0.5 | 5.8 | 0.5 | 7.5 | 0.5 | 5.6 |
| 0.55 | 3.1 | 0.55 | 5.7 | 0.55 | 5.8 | 0.55 | 7.5 | 0.55 | 5.6 |
| 0.6 | 3.1 | 0.6 | 5.7 | 0.6 | 5.8 | 0.6 | 7.5 | 0.6 | 5.6 |
| 0.65 | 3.1 | 0.65 | 5.6 | 0.65 | 5.8 | 0.65 | 7.5 | 0.65 | 5.7 |
| 0.7 | 3.1 | 0.7 | 5.4 | 0.7 | 5.8 | 0.7 | 7.5 | 0.7 | 5.7 |
| 0.75 | 3.1 | 0.75 | 5.2 | 0.75 | 5.8 | 0.75 | 7.3 | 0.75 | 5.5 |
| 0.8 | 2.9 | 0.8 | 4.9 | 0.8 | 5.8 | 0.8 | 7.0 | 0.8 | 5.3 |
| 0.85 | 2.7 | 0.85 | 4.4 | 0.85 | 5.7 | 0.85 | 6.4 | 0.85 | 4.8 |
| 0.9 | 2.4 | 0.9 | 3.7 | 0.9 | 4.9 | 0.9 | 5.4 | 0.9 | 4.1 |
| 0.95 | 1.9 | 0.95 | 2.6 | 0.95 | 3.5 | 0.95 | 3.7 | 0.95 | 2.9 |
| 1 | 1.2 | 1 | 1.2 | 1 | 1.2 | 1 | 1.2 | 1 | 1.2 |

| HF-HCFO-1233xf-HFC-245cb-HFO-1234zeZ-HFO-1234yf | | | | | | | | | |
|---|---|---|---|---|---|---|---|---|---|
| Organics 0.9 F1233xf + 0.033 F1234zeZ + 0.033 F245cb + 0.034 F1234yf | | Organics 0.033 F1233xf + 0.9 F1234zeZ + 0.033 F245cb + 0.034 F1234yf | | Organics 0.033 F1233xf + 0.033 F1234zeZ + 0.9 F245cb + 0.034 F1234yf | | Organics 0.034 F1233xf + 0.033 F1234zeZ + 0.033 F245cb + 0.9 F1234y4 | | Organics 0.25 F1233xf + 0.25 F1234zeZ + 0.25 F245cb + 0.25 F1234yf | |
| MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar | MASSFRAC HF | TOTAL PRESSURE bar |
| 0 | 1.9 | 0 | 2.1 | 0 | 4.5 | 0 | 6.4 | 0 | 3.7 |
| 0.05 | 3.0 | 0.05 | 3.2 | 0.05 | 5.7 | 0.05 | 7.4 | 0.05 | 4.9 |
| 0.1 | 3.0 | 0.1 | 3.2 | 0.1 | 5.7 | 0.1 | 7.4 | 0.1 | 4.9 |
| 0.15 | 3.0 | 0.15 | 3.2 | 0.15 | 5.7 | 0.15 | 7.4 | 0.15 | 4.9 |
| 0.2 | 3.0 | 0.2 | 3.2 | 0.2 | 5.7 | 0.2 | 7.4 | 0.2 | 4.9 |
| 0.25 | 3.0 | 0.25 | 3.2 | 0.25 | 5.7 | 0.25 | 7.4 | 0.25 | 4.9 |
| 0.3 | 3.0 | 0.3 | 3.2 | 0.3 | 5.7 | 0.3 | 7.4 | 0.3 | 4.9 |
| 0.35 | 3.0 | 0.35 | 3.2 | 0.35 | 5.7 | 0.35 | 7.4 | 0.35 | 4.9 |
| 0.4 | 3.0 | 0.4 | 3.2 | 0.4 | 5.7 | 0.4 | 7.4 | 0.4 | 4.9 |
| 0.45 | 3.0 | 0.45 | 3.2 | 0.45 | 5.7 | 0.45 | 7.4 | 0.45 | 4.9 |
| 0.5 | 3.0 | 0.5 | 3.2 | 0.5 | 5.7 | 0.5 | 7.4 | 0.5 | 4.9 |
| 0.55 | 3.0 | 0.55 | 3.2 | 0.55 | 5.7 | 0.55 | 7.4 | 0.55 | 4.9 |
| 0.6 | 3.0 | 0.6 | 3.2 | 0.6 | 5.7 | 0.6 | 7.4 | 0.6 | 4.9 |
| 0.65 | 3.0 | 0.65 | 3.2 | 0.65 | 5.7 | 0.65 | 7.4 | 0.65 | 4.9 |
| 0.7 | 3.0 | 0.7 | 3.2 | 0.7 | 5.7 | 0.7 | 7.4 | 0.7 | 4.9 |
| 0.75 | 3.0 | 0.75 | 3.2 | 0.75 | 5.7 | 0.75 | 7.2 | 0.75 | 5.0 |
| 0.8 | 2.8 | 0.8 | 3.0 | 0.8 | 5.7 | 0.8 | 6.9 | 0.8 | 4.8 |
| 0.85 | 2.6 | 0.85 | 2.8 | 0.85 | 5.7 | 0.85 | 6.4 | 0.85 | 4.4 |
| 0.9 | 2.3 | 0.9 | 2.5 | 0.9 | 4.9 | 0.9 | 5.4 | 0.9 | 3.8 |
| 0.95 | 1.8 | 0.95 | 2.0 | 0.95 | 3.5 | 0.95 | 3.7 | 0.95 | 2.7 |
| 1 | 1.2 | 1 | 1.2 | 1 | 1.2 | 1 | 1.2 | 1 | 1.2 |

| HF-HCFO-1233xf-HFO-1234yf-HFC-245cb-HCFC-244bb | | | | | |
|---|---|---|---|---|---|
| MASSFRAC HF | Organics 0.25 F1233xf + 0.25 F1234yf + +0.25 F245cb + 0.25 F244bb TOTAL PRESSURE bar | Organics 0.97 F1233xf + 0.01 F1234yf + 0.01 F245cb + 0.01 F244bb TOTAL HF bar | Organics 0.01 F1233xf + 0.97 F1234yf + 0.01 F245cb + 0.01 F244bb TOTAL PRESSURE bar | Organics 0.01 F1233xf + 0.01 F1234yf + 0.97 F245cb + 0.01 F244bb TOTAL HF bar | Organics 0.01 F1233xf + 0.01 F1234yf + 0.01 F245cb + 0.97 F244bb TOTAL PRESSURE bar |
| 0 | 3.6 | 1.6 | 6.7 | 4.6 | 0.8 |
| 0.05 | 4.7 | 2.7 | 7.6 | 5.8 | 1.9 |
| 0.1 | 4.7 | 2.7 | 7.7 | 5.8 | 1.9 |
| 0.15 | 4.7 | 2.7 | 7.6 | 5.8 | 1.9 |
| 0.2 | 4.7 | 2.7 | 7.6 | 5.8 | 1.9 |
| 0.25 | 4.7 | 2.7 | 7.6 | 5.8 | 1.9 |
| 0.3 | 4.7 | 2.7 | 7.6 | 5.8 | 1.9 |
| 0.35 | 4.7 | 2.7 | 7.6 | 5.8 | 1.9 |
| 0.4 | 4.7 | 2.7 | 7.6 | 5.8 | 1.9 |
| 0.45 | 4.7 | 2.7 | 7.6 | 5.8 | 1.9 |
| 0.5 | 4.7 | 2.7 | 7.6 | 5.8 | 1.9 |
| 0.55 | 4.7 | 2.7 | 7.6 | 5.8 | 1.9 |
| 0.6 | 4.7 | 2.7 | 7.6 | 5.8 | 1.9 |
| 0.65 | 4.7 | 2.7 | 7.6 | 5.8 | 1.9 |
| 0.7 | 4.6 | 2.7 | 7.6 | 5.8 | 1.9 |
| 0.75 | 4.6 | 2.7 | 7.5 | 5.8 | 1.9 |
| 0.8 | 4.6 | 2.6 | 7.2 | 5.8 | 1.9 |
| 0.85 | 4.2 | 2.4 | 6.6 | 5.8 | 1.9 |
| 0.9 | 3.6 | 2.1 | 5.5 | 5.0 | 1.8 |
| 0.95 | 2.7 | 1.7 | 3.8 | 3.5 | 1.5 |
| 1 | 1.2 | 1.2 | 1.2 | 1.2 | 1.2 |

EXAMPLE 4

Mixtures with Six Compounds

| HF - HCFO-1233xf - HFO-1234yf - HFC-245cb - HFO-1234zeE- HFO-1234zeZ | | | | | | | | | | | |
|---|---|---|---|---|---|---|---|---|---|---|---|
| Organics 0.2 F1233xf + 0.2 F1234yf + 0.2 F245cb 0.2 F1234zeE + 0.2 F1234zeZ | | Organics 0.96 F1233xf + 0.01 F1234yf + 0.01 F245cb + 0.01 F1234zeE + 0.01 F1234zeZ | | Organics 0.01 F1233xf + 0.96 F1234yf + 0.01 F245cb + 0.01 F1234zeE + 0.01 F1234zeZ | | Organics 0.01 F1233xf + 0.01 F1234yf + 0.96 F245cb + 0.01 F1234zeE + 0.01 F1234zeZ | | Organics 0.01 F1233xf + 0.01 F1234yf + 0.01 F245cb + 0.96 F1234zeE + 0.01 F1234zeZ | | Organics 0.01 F1233xf + 0.01 F1234yf + 0.01 F245cb + 0.01 F1234zeE + 0.96 F1234zeZ | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.0 | 0 | 1.7 | 0 | 6.7 | 0 | 4.6 | 0 | 4.8 | 0 | 1.9 |
| 0.05 | 5.1 | 0.05 | 2.8 | 0.05 | 7.6 | 0.05 | 5.8 | 0.05 | 5.8 | 0.05 | 3.0 |
| 0.1 | 5.1 | 0.1 | 2.8 | 0.1 | 7.6 | 0.1 | 5.8 | 0.1 | 5.8 | 0.1 | 3.0 |
| 0.15 | 5.1 | 0.15 | 2.8 | 0.15 | 7.6 | 0.15 | 5.8 | 0.15 | 5.8 | 0.15 | 3.0 |
| 0.2 | 5.1 | 0.2 | 2.8 | 0.2 | 7.6 | 0.2 | 5.8 | 0.2 | 5.8 | 0.2 | 3.0 |
| 0.25 | 5.1 | 0.25 | 2.8 | 0.25 | 7.6 | 0.25 | 5.8 | 0.25 | 5.8 | 0.25 | 3.0 |
| 0.3 | 5.1 | 0.3 | 2.8 | 0.3 | 7.6 | 0.3 | 5.8 | 0.3 | 5.8 | 0.3 | 3.0 |
| 0.35 | 5.1 | 0.35 | 2.8 | 0.35 | 7.6 | 0.35 | 5.8 | 0.35 | 5.8 | 0.35 | 3.0 |
| 0.4 | 5.1 | 0.4 | 2.8 | 0.4 | 7.6 | 0.4 | 5.8 | 0.4 | 5.8 | 0.4 | 3.0 |
| 0.45 | 5.1 | 0.45 | 2.8 | 0.45 | 7.6 | 0.45 | 5.8 | 0.45 | 5.8 | 0.45 | 3.0 |
| 0.5 | 5.1 | 0.5 | 2.8 | 0.5 | 7.6 | 0.5 | 5.8 | 0.5 | 5.7 | 0.5 | 3.0 |
| 0.55 | 5.1 | 0.55 | 2.8 | 0.55 | 7.6 | 0.55 | 5.8 | 0.55 | 5.7 | 0.55 | 3.0 |
| 0.6 | 5.1 | 0.6 | 2.8 | 0.6 | 7.6 | 0.6 | 5.8 | 0.6 | 5.6 | 0.6 | 3.0 |
| 0.65 | 5.1 | 0.65 | 2.8 | 0.65 | 7.6 | 0.65 | 5.8 | 0.65 | 5.5 | 0.65 | 3.0 |
| 0.7 | 5.1 | 0.7 | 2.8 | 0.7 | 7.6 | 0.7 | 5.8 | 0.7 | 5.4 | 0.7 | 3.0 |
| 0.75 | 5.0 | 0.75 | 2.8 | 0.75 | 7.5 | 0.75 | 5.8 | 0.75 | 5.1 | 0.75 | 3.0 |
| 0.8 | 4.8 | 0.8 | 2.6 | 0.8 | 7.1 | 0.8 | 5.8 | 0.8 | 4.8 | 0.8 | 2.9 |
| 0.85 | 4.4 | 0.85 | 2.5 | 0.85 | 6.5 | 0.85 | 5.8 | 0.85 | 4.3 | 0.85 | 2.7 |
| 0.9 | 3.7 | 0.9 | 2.2 | 0.9 | 5.5 | 0.9 | 5.0 | 0.9 | 3.6 | 0.9 | 2.4 |
| 0.95 | 2.7 | 0.95 | 1.8 | 0.95 | 3.8 | 0.95 | 3.5 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFC-245cb - HFO-1234zeE- HCFO-1233zdE | | | | | | | | | | | |
|---|---|---|---|---|---|---|---|---|---|---|---|
| Organics 0.2 F1233xf + 0.2 F1234yf + 0.2 F245cb 0.2 F1234zeE + 0.2 F1233zdE | | Organics 0.96 F1233xf + 0.01 F1234yf + 0.01 F245cb + 0.01 F1234zeE + 0.01 F1233zdE | | Organics 0.01 F1233xf + 0.96 F1234yf + 0.01 F245cb + 0.01 F1234zeE + 0.01 F1233zdE | | Organics 0.01 F1233xf + 0.01 F1234yf + 0.96 F245cb + 0.01 F1234zeE + 0.01 F1233zdE | | Organics 0.01 F1233xf + 0.01 F1234yf + 0.01 F245cb + 0.96 F1234zeE + 0.01 F1233zdE | | Organics 0.01 F1233xf + 0.01 F1234yf + 0.01 F245cb + 0.01 F1234zeE + 0.96 F1233zdE | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.9 | 0 | 1.7 | 0 | 6.7 | 0 | 4.6 | 0 | 4.8 | 0 | 1.5 |
| 0.05 | 5.0 | 0.05 | 2.8 | 0.05 | 7.6 | 0.05 | 5.8 | 0.05 | 5.8 | 0.05 | 2.6 |
| 0.1 | 5.0 | 0.1 | 2.8 | 0.1 | 7.6 | 0.1 | 5.8 | 0.1 | 5.8 | 0.1 | 2.6 |
| 0.15 | 5.0 | 0.15 | 2.8 | 0.15 | 7.6 | 0.15 | 5.8 | 0.15 | 5.8 | 0.15 | 2.6 |
| 0.2 | 5.0 | 0.2 | 2.8 | 0.2 | 7.6 | 0.2 | 5.8 | 0.2 | 5.8 | 0.2 | 2.6 |
| 0.25 | 5.0 | 0.25 | 2.8 | 0.25 | 7.6 | 0.25 | 5.8 | 0.25 | 5.8 | 0.25 | 2.6 |
| 0.3 | 5.0 | 0.3 | 2.8 | 0.3 | 7.6 | 0.3 | 5.8 | 0.3 | 5.8 | 0.3 | 2.6 |
| 0.35 | 5.0 | 0.35 | 2.8 | 0.35 | 7.6 | 0.35 | 5.8 | 0.35 | 5.8 | 0.35 | 2.6 |
| 0.4 | 5.0 | 0.4 | 2.8 | 0.4 | 7.6 | 0.4 | 5.8 | 0.4 | 5.8 | 0.4 | 2.6 |
| 0.45 | 5.0 | 0.45 | 2.8 | 0.45 | 7.6 | 0.45 | 5.8 | 0.45 | 5.8 | 0.45 | 2.6 |
| 0.5 | 5.0 | 0.5 | 2.8 | 0.5 | 7.6 | 0.5 | 5.8 | 0.5 | 5.7 | 0.5 | 2.6 |
| 0.55 | 5.0 | 0.55 | 2.8 | 0.55 | 7.6 | 0.55 | 5.8 | 0.55 | 5.7 | 0.55 | 2.6 |
| 0.6 | 5.0 | 0.6 | 2.8 | 0.6 | 7.6 | 0.6 | 5.8 | 0.6 | 5.6 | 0.6 | 2.6 |
| 0.65 | 5.0 | 0.65 | 2.8 | 0.65 | 7.6 | 0.65 | 5.8 | 0.65 | 5.5 | 0.65 | 2.6 |
| 0.7 | 5.1 | 0.7 | 2.8 | 0.7 | 7.6 | 0.7 | 5.8 | 0.7 | 5.4 | 0.7 | 2.6 |
| 0.75 | 5.0 | 0.75 | 2.8 | 0.75 | 7.5 | 0.75 | 5.8 | 0.75 | 5.1 | 0.75 | 2.6 |
| 0.8 | 4.7 | 0.8 | 2.6 | 0.8 | 7.1 | 0.8 | 5.8 | 0.8 | 4.8 | 0.8 | 2.4 |
| 0.85 | 4.3 | 0.85 | 2.5 | 0.85 | 6.5 | 0.85 | 5.8 | 0.85 | 4.3 | 0.85 | 2.3 |
| 0.9 | 3.7 | 0.9 | 2.2 | 0.9 | 5.5 | 0.9 | 5.0 | 0.9 | 3.6 | 0.9 | 2.0 |
| 0.95 | 2.7 | 0.95 | 1.8 | 0.95 | 3.8 | 0.95 | 3.5 | 0.95 | 2.6 | 0.95 | 1.7 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFC-245cb - HFO-1234zeE- HFO-1243zf | | | | | | | | | | | |
|---|---|---|---|---|---|---|---|---|---|---|---|
| Organics 0.2 F1233xf + 0.2 F1234yf + 0.2 F245cb 0.2 F1234zeE + 0.2 F1243zf | | Organics 0.96 F1233xf + 0.01 F1234yf + 0.01 F245cb + 0.01 F1234zeE + 0.01 F1243zf | | Organics 0.01 F1233xf + 0.96 F1234yf + 0.01 F245cb + 0.01 F1234zeE + 0.01 F1243zf | | Organics 0.01 F1233xf + 0.01 F1234yf + 0.96 F245cb + 0.01 F1234zeE + 0.01 F1243zf | | Organics 0.01 F1233xf + 0.01 F1234yf + 0.01 F245cb + 0.96 F1234zeE + 0.01 F1243zf | | Organics 0.01 F1233xf + 0.01 F1234yf + 0.01 F245cb + 0.01 F1234zeE + 0.96 F1243zf | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.9 | 0 | 1.7 | 0 | 6.7 | 0 | 4.7 | 0 | 4.9 | 0 | 5.8 |
| 0.05 | 5.9 | 0.05 | 2.8 | 0.05 | 7.7 | 0.05 | 5.8 | 0.05 | 5.8 | 0.05 | 6.7 |
| 0.1 | 5.9 | 0.1 | 2.8 | 0.1 | 7.7 | 0.1 | 5.8 | 0.1 | 5.9 | 0.1 | 6.8 |
| 0.15 | 5.9 | 0.15 | 2.8 | 0.15 | 7.7 | 0.15 | 5.8 | 0.15 | 5.8 | 0.15 | 6.8 |
| 0.2 | 5.9 | 0.2 | 2.8 | 0.2 | 7.7 | 0.2 | 5.8 | 0.2 | 5.8 | 0.2 | 6.8 |
| 0.25 | 5.9 | 0.25 | 2.8 | 0.25 | 7.7 | 0.25 | 5.8 | 0.25 | 5.8 | 0.25 | 6.8 |
| 0.3 | 5.9 | 0.3 | 2.8 | 0.3 | 7.7 | 0.3 | 5.8 | 0.3 | 5.8 | 0.3 | 6.8 |
| 0.35 | 5.9 | 0.35 | 2.8 | 0.35 | 7.7 | 0.35 | 5.8 | 0.35 | 5.8 | 0.35 | 6.8 |
| 0.4 | 5.9 | 0.4 | 2.8 | 0.4 | 7.7 | 0.4 | 5.8 | 0.4 | 5.8 | 0.4 | 6.8 |
| 0.45 | 5.9 | 0.45 | 2.8 | 0.45 | 7.7 | 0.45 | 5.8 | 0.45 | 5.8 | 0.45 | 6.7 |
| 0.5 | 5.9 | 0.5 | 2.8 | 0.5 | 7.7 | 0.5 | 5.8 | 0.5 | 5.8 | 0.5 | 6.7 |
| 0.55 | 5.9 | 0.55 | 2.8 | 0.55 | 7.7 | 0.55 | 5.8 | 0.55 | 5.7 | 0.55 | 6.7 |
| 0.6 | 5.9 | 0.6 | 2.8 | 0.6 | 7.7 | 0.6 | 5.8 | 0.6 | 5.7 | 0.6 | 6.7 |
| 0.65 | 5.9 | 0.65 | 2.8 | 0.65 | 7.7 | 0.65 | 5.8 | 0.65 | 5.6 | 0.65 | 6.6 |
| 0.7 | 5.9 | 0.7 | 2.8 | 0.7 | 7.6 | 0.7 | 5.8 | 0.7 | 5.4 | 0.7 | 6.5 |
| 0.75 | 5.7 | 0.75 | 2.8 | 0.75 | 7.5 | 0.75 | 5.8 | 0.75 | 5.2 | 0.75 | 6.4 |
| 0.8 | 5.5 | 0.8 | 2.7 | 0.8 | 7.2 | 0.8 | 5.8 | 0.8 | 4.8 | 0.8 | 6.1 |
| 0.85 | 5.0 | 0.85 | 2.5 | 0.85 | 6.6 | 0.85 | 5.8 | 0.85 | 4.3 | 0.85 | 5.6 |
| 0.9 | 4.2 | 0.9 | 2.2 | 0.9 | 5.5 | 0.9 | 5.0 | 0.9 | 3.6 | 0.9 | 4.8 |
| 0.95 | 3.0 | 0.95 | 1.8 | 0.95 | 3.8 | 0.95 | 3.5 | 0.95 | 2.6 | 0.95 | 3.4 |
| 1 | 1.2 | 1 | 1.2 | 1 | 1.2 | 1 | 1.2 | 1 | 1.2 | 1 | 1.2 |

HF - HCFO-1233xf - HFO-1234yf - HFC-245cb - HFO-1234zeZ- HCFO-1233zdE

| Organics 0.2 F1233xf + 0.2 F1234yf + 0.2 F245cb 0.2 F1234zeZ + 0.2 F1233zdE | | Organics 0.96 F1233xf + 0.01 F1234yf + 0.01 F245cb + 0.01 F1234zeZ + 0.01 F1233zdE | | Organics 0.01 F1233xf + 0.96 F1234yf + 0.01 F245cb + 0.01 F1234zeZ + 0.01 F1233zdE | | Organics 0.01 F1233xf + 0.01 F1234yf + 0.96 F245cb + 0.01 F1234zeZ + 0.01 F1233zdE | | Organics 0.01 F1233xf + 0.01 F1234yf + 0.01 F245cb + 0.96 F1234zeZ + 0.01 F1233zdE | | Organics 0.01 F1233xf + 0.01 F1234yf + 0.01 F245cb + 0.01 F1234zeZ + 0.96 F1233zdE | |
|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.3 | 0 | 1.6 | 0 | 6.6 | 0 | 4.6 | 0 | 1.9 | 0 | 1.4 |
| 0.05 | 4.4 | 0.05 | 2.8 | 0.05 | 7.6 | 0.05 | 5.8 | 0.05 | 3.0 | 0.05 | 2.5 |
| 0.1 | 4.4 | 0.1 | 2.8 | 0.1 | 7.6 | 0.1 | 5.8 | 0.1 | 3.0 | 0.1 | 2.5 |
| 0.15 | 4.4 | 0.15 | 2.8 | 0.15 | 7.6 | 0.15 | 5.8 | 0.15 | 3.0 | 0.15 | 2.5 |
| 0.2 | 4.4 | 0.2 | 2.8 | 0.2 | 7.6 | 0.2 | 5.8 | 0.2 | 3.0 | 0.2 | 2.5 |
| 0.25 | 4.4 | 0.25 | 2.8 | 0.25 | 7.6 | 0.25 | 5.8 | 0.25 | 3.0 | 0.25 | 2.5 |
| 0.3 | 4.4 | 0.3 | 2.8 | 0.3 | 7.6 | 0.3 | 5.8 | 0.3 | 3.0 | 0.3 | 2.5 |
| 0.35 | 4.4 | 0.35 | 2.8 | 0.35 | 7.6 | 0.35 | 5.8 | 0.35 | 3.0 | 0.35 | 2.5 |
| 0.4 | 4.4 | 0.4 | 2.8 | 0.4 | 7.6 | 0.4 | 5.8 | 0.4 | 3.0 | 0.4 | 2.5 |
| 0.45 | 4.4 | 0.45 | 2.8 | 0.45 | 7.6 | 0.45 | 5.8 | 0.45 | 3.0 | 0.45 | 2.5 |
| 0.5 | 4.4 | 0.5 | 2.8 | 0.5 | 7.6 | 0.5 | 5.8 | 0.5 | 3.0 | 0.5 | 2.5 |
| 0.55 | 4.4 | 0.55 | 2.8 | 0.55 | 7.6 | 0.55 | 5.8 | 0.55 | 3.0 | 0.55 | 2.5 |
| 0.6 | 4.4 | 0.6 | 2.8 | 0.6 | 7.6 | 0.6 | 5.8 | 0.6 | 3.0 | 0.6 | 2.5 |
| 0.65 | 4.5 | 0.65 | 2.8 | 0.65 | 7.6 | 0.65 | 5.8 | 0.65 | 3.0 | 0.65 | 2.5 |
| 0.7 | 4.5 | 0.7 | 2.8 | 0.7 | 7.6 | 0.7 | 5.8 | 0.7 | 3.0 | 0.7 | 2.5 |
| 0.75 | 4.5 | 0.75 | 2.8 | 0.75 | 7.4 | 0.75 | 5.8 | 0.75 | 3.0 | 0.75 | 2.5 |
| 0.8 | 4.3 | 0.8 | 2.6 | 0.8 | 7.1 | 0.8 | 5.8 | 0.8 | 2.9 | 0.8 | 2.4 |
| 0.85 | 4.0 | 0.85 | 2.4 | 0.85 | 6.5 | 0.85 | 5.8 | 0.85 | 2.7 | 0.85 | 2.3 |
| 0.9 | 3.4 | 0.9 | 2.2 | 0.9 | 5.5 | 0.9 | 5.0 | 0.9 | 2.3 | 0.9 | 2.0 |
| 0.95 | 2.5 | 0.95 | 1.7 | 0.95 | 3.8 | 0.95 | 3.5 | 0.95 | 1.9 | 0.95 | 1.7 |
| 1 | 1.2 | 1 | 1.2 | 1 | 1.2 | 1 | 1.2 | 1 | 1.2 | 1 | 1.2 |

HF - HCFO-1233xf - HFO-1234yf - HFC-245cb - HFO-1234zeZ- HFO-1243zf

| Organics 0.2 F1233xf + 0.2 F1234yf + 0.2 F245cb 0.2 F1234zeZ + 0.2 F1243zf | | Organics 0.96 F1233xf + 0.01 F1234yf + 0.01 F245cb + 0.01 F1234zeZ + 0.01 F1243zf | | Organics 0.01 F1233xf + 0.96 F1234yf + 0.01 F245cb + 0.01 F1234zeZ + 0.01 F1243zf | | Organics 0.01 F1233xf + 0.01 F1234yf + 0.96 F245cb + 0.01 F1234zeZ + 0.01 F1243zf | | Organics 0.01 F1233xf + 0.01 F1234yf + 0.01 F245cb + 0.96 F1234zeZ + 0.01 F1243zf | | Organics 0.01 F1233xf + 0.01 F1234yf + 0.01 F245cb + 0.01 F1234zeZ + 0.96 F1243zf | |
|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.2 | 0 | 1.7 | 0 | 6.7 | 0 | 4.6 | 0 | 1.9 | 0 | 5.8 |
| 0.05 | 5.3 | 0.05 | 2.8 | 0.05 | 7.6 | 0.05 | 5.8 | 0.05 | 3.0 | 0.05 | 6.7 |
| 0.1 | 5.3 | 0.1 | 2.8 | 0.1 | 7.7 | 0.1 | 5.8 | 0.1 | 3.0 | 0.1 | 6.8 |
| 0.15 | 5.3 | 0.15 | 2.8 | 0.15 | 7.6 | 0.15 | 5.8 | 0.15 | 3.0 | 0.15 | 6.7 |
| 0.2 | 5.3 | 0.2 | 2.8 | 0.2 | 7.6 | 0.2 | 5.8 | 0.2 | 3.0 | 0.2 | 6.7 |
| 0.25 | 5.3 | 0.25 | 2.8 | 0.25 | 7.6 | 0.25 | 5.8 | 0.25 | 3.0 | 0.25 | 6.7 |
| 0.3 | 5.3 | 0.3 | 2.8 | 0.3 | 7.6 | 0.3 | 5.8 | 0.3 | 3.0 | 0.3 | 6.7 |
| 0.35 | 5.3 | 0.35 | 2.8 | 0.35 | 7.6 | 0.35 | 5.8 | 0.35 | 3.0 | 0.35 | 6.7 |
| 0.4 | 5.3 | 0.4 | 2.8 | 0.4 | 7.6 | 0.4 | 5.8 | 0.4 | 3.0 | 0.4 | 6.7 |
| 0.45 | 5.3 | 0.45 | 2.8 | 0.45 | 7.6 | 0.45 | 5.8 | 0.45 | 3.0 | 0.45 | 6.7 |
| 0.5 | 5.3 | 0.5 | 2.8 | 0.5 | 7.6 | 0.5 | 5.8 | 0.5 | 3.0 | 0.5 | 6.7 |
| 0.55 | 5.3 | 0.55 | 2.8 | 0.55 | 7.6 | 0.55 | 5.8 | 0.55 | 3.0 | 0.55 | 6.7 |
| 0.6 | 5.3 | 0.6 | 2.8 | 0.6 | 7.6 | 0.6 | 5.8 | 0.6 | 3.0 | 0.6 | 6.7 |
| 0.65 | 5.3 | 0.65 | 2.8 | 0.65 | 7.6 | 0.65 | 5.8 | 0.65 | 3.0 | 0.65 | 6.6 |
| 0.7 | 5.3 | 0.7 | 2.8 | 0.7 | 7.6 | 0.7 | 5.8 | 0.7 | 3.0 | 0.7 | 6.5 |
| 0.75 | 5.3 | 0.75 | 2.8 | 0.75 | 7.5 | 0.75 | 5.8 | 0.75 | 3.0 | 0.75 | 6.4 |
| 0.8 | 5.1 | 0.8 | 2.7 | 0.8 | 7.2 | 0.8 | 5.8 | 0.8 | 2.9 | 0.8 | 6.1 |
| 0.85 | 4.7 | 0.85 | 2.5 | 0.85 | 6.6 | 0.85 | 5.8 | 0.85 | 2.7 | 0.85 | 5.6 |
| 0.9 | 4.0 | 0.9 | 2.2 | 0.9 | 5.5 | 0.9 | 5.0 | 0.9 | 2.4 | 0.9 | 4.7 |
| 0.95 | 2.9 | 0.95 | 1.8 | 0.95 | 3.8 | 0.95 | 3.5 | 0.95 | 1.9 | 0.95 | 3.4 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFC-245cb - HCFO-1233zdE- HFO-1243zf | | | | | | | | | | | |
|---|---|---|---|---|---|---|---|---|---|---|---|
| Organics 0.2 F1233xf + 0.2 F1234yf + 0.2 F245cb 0.2 F1233zdE + 0.2 F1243zf | | Organics 0.96 F1233xf + 0.01 F1234yf + 0.01 F245cb + 0.01 F1233zdE + 0.01 F1243zf | | Organics 0.01 F1233xf + 0.96 F1234yf + 0.01 F245cb + 0.01 F1233zdE + 0.01 F1243zf | | Organics 0.01 F1233xf + 0.01 F1234yf + 0.96 F245cb + 0.01 F1233zdE + 0.01 F1243zf | | Organics 0.01 F1233xf + 0.01 F1234yf + 0.01 F245cb + 0.96 F1233zdE + 0.01 F1243zf | | Organics 0.01 F1233xf + 0.01 F1234yf + 0.01 F245cb + 0.01 F1233zdE + 0.96 F1243zf | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.2 | 0 | 1.7 | 0 | 6.7 | 0 | 4.6 | 0 | 1.5 | 0 | 5.8 |
| 0.05 | 5.3 | 0.05 | 2.8 | 0.05 | 7.6 | 0.05 | 5.8 | 0.05 | 2.6 | 0.05 | 6.7 |
| 0.1 | 5.3 | 0.1 | 2.8 | 0.1 | 7.7 | 0.1 | 5.8 | 0.1 | 2.6 | 0.1 | 6.8 |
| 0.15 | 5.3 | 0.15 | 2.8 | 0.15 | 7.6 | 0.15 | 5.8 | 0.15 | 2.6 | 0.15 | 6.7 |
| 0.2 | 5.3 | 0.2 | 2.8 | 0.2 | 7.6 | 0.2 | 5.8 | 0.2 | 2.6 | 0.2 | 6.7 |
| 0.25 | 5.3 | 0.25 | 2.8 | 0.25 | 7.6 | 0.25 | 5.8 | 0.25 | 2.6 | 0.25 | 6.7 |
| 0.3 | 5.3 | 0.3 | 2.8 | 0.3 | 7.6 | 0.3 | 5.8 | 0.3 | 2.6 | 0.3 | 6.7 |
| 0.35 | 5.3 | 0.35 | 2.8 | 0.35 | 7.6 | 0.35 | 5.8 | 0.35 | 2.6 | 0.35 | 6.7 |
| 0.4 | 5.3 | 0.4 | 2.8 | 0.4 | 7.6 | 0.4 | 5.8 | 0.4 | 2.6 | 0.4 | 6.7 |
| 0.45 | 5.3 | 0.45 | 2.8 | 0.45 | 7.6 | 0.45 | 5.8 | 0.45 | 2.6 | 0.45 | 6.7 |
| 0.5 | 5.3 | 0.5 | 2.8 | 0.5 | 7.6 | 0.5 | 5.8 | 0.5 | 2.6 | 0.5 | 6.7 |
| 0.55 | 5.3 | 0.55 | 2.8 | 0.55 | 7.6 | 0.55 | 5.8 | 0.55 | 2.6 | 0.55 | 6.7 |
| 0.6 | 5.3 | 0.6 | 2.8 | 0.6 | 7.6 | 0.6 | 5.8 | 0.6 | 2.6 | 0.6 | 6.7 |
| 0.65 | 5.3 | 0.65 | 2.8 | 0.65 | 7.6 | 0.65 | 5.8 | 0.65 | 2.6 | 0.65 | 6.6 |
| 0.7 | 5.3 | 0.7 | 2.8 | 0.7 | 7.6 | 0.7 | 5.8 | 0.7 | 2.6 | 0.7 | 6.5 |
| 0.75 | 5.2 | 0.75 | 2.8 | 0.75 | 7.5 | 0.75 | 5.8 | 0.75 | 2.6 | 0.75 | 6.4 |
| 0.8 | 5.0 | 0.8 | 2.7 | 0.8 | 7.2 | 0.8 | 5.8 | 0.8 | 2.5 | 0.8 | 6.1 |
| 0.85 | 4.6 | 0.85 | 2.5 | 0.85 | 6.6 | 0.85 | 5.8 | 0.85 | 2.3 | 0.85 | 5.6 |
| 0.9 | 3.9 | 0.9 | 2.2 | 0.9 | 5.5 | 0.9 | 5.0 | 0.9 | 2.0 | 0.9 | 4.7 |
| 0.95 | 2.8 | 0.95 | 1.8 | 0.95 | 3.8 | 0.95 | 3.5 | 0.95 | 1.7 | 0.95 | 3.4 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFO-1234zeE - HFO-1234zeZ - HCFO-1233zdE | | | | | | | | | | | |
|---|---|---|---|---|---|---|---|---|---|---|---|
| Organics 0.2 F1233xf + 0.2 F1234yf + 0.2 F1233zdE 0.2 F1234zeE + 0.2 F1234zeZ | | Organics 0.96 F1233xf + 0.01 F1234yf + 0.01 F1233zdE + 0.01 F1234zeE + 0.01 F1234zeZ | | Organics 0.01 F1233xf + 0.96 F1234yf + 0.01 F1233zdE + 0.01 F1234zeE + 0.01 F1234zeZ | | Organics 0.01 F1233xf + 0.01 F1234yf + 0.96 F1233zdE + 0.01 F1234zeE + 0.01 F1234zeZ | | Organics 0.01 F1233xf + 0.01 F1234yf + 0.01 F1233zdE + 0.96 F1234zeE + 0.01 F1234zeZ | | Organics 0.01 F1233xf + 0.01 F1234yf + 0.01 F1233zdE + 0.01 F1234zeE + 0.96 F1234zeZ | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.4 | 0 | 1.6 | 0 | 6.6 | 0 | 1.4 | 0 | 4.8 | 0 | 1.9 |
| 0.05 | 4.4 | 0.05 | 2.8 | 0.05 | 7.6 | 0.05 | 2.5 | 0.05 | 5.8 | 0.05 | 3.0 |
| 0.1 | 4.4 | 0.1 | 2.8 | 0.1 | 7.6 | 0.1 | 2.5 | 0.1 | 5.8 | 0.1 | 3.0 |
| 0.15 | 4.4 | 0.15 | 2.8 | 0.15 | 7.6 | 0.15 | 2.5 | 0.15 | 5.8 | 0.15 | 3.0 |
| 0.2 | 4.4 | 0.2 | 2.8 | 0.2 | 7.6 | 0.2 | 2.5 | 0.2 | 5.8 | 0.2 | 3.0 |
| 0.25 | 4.4 | 0.25 | 2.8 | 0.25 | 7.6 | 0.25 | 2.5 | 0.25 | 5.8 | 0.25 | 3.0 |
| 0.3 | 4.4 | 0.3 | 2.8 | 0.3 | 7.6 | 0.3 | 2.5 | 0.3 | 5.8 | 0.3 | 3.0 |
| 0.35 | 4.4 | 0.35 | 2.8 | 0.35 | 7.6 | 0.35 | 2.5 | 0.35 | 5.8 | 0.35 | 3.0 |
| 0.4 | 4.4 | 0.4 | 2.8 | 0.4 | 7.6 | 0.4 | 2.5 | 0.4 | 5.8 | 0.4 | 3.0 |
| 0.45 | 4.4 | 0.45 | 2.7 | 0.45 | 7.6 | 0.45 | 2.5 | 0.45 | 5.7 | 0.45 | 3.0 |
| 0.5 | 4.4 | 0.5 | 2.7 | 0.5 | 7.6 | 0.5 | 2.5 | 0.5 | 5.7 | 0.5 | 3.0 |
| 0.55 | 4.4 | 0.55 | 2.7 | 0.55 | 7.6 | 0.55 | 2.5 | 0.55 | 5.7 | 0.55 | 3.0 |
| 0.6 | 4.4 | 0.6 | 2.7 | 0.6 | 7.6 | 0.6 | 2.5 | 0.6 | 5.6 | 0.6 | 3.0 |
| 0.65 | 4.4 | 0.65 | 2.7 | 0.65 | 7.6 | 0.65 | 2.5 | 0.65 | 5.5 | 0.65 | 3.0 |
| 0.7 | 4.4 | 0.7 | 2.7 | 0.7 | 7.6 | 0.7 | 2.5 | 0.7 | 5.3 | 0.7 | 3.0 |
| 0.75 | 4.2 | 0.75 | 2.7 | 0.75 | 7.4 | 0.75 | 2.5 | 0.75 | 5.1 | 0.75 | 3.0 |
| 0.8 | 4.0 | 0.8 | 2.6 | 0.8 | 7.1 | 0.8 | 2.4 | 0.8 | 4.8 | 0.8 | 2.8 |
| 0.85 | 3.6 | 0.85 | 2.4 | 0.85 | 6.5 | 0.85 | 2.2 | 0.85 | 4.3 | 0.85 | 2.6 |
| 0.9 | 3.1 | 0.9 | 2.1 | 0.9 | 5.5 | 0.9 | 2.0 | 0.9 | 3.6 | 0.9 | 2.3 |
| 0.95 | 2.3 | 0.95 | 1.7 | 0.95 | 3.8 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFO-1234zeE - HFO-1234zeZ - HFO-1243zf | | | | | | | | | | | |
|---|---|---|---|---|---|---|---|---|---|---|---|
| Organics 0.2 F1233xf + 0.2 F1234yf + 0.2 F1243zf 0.2 F1234zeE + 0.2 F1234zeZ | | Organics 0.96 F1233xf + 0.01 F1234yf + 0.01 F1243zf + 0.01 F1234zeE + 0.01 F1234zeZ | | Organics 0.01 F1233xf + 0.96 F1234yf + 0.01 F1243zf + 0.01 F1234zeE + 0.01 F1234zeZ | | Organics 0.0 F1233xf + 0.01 F1234yf + 0.96 F1243zf + 0.01 F1234zeE + 0.01 F1234zeZ | | Organics 0.01 F1233xf + 0.01 F1234yf + 0.01 F1243zf + 0.96 F1234zeE + 0.01 F1234zeZ | | Organics 0.01 F1233xf + 0.01 F1234yf + 0.01 F1243zf + 0.01 F1234zeE + 0.96 F1234zeZ | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.3 | 0 | 1.7 | 0 | 6.7 | 0 | 5.8 | 0 | 4.8 | 0 | 1.9 |
| 0.05 | 5.3 | 0.05 | 2.8 | 0.05 | 7.6 | 0.05 | 6.7 | 0.05 | 5.8 | 0.05 | 3.0 |
| 0.1 | 5.3 | 0.1 | 2.8 | 0.1 | 7.6 | 0.1 | 6.7 | 0.1 | 5.8 | 0.1 | 3.0 |
| 0.15 | 5.3 | 0.15 | 2.8 | 0.15 | 7.6 | 0.15 | 6.7 | 0.15 | 5.8 | 0.15 | 3.0 |
| 0.2 | 5.3 | 0.2 | 2.8 | 0.2 | 7.6 | 0.2 | 6.7 | 0.2 | 5.8 | 0.2 | 3.0 |
| 0.25 | 5.3 | 0.25 | 2.8 | 0.25 | 7.6 | 0.25 | 6.7 | 0.25 | 5.8 | 0.25 | 3.0 |
| 0.3 | 5.3 | 0.3 | 2.8 | 0.3 | 7.6 | 0.3 | 6.7 | 0.3 | 5.8 | 0.3 | 3.0 |
| 0.35 | 5.3 | 0.35 | 2.8 | 0.35 | 7.6 | 0.35 | 6.7 | 0.35 | 5.8 | 0.35 | 3.0 |
| 0.4 | 5.3 | 0.4 | 2.8 | 0.4 | 7.6 | 0.4 | 6.7 | 0.4 | 5.8 | 0.4 | 3.0 |
| 0.45 | 5.3 | 0.45 | 2.8 | 0.45 | 7.6 | 0.45 | 6.7 | 0.45 | 5.8 | 0.45 | 3.0 |
| 0.5 | 5.3 | 0.5 | 2.8 | 0.5 | 7.6 | 0.5 | 6.7 | 0.5 | 5.8 | 0.5 | 3.0 |
| 0.55 | 5.3 | 0.55 | 2.8 | 0.55 | 7.6 | 0.55 | 6.7 | 0.55 | 5.7 | 0.55 | 3.0 |
| 0.6 | 5.3 | 0.6 | 2.8 | 0.6 | 7.6 | 0.6 | 6.7 | 0.6 | 5.6 | 0.6 | 3.0 |
| 0.65 | 5.3 | 0.65 | 2.8 | 0.65 | 7.6 | 0.65 | 6.6 | 0.65 | 5.5 | 0.65 | 3.0 |
| 0.7 | 5.2 | 0.7 | 2.8 | 0.7 | 7.6 | 0.7 | 6.5 | 0.7 | 5.4 | 0.7 | 3.0 |
| 0.75 | 5.0 | 0.75 | 2.8 | 0.75 | 7.5 | 0.75 | 6.3 | 0.75 | 5.1 | 0.75 | 3.0 |
| 0.8 | 4.8 | 0.8 | 2.7 | 0.8 | 7.1 | 0.8 | 6.1 | 0.8 | 4.8 | 0.8 | 2.9 |
| 0.85 | 4.3 | 0.85 | 2.5 | 0.85 | 6.5 | 0.85 | 5.6 | 0.85 | 4.3 | 0.85 | 2.7 |
| 0.9 | 3.7 | 0.9 | 2.2 | 0.9 | 5.5 | 0.9 | 4.7 | 0.9 | 3.6 | 0.9 | 2.4 |
| 0.95 | 2.7 | 0.95 | 1.8 | 0.95 | 3.8 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFO-1234zeE - HCFO-1233zdE - HFO-1243zf | | | | | | | | | | | |
|---|---|---|---|---|---|---|---|---|---|---|---|
| Organics 0.2 F1233xf + 0.2 F1234yf + 0.2 F1243zf + 0.2 F1234zeE + 0.2 F1233zdE | | Organics 0.96 F1233xf + 0.01 F1234yf + 0.01 F1243zf + 0.01 F1234zeE + 0.01 F1233zdE | | Organics 0.01 F1233xf + 0.96 F1234yf + 0.01 F1243zf + 0.01 F1234zeE + 0.01 F1233zdE | | Organics 0.01 F1233xf + 0.01 F1234yf + 0.96 F1243zf + 0.01 F1234zeE + 0.01 F1233zdE | | Organics 0.01 F1233xf + 0.01 F1234yf + 0.01 F1243zf + 0.96 F1234zeE + 0.01 F1233zdE | | Organics 0.01 F1233xf + 0.01 F1234yf + 0.01 F1243zf + 0.01 F1234zeE + 0.96 F1233zdE | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.3 | 0 | 1.7 | 0 | 6.7 | 0 | 5.8 | 0 | 4.8 | 0 | 1.5 |
| 0.05 | 5.3 | 0.05 | 2.8 | 0.05 | 7.6 | 0.05 | 6.7 | 0.05 | 5.8 | 0.05 | 2.6 |
| 0.1 | 5.3 | 0.1 | 2.8 | 0.1 | 7.6 | 0.1 | 6.7 | 0.1 | 5.8 | 0.1 | 2.6 |
| 0.15 | 5.3 | 0.15 | 2.8 | 0.15 | 7.6 | 0.15 | 6.7 | 0.15 | 5.8 | 0.15 | 2.6 |
| 0.2 | 5.3 | 0.2 | 2.8 | 0.2 | 7.6 | 0.2 | 6.7 | 0.2 | 5.8 | 0.2 | 2.6 |
| 0.25 | 5.3 | 0.25 | 2.8 | 0.25 | 7.6 | 0.25 | 6.7 | 0.25 | 5.8 | 0.25 | 2.6 |
| 0.3 | 5.3 | 0.3 | 2.8 | 0.3 | 7.6 | 0.3 | 6.7 | 0.3 | 5.8 | 0.3 | 2.6 |
| 0.35 | 5.3 | 0.35 | 2.8 | 0.35 | 7.6 | 0.35 | 6.7 | 0.35 | 5.8 | 0.35 | 2.6 |
| 0.4 | 5.3 | 0.4 | 2.8 | 0.4 | 7.6 | 0.4 | 6.7 | 0.4 | 5.8 | 0.4 | 2.6 |
| 0.45 | 5.3 | 0.45 | 2.8 | 0.45 | 7.6 | 0.45 | 6.7 | 0.45 | 5.8 | 0.45 | 2.6 |
| 0.5 | 5.3 | 0.5 | 2.8 | 0.5 | 7.6 | 0.5 | 6.7 | 0.5 | 5.8 | 0.5 | 2.6 |
| 0.55 | 5.3 | 0.55 | 2.8 | 0.55 | 7.6 | 0.55 | 6.7 | 0.55 | 5.7 | 0.55 | 2.6 |
| 0.6 | 5.3 | 0.6 | 2.8 | 0.6 | 7.6 | 0.6 | 6.7 | 0.6 | 5.6 | 0.6 | 2.6 |
| 0.65 | 5.2 | 0.65 | 2.8 | 0.65 | 7.6 | 0.65 | 6.6 | 0.65 | 5.5 | 0.65 | 2.6 |
| 0.7 | 5.1 | 0.7 | 2.8 | 0.7 | 7.6 | 0.7 | 6.5 | 0.7 | 5.4 | 0.7 | 2.6 |
| 0.75 | 5.0 | 0.75 | 2.8 | 0.75 | 7.5 | 0.75 | 6.3 | 0.75 | 5.1 | 0.75 | 2.6 |
| 0.8 | 4.7 | 0.8 | 2.6 | 0.8 | 7.1 | 0.8 | 6.1 | 0.8 | 4.8 | 0.8 | 2.4 |
| 0.85 | 4.3 | 0.85 | 2.5 | 0.85 | 6.5 | 0.85 | 5.6 | 0.85 | 4.3 | 0.85 | 2.3 |
| 0.9 | 3.6 | 0.9 | 2.2 | 0.9 | 5.5 | 0.9 | 4.7 | 0.9 | 3.6 | 0.9 | 2.0 |
| 0.95 | 2.6 | 0.95 | 1.8 | 0.95 | 3.8 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

| HF - HCFO-1233xf - HFO-1234yf - HFO-1234zeZ - HCFO-1233zdE - HFO-1243zf | | | | | | | | | | | |
|---|---|---|---|---|---|---|---|---|---|---|---|
| Organics 0.2 F1233xf + 0.2 F1234yf + 0.2 F1243zf + 0.2 F1234zeZ + 0.2 F1233zdE | | Organics 0.96 F1233xf + 0.01 F1234yf + 0.01 F1243zf + 0.01 F1234zeZ + 0.01 F1233zdE | | Organics 0.01 F1233xf + 0.96 F1234yf + 0.01 F1243zf + 0.01 F1234zeZ + 0.01 F1233zdE | | Organics 0.01 F1233xf + 0.01 F1234yf + 0.96 F1243zf + 0.01 F1234zeZ + 0.01 F1233zdE | | Organics 0.01 F1233xf + 0.01 F1234yf + 0.01 F1243zf + 0.96 F1234zeZ + 0.01 F1233zdE | | Organics 0.01 F1233xf + 0.01 F1234yf + 0.01 F1243zf + 0.01 F1234zeZ + 0.96 F1233zdE | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.6 | 0 | 1.7 | 0 | 6.6 | 0 | 5.7 | 0 | 1.9 | 0 | 1.4 |
| 0.05 | 4.7 | 0.05 | 2.8 | 0.05 | 7.6 | 0.05 | 6.7 | 0.05 | 3.0 | 0.05 | 2.6 |
| 0.1 | 4.7 | 0.1 | 2.8 | 0.1 | 7.6 | 0.1 | 6.7 | 0.1 | 3.0 | 0.1 | 2.6 |
| 0.15 | 4.7 | 0.15 | 2.8 | 0.15 | 7.6 | 0.15 | 6.7 | 0.15 | 3.0 | 0.15 | 2.6 |
| 0.2 | 4.7 | 0.2 | 2.8 | 0.2 | 7.6 | 0.2 | 6.7 | 0.2 | 3.0 | 0.2 | 2.6 |
| 0.25 | 4.7 | 0.25 | 2.8 | 0.25 | 7.6 | 0.25 | 6.7 | 0.25 | 3.0 | 0.25 | 2.6 |
| 0.3 | 4.7 | 0.3 | 2.8 | 0.3 | 7.6 | 0.3 | 6.7 | 0.3 | 3.0 | 0.3 | 2.6 |
| 0.35 | 4.7 | 0.35 | 2.8 | 0.35 | 7.6 | 0.35 | 6.7 | 0.35 | 3.0 | 0.35 | 2.5 |
| 0.4 | 4.7 | 0.4 | 2.8 | 0.4 | 7.6 | 0.4 | 6.7 | 0.4 | 3.0 | 0.4 | 2.5 |
| 0.45 | 4.7 | 0.45 | 2.8 | 0.45 | 7.6 | 0.45 | 6.7 | 0.45 | 3.0 | 0.45 | 2.5 |
| 0.5 | 4.7 | 0.5 | 2.8 | 0.5 | 7.6 | 0.5 | 6.7 | 0.5 | 3.0 | 0.5 | 2.5 |
| 0.55 | 4.7 | 0.55 | 2.8 | 0.55 | 7.6 | 0.55 | 6.7 | 0.55 | 3.0 | 0.55 | 2.5 |
| 0.6 | 4.7 | 0.6 | 2.8 | 0.6 | 7.6 | 0.6 | 6.6 | 0.6 | 3.0 | 0.6 | 2.5 |
| 0.65 | 4.7 | 0.65 | 2.8 | 0.65 | 7.6 | 0.65 | 6.6 | 0.65 | 3.0 | 0.65 | 2.5 |
| 0.7 | 4.7 | 0.7 | 2.8 | 0.7 | 7.6 | 0.7 | 6.5 | 0.7 | 3.0 | 0.7 | 2.5 |
| 0.75 | 4.5 | 0.75 | 2.8 | 0.75 | 7.4 | 0.75 | 6.3 | 0.75 | 3.0 | 0.75 | 2.5 |
| 0.8 | 4.3 | 0.8 | 2.6 | 0.8 | 7.1 | 0.8 | 6.0 | 0.8 | 2.9 | 0.8 | 2.4 |
| 0.85 | 3.9 | 0.85 | 2.4 | 0.85 | 6.5 | 0.85 | 5.5 | 0.85 | 2.7 | 0.85 | 2.3 |
| 0.9 | 3.4 | 0.9 | 2.2 | 0.9 | 5.5 | 0.9 | 4.7 | 0.9 | 2.3 | 0.9 | 2.0 |
| 0.95 | 2.5 | 0.95 | 1.7 | 0.95 | 3.8 | 0.95 | 3.3 | 0.95 | 1.9 | 0.95 | 1.7 |
| 1 | 1.2 | 1 | 1.2 | 1 | 1.2 | 1 | 1.2 | 1 | 1.2 | 1 | 1.2 |

| HF - HFO-1234yf - HFC-245cb - HFO-1234zeE - HFO-1234zeZ - HCFO-1233zdE | | | | | | | | | | | |
|---|---|---|---|---|---|---|---|---|---|---|---|
| Organics 0.2 F1234yf + 0.2 F245cb + 0.2 F1233zdE + 0.2 F1234zeE + 0.2 F1234zeZ | | Organics 0.96 F1234yf + 0.01 F245cb + 0.01 F1233zdE + 0.01 F1234zeE + 0.01 F1234zeZ | | Organics 0.01 F1234yf + 0.96 F245cb + 0.01 F1233zdE + 0.01 F1234zeE + 0.01 F1234zeZ | | Organics 0.01 F1234yf + 0.01 F245cb + 0.96 F1233zdE + 0.01 F1234zeE + 0.01 F1234zeZ | | Organics 0.01 F1234yf + 0.01 F245cb + 0.01 F1233zdE + 0.96 F1234zeE + 0.01 F1234zeZ | | Organics 0.01 F1234yf + 0.01 F245cb + 0.01 F1233zdE + 0.01 F1234zeE + 0.96 F1234zeZ | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.9 | 0 | 6.7 | 0 | 4.6 | 0 | 1.5 | 0 | 4.8 | 0 | 1.9 |
| 0.05 | 5.0 | 0.05 | 7.6 | 0.05 | 5.8 | 0.05 | 2.6 | 0.05 | 5.8 | 0.05 | 3.0 |
| 0.1 | 5.0 | 0.1 | 7.6 | 0.1 | 5.8 | 0.1 | 2.6 | 0.1 | 5.8 | 0.1 | 3.0 |
| 0.15 | 5.0 | 0.15 | 7.6 | 0.15 | 5.8 | 0.15 | 2.6 | 0.15 | 5.8 | 0.15 | 3.0 |
| 0.2 | 5.0 | 0.2 | 7.6 | 0.2 | 5.8 | 0.2 | 2.6 | 0.2 | 5.8 | 0.2 | 3.0 |
| 0.25 | 5.0 | 0.25 | 7.6 | 0.25 | 5.8 | 0.25 | 2.6 | 0.25 | 5.8 | 0.25 | 3.0 |
| 0.3 | 5.0 | 0.3 | 7.6 | 0.3 | 5.8 | 0.3 | 2.6 | 0.3 | 5.8 | 0.3 | 3.0 |
| 0.35 | 5.0 | 0.35 | 7.6 | 0.35 | 5.8 | 0.35 | 2.6 | 0.35 | 5.8 | 0.35 | 3.0 |
| 0.4 | 5.0 | 0.4 | 7.6 | 0.4 | 5.8 | 0.4 | 2.6 | 0.4 | 5.8 | 0.4 | 3.0 |
| 0.45 | 5.0 | 0.45 | 7.6 | 0.45 | 5.8 | 0.45 | 2.6 | 0.45 | 5.8 | 0.45 | 3.0 |
| 0.5 | 5.0 | 0.5 | 7.6 | 0.5 | 5.8 | 0.5 | 2.6 | 0.5 | 5.7 | 0.5 | 3.0 |
| 0.55 | 5.0 | 0.55 | 7.6 | 0.55 | 5.8 | 0.55 | 2.6 | 0.55 | 5.7 | 0.55 | 3.0 |
| 0.6 | 5.0 | 0.6 | 7.6 | 0.6 | 5.8 | 0.6 | 2.6 | 0.6 | 5.6 | 0.6 | 3.0 |
| 0.65 | 5.0 | 0.65 | 7.6 | 0.65 | 5.8 | 0.65 | 2.6 | 0.65 | 5.5 | 0.65 | 3.0 |
| 0.7 | 5.1 | 0.7 | 7.6 | 0.7 | 5.8 | 0.7 | 2.6 | 0.7 | 5.4 | 0.7 | 3.0 |
| 0.75 | 5.0 | 0.75 | 7.5 | 0.75 | 5.8 | 0.75 | 2.6 | 0.75 | 5.1 | 0.75 | 3.0 |
| 0.8 | 4.7 | 0.8 | 7.1 | 0.8 | 5.8 | 0.8 | 2.5 | 0.8 | 4.8 | 0.8 | 2.9 |
| 0.85 | 4.3 | 0.85 | 6.5 | 0.85 | 5.8 | 0.85 | 2.3 | 0.85 | 4.3 | 0.85 | 2.7 |
| 0.9 | 3.7 | 0.9 | 5.5 | 0.9 | 5.0 | 0.9 | 2.0 | 0.9 | 3.6 | 0.9 | 2.4 |
| 0.95 | 2.7 | 0.95 | 3.8 | 0.95 | 3.5 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF - HFO-1234yf - HFC-245cb - HFO-1234zeE - HFO-1234zeZ - HFO-1243zf

| Organics 0.2 F1234yf + 0.2 F245cb + 0.2 F1243zf + 0.2 F1234zeE + 0.2 F1234zeZ | | Organics 0.96 F1234yf + 0.01 F245cb + 0.01 F1243zf + 0.01 F1234zeE + 0.01 F1234zeZ | | Organics 0.01 F1234yf + 0.96 F245cb + 0.01 F1243zf + 0.01 F1234zeE + 0.01 F1234zeZ | | Organics 0.01 F1234yf + 0.01 F245cb + 0.96 F1243zf + 0.01 F1234zeE + 0.01 F1234zeZ | | Organics 0.01 F1234yf + 0.01 F245cb + 0.01 F1243zf + 0.96 F1234zeE + 0.01 F1234zeZ | | Organics 0.01 F1234yf + 0.01 F245cb + 0.01 F1243zf + 0.01 F1234zeE + 0.96 F1234zeZ | |
|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.8 | 0 | 6.7 | 0 | 4.7 | 0 | 5.8 | 0 | 4.9 | 0 | 2.0 |
| 0.05 | 5.9 | 0.05 | 7.7 | 0.05 | 5.8 | 0.05 | 6.7 | 0.05 | 5.8 | 0.05 | 3.1 |
| 0.1 | 5.9 | 0.1 | 7.7 | 0.1 | 5.8 | 0.1 | 6.8 | 0.1 | 5.9 | 0.1 | 3.1 |
| 0.15 | 5.9 | 0.15 | 7.7 | 0.15 | 5.8 | 0.15 | 6.8 | 0.15 | 5.8 | 0.15 | 3.1 |
| 0.2 | 5.9 | 0.2 | 7.7 | 0.2 | 5.8 | 0.2 | 6.8 | 0.2 | 5.8 | 0.2 | 3.1 |
| 0.25 | 5.9 | 0.25 | 7.6 | 0.25 | 5.8 | 0.25 | 6.8 | 0.25 | 5.8 | 0.25 | 3.1 |
| 0.3 | 5.9 | 0.3 | 7.6 | 0.3 | 5.8 | 0.3 | 6.8 | 0.3 | 5.8 | 0.3 | 3.1 |
| 0.35 | 5.9 | 0.35 | 7.6 | 0.35 | 5.8 | 0.35 | 6.8 | 0.35 | 5.8 | 0.35 | 3.1 |
| 0.4 | 5.9 | 0.4 | 7.6 | 0.4 | 5.8 | 0.4 | 6.7 | 0.4 | 5.8 | 0.4 | 3.1 |
| 0.45 | 5.9 | 0.45 | 7.6 | 0.45 | 5.8 | 0.45 | 6.7 | 0.45 | 5.8 | 0.45 | 3.1 |
| 0.5 | 5.9 | 0.5 | 7.7 | 0.5 | 5.8 | 0.5 | 6.7 | 0.5 | 5.8 | 0.5 | 3.1 |
| 0.55 | 5.9 | 0.55 | 7.7 | 0.55 | 5.8 | 0.55 | 6.7 | 0.55 | 5.7 | 0.55 | 3.1 |
| 0.6 | 5.9 | 0.6 | 7.7 | 0.6 | 5.8 | 0.6 | 6.7 | 0.6 | 5.7 | 0.6 | 3.1 |
| 0.65 | 5.9 | 0.65 | 7.7 | 0.65 | 5.8 | 0.65 | 6.6 | 0.65 | 5.6 | 0.65 | 3.1 |
| 0.7 | 5.9 | 0.7 | 7.6 | 0.7 | 5.8 | 0.7 | 6.5 | 0.7 | 5.4 | 0.7 | 3.1 |
| 0.75 | 5.7 | 0.75 | 7.5 | 0.75 | 5.8 | 0.75 | 6.4 | 0.75 | 5.2 | 0.75 | 3.1 |
| 0.8 | 5.5 | 0.8 | 7.2 | 0.8 | 5.8 | 0.8 | 6.1 | 0.8 | 4.8 | 0.8 | 2.9 |
| 0.85 | 5.0 | 0.85 | 6.6 | 0.85 | 5.8 | 0.85 | 5.6 | 0.85 | 4.3 | 0.85 | 2.7 |
| 0.9 | 4.3 | 0.9 | 5.5 | 0.9 | 5.0 | 0.9 | 4.8 | 0.9 | 3.6 | 0.9 | 2.4 |
| 0.95 | 3.0 | 0.95 | 3.8 | 0.95 | 3.5 | 0.95 | 3.4 | 0.95 | 2.6 | 0.95 | 1.9 |
| 1 | 1.2 | 1 | 1.2 | 1 | 1.2 | 1 | 1.2 | 1 | 1.2 | 1 | 1.2 |

HF - HFO-1234yf - HFC-245cb - HFO-1234zeE - HCFO-1233zdE- HFO-1243zf

| Organics 0.2 F1234yf + 0.2 F245cb + 0.2 F1243zf + 0.2 F1234zeE + 0.2 F1233zdE | | Organics 0.96 F1234yf + 0.01 F245cb + 0.01 F1243zf + 0.01 F1234zeE + 0.01 F1233zdE | | Organics 0.01 F1234yf + 0.96 F245cb + 0.01 F1243zf + 0.01 F1234zeE + 0.01 F1233zdE | | Organics 0.01 F1234yf + 0.01 F245cb + 0.96 F1243zf + 0.01 F1234zeE + 0.01 F1233zdE | | Organics 0.01 F1234yf + 0.01 F245cb + 0.01 F1243zf + 0.96 F1234zeE + 0.01 F1233zdE | | Organics 0.01 F1234yf + 0.01 F245cb + 0.01 F1243zf + 0.01 F1234zeE + 0.96 F1233zdE | |
|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.8 | 0 | 6.7 | 0 | 4.7 | 0 | 5.8 | 0 | 4.9 | 0 | 1.5 |
| 0.05 | 5.9 | 0.05 | 7.7 | 0.05 | 5.8 | 0.05 | 6.7 | 0.05 | 5.8 | 0.05 | 2.6 |
| 0.1 | 5.9 | 0.1 | 7.7 | 0.1 | 5.8 | 0.1 | 6.8 | 0.1 | 5.8 | 0.1 | 2.6 |
| 0.15 | 5.9 | 0.15 | 7.7 | 0.15 | 5.8 | 0.15 | 6.8 | 0.15 | 5.8 | 0.15 | 2.6 |
| 0.2 | 5.9 | 0.2 | 7.7 | 0.2 | 5.8 | 0.2 | 6.8 | 0.2 | 5.8 | 0.2 | 2.6 |
| 0.25 | 5.9 | 0.25 | 7.6 | 0.25 | 5.8 | 0.25 | 6.8 | 0.25 | 5.8 | 0.25 | 2.6 |
| 0.3 | 5.9 | 0.3 | 7.6 | 0.3 | 5.8 | 0.3 | 6.8 | 0.3 | 5.8 | 0.3 | 2.6 |
| 0.35 | 5.9 | 0.35 | 7.6 | 0.35 | 5.8 | 0.35 | 6.8 | 0.35 | 5.8 | 0.35 | 2.6 |
| 0.4 | 5.9 | 0.4 | 7.7 | 0.4 | 5.8 | 0.4 | 6.7 | 0.4 | 5.8 | 0.4 | 2.6 |
| 0.45 | 5.9 | 0.45 | 7.7 | 0.45 | 5.8 | 0.45 | 6.7 | 0.45 | 5.8 | 0.45 | 2.6 |
| 0.5 | 5.9 | 0.5 | 7.7 | 0.5 | 5.8 | 0.5 | 6.7 | 0.5 | 5.8 | 0.5 | 2.6 |
| 0.55 | 5.9 | 0.55 | 7.7 | 0.55 | 5.8 | 0.55 | 6.7 | 0.55 | 5.7 | 0.55 | 2.6 |
| 0.6 | 5.9 | 0.6 | 7.7 | 0.6 | 5.8 | 0.6 | 6.7 | 0.6 | 5.7 | 0.6 | 2.6 |
| 0.65 | 5.9 | 0.65 | 7.7 | 0.65 | 5.8 | 0.65 | 6.6 | 0.65 | 5.6 | 0.65 | 2.6 |
| 0.7 | 5.9 | 0.7 | 7.6 | 0.7 | 5.8 | 0.7 | 6.5 | 0.7 | 5.4 | 0.7 | 2.6 |
| 0.75 | 5.7 | 0.75 | 7.5 | 0.75 | 5.8 | 0.75 | 6.4 | 0.75 | 5.2 | 0.75 | 2.6 |
| 0.8 | 5.4 | 0.8 | 7.2 | 0.8 | 5.8 | 0.8 | 6.1 | 0.8 | 4.8 | 0.8 | 2.5 |
| 0.85 | 5.0 | 0.85 | 6.6 | 0.85 | 5.8 | 0.85 | 5.6 | 0.85 | 4.3 | 0.85 | 2.3 |
| 0.9 | 4.2 | 0.9 | 5.5 | 0.9 | 5.0 | 0.9 | 4.8 | 0.9 | 3.6 | 0.9 | 2.1 |
| 0.95 | 3.0 | 0.95 | 3.8 | 0.95 | 3.5 | 0.95 | 3.4 | 0.95 | 2.6 | 0.95 | 1.7 |
| 1 | 1.2 | 1 | 1.2 | 1 | 1.2 | 1 | 1.2 | 1 | 1.2 | 1 | 1.2 |

| HF - HFO-1234yf - HFC-245cb - HFO-1234zeZ - HCFO-1233zdE- HFO-1243zf | | | | | | | | | | | |
|---|---|---|---|---|---|---|---|---|---|---|---|
| Organics 0.2 F1234yf + 0.2 F245cb + 0.2 F1243zf + 0.2 F1234zeZ + 0.2 F1233zdE | | Organics 0.96 F1234yf + 0.01 F245cb + 0.01 F1243zf + 0.01 F1234zeZ + 0.01 F1233zdE | | Organics 0.01 F1234yf + 0.96 F245cb + 0.01 F1243zf + 0.01 F1234zeZ + 0.01 F1233zdE | | Organics 0.01 F1234yf + 0.01 F245cb + 0.96 F1243zf + 0.01 F1234zeZ + 0.01 F1233zdE | | Organics 0.01 F1234yf + 0.01 F245cb + 0.01 F1243zf + 0.96 F1234zeZ + 0.01 F1233zdE | | Organics 0.01 F1234yf + 0.01 F245cb + 0.01 F1243zf + 0.01 F1234zeZ + 0.96 F1233zdE | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.2 | 0 | 6.7 | 0 | 4.6 | 0 | 5.8 | 0 | 1.9 | 0 | 1.5 |
| 0.05 | 5.3 | 0.05 | 7.6 | 0.05 | 5.8 | 0.05 | 6.7 | 0.05 | 3.0 | 0.05 | 2.6 |
| 0.1 | 5.3 | 0.1 | 7.6 | 0.1 | 5.8 | 0.1 | 6.7 | 0.1 | 3.0 | 0.1 | 2.6 |
| 0.15 | 5.3 | 0.15 | 7.6 | 0.15 | 5.8 | 0.15 | 6.7 | 0.15 | 3.0 | 0.15 | 2.6 |
| 0.2 | 5.3 | 0.2 | 7.6 | 0.2 | 5.8 | 0.2 | 6.7 | 0.2 | 3.0 | 0.2 | 2.6 |
| 0.25 | 5.3 | 0.25 | 7.6 | 0.25 | 5.8 | 0.25 | 6.7 | 0.25 | 3.0 | 0.25 | 2.6 |
| 0.3 | 5.3 | 0.3 | 7.6 | 0.3 | 5.8 | 0.3 | 6.7 | 0.3 | 3.0 | 0.3 | 2.6 |
| 0.35 | 5.3 | 0.35 | 7.6 | 0.35 | 5.8 | 0.35 | 6.7 | 0.35 | 3.0 | 0.35 | 2.6 |
| 0.4 | 5.3 | 0.4 | 7.6 | 0.4 | 5.8 | 0.4 | 6.7 | 0.4 | 3.0 | 0.4 | 2.6 |
| 0.45 | 5.3 | 0.45 | 7.6 | 0.45 | 5.8 | 0.45 | 6.7 | 0.45 | 3.0 | 0.45 | 2.6 |
| 0.5 | 5.3 | 0.5 | 7.6 | 0.5 | 5.8 | 0.5 | 6.7 | 0.5 | 3.0 | 0.5 | 2.6 |
| 0.55 | 5.3 | 0.55 | 7.6 | 0.55 | 5.8 | 0.55 | 6.7 | 0.55 | 3.0 | 0.55 | 2.6 |
| 0.6 | 5.3 | 0.6 | 7.6 | 0.6 | 5.8 | 0.6 | 6.7 | 0.6 | 3.0 | 0.6 | 2.6 |
| 0.65 | 5.3 | 0.65 | 7.6 | 0.65 | 5.8 | 0.65 | 6.6 | 0.65 | 3.0 | 0.65 | 2.6 |
| 0.7 | 5.3 | 0.7 | 7.6 | 0.7 | 5.8 | 0.7 | 6.5 | 0.7 | 3.0 | 0.7 | 2.6 |
| 0.75 | 5.2 | 0.75 | 7.5 | 0.75 | 5.8 | 0.75 | 6.4 | 0.75 | 3.0 | 0.75 | 2.6 |
| 0.8 | 5.0 | 0.8 | 7.2 | 0.8 | 5.8 | 0.8 | 6.1 | 0.8 | 2.9 | 0.8 | 2.5 |
| 0.85 | 4.6 | 0.85 | 6.6 | 0.85 | 5.8 | 0.85 | 5.6 | 0.85 | 2.7 | 0.85 | 2.3 |
| 0.9 | 3.9 | 0.9 | 5.5 | 0.9 | 5.0 | 0.9 | 4.7 | 0.9 | 2.4 | 0.9 | 2.0 |
| 0.95 | 2.9 | 0.95 | 3.8 | 0.95 | 3.5 | 0.95 | 3.4 | 0.95 | 1.9 | 0.95 | 1.7 |
| 1 | 1.2 | 1 | 1.2 | 1 | 1.2 | 1 | 1.2 | 1 | 1.2 | 1 | 1.2 |

| HF - HFO-1234yf - HFO-1234zeE - HFO-1234zeZ - HCFO-1233zdE- HFO-1243zf | | | | | | | | | | | |
|---|---|---|---|---|---|---|---|---|---|---|---|
| Organics 0.2 F1234yf + 0.2 F1243zf + 0.2 F1233zdE 0.2 F1234zeE + 0.2 F1234zeZ | | Organics 0.96 F1234yf + 0.01 F1243zf + 0.01 F1233zdE + 0.01 F1234zeE + 0.01 F1234zeZ | | Organics 0.01 F1234yf + 0.96 F1243zf + 0.01 F1233zdE + 0.01 F1234zeE + 0.01 F1234zeZ | | Organics 0.01 F1234yf + 0.01 F1243zf + 0.96 F1233zdE + 0.01 F1234zeE + 0.01 F1234zeZ | | Organics 0.01 F1234yf + 0.01 F1243zf + 0.01 F1233zdE + 0.96 F1234zeE + 0.01 F1234zeZ | | Organics 0.01 F1234yf + 0.01 F1243zf + 0.01 F1233zdE + 0.01 F1234zeE + 0.96 F1234zeZ | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.2 | 0 | 6.7 | 0 | 5.8 | 0 | 1.5 | 0 | 4.8 | 0 | 1.9 |
| 0.05 | 5.3 | 0.05 | 7.6 | 0.05 | 6.7 | 0.05 | 2.6 | 0.05 | 5.8 | 0.05 | 3.0 |
| 0.1 | 5.3 | 0.1 | 7.6 | 0.1 | 6.7 | 0.1 | 2.6 | 0.1 | 5.8 | 0.1 | 3.0 |
| 0.15 | 5.3 | 0.15 | 7.6 | 0.15 | 6.7 | 0.15 | 2.6 | 0.15 | 5.8 | 0.15 | 3.0 |
| 0.2 | 5.3 | 0.2 | 7.6 | 0.2 | 6.7 | 0.2 | 2.6 | 0.2 | 5.8 | 0.2 | 3.0 |
| 0.25 | 5.3 | 0.25 | 7.6 | 0.25 | 6.7 | 0.25 | 2.6 | 0.25 | 5.8 | 0.25 | 3.0 |
| 0.3 | 5.3 | 0.3 | 7.6 | 0.3 | 6.7 | 0.3 | 2.6 | 0.3 | 5.8 | 0.3 | 3.0 |
| 0.35 | 5.3 | 0.35 | 7.6 | 0.35 | 6.7 | 0.35 | 2.6 | 0.35 | 5.8 | 0.35 | 3.0 |
| 0.4 | 5.3 | 0.4 | 7.6 | 0.4 | 6.7 | 0.4 | 2.6 | 0.4 | 5.8 | 0.4 | 3.0 |
| 0.45 | 5.3 | 0.45 | 7.6 | 0.45 | 6.7 | 0.45 | 2.6 | 0.45 | 5.8 | 0.45 | 3.0 |
| 0.5 | 5.3 | 0.5 | 7.6 | 0.5 | 6.7 | 0.5 | 2.6 | 0.5 | 5.8 | 0.5 | 3.0 |
| 0.55 | 5.3 | 0.55 | 7.6 | 0.55 | 6.7 | 0.55 | 2.6 | 0.55 | 5.7 | 0.55 | 3.0 |
| 0.6 | 5.2 | 0.6 | 7.6 | 0.6 | 6.7 | 0.6 | 2.6 | 0.6 | 5.6 | 0.6 | 3.0 |
| 0.65 | 5.2 | 0.65 | 7.6 | 0.65 | 6.6 | 0.65 | 2.6 | 0.65 | 5.5 | 0.65 | 3.0 |
| 0.7 | 5.2 | 0.7 | 7.6 | 0.7 | 6.5 | 0.7 | 2.6 | 0.7 | 5.4 | 0.7 | 3.0 |
| 0.75 | 5.0 | 0.75 | 7.5 | 0.75 | 6.3 | 0.75 | 2.6 | 0.75 | 5.1 | 0.75 | 3.0 |
| 0.8 | 4.7 | 0.8 | 7.1 | 0.8 | 6.1 | 0.8 | 2.5 | 0.8 | 4.8 | 0.8 | 2.9 |
| 0.85 | 4.3 | 0.85 | 6.5 | 0.85 | 5.6 | 0.85 | 2.3 | 0.85 | 4.3 | 0.85 | 2.7 |
| 0.9 | 3.7 | 0.9 | 5.5 | 0.9 | 4.7 | 0.9 | 2.0 | 0.9 | 3.6 | 0.9 | 2.4 |
| 0.95 | 2.7 | 0.95 | 3.8 | 0.95 | 3.4 | 0.95 | 1.7 | 0.95 | 2.6 | 0.95 | 1.9 |
| 1 | 1.2 | 1 | 1.2 | 1 | 1.2 | 1 | 1.2 | 1 | 1.2 | 1 | 1.2 |

| HF - HCFC-244bb- HFC-245fa - Trifluoropropyne- HFO-1225yeZ- HFO-1225zc | | | | | | |
|---|---|---|---|---|---|---|
| MASSFRAC HF | Organics 0.2 F244bb + 0.2 F245fa + 0.2 TFP + 0.2 F1225yeZ + 0.2 F1225zc TOTAL PRESSURE bar | Organics 0.96 F244bb + 0.01 F245fa + 0.01 TFP + 0.01 F1225yeZ + 0.01 F1225zc TOTAL PRES bar | Organics 0.01 F244bb + 0.96 F245fa + 0.01 TFP + 0.01 F1225yeZ + 0.01 F1225zc TOTAL PRES bar | Organics 0.01 F244bb + 0.01 F245fa + 0.96 TFP + 0.01 F1225yeZ + 0.01 F1225zc TOTAL PRES bar | Organics 0.01 F244bb + 0.01 F245fa + 0.01 TFP + 0.96 F1225yeZ + 0.01 F1225zc TOTAL PRES bar | Organics 0.01 F244bb + 0.01 F245fa + 0.01 TFP + 0.01 F1225yeZ + 0.96 F1225zc TOTAL PRES bar |
| 0 | 5.4 | 0.9 | 1.7 | 11.4 | 5.2 | 5.3 |
| 0.05 | 6.4 | 2.1 | 2.8 | 12.1 | 6.2 | 6.3 |
| 0.1 | 6.4 | 2.1 | 2.8 | 12.1 | 6.2 | 6.3 |
| 0.15 | 6.4 | 2.1 | 2.8 | 12.0 | 6.2 | 6.3 |
| 0.2 | 6.4 | 2.1 | 2.8 | 11.8 | 6.2 | 6.3 |
| 0.25 | 6.4 | 2.1 | 2.8 | 11.7 | 6.2 | 6.3 |
| 0.3 | 6.4 | 2.1 | 2.8 | 11.7 | 6.2 | 6.3 |
| 0.35 | 6.3 | 2.0 | 2.8 | 11.6 | 6.2 | 6.3 |
| 0.4 | 6.3 | 2.0 | 2.8 | 11.5 | 6.2 | 6.3 |
| 0.45 | 6.3 | 2.0 | 2.8 | 11.5 | 6.2 | 6.3 |
| 0.5 | 6.3 | 2.0 | 2.8 | 11.6 | 6.2 | 6.2 |
| 0.55 | 6.2 | 2.0 | 2.8 | 11.6 | 6.2 | 6.2 |
| 0.6 | 6.2 | 2.0 | 2.8 | 11.6 | 6.2 | 6.1 |
| 0.65 | 6.1 | 2.0 | 2.8 | 11.6 | 6.2 | 6.0 |
| 0.7 | 6.1 | 2.0 | 2.8 | 11.6 | 6.1 | 5.9 |
| 0.75 | 5.9 | 2.0 | 2.8 | 11.6 | 5.9 | 5.6 |
| 0.8 | 5.6 | 2.0 | 2.7 | 11.4 | 5.6 | 5.2 |
| 0.85 | 5.1 | 1.9 | 2.5 | 10.6 | 5.1 | 4.7 |
| 0.9 | 4.3 | 1.8 | 2.2 | 8.9 | 4.2 | 3.8 |
| 0.95 | 3.0 | 1.6 | 1.8 | 6.0 | 3.0 | 2.7 |
| 1 | 1.2 | 1.2 | 1.2 | 1.2 | 1.2 | 1.2 |

EXAMPLE 5

Mixtures with Seven Compounds

| HF - HCFO-1233xf - HFO-1234yf - HFC-245cb - HCFO-1233zdE - HFO-1234zeE - HFO-1234zeZ | | | | | | | | | | | | | |
|---|---|---|---|---|---|---|---|---|---|---|---|---|---|
| Organics 0.15 F1233xf + 0.17 F1234yf + 0.17 F245cb + 0.17 F1233zdE + 0.17 F1234zeE + 0.17 F1234zeZ | | Organics 0.01 F1233xf + 0.95 F1234yf + 0.01 F245cb + 0.01 F1233zdE + 0.01 F1234zeE + 0.01 F1234zeZ | | Organics 0.01 F1233xf + 0.01 F1234yf + 0.95 F245cb + 0.01 F1233zdE + 0.01 F1234zeE + 0.01 F1234zeZ | | Organics 0.01 F1233xf + 0.01 F1234yf + 0.01 F245cb + 0.95 F1233zdE + 0.01 F1234zeE + 0.01 F1234zeZ | | Organics 0.01 F1233xf + 0.01 F1234yf + 0.01 F245cb + 0.01 F1233zdE + 0.95 F1234zeE + 0.01 F1234zeZ | | Organics 0.01 F1233xf + 0.01 F1234yf + 0.01 F245cb + 0.01 F1233zdE + 0.01 F1234zeE + 0.95 F1234zeZ | | Organics 0.95 F1233xf + 0.01 F1234yf + 0.01 F245cb + 0.01 F1233zdE + 0.01 F1234zeE + 0.01 F1234zeZ | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.6 | 0 | 6.6 | 0 | 4.6 | 0 | 1.5 | 0 | 4.8 | 0 | 1.9 | 0 | 1.7 |
| 0.05 | 4.7 | 0.05 | 7.6 | 0.05 | 5.8 | 0.05 | 2.6 | 0.05 | 5.8 | 0.05 | 3.0 | 0.05 | 2.8 |
| 0.1 | 4.7 | 0.1 | 7.6 | 0.1 | 5.8 | 0.1 | 2.6 | 0.1 | 5.8 | 0.1 | 3.0 | 0.1 | 2.8 |
| 0.15 | 4.7 | 0.15 | 7.6 | 0.15 | 5.8 | 0.15 | 2.6 | 0.15 | 5.8 | 0.15 | 3.0 | 0.15 | 2.8 |
| 0.2 | 4.7 | 0.2 | 7.6 | 0.2 | 5.8 | 0.2 | 2.6 | 0.2 | 5.8 | 0.2 | 3.0 | 0.2 | 2.8 |
| 0.25 | 4.7 | 0.25 | 7.6 | 0.25 | 5.8 | 0.25 | 2.6 | 0.25 | 5.8 | 0.25 | 3.0 | 0.25 | 2.8 |
| 0.3 | 4.7 | 0.3 | 7.6 | 0.3 | 5.8 | 0.3 | 2.6 | 0.3 | 5.8 | 0.3 | 3.0 | 0.3 | 2.8 |
| 0.35 | 4.7 | 0.35 | 7.6 | 0.35 | 5.8 | 0.35 | 2.6 | 0.35 | 5.8 | 0.35 | 3.0 | 0.35 | 2.8 |
| 0.4 | 4.7 | 0.4 | 7.6 | 0.4 | 5.8 | 0.4 | 2.6 | 0.4 | 5.8 | 0.4 | 3.0 | 0.4 | 2.8 |
| 0.45 | 4.7 | 0.45 | 7.6 | 0.45 | 5.8 | 0.45 | 2.6 | 0.45 | 5.7 | 0.45 | 3.0 | 0.45 | 2.8 |
| 0.5 | 4.7 | 0.5 | 7.6 | 0.5 | 5.8 | 0.5 | 2.6 | 0.5 | 5.7 | 0.5 | 3.0 | 0.5 | 2.8 |
| 0.55 | 4.7 | 0.55 | 7.6 | 0.55 | 5.8 | 0.55 | 2.6 | 0.55 | 5.7 | 0.55 | 3.0 | 0.55 | 2.8 |
| 0.6 | 4.7 | 0.6 | 7.6 | 0.6 | 5.8 | 0.6 | 2.6 | 0.6 | 5.6 | 0.6 | 3.0 | 0.6 | 2.8 |
| 0.65 | 4.7 | 0.65 | 7.6 | 0.65 | 5.8 | 0.65 | 2.6 | 0.65 | 5.5 | 0.65 | 3.0 | 0.65 | 2.8 |
| 0.7 | 4.7 | 0.7 | 7.6 | 0.7 | 5.8 | 0.7 | 2.6 | 0.7 | 5.3 | 0.7 | 3.0 | 0.7 | 2.8 |
| 0.75 | 4.6 | 0.75 | 7.4 | 0.75 | 5.8 | 0.75 | 2.6 | 0.75 | 5.1 | 0.75 | 3.0 | 0.75 | 2.8 |
| 0.8 | 4.4 | 0.8 | 7.1 | 0.8 | 5.8 | 0.8 | 2.5 | 0.8 | 4.8 | 0.8 | 2.9 | 0.8 | 2.6 |
| 0.85 | 4.1 | 0.85 | 6.5 | 0.85 | 5.8 | 0.85 | 2.3 | 0.85 | 4.3 | 0.85 | 2.7 | 0.85 | 2.5 |
| 0.9 | 3.5 | 0.9 | 5.5 | 0.9 | 5.0 | 0.9 | 2.0 | 0.9 | 3.6 | 0.9 | 2.4 | 0.9 | 2.2 |
| 0.95 | 2.5 | 0.95 | 3.8 | 0.95 | 3.5 | 0.95 | 1.7 | 0.95 | 2.6 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

| HF - HCFO-1233xf - HFO-1234yf - HFC-245cb - HCFO-1233zdE - HFO-1234zeE - HFO-1243zf | | | | | | | | | | | | | |
|---|---|---|---|---|---|---|---|---|---|---|---|---|---|
| Organics 0.15<br>F1233xf + 0.17<br>F1234yf + 0.17<br>F245cb + 0.17<br>F1233zdE + 0.17<br>F1234zeE + 0.17<br>F1243zf | | Organics 0.01<br>F1233xf + 0.95<br>F1234yf + 0.01<br>F245cb + 0.01<br>F1233zdE + 0.01<br>F1234zeE + 0.01<br>F1243zf | | Organics 0.01<br>F1233xf + 0.01<br>F1234yf + 0.95<br>F245cb + 0.01<br>F1233zdE + 0.01<br>F1234zeE + 0.01<br>F1243zf | | Organics 0.01<br>F1233xf + 0.01<br>F1234yf + 0.01<br>F245cb + 0.95<br>F1233zdE 0.01<br>F1234zeE + 0.01<br>F1243zf | | Organics 0.01<br>F1233xf + 0.01<br>F1234yf + 0.01<br>F245cb + 0.01<br>F1233zdE + 0.95<br>F1234zeE + 0.01<br>F1243zf | | Organics 0.01<br>F1233xf + 0.01<br>F1234yf + 0.01<br>F245cb + 0.01<br>F1233zdE + 0.01<br>F1234zeE + 0.95<br>F1243zf | | Organics 0.95<br>F1233xf + 0.01<br>F1234yf + 0.01<br>F245cb + 0.01<br>F1233zdE + 0.01<br>F1234zeE + 0.01<br>F1243zf | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.4 | 0 | 6.6 | 0 | 4.6 | 0 | 1.5 | 0 | 4.8 | 0 | 5.8 | 0 | 1.7 |
| 0.05 | 5.4 | 0.05 | 7.6 | 0.05 | 5.8 | 0.05 | 2.6 | 0.05 | 5.8 | 0.05 | 6.7 | 0.05 | 2.8 |
| 0.1 | 5.4 | 0.1 | 7.6 | 0.1 | 5.8 | 0.1 | 2.6 | 0.1 | 5.8 | 0.1 | 6.7 | 0.1 | 2.8 |
| 0.15 | 5.4 | 0.15 | 7.6 | 0.15 | 5.8 | 0.15 | 2.6 | 0.15 | 5.8 | 0.15 | 6.7 | 0.15 | 2.8 |
| 0.2 | 5.4 | 0.2 | 7.6 | 0.2 | 5.8 | 0.2 | 2.6 | 0.2 | 5.8 | 0.2 | 6.7 | 0.2 | 2.8 |
| 0.25 | 5.4 | 0.25 | 7.6 | 0.25 | 5.8 | 0.25 | 2.6 | 0.25 | 5.8 | 0.25 | 6.7 | 0.25 | 2.8 |
| 0.3 | 5.4 | 0.3 | 7.6 | 0.3 | 5.8 | 0.3 | 2.6 | 0.3 | 5.8 | 0.3 | 6.7 | 0.3 | 2.8 |
| 0.35 | 5.4 | 0.35 | 7.6 | 0.35 | 5.8 | 0.35 | 2.6 | 0.35 | 5.8 | 0.35 | 6.7 | 0.35 | 2.8 |
| 0.4 | 5.4 | 0.4 | 7.6 | 0.4 | 5.8 | 0.4 | 2.6 | 0.4 | 5.8 | 0.4 | 6.7 | 0.4 | 2.8 |
| 0.45 | 5.4 | 0.45 | 7.6 | 0.45 | 5.8 | 0.45 | 2.6 | 0.45 | 5.8 | 0.45 | 6.7 | 0.45 | 2.8 |
| 0.5 | 5.4 | 0.5 | 7.6 | 0.5 | 5.8 | 0.5 | 2.6 | 0.5 | 5.8 | 0.5 | 6.7 | 0.5 | 2.8 |
| 0.55 | 5.4 | 0.55 | 7.6 | 0.55 | 5.8 | 0.55 | 2.6 | 0.55 | 5.7 | 0.55 | 6.7 | 0.55 | 2.8 |
| 0.6 | 5.4 | 0.6 | 7.6 | 0.6 | 5.8 | 0.6 | 2.6 | 0.6 | 5.6 | 0.6 | 6.7 | 0.6 | 2.8 |
| 0.65 | 5.4 | 0.65 | 7.6 | 0.65 | 5.8 | 0.65 | 2.6 | 0.65 | 5.5 | 0.65 | 6.6 | 0.65 | 2.8 |
| 0.7 | 5.4 | 0.7 | 7.6 | 0.7 | 5.8 | 0.7 | 2.6 | 0.7 | 5.4 | 0.7 | 6.5 | 0.7 | 2.8 |
| 0.75 | 5.3 | 0.75 | 7.4 | 0.75 | 5.8 | 0.75 | 2.6 | 0.75 | 5.1 | 0.75 | 6.3 | 0.75 | 2.8 |
| 0.8 | 5.0 | 0.8 | 7.1 | 0.8 | 5.8 | 0.8 | 2.5 | 0.8 | 4.8 | 0.8 | 6.1 | 0.8 | 2.7 |
| 0.85 | 4.6 | 0.85 | 6.5 | 0.85 | 5.8 | 0.85 | 2.3 | 0.85 | 4.3 | 0.85 | 5.6 | 0.85 | 2.5 |
| 0.9 | 3.9 | 0.9 | 5.5 | 0.9 | 5.0 | 0.9 | 2.1 | 0.9 | 3.6 | 0.9 | 4.7 | 0.9 | 2.2 |
| 0.95 | 2.8 | 0.95 | 3.8 | 0.95 | 3.5 | 0.95 | 1.7 | 0.95 | 2.6 | 0.95 | 3.4 | 0.95 | 1.8 |
| 1 | 1.2 | 1 | 1.2 | 1 | 1.2 | 1 | 1.2 | 1 | 1.2 | 1 | 1.2 | 1 | 1.2 |

| HF - HCFO-1233xf - HFO-1234yf - HFC-245cb - HCFO-1233zdE - HFO-1234zeZ - HFO-1243zf | | | | | | | | | | | | | |
|---|---|---|---|---|---|---|---|---|---|---|---|---|---|
| Organics 0.15<br>F1233xf + 0.17<br>F1234yf + 0.17<br>F245cb + 0.17<br>F1243zf + 0.17<br>F1233zdE + 0.17<br>F1234zeZ | | Organics 0.01<br>F1233xf + 0.95<br>F1234yf + 0.01<br>F245cb + 0.01<br>F1243zf + 0.01<br>F1233zdE + 0.01<br>F1234zeZ | | Organics 0.01<br>F1233xf + 0.01<br>F1234yf + 0.95<br>F245cb + 0.01<br>F1243zf + 0.01<br>F1233zdE + 0.01<br>F1234zeZ | | Organics 0.01<br>F1233xf + 0.01<br>F1234yf + 0.01<br>F245cb + 0.95<br>F1243zf + 0.01<br>F1233zdE + 0.01<br>F1234zeZ | | Organics 0.01<br>F1233xf + 0.01<br>F1234yf + 0.01<br>F245cb + 0.01<br>F1243zf + 0.95<br>F1233zdE + 0.01<br>F1234zeZ | | Organics 0.01<br>F1233xf + 0.01<br>F1234yf + 0.01<br>F245cb + 0.01<br>F1243zf + 0.01<br>F1233zdE + 0.95<br>F1234zeZ | | Organics 0.95<br>F1233xf + 0.01<br>F1234yf + 0.01<br>F245cb + 0.01<br>F1243zf + 0.01<br>F1233zdE + 0.01<br>F1234zeZ | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.8 | 0 | 6.6 | 0 | 4.6 | 0 | 5.7 | 0 | 1.5 | 0 | 1.9 | 0 | 1.7 |
| 0.05 | 4.9 | 0.05 | 7.6 | 0.05 | 5.8 | 0.05 | 6.7 | 0.05 | 2.6 | 0.05 | 3.0 | 0.05 | 2.8 |
| 0.1 | 4.9 | 0.1 | 7.6 | 0.1 | 5.8 | 0.1 | 6.7 | 0.1 | 2.6 | 0.1 | 3.0 | 0.1 | 2.8 |
| 0.15 | 4.9 | 0.15 | 7.6 | 0.15 | 5.8 | 0.15 | 6.7 | 0.15 | 2.6 | 0.15 | 3.0 | 0.15 | 2.8 |
| 0.2 | 4.9 | 0.2 | 7.6 | 0.2 | 5.8 | 0.2 | 6.7 | 0.2 | 2.6 | 0.2 | 3.0 | 0.2 | 2.8 |
| 0.25 | 4.9 | 0.25 | 7.6 | 0.25 | 5.8 | 0.25 | 6.7 | 0.25 | 2.6 | 0.25 | 3.0 | 0.25 | 2.8 |
| 0.3 | 4.9 | 0.3 | 7.6 | 0.3 | 5.8 | 0.3 | 6.7 | 0.3 | 2.6 | 0.3 | 3.0 | 0.3 | 2.8 |
| 0.35 | 4.9 | 0.35 | 7.6 | 0.35 | 5.8 | 0.35 | 6.7 | 0.35 | 2.6 | 0.35 | 3.0 | 0.35 | 2.8 |
| 0.4 | 4.9 | 0.4 | 7.6 | 0.4 | 5.8 | 0.4 | 6.7 | 0.4 | 2.6 | 0.4 | 3.0 | 0.4 | 2.8 |
| 0.45 | 4.9 | 0.45 | 7.6 | 0.45 | 5.8 | 0.45 | 6.7 | 0.45 | 2.6 | 0.45 | 3.0 | 0.45 | 2.8 |
| 0.5 | 4.9 | 0.5 | 7.6 | 0.5 | 5.8 | 0.5 | 6.7 | 0.5 | 2.6 | 0.5 | 3.0 | 0.5 | 2.8 |
| 0.55 | 4.9 | 0.55 | 7.6 | 0.55 | 5.8 | 0.55 | 6.7 | 0.55 | 2.6 | 0.55 | 3.0 | 0.55 | 2.8 |
| 0.6 | 4.9 | 0.6 | 7.6 | 0.6 | 5.8 | 0.6 | 6.6 | 0.6 | 2.6 | 0.6 | 3.0 | 0.6 | 2.8 |
| 0.65 | 4.9 | 0.65 | 7.6 | 0.65 | 5.8 | 0.65 | 6.6 | 0.65 | 2.6 | 0.65 | 3.0 | 0.65 | 2.8 |
| 0.7 | 4.9 | 0.7 | 7.6 | 0.7 | 5.8 | 0.7 | 6.5 | 0.7 | 2.6 | 0.7 | 3.0 | 0.7 | 2.8 |
| 0.75 | 4.9 | 0.75 | 7.4 | 0.75 | 5.8 | 0.75 | 6.3 | 0.75 | 2.6 | 0.75 | 3.0 | 0.75 | 2.8 |
| 0.8 | 4.7 | 0.8 | 7.1 | 0.8 | 5.8 | 0.8 | 6.0 | 0.8 | 2.5 | 0.8 | 2.9 | 0.8 | 2.7 |
| 0.85 | 4.3 | 0.85 | 6.5 | 0.85 | 5.8 | 0.85 | 5.5 | 0.85 | 2.3 | 0.85 | 2.7 | 0.85 | 2.5 |
| 0.9 | 3.7 | 0.9 | 5.5 | 0.9 | 5.0 | 0.9 | 4.7 | 0.9 | 2.0 | 0.9 | 2.4 | 0.9 | 2.2 |
| 0.95 | 2.7 | 0.95 | 3.8 | 0.95 | 3.5 | 0.95 | 3.3 | 0.95 | 1.7 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

HF - HCFO-1233xf - HFO-1234yf - HFC-245cb -HFO-1234zeE - HFO-1234zeZ - HFO- 1243zf

| Organics 0.15<br>F1233xf + 0.17<br>F1234yf + 0.17<br>F245cb + 0.17<br>F1243zf + 0.17<br>F1234zeE + 0.17<br>F1234zeZ | | Organics 0.01<br>F1233xf + 0.95<br>F1234yf + 0.01<br>F245cb + 0.01<br>F1243zf + 0.01<br>F1234zeE + 0.01<br>F1234zeZ | | Organics 0.01<br>F1233xf + 0.01<br>F1234yf + 0.95<br>F245cb + 0.01<br>F1243zf + 0.01<br>F1234zeE + 0.01<br>F1234zeZ | | Organics 0.01<br>F1233xf + 0.01<br>F1234yf + 0.01<br>F245cb + 0.95<br>F1243zf + 0.01<br>F1234zeE + 0.01<br>F1234zeZ | | Organics 0.01<br>F1233xf + 0.01<br>F1234yf + 0.01<br>F245cb + 0.01<br>F1243zf + 0.95<br>F1234zeE + 0.01<br>F1234zeZ | | Organics 0.01<br>F1233xf + 0.01<br>F1234yf + 0.01<br>F245cb + 0.01<br>F1243zf + 0.01<br>F1234zeE + 0.95<br>F1234zeZ | | Organics 0.95<br>F1233xf + 0.01<br>F1234yf + 0.01<br>F245cb + 0.01<br>F1243zf + 0.01<br>F1234zeE + 0.01<br>F1234zeZ | |
|---|---|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.4 | 0 | 6.6 | 0 | 4.6 | 0 | 5.8 | 0 | 4.8 | 0 | 2.0 | 0 | 1.7 |
| 0.05 | 5.5 | 0.05 | 7.6 | 0.05 | 5.8 | 0.05 | 6.7 | 0.05 | 5.8 | 0.05 | 3.1 | 0.05 | 2.8 |
| 0.1 | 5.5 | 0.1 | 7.6 | 0.1 | 5.8 | 0.1 | 6.7 | 0.1 | 5.8 | 0.1 | 3.1 | 0.1 | 2.8 |
| 0.15 | 5.5 | 0.15 | 7.6 | 0.15 | 5.8 | 0.15 | 6.7 | 0.15 | 5.8 | 0.15 | 3.1 | 0.15 | 2.8 |
| 0.2 | 5.5 | 0.2 | 7.6 | 0.2 | 5.8 | 0.2 | 6.7 | 0.2 | 5.8 | 0.2 | 3.1 | 0.2 | 2.8 |
| 0.25 | 5.5 | 0.25 | 7.6 | 0.25 | 5.8 | 0.25 | 6.7 | 0.25 | 5.8 | 0.25 | 3.1 | 0.25 | 2.8 |
| 0.3 | 5.5 | 0.3 | 7.6 | 0.3 | 5.8 | 0.3 | 6.7 | 0.3 | 5.8 | 0.3 | 3.1 | 0.3 | 2.8 |
| 0.35 | 5.5 | 0.35 | 7.6 | 0.35 | 5.8 | 0.35 | 6.7 | 0.35 | 5.8 | 0.35 | 3.1 | 0.35 | 2.8 |
| 0.4 | 5.5 | 0.4 | 7.6 | 0.4 | 5.8 | 0.4 | 6.7 | 0.4 | 5.8 | 0.4 | 3.1 | 0.4 | 2.8 |
| 0.45 | 5.5 | 0.45 | 7.6 | 0.45 | 5.8 | 0.45 | 6.7 | 0.45 | 5.8 | 0.45 | 3.1 | 0.45 | 2.8 |
| 0.5 | 5.5 | 0.5 | 7.6 | 0.5 | 5.8 | 0.5 | 6.7 | 0.5 | 5.8 | 0.5 | 3.1 | 0.5 | 2.8 |
| 0.55 | 5.5 | 0.55 | 7.6 | 0.55 | 5.8 | 0.55 | 6.7 | 0.55 | 5.7 | 0.55 | 3.1 | 0.55 | 2.8 |
| 0.6 | 5.5 | 0.6 | 7.6 | 0.6 | 5.8 | 0.6 | 6.7 | 0.6 | 5.6 | 0.6 | 3.1 | 0.6 | 2.8 |
| 0.65 | 5.5 | 0.65 | 7.6 | 0.65 | 5.8 | 0.65 | 6.6 | 0.65 | 5.5 | 0.65 | 3.1 | 0.65 | 2.8 |
| 0.7 | 5.5 | 0.7 | 7.6 | 0.7 | 5.8 | 0.7 | 6.5 | 0.7 | 5.4 | 0.7 | 3.1 | 0.7 | 2.8 |
| 0.75 | 5.3 | 0.75 | 7.4 | 0.75 | 5.8 | 0.75 | 6.3 | 0.75 | 5.1 | 0.75 | 3.1 | 0.75 | 2.8 |
| 0.8 | 5.1 | 0.8 | 7.1 | 0.8 | 5.8 | 0.8 | 6.1 | 0.8 | 4.8 | 0.8 | 2.9 | 0.8 | 2.7 |
| 0.85 | 4.6 | 0.85 | 6.5 | 0.85 | 5.8 | 0.85 | 5.6 | 0.85 | 4.3 | 0.85 | 2.7 | 0.85 | 2.5 |
| 0.9 | 3.9 | 0.9 | 5.5 | 0.9 | 5.0 | 0.9 | 4.7 | 0.9 | 3.6 | 0.9 | 2.4 | 0.9 | 2.2 |
| 0.95 | 2.8 | 0.95 | 3.8 | 0.95 | 3.5 | 0.95 | 3.4 | 0.95 | 2.6 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

HF - HCFO-1233xf - HFO-1234yf - HCFO-1233zdE -HFO-1234zeE - HFO-1234zeZ - HFO-1243zf

| Organics 0.15<br>F1233xf + 0.17<br>F1234yf + 0.17<br>F1233zdE + 0.17<br>F1243zf + 0.17<br>F1234zeE + 0.17<br>F1234zeZ | | Organics 0.01<br>F1233xf + 0.95<br>F1234yf + 0.01<br>F1233zdE+ 0.01<br>F1243zf + 0.01<br>F1234zeE + 0.01<br>F1234zeZ | | Organics 0.01<br>F1233xf + 0.01<br>F1234yf + 0.95<br>F1233zdE + 0.01<br>F1243zf + 0.01<br>F1234zeE + 0.01<br>F1234zeZ | | Organics 0.01<br>F1233xf + 0.01<br>F1234yf + 0.01<br>F1233zdE + 0.95<br>F1243zf + 0.01<br>F1234zeE + 0.01<br>F1234zeZ | | Organics 0.01<br>F1233xf + 0.01<br>F1234yf + 0.01<br>F1233zdE + 0.01<br>F1243zf + 0.95<br>F1234zeE + 0.01<br>F1234zeZ | | Organics 0.01<br>F1233xf + 0.01<br>F1234yf + 0.01<br>F1233zdE + 0.01<br>F1243zf + 0.01<br>F1234zeE + 0.95<br>F1234zeZ | | Organics 0.95<br>F1233xf + 0.01<br>F1234yf + 0.01<br>F1233zdE + 0.01<br>F1243zf + 0.01<br>F1234zeE + 0.01<br>F1234zeZ | |
|---|---|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 3.9 | 0 | 6.6 | 0 | 1.5 | 0 | 5.7 | 0 | 4.8 | 0 | 1.9 | 0 | 1.7 |
| 0.05 | 5.0 | 0.05 | 7.6 | 0.05 | 2.6 | 0.05 | 6.7 | 0.05 | 5.8 | 0.05 | 3.0 | 0.05 | 2.8 |
| 0.1 | 4.9 | 0.1 | 7.6 | 0.1 | 2.6 | 0.1 | 6.7 | 0.1 | 5.8 | 0.1 | 3.0 | 0.1 | 2.8 |
| 0.15 | 4.9 | 0.15 | 7.6 | 0.15 | 2.6 | 0.15 | 6.7 | 0.15 | 5.8 | 0.15 | 3.0 | 0.15 | 2.8 |
| 0.2 | 4.9 | 0.2 | 7.6 | 0.2 | 2.6 | 0.2 | 6.7 | 0.2 | 5.8 | 0.2 | 3.0 | 0.2 | 2.8 |
| 0.25 | 4.9 | 0.25 | 7.6 | 0.25 | 2.6 | 0.25 | 6.7 | 0.25 | 5.8 | 0.25 | 3.0 | 0.25 | 2.8 |
| 0.3 | 4.9 | 0.3 | 7.6 | 0.3 | 2.6 | 0.3 | 6.7 | 0.3 | 5.8 | 0.3 | 3.0 | 0.3 | 2.8 |
| 0.35 | 4.9 | 0.35 | 7.6 | 0.35 | 2.6 | 0.35 | 6.7 | 0.35 | 5.8 | 0.35 | 3.0 | 0.35 | 2.8 |
| 0.4 | 4.9 | 0.4 | 7.6 | 0.4 | 2.6 | 0.4 | 6.7 | 0.4 | 5.8 | 0.4 | 3.0 | 0.4 | 2.8 |
| 0.45 | 4.9 | 0.45 | 7.6 | 0.45 | 2.6 | 0.45 | 6.7 | 0.45 | 5.8 | 0.45 | 3.0 | 0.45 | 2.8 |
| 0.5 | 4.9 | 0.5 | 7.6 | 0.5 | 2.6 | 0.5 | 6.7 | 0.5 | 5.7 | 0.5 | 3.0 | 0.5 | 2.8 |
| 0.55 | 4.9 | 0.55 | 7.6 | 0.55 | 2.6 | 0.55 | 6.7 | 0.55 | 5.7 | 0.55 | 3.0 | 0.55 | 2.8 |
| 0.6 | 4.9 | 0.6 | 7.6 | 0.6 | 2.6 | 0.6 | 6.6 | 0.6 | 5.6 | 0.6 | 3.0 | 0.6 | 2.8 |
| 0.65 | 4.9 | 0.65 | 7.6 | 0.65 | 2.6 | 0.65 | 6.6 | 0.65 | 5.5 | 0.65 | 3.0 | 0.65 | 2.8 |
| 0.7 | 4.8 | 0.7 | 7.6 | 0.7 | 2.6 | 0.7 | 6.5 | 0.7 | 5.3 | 0.7 | 3.0 | 0.7 | 2.8 |
| 0.75 | 4.7 | 0.75 | 7.4 | 0.75 | 2.6 | 0.75 | 6.3 | 0.75 | 5.1 | 0.75 | 3.0 | 0.75 | 2.8 |
| 0.8 | 4.4 | 0.8 | 7.1 | 0.8 | 2.5 | 0.8 | 6.0 | 0.8 | 4.8 | 0.8 | 2.9 | 0.8 | 2.6 |
| 0.85 | 4.0 | 0.85 | 6.5 | 0.85 | 2.3 | 0.85 | 5.5 | 0.85 | 4.3 | 0.85 | 2.7 | 0.85 | 2.5 |
| 0.9 | 3.4 | 0.9 | 5.5 | 0.9 | 2.0 | 0.9 | 4.7 | 0.9 | 3.6 | 0.9 | 2.4 | 0.9 | 2.2 |
| 0.95 | 2.5 | 0.95 | 3.8 | 0.95 | 1.7 | 0.95 | 3.3 | 0.95 | 2.6 | 0.95 | 1.9 | 0.95 | 1.8 |
| 1 | 1.2 | 1 | 1.2 | 1 | 1.2 | 1 | 1.2 | 1 | 1.2 | 1 | 1.2 | 1 | 1.2 |

HF - HFO-1234yf - HFC-245cb - HCFO-1233zdE -HFO-1234zeE - HFO-1234zeZ - HFO-1243zf

| Organics 0.15 F1234yf + 0.17 F245cb + 0.17 F1233zdE + 0.17 F1234zeE + 0.17 F1234zeZ + 0.17 F1243zf | | Organics 0.95 F1234yf + 0.01 F245cb + 0.01 F1233zdE + 0.01 F1234zeE + 0.01 F1234zeZ + 0.01 F1243zf | | Organics 0.01 F1234yf + 0.95 F245cb + 0.01 F1233zdE + 0.01 F1234zeE + 0.01 F1234zeZ + 0.01 F1243zf | | Organics 0.01 F1234yf + 0.01 F245cb + 0.95 F1233zdE + 0.01 F1234zeE + 0.01 F1234zeZ + 0.01 F1243zf | | Organics 0.01 F1234yf + 0.01 F245cb + 0.01 F1233zdE + 0.95 F1234zeE + 0.01 F1234zeZ + 0.01 F1243zf | | Organics 0.01 F1234yf + 0.01 F245cb + 0.01 F1233zdE + 0.01 F1234zeE + 0.95 F1234zeZ + 0.01 F1243zf | | Organics 0.01 F1234yf + 0.01 F245cb + 0.01 F1233zdE + 0.01 F1234zeE + 0.95 F1234zeZ + 0.01 F1243zf | |
|---|---|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 4.3 | 0 | 6.6 | 0 | 4.6 | 0 | 1.5 | 0 | 4.8 | 0 | 5.8 | 0 | 2.0 |
| 0.05 | 5.3 | 0.05 | 7.6 | 0.05 | 5.8 | 0.05 | 2.6 | 0.05 | 5.8 | 0.05 | 6.7 | 0.05 | 3.1 |
| 0.1 | 5.3 | 0.1 | 7.6 | 0.1 | 5.8 | 0.1 | 2.6 | 0.1 | 5.8 | 0.1 | 6.7 | 0.1 | 3.1 |
| 0.15 | 5.3 | 0.15 | 7.6 | 0.15 | 5.8 | 0.15 | 2.6 | 0.15 | 5.8 | 0.15 | 6.7 | 0.15 | 3.1 |
| 0.2 | 5.3 | 0.2 | 7.6 | 0.2 | 5.8 | 0.2 | 2.6 | 0.2 | 5.8 | 0.2 | 6.7 | 0.2 | 3.1 |
| 0.25 | 5.3 | 0.25 | 7.6 | 0.25 | 5.8 | 0.25 | 2.6 | 0.25 | 5.8 | 0.25 | 6.7 | 0.25 | 3.1 |
| 0.3 | 5.3 | 0.3 | 7.6 | 0.3 | 5.8 | 0.3 | 2.6 | 0.3 | 5.8 | 0.3 | 6.7 | 0.3 | 3.1 |
| 0.35 | 5.3 | 0.35 | 7.6 | 0.35 | 5.8 | 0.35 | 2.6 | 0.35 | 5.8 | 0.35 | 6.7 | 0.35 | 3.1 |
| 0.4 | 5.3 | 0.4 | 7.6 | 0.4 | 5.8 | 0.4 | 2.6 | 0.4 | 5.8 | 0.4 | 6.7 | 0.4 | 3.1 |
| 0.45 | 5.3 | 0.45 | 7.6 | 0.45 | 5.8 | 0.45 | 2.6 | 0.45 | 5.8 | 0.45 | 6.7 | 0.45 | 3.1 |
| 0.5 | 5.3 | 0.5 | 7.6 | 0.5 | 5.8 | 0.5 | 2.6 | 0.5 | 5.8 | 0.5 | 6.7 | 0.5 | 3.1 |
| 0.55 | 5.3 | 0.55 | 7.6 | 0.55 | 5.8 | 0.55 | 2.6 | 0.55 | 5.7 | 0.55 | 6.7 | 0.55 | 3.1 |
| 0.6 | 5.3 | 0.6 | 7.6 | 0.6 | 5.8 | 0.6 | 2.6 | 0.6 | 5.6 | 0.6 | 6.7 | 0.6 | 3.1 |
| 0.65 | 5.3 | 0.65 | 7.6 | 0.65 | 5.8 | 0.65 | 2.6 | 0.65 | 5.5 | 0.65 | 6.6 | 0.65 | 3.1 |
| 0.7 | 5.3 | 0.7 | 7.6 | 0.7 | 5.8 | 0.7 | 2.6 | 0.7 | 5.4 | 0.7 | 6.5 | 0.7 | 3.1 |
| 0.75 | 5.2 | 0.75 | 7.4 | 0.75 | 5.8 | 0.75 | 2.6 | 0.75 | 5.1 | 0.75 | 6.3 | 0.75 | 3.1 |
| 0.8 | 4.9 | 0.8 | 7.1 | 0.8 | 5.8 | 0.8 | 2.5 | 0.8 | 4.8 | 0.8 | 6.1 | 0.8 | 2.9 |
| 0.85 | 4.5 | 0.85 | 6.5 | 0.85 | 5.8 | 0.85 | 2.3 | 0.85 | 4.3 | 0.85 | 5.6 | 0.85 | 2.7 |
| 0.9 | 3.9 | 0.9 | 5.5 | 0.9 | 5.0 | 0.9 | 2.1 | 0.9 | 3.6 | 0.9 | 4.7 | 0.9 | 2.4 |
| 0.95 | 2.8 | 0.95 | 3.8 | 0.95 | 3.5 | 0.95 | 1.7 | 0.95 | 2.6 | 0.95 | 3.4 | 0.95 | 1.9 |
| 1 | 1.2 | 1 | 1.2 | 1 | 1.2 | 1 | 1.2 | 1 | 1.2 | 1 | 1.2 | 1 | 1.2 |

HF - HFO-1234yf - HCFC-244bb- HFC-245fa - Trifluoropropyne- HFO-1225yeZ- HFO-1225zc

| MASSFRAC HF | Organics 0.15 F1234yf + 0.17 F244bb + 0.17 F245fa + 0.17 TFP + 0.17 F1225yeZ + 0.17 F1225zc TOTAL PRESSURE bar | Organics 0.95 F1234yf + 0.01 F244bb + 0.01 F245fa + 0.01 TFP + 0.01 F1225yeZ + 0.01 F1225zc TOTAL PRESSURE bar | Organics 0.01 F1234yf + 0.95 F244bb + 0.01 F245fa + 0.01 TFP + 0.01 F1225yeZ + 0.01 F1225zc TOTAL PRESSURE bar | Organics 0.01 F1234yf + 0.01 F244bb + 0.95 F245fa + 0.01 TFP + 0.01 F1225yeZ + 0.01 F1225zc TOTAL PRESSURE bar | Organics 0.01 F1234yf + 0.01 F244bb + 0.01 F245fa + 0.95 TFP + 0.01 F1225yeZ + 0.01 F1225zc TOTAL PRESSURE bar | Organics 0.01 F1234yf + 0.01 F244bb + 0.01 F245fa + 0.01 TFP + 0.95 F1225yeZ + 0.01 F1225zc TOTAL PRESSURE bar | Organics 0.01 F1234yf + 0.01 F244bb + 0.01 F245fa + 0.01 TFP + 0.01 F1225yeZ + 0.95 F1225zc TOTAL PRESSURE bar |
|---|---|---|---|---|---|---|---|
| 0 | 5.6 | 6.7 | 1.0 | 1.8 | 11.3 | 5.2 | 5.3 |
| 0.05 | 6.6 | 7.7 | 2.1 | 2.9 | 12.1 | 6.2 | 6.3 |
| 0.1 | 6.6 | 7.7 | 2.1 | 2.9 | 12.0 | 6.2 | 6.3 |
| 0.15 | 6.6 | 7.7 | 2.1 | 2.9 | 11.9 | 6.2 | 6.3 |
| 0.2 | 6.6 | 7.7 | 2.1 | 2.9 | 11.8 | 6.2 | 6.3 |
| 0.25 | 6.6 | 7.7 | 2.1 | 2.9 | 11.7 | 6.2 | 6.3 |
| 0.3 | 6.6 | 7.7 | 2.1 | 2.9 | 11.6 | 6.2 | 6.3 |
| 0.35 | 6.5 | 7.7 | 2.1 | 2.9 | 11.5 | 6.2 | 6.3 |
| 0.4 | 6.5 | 7.7 | 2.1 | 2.9 | 11.5 | 6.2 | 6.3 |
| 0.45 | 6.5 | 7.7 | 2.1 | 2.9 | 11.5 | 6.2 | 6.3 |
| 0.5 | 6.5 | 7.7 | 2.1 | 2.9 | 11.5 | 6.2 | 6.3 |
| 0.55 | 6.5 | 7.7 | 2.1 | 2.9 | 11.5 | 6.2 | 6.2 |
| 0.6 | 6.4 | 7.7 | 2.1 | 2.9 | 11.5 | 6.2 | 6.2 |
| 0.65 | 6.4 | 7.7 | 2.1 | 2.9 | 11.5 | 6.2 | 6.0 |
| 0.7 | 6.3 | 7.7 | 2.1 | 2.9 | 11.5 | 6.1 | 5.9 |
| 0.75 | 6.2 | 7.5 | 2.1 | 2.9 | 11.6 | 5.9 | 5.6 |
| 0.8 | 5.9 | 7.2 | 2.0 | 2.8 | 11.3 | 5.6 | 5.2 |
| 0.85 | 5.3 | 6.6 | 2.0 | 2.6 | 10.5 | 5.1 | 4.7 |
| 0.9 | 4.5 | 5.5 | 1.9 | 2.3 | 8.9 | 4.2 | 3.9 |
| 0.95 | 3.2 | 3.8 | 1.6 | 1.8 | 6.0 | 3.0 | 2.7 |
| 1 | 1.2 | 1.2 | 1.2 | 1.2 | 1.2 | 1.2 | 1.2 |

HF - HFC-245cb - HCFC-244bb- HFC-245fa - Trifluoropropyne- HFO-1225yeZ- HFO-1225zc

| MASSFRAC HF | Organics 0.15 F245cb + 0.17 F244bb + 0.17 F245fa + 0.17 TFP + 0.17 F1225yeZ + 0.17 F1225zc TOTAL PRESSURE bar | Organics 0.95 F245cb + 0.01 F244bb + 0.01 F245fa + 0.01 TFP + 0.01 F1225yeZ + 0.01 F1225zc TOTAL PRESSURE bar | Organics 0.01 F245cb + 0.95 F244bb + 0.01 F245fa + 0.01 TFP + 0.01 F1225yeZ + 0.01 F1225zc TOTAL PRESSURE bar | Organics 0.01 F245cb + 0.01 F244bb + 0.95 F245fa + 0.01 TFP + 0.01 F1225yeZ + 0.01 F1225zc TOTAL PRESSURE bar | Organics 0.01 F245cb + 0.01 F244bb + 0.01 F245fa + 0.95 TFP + 0.01 F1225yeZ + 0.01 F1225zc TOTAL PRESSURE bar | Organics 0.01 F245cb + 0.01 F244bb + 0.01 F245fa + 0.01 TFP + 0.95 F1225yeZ + 0.01 F1225zc TOTAL PRESSURE bar | Organics 0.01 F245cb + 0.01 F244bb + 0.01 F245fa + 0.01 TFP + 0.01 F1225yeZ + 0.95 F1225zc TOTAL PRESSURE bar |
|---|---|---|---|---|---|---|---|
| 0 | 5.3 | 4.7 | 1.0 | 1.8 | 11.3 | 5.2 | 5.3 |
| 0.05 | 6.3 | 5.9 | 2.1 | 2.9 | 12.1 | 6.2 | 6.3 |
| 0.1 | 6.3 | 5.9 | 2.1 | 2.9 | 12.0 | 6.2 | 6.3 |
| 0.15 | 6.3 | 5.9 | 2.1 | 2.9 | 11.9 | 6.2 | 6.3 |
| 0.2 | 6.3 | 5.9 | 2.1 | 2.9 | 11.8 | 6.2 | 6.3 |
| 0.25 | 6.3 | 5.9 | 2.1 | 2.9 | 11.7 | 6.2 | 6.3 |
| 0.3 | 6.3 | 5.9 | 2.1 | 2.9 | 11.6 | 6.2 | 6.3 |
| 0.35 | 6.3 | 5.9 | 2.1 | 2.9 | 11.5 | 6.2 | 6.3 |
| 0.4 | 6.2 | 5.9 | 2.1 | 2.9 | 11.5 | 6.2 | 6.3 |
| 0.45 | 6.2 | 5.9 | 2.1 | 2.9 | 11.5 | 6.2 | 6.3 |
| 0.5 | 6.2 | 5.9 | 2.1 | 2.9 | 11.5 | 6.2 | 6.2 |
| 0.55 | 6.2 | 5.9 | 2.1 | 2.9 | 11.5 | 6.2 | 6.2 |
| 0.6 | 6.2 | 5.9 | 2.1 | 2.9 | 11.5 | 6.2 | 6.1 |
| 0.65 | 6.1 | 5.9 | 2.1 | 2.9 | 11.5 | 6.2 | 6.0 |
| 0.7 | 6.1 | 5.9 | 2.0 | 2.8 | 11.5 | 6.1 | 5.9 |
| 0.75 | 6.0 | 5.8 | 2.0 | 2.8 | 11.5 | 5.9 | 5.6 |
| 0.8 | 5.7 | 5.8 | 2.0 | 2.8 | 11.3 | 5.6 | 5.2 |
| 0.85 | 5.2 | 5.8 | 2.0 | 2.6 | 10.5 | 5.1 | 4.7 |
| 0.9 | 4.4 | 5.0 | 1.9 | 2.3 | 8.9 | 4.2 | 3.9 |
| 0.95 | 3.1 | 3.5 | 1.6 | 1.8 | 6.0 | 3.0 | 2.7 |
| 1 | 1.2 | 1.2 | 1.2 | 1.2 | 1.2 | 1.2 | 1.2 |

EXAMPLE 6

Systems with 8 Compounds

HF - HCFO-1233xf - HFO-1234yf - HFC-245cb - HCFO-1233zdE - HFO-1234zeE - HFO-1234zeZ - HFO-1243zf

| Organics 0.01 F1233xf + 0.94 F1234yf + 0.01 F245cb + 0.01 F1233zdE + 0.01 F1234zeE + 0.01 F1234zeZ + 0.01 F1243zf | | Organics 0.01 F1233xf + 0.01 F1234yf + 0.94 F245cb + 0.01 F1233zdE + 0.01 F1234zeE + 0.01 F1234zeZ + 0.01 F1243zf | | Organics 0.01 F1233xf + 0.01 F1234yf + 0.01 F245cb + 0.94 F1233zdE + 0.01 F1234zeE + 0.01 F1234zeZ + 0.01 F1243zf | | Organics 0.01 F1233xf + 0.01 F1234yf + 0.01 F245cb + 0.01 F1233zdE + 0.94 F1234zeE + 0.01 F1234zeZ + 0.01 F1243zf | | Organics 0.01 F1233xf + 0.01 F1234yf + 0.01 F245cb + 0.01 F1233zdE + 0.01 F1234zeE + 0.94 F1234zeZ + 0.01 F1243zf | | Organics 0.01 F1233xf + 0.01 F1234yf + 0.01 F245cb + 0.01 F1233zdE + 0.01 F1234zeE + 0.01 F1234zeZ + 0.94 F1243zf | | Organics 0.16 F1233xf + 0.14 F1234yf + 0.14 F245cb + 0.14 F1233zdE + 0.14 F1234zeE + 0.14 F1234zeZ + 0.14 F1243zf | |
|---|---|---|---|---|---|---|---|---|---|---|---|---|---|
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0 | 6.6 | 0 | 4.6 | 0 | 1.5 | 0 | 4.8 | 0 | 2.0 | 0 | 5.7 | 0 | 3.9 |
| 0.05 | 7.6 | 0.05 | 5.8 | 0.05 | 2.6 | 0.05 | 5.8 | 0.05 | 3.1 | 0.05 | 6.7 | 0.05 | 5.0 |
| 0.1 | 7.6 | 0.1 | 5.8 | 0.1 | 2.6 | 0.1 | 5.8 | 0.1 | 3.1 | 0.1 | 6.7 | 0.1 | 5.0 |
| 0.15 | 7.6 | 0.15 | 5.8 | 0.15 | 2.6 | 0.15 | 5.8 | 0.15 | 3.1 | 0.15 | 6.7 | 0.15 | 5.0 |
| 0.2 | 7.6 | 0.2 | 5.8 | 0.2 | 2.6 | 0.2 | 5.8 | 0.2 | 3.1 | 0.2 | 6.7 | 0.2 | 5.0 |
| 0.25 | 7.6 | 0.25 | 5.8 | 0.25 | 2.6 | 0.25 | 5.8 | 0.25 | 3.1 | 0.25 | 6.7 | 0.25 | 5.0 |
| 0.3 | 7.6 | 0.3 | 5.8 | 0.3 | 2.6 | 0.3 | 5.8 | 0.3 | 3.1 | 0.3 | 6.7 | 0.3 | 5.0 |
| 0.35 | 7.6 | 0.35 | 5.8 | 0.35 | 2.6 | 0.35 | 5.8 | 0.35 | 3.1 | 0.35 | 6.7 | 0.35 | 5.0 |
| 0.4 | 7.6 | 0.4 | 5.8 | 0.4 | 2.6 | 0.4 | 5.8 | 0.4 | 3.1 | 0.4 | 6.7 | 0.4 | 5.0 |
| 0.45 | 7.6 | 0.45 | 5.8 | 0.45 | 2.6 | 0.45 | 5.8 | 0.45 | 3.1 | 0.45 | 6.7 | 0.45 | 5.0 |
| 0.5 | 7.6 | 0.5 | 5.8 | 0.5 | 2.6 | 0.5 | 5.7 | 0.5 | 3.1 | 0.5 | 6.7 | 0.5 | 5.0 |
| 0.55 | 7.6 | 0.55 | 5.8 | 0.55 | 2.6 | 0.55 | 5.7 | 0.55 | 3.1 | 0.55 | 6.7 | 0.55 | 5.0 |
| 0.6 | 7.6 | 0.6 | 5.8 | 0.6 | 2.6 | 0.6 | 5.6 | 0.6 | 3.1 | 0.6 | 6.6 | 0.6 | 5.0 |
| 0.65 | 7.6 | 0.65 | 5.8 | 0.65 | 2.6 | 0.65 | 5.5 | 0.65 | 3.1 | 0.65 | 6.6 | 0.65 | 5.0 |
| 0.7 | 7.5 | 0.7 | 5.8 | 0.7 | 2.6 | 0.7 | 5.4 | 0.7 | 3.1 | 0.7 | 6.5 | 0.7 | 5.0 |
| 0.75 | 7.4 | 0.75 | 5.8 | 0.75 | 2.6 | 0.75 | 5.1 | 0.75 | 3.1 | 0.75 | 6.3 | 0.75 | 4.9 |
| 0.8 | 7.1 | 0.8 | 5.8 | 0.8 | 2.5 | 0.8 | 4.8 | 0.8 | 2.9 | 0.8 | 6.0 | 0.8 | 4.6 |
| 0.85 | 6.5 | 0.85 | 5.8 | 0.85 | 2.3 | 0.85 | 4.3 | 0.85 | 2.7 | 0.85 | 5.5 | 0.85 | 4.2 |

-continued

| HF - HCFO-1233xf - HFO-1234yf - HFC-245cb - HCFO-1233zdE - HFO-1234zeE - HFO-1234zeZ - HFO-1243zf | | | | | | | | | | | | | |
|---|---|---|---|---|---|---|---|---|---|---|---|---|---|
| Organics 0.01 F1233xf + 0.94 F1234yf + 0.01 F245cb + 0.01 F1233zdE + 0.01 F1234zeE + 0.01 F1234zeZ + 0.01 F1243zf | | Organics 0.01 F1233xf + 0.01 F1234yf + 0.94 F245cb + 0.01 F1233zdE + 0.01 F1234zeE + 0.01 F1234zeZ + 0.01 F1243zf | | Organics 0.01 F1233xf + 0.01 F1234yf + 0.01 F245cb + 0.94 F1233zdE + 0.01 F1234zeE + 0.01 F1234zeZ + 0.01 F1243zf | | Organics 0.01 F1233xf + 0.01 F1234yf + 0.01 F245cb + 0.01 F1233zdE + 0.94 F1234zeE + 0.01 F1234zeZ + 0.01 F1243zf | | Organics 0.01 F1233xf + 0.01 F1234yf + 0.01 F245cb + 0.01 F1233zdE + 0.01 F1234zeE + 0.94 F1234zeZ + 0.01 F1243zf | | Organics 0.01 F1233xf + 0.01 F1234yf + 0.01 F245cb + 0.01 F1233zdE + 0.01 F1234zeE + 0.01 F1234zeZ + 0.94 F1243zf | | Organics 0.16 F1233xf + 0.14 F1234yf + 0.14 F245cb + 0.14 F1233zdE + 0.14 F1234zeE + 0.14 F1234zeZ + 0.14 F1243zf | |
| MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar | MASS-FRAC HF | TOTAL PRES-SURE bar |
| 0.9 | 5.5 | 0.9 | 5.0 | 0.9 | 2.1 | 0.9 | 3.6 | 0.9 | 2.4 | 0.9 | 4.7 | 0.9 | 3.6 |
| 0.95 | 3.8 | 0.95 | 3.5 | 0.95 | 1.7 | 0.95 | 2.6 | 0.95 | 1.9 | 0.95 | 3.3 | 0.95 | 2.6 |
| 1 | 1.2 | 1 | 1.2 | 1 | 1.2 | 1 | 1.2 | 1 | 1.2 | 1 | 1.2 | 1 | 1.2 |

| HF-HFO-1234yf-HFC-245cb-HCFO-1233xf-HFO-1234zeE-HFO-1234zeZ-HCFO-1233zdE-HCFC-244bb | | | | |
|---|---|---|---|---|
| MASSFRAC HF | Organics 0.94 F1233xf + 0.01 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.94 F1234yf + 0.01 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.94 F245cb + 0.01 F1233zdE + 0.01 F1234zeE + 0.01 F1234zeZ + 0.01 F244bb TOTAL PRESSURE bar | Organics 0.01 F1233xf + 0.01 F1234yf + 0.01 F245cb + 0.94 F1233zdE + 0.01 F1234zeE + 0.01 F1234zeZ + 0.01 F244bb TOTAL PRESSURE bar |
| 0 | 1.7 | 6.6 | 4.5 | 1.5 |
| 0.05 | 2.8 | 7.5 | 5.7 | 2.6 |
| 0.1 | 2.8 | 7.5 | 5.7 | 2.6 |
| 0.15 | 2.8 | 7.5 | 5.7 | 2.6 |
| 0.2 | 2.8 | 7.5 | 5.7 | 2.6 |
| 0.25 | 2.8 | 7.5 | 5.7 | 2.6 |
| 0.3 | 2.8 | 7.5 | 5.7 | 2.6 |
| 0.35 | 2.8 | 7.5 | 5.7 | 2.6 |
| 0.4 | 2.8 | 7.5 | 5.7 | 2.6 |
| 0.45 | 2.8 | 7.5 | 5.7 | 2.6 |
| 0.5 | 2.8 | 7.5 | 5.7 | 2.6 |
| 0.55 | 2.8 | 7.5 | 5.7 | 2.6 |
| 0.6 | 2.8 | 7.5 | 5.7 | 2.6 |
| 0.65 | 2.8 | 7.5 | 5.7 | 2.6 |
| 0.7 | 2.8 | 7.5 | 5.7 | 2.6 |
| 0.75 | 2.8 | 7.4 | 5.7 | 2.6 |
| 0.8 | 2.6 | 7.0 | 5.7 | 2.4 |
| 0.85 | 2.4 | 6.5 | 5.7 | 2.3 |
| 0.9 | 2.2 | 5.4 | 4.9 | 2.0 |
| 0.95 | 1.8 | 3.8 | 3.5 | 1.7 |
| 1 | 1.2 | 1.2 | 1.2 | 1.2 |
| MASSFRAC HF | Organics 0.01 F1233xf + 0.01 F1234yf + 0.01 F245cb + 0.01 F1233zdE + 0.94 F1234zeE + 0.01 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.94 F1234zeZ + 0.01 F244bb TOTAL PRESSURE bar | Organics 0.01 F1233xf + 0.01 F1234yf + 0.01 F245cb + 0.01 F1233zdE + 0.01 F1234zeE + 0.01 F1234zeZ + 0.94 F244bb TOTAL PRESSURE bar | Organics 0.16 F1233xf + 0.14 F1234yf + 0.14 F245cb + 0.14 F1233zdE + 0.14 F1234zeE + 0.14 F1234zeZ + 0.14 F244bb TOTAL PRESSURE bar |
| 0 | 4.8 | 1.9 | 0.8 | 3.2 |
| 0.05 | 5.7 | 3.0 | 2.0 | 4.3 |
| 0.1 | 5.7 | 3.0 | 2.0 | 4.3 |
| 0.15 | 5.7 | 3.0 | 2.0 | 4.3 |
| 0.2 | 5.7 | 3.0 | 2.0 | 4.3 |
| 0.25 | 5.7 | 3.0 | 2.0 | 4.3 |
| 0.3 | 5.7 | 3.0 | 2.0 | 4.3 |

-continued

| HF-HFO-1234yf-HFC-245cb-HCFO-1233xf-HFO-1234zeE-HFO-1234zeZ-HCFO-1233zdE-HCFC-244bb | | | | |
|---|---|---|---|---|
| 0.35 | 5.7 | 3.0 | 2.0 | 4.3 |
| 0.4 | 5.7 | 3.0 | 2.0 | 4.3 |
| 0.45 | 5.7 | 3.0 | 2.0 | 4.3 |
| 0.5 | 5.7 | 3.0 | 2.0 | 4.3 |
| 0.55 | 5.6 | 3.0 | 2.0 | 4.2 |
| 0.6 | 5.6 | 3.0 | 2.0 | 4.2 |
| 0.65 | 5.5 | 3.0 | 2.0 | 4.2 |
| 0.7 | 5.3 | 3.0 | 2.0 | 4.2 |
| 0.75 | 5.1 | 3.0 | 1.9 | 4.2 |
| 0.8 | 4.7 | 2.9 | 1.9 | 4.0 |
| 0.85 | 4.3 | 2.7 | 1.9 | 3.7 |
| 0.9 | 3.6 | 2.4 | 1.8 | 3.2 |
| 0.95 | 2.6 | 1.9 | 1.6 | 2.4 |
| 1 | 1.2 | 1.2 | 1.2 | 1.2 |

| HF-HFO-1234yf-HFC-245cb-HCFO-1233xf-HFO-1234zeE-HFO-1234zeZ-HCFO-1233zdE-Trifluoropropyne | | | | |
|---|---|---|---|---|
| MASSFRAC HF | Organics 0.16 F1234yf + 0.14 F245cb + 0.14 F1233xf + 0.14 F1234zeE + 0.14 F1234zeZ + 0.14 F1233zdE + 0.14 TPF TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 TPF TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 TPF TOTAL PRESSURE bar |
| 0 | 5.0 | 6.7 | 4.7 | 1.8 |
| 0.05 | 6.0 | 7.6 | 5.8 | 2.9 |
| 0.1 | 6.0 | 7.6 | 5.8 | 2.9 |
| 0.15 | 6.0 | 7.6 | 5.8 | 2.9 |
| 0.2 | 6.0 | 7.6 | 5.8 | 2.9 |
| 0.25 | 6.0 | 7.6 | 5.8 | 2.9 |
| 0.3 | 6.0 | 7.6 | 5.8 | 2.9 |
| 0.35 | 6.0 | 7.6 | 5.8 | 2.9 |
| 0.4 | 6.0 | 7.6 | 5.8 | 2.9 |
| 0.45 | 6.0 | 7.6 | 5.8 | 2.9 |
| 0.5 | 6.0 | 7.6 | 5.8 | 2.9 |
| 0.55 | 6.0 | 7.6 | 5.8 | 2.9 |
| 0.6 | 6.0 | 7.6 | 5.8 | 2.9 |
| 0.65 | 6.0 | 7.6 | 5.8 | 2.9 |
| 0.7 | 6.0 | 7.6 | 5.8 | 2.9 |
| 0.75 | 5.9 | 7.5 | 5.8 | 2.9 |
| 0.8 | 5.6 | 7.1 | 5.8 | 2.8 |
| 0.85 | 5.1 | 6.6 | 5.8 | 2.6 |
| 0.9 | 4.3 | 5.5 | 5.0 | 2.2 |
| 0.95 | 3.1 | 3.8 | 3.5 | 1.8 |
| 1 | 1.2 | 1.2 | 1.2 | 1.2 |
| MASSFRAC HF | Organics 0.01 F1234yf + 0.01 F245cb + 0.01 F1233xf + 0.94 F1234zeE + 0.01 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 TPF TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 TPF TOTAL PRESSURE bar |
| 0 | 4.9 | 2.0 | 1.6 | 11.2 |
| 0.05 | 5.8 | 3.1 | 2.7 | 12.0 |
| 0.1 | 5.9 | 3.1 | 2.7 | 11.9 |
| 0.15 | 5.9 | 3.1 | 2.7 | 11.8 |
| 0.2 | 5.9 | 3.1 | 2.7 | 11.7 |
| 0.25 | 5.8 | 3.1 | 2.7 | 11.6 |
| 0.3 | 5.8 | 3.1 | 2.7 | 11.5 |
| 0.35 | 5.8 | 3.1 | 2.7 | 11.5 |
| 0.4 | 5.8 | 3.1 | 2.7 | 11.4 |

-continued

| HF-HFO-1234yf-HFC-245cb-HCFO-1233xf-HFO-1234zeE-HFO-1234zeZ-HCFO-1233zdE-Trifluoropropyne | | | | |
|---|---|---|---|---|
| 0.45 | 5.8 | 3.1 | 2.7 | 11.4 |
| 0.5 | 5.8 | 3.1 | 2.7 | 11.4 |
| 0.55 | 5.8 | 3.1 | 2.7 | 11.5 |
| 0.6 | 5.7 | 3.1 | 2.7 | 11.5 |
| 0.65 | 5.6 | 3.1 | 2.7 | 11.5 |
| 0.7 | 5.4 | 3.1 | 2.7 | 11.5 |
| 0.75 | 5.2 | 3.1 | 2.7 | 11.5 |
| 0.8 | 4.9 | 3.0 | 2.6 | 11.2 |
| 0.85 | 4.4 | 2.8 | 2.4 | 10.4 |
| 0.9 | 3.6 | 2.4 | 2.1 | 8.8 |
| 0.95 | 2.6 | 1.9 | 1.7 | 5.9 |
| 1 | 1.2 | 1.2 | 1.2 | 1.2 |

| HF-HFO-1234yf-HFC-245cb-HCFO-1233xf-HFO-1234zeE-HFO-1234zeZ-HCFO-1233zdE-HFC-245fa | | | | |
|---|---|---|---|---|
| MASSFRAC HF | Organics 0.16 F1234yf + 0.14 F245cb + 0.14 F1233xf + 0.14 F1234zeE + 0.14 F1234zeZ + 0.14 F1233zdE + 0.14 F245fa TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F245fa TOTAL PRESSURE bar | Organics 0.01 F1234yf + 0.01 F245cb t 0.94 F1233xf + 0.01 F1234zeE + 0.01 F1234zeZ + 0.01 F1233zdE + 0.01 F245fa TOTAL PRESSURE bar |
| 0 | 3.4 | 6.6 | 4.5 | 1.7 |
| 0.05 | 4.5 | 7.5 | 5.7 | 2.8 |
| 0.1 | 4.5 | 7.5 | 5.7 | 2.8 |
| 0.15 | 4.5 | 7.5 | 5.7 | 2.8 |
| 0.2 | 4.5 | 7.5 | 5.7 | 2.8 |
| 0.25 | 4.5 | 7.5 | 5.7 | 2.8 |
| 0.3 | 4.5 | 7.5 | 5.7 | 2.8 |
| 0.35 | 4.5 | 7.5 | 5.7 | 2.8 |
| 0.4 | 4.5 | 7.5 | 5.7 | 2.8 |
| 0.45 | 4.5 | 7.5 | 5.7 | 2.8 |
| 0.5 | 4.5 | 7.5 | 5.7 | 2.8 |
| 0.55 | 4.5 | 7.5 | 5.7 | 2.8 |
| 0.6 | 4.5 | 7.5 | 5.7 | 2.8 |
| 0.65 | 4.5 | 7.5 | 5.7 | 2.8 |
| 0.7 | 4.5 | 7.5 | 5.7 | 2.8 |
| 0.75 | 4.4 | 7.4 | 5.7 | 2.8 |
| 0.8 | 4.2 | 7.1 | 5.8 | 2.6 |
| 0.85 | 3.9 | 6.5 | 5.7 | 2.5 |
| 0.9 | 3.3 | 5.4 | 4.9 | 2.2 |
| 0.95 | 2.4 | 3.8 | 3.5 | 1.8 |
| 1 | 1.2 | 1.2 | 1.2 | 1.2 |
| MASSFRAC HF | Organics 0.01 F1234yf + 0.01 F245cb + 0.01 F1233xf + 0.94 F1234zeE + 0.01 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F245fa TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F245fa TOTAL PRESSURE bar |
| 0 | 4.8 | 1.9 | 1.5 | 1.6 |
| 0.05 | 5.7 | 3.0 | 2.6 | 2.8 |
| 0.1 | 5.7 | 3.0 | 2.6 | 2.8 |
| 0.15 | 5.7 | 3.0 | 2.6 | 2.8 |
| 0.2 | 5.7 | 3.0 | 2.6 | 2.8 |
| 0.25 | 5.7 | 3.0 | 2.6 | 2.8 |
| 0.3 | 5.7 | 3.0 | 2.6 | 2.8 |
| 0.35 | 5.7 | 3.0 | 2.6 | 2.8 |
| 0.4 | 5.7 | 3.0 | 2.6 | 2.8 |
| 0.45 | 5.7 | 3.0 | 2.6 | 2.8 |
| 0.5 | 5.7 | 3.0 | 2.6 | 2.8 |

-continued

| HF-HFO-1234yf-HFC-245cb-HCFO-1233xf-HFO-1234zeE-HFO-1234zeZ-HCFO-1233zdE-HFC-245fa | | | | |
|---|---|---|---|---|
| 0.55 | 5.6 | 3.0 | 2.6 | 2.8 |
| 0.6 | 5.6 | 3.0 | 2.6 | 2.8 |
| 0.65 | 5.5 | 3.0 | 2.6 | 2.8 |
| 0.7 | 5.3 | 3.0 | 2.6 | 2.8 |
| 0.75 | 5.1 | 3.0 | 2.6 | 2.8 |
| 0.8 | 4.7 | 2.9 | 2.5 | 2.7 |
| 0.85 | 4.3 | 2.7 | 2.3 | 2.5 |
| 0.9 | 3.6 | 2.4 | 2.0 | 2.2 |
| 0.95 | 2.6 | 1.9 | 1.7 | 1.8 |
| 1 | 1.2 | 1.2 | 1.2 | 1.2 |

| HF-HFO-1234yf-HFC-245cb-HCFO-1233xf-HFO-1234zeE-HFO-1234zeZ-HCFO-1233zdE-HFO-1225yeZ | | | | |
|---|---|---|---|---|
| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225yeZ TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225yeZ TOTAL PRESSURE bar | Organics 0.01 F1234yf + 0.01 F245cb + 0.94 F1233xf + 0.01 F1234zeE + 0.01 F1234zeZ + 0.01 F1233zdE + 0.01 F1225yeZ TOTAL PRESSURE bar |
| 0 | 3.8 | 6.6 | 4.6 | 1.7 |
| 0.05 | 4.9 | 7.6 | 5.8 | 2.8 |
| 0.1 | 4.9 | 7.6 | 5.8 | 2.8 |
| 0.15 | 4.9 | 7.6 | 5.8 | 2.8 |
| 0.2 | 4.9 | 7.5 | 5.8 | 2.8 |
| 0.25 | 4.9 | 7.6 | 5.8 | 2.8 |
| 0.3 | 4.9 | 7.6 | 5.8 | 2.8 |
| 0.35 | 4.9 | 7.6 | 5.8 | 2.8 |
| 0.4 | 4.9 | 7.6 | 5.8 | 2.8 |
| 0.45 | 4.9 | 7.6 | 5.8 | 2.8 |
| 0.5 | 4.9 | 7.6 | 5.8 | 2.8 |
| 0.55 | 4.9 | 7.6 | 5.8 | 2.8 |
| 0.6 | 4.9 | 7.6 | 5.8 | 2.8 |
| 0.65 | 4.9 | 7.6 | 5.8 | 2.8 |
| 0.7 | 5.0 | 7.5 | 5.8 | 2.8 |
| 0.75 | 4.8 | 7.4 | 5.8 | 2.8 |
| 0.8 | 4.6 | 7.1 | 5.8 | 2.7 |
| 0.85 | 4.2 | 6.5 | 5.8 | 2.5 |
| 0.9 | 3.6 | 5.5 | 4.9 | 2.2 |
| 0.95 | 2.6 | 3.8 | 3.5 | 1.8 |
| 1 | 1.2 | 1.2 | 1.2 | 1.2 |
| MASSFRAC HF | Organics 0.01 F1234yf + 0.01 F245cb + 0.01 F1233xf + 0.94 F1234zeE + 0.01 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225yeZ TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225yeZ TOTAL PRESSURE bar |
| 0 | 4.8 | 1.9 | 1.5 | 5.1 |
| 0.05 | 5.8 | 3.0 | 2.6 | 6.1 |
| 0.1 | 5.8 | 3.0 | 2.6 | 6.1 |
| 0.15 | 5.8 | 3.0 | 2.6 | 6.1 |
| 0.2 | 5.8 | 3.0 | 2.6 | 6.1 |
| 0.25 | 5.8 | 3.0 | 2.6 | 6.1 |
| 0.3 | 5.8 | 3.0 | 2.6 | 6.1 |
| 0.35 | 5.8 | 3.0 | 2.6 | 6.1 |
| 0.4 | 5.8 | 3.0 | 2.6 | 6.1 |
| 0.45 | 5.8 | 3.0 | 2.6 | 6.1 |
| 0.5 | 5.7 | 3.0 | 2.6 | 6.1 |
| 0.55 | 5.7 | 3.0 | 2.6 | 6.1 |
| 0.6 | 5.6 | 3.0 | 2.6 | 6.1 |

-continued

| HF-HFO-1234yf-HFC-245cb-HCFO-1233xf-HFO-1234zeE-HFO-1234zeZ-HCFO-1233zdE-HFO-1225yeZ | | | | |
|---|---|---|---|---|
| 0.65 | 5.5 | 3.0 | 2.6 | 6.1 |
| 0.7 | 5.3 | 3.0 | 2.6 | 6.0 |
| 0.75 | 5.1 | 3.0 | 2.6 | 5.8 |
| 0.8 | 4.8 | 2.9 | 2.5 | 5.5 |
| 0.85 | 4.3 | 2.7 | 2.3 | 5.0 |
| 0.9 | 3.6 | 2.4 | 2.1 | 4.2 |
| 0.95 | 2.6 | 1.9 | 1.7 | 2.9 |
| 1 | 1.2 | 1.2 | 1.2 | 1.2 |

| HF-HFO-1234yf-HFC-245cb-HCFO-1233xf-HFO-1234zeE-HFO-1234zeZ-HCFC-1233zdE-HFO-1225zc | | | | |
|---|---|---|---|---|
| MASSFRAC HF | Organics 0.16 F1234yf + 0.14 F245cb + 0.14 F1233xf + 0.14 F1234zeE + 0.14 F1234zeZ + 0.14 F1233zdE + 0.14 F1225zc TOTAL PRESSURE bar | Organics 0.94 F1234yf + 0.01 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yf + 0.94 F245cb + 0.01 F1233xf + 0.01 F1234zeE + 0.01 F1234zeZ + 0.01 F1233zdE + 0.01 F1225zc TOTAL PRESSURE bar | Organics 0.01 F1234yft 0.01 F245cb + 0.94 F1233xf + 0.01 F1234zeE + 0.01 F1234zeZ + 0.01 F1233zdE + 0.01 F1225zc TOTAL PRESSURE bar |
| 0 | 3.9 | 6.6 | 4.6 | 1.7 |
| 0.05 | 4.9 | 7.6 | 5.8 | 2.8 |
| 0.1 | 4.9 | 7.6 | 5.8 | 2.8 |
| 0.15 | 4.9 | 7.6 | 5.8 | 2.8 |
| 0.2 | 4.9 | 7.6 | 5.8 | 2.8 |
| 0.25 | 4.9 | 7.6 | 5.8 | 2.8 |
| 0.3 | 4.9 | 7.6 | 5.8 | 2.8 |
| 0.35 | 4.9 | 7.6 | 5.8 | 2.8 |
| 0.4 | 4.9 | 7.6 | 5.8 | 2.8 |
| 0.45 | 4.9 | 7.6 | 5.8 | 2.8 |
| 0.5 | 4.9 | 7.6 | 5.8 | 2.8 |
| 0.55 | 4.9 | 7.6 | 5.8 | 2.8 |
| 0.6 | 4.9 | 7.6 | 5.8 | 2.8 |
| 0.65 | 4.9 | 7.6 | 5.8 | 2.8 |
| 0.7 | 4.9 | 7.5 | 5.8 | 2.8 |
| 0.75 | 4.8 | 7.4 | 5.8 | 2.8 |
| 0.8 | 4.6 | 7.1 | 5.8 | 2.7 |
| 0.85 | 4.2 | 6.5 | 5.8 | 2.5 |
| 0.9 | 3.5 | 5.5 | 4.9 | 2.2 |
| 0.95 | 2.6 | 3.8 | 3.5 | 1.8 |
| 1 | 1.2 | 1.2 | 1.2 | 1.2 |
| MASSFRAC HF | Organics 0.01 F1234yf + 0.01 F245cb + 0.01 F1233xf + 0.94 F1234zeE + 0.01 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.94 F1234zeZ + 0.01 F1233zdE + 0.01 F1225zc TOTAL PRESSURE bar | Organics 0.01 F1234yf + 0.01 F245cb + 0.01 F1233xf + 0.01 F1234zeE + 0.01 F1234zeZ + 0.94 F1233zdE + 0.01 F1225zc TOTAL PRESSURE bar | Organics 0.01 F1234yf + 0.01 F245cb + 0.01 F1233xf + 0.01 F1234zeE + 0.01 F1234zeZ + 0.01 F1233zdE + 0.94 F1225zc TOTAL PRESSURE bar |
| 0 | 4.8 | 1.9 | 1.5 | 5.2 |
| 0.05 | 5.8 | 3.0 | 2.6 | 6.2 |
| 0.1 | 5.8 | 3.0 | 2.6 | 6.2 |
| 0.15 | 5.8 | 3.0 | 2.6 | 6.2 |
| 0.2 | 5.8 | 3.0 | 2.6 | 6.2 |
| 0.25 | 5.8 | 3.0 | 2.6 | 6.2 |
| 0.3 | 5.8 | 3.0 | 2.6 | 6.2 |
| 0.35 | 5.8 | 3.0 | 2.6 | 6.2 |
| 0.4 | 5.8 | 3.0 | 2.6 | 6.2 |
| 0.45 | 5.8 | 3.0 | 2.6 | 6.2 |
| 0.5 | 5.7 | 3.0 | 2.6 | 6.1 |
| 0.55 | 5.7 | 3.0 | 2.6 | 6.1 |
| 0.6 | 5.6 | 3.0 | 2.6 | 6.0 |
| 0.65 | 5.5 | 3.0 | 2.6 | 5.9 |
| 0.7 | 5.3 | 3.0 | 2.6 | 5.8 |

-continued

| HF-HFO-1234yf-HFC-245cb-HCFO-1233xf-HFO-1234zeE-HFO-1234zeZ-HCFC-1233zdE-HFO-1225zc | | | | |
|---|---|---|---|---|
| 0.75 | 5.1 | 3.0 | 2.6 | 5.5 |
| 0.8 | 4.8 | 2.9 | 2.5 | 5.1 |
| 0.85 | 4.3 | 2.7 | 2.3 | 4.6 |
| 0.9 | 3.6 | 2.4 | 2.1 | 3.8 |
| 0.95 | 2.6 | 1.9 | 1.7 | 2.7 |
| 1 | 1.2 | 1.2 | 1.2 | 1.2 |

EXAMPLE 7

Systems with 13 Compounds

| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | | | | | |
|---|---|---|---|---|---|
| MASSFRAC HF | Organics 0.087 F123414 + 0.083 F245cb + 0.083 F1233xf + 0.083 F1233zdE + 0.083 F1234zeE + 0.083 F1234zeZ + 0.083 F1243zf + 0.083 F244bb + 0.083 F245fa + 0.083 TFP + 0.083 F1225yeZ + 0.83 F1225zc TOTAL PRESSURE bar | Organics 0.89 F1234yf + 0.01 F245cb + 0.01 F1233xf+ 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.89 F1233xf+ 0.01 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf+ 0.01 F1233zdE + 0.89 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar | Organics 0.01 F1234yf + 0.01 F245cb + 0.01 F1233xf + 0.89 F1233zdE + 0.01 F1234zeE + 0.01 F1234zeZ + 0.01 F1243zf + 0.01 F244bb + 0.01 F245fa + 0.01 TFP + 0.01 F1225yeZ + 0.1 F1225zc TOTAL PRESSURE bar |
| 0 | 4.5 | 6.5 | 1.9 | 4.8 | 1.7 |
| 0.05 | 5.6 | 7.5 | 3.0 | 5.8 | 2.9 |
| 0.1 | 5.6 | 7.5 | 3.0 | 5.8 | 2.9 |
| 0.15 | 5.6 | 7.5 | 3.0 | 5.8 | 2.8 |
| 0.2 | 5.6 | 7.5 | 3.0 | 5.8 | 2.8 |
| 0.25 | 5.6 | 7.5 | 3.0 | 5.8 | 2.8 |
| 0.3 | 5.6 | 7.5 | 3.0 | 5.8 | 2.8 |
| 0.35 | 5.6 | 7.5 | 3.0 | 5.8 | 2.8 |
| 0.4 | 5.6 | 7.5 | 3.0 | 5.8 | 2.8 |
| 0.45 | 5.5 | 7.5 | 3.0 | 5.8 | 2.8 |
| 0.5 | 5.5 | 7.5 | 3.0 | 5.8 | 2.8 |
| 0.55 | 5.5 | 7.5 | 3.0 | 5.7 | 2.8 |
| 0.6 | 5.5 | 7.5 | 3.0 | 5.6 | 2.8 |
| 0.65 | 5.5 | 7.5 | 3.0 | 5.5 | 2.8 |
| 0.7 | 5.4 | 7.5 | 3.0 | 5.4 | 2.8 |
| 0.75 | 5.3 | 7.3 | 3.0 | 5.2 | 2.8 |
| 0.8 | 5.1 | 7.0 | 2.8 | 4.8 | 2.7 |
| 0.85 | 4.6 | 6.4 | 2.6 | 4.3 | 2.5 |
| 0.9 | 3.9 | 5.4 | 2.3 | 3.6 | 2.2 |
| 0.95 | 2.8 | 3.7 | 1.8 | 2.6 | 1.8 |
| 1 | 1.2 | 1.2 | 1.2 | 1.2 | 1.2 |

EXAMPLE 8

Temperature and Pressure Range of Ternary Mixture

| | Boiling point range | |
|---|---|---|
| Ternary | Temperature ° C. | Pressure bar abs |
| HF-HFO-1234yf-HFC-245cb | 0 to 40 | ~2.4 to ~11.8 |
| HF-HFO-1234yf-HFO-1234zeE | 0 to 40 | ~2.6 to ~11.6 |
| HF-HFO-1234yf-HFO-1234zeZ | 0 to 40 | ~1.3 to ~11.4 |
| HF-HFO-1234yf-HFO-1243zf | 0 to 40 | ~3.0 to ~11.7 |
| HF-HFO-1234yf-HCFO-1233xf | 0 to 40 | ~1.1 to ~11.4 |
| HF-HFO-1234yf-HCFO-1233zdE | 0 to 40 | ~1.0 to ~11.4 |
| HF-HFO-1234yf-Trifluoropropyne | 0 to 40 | ~8.0 to ~12.2 |
| HF-HFO-1234yf-HFC-244bb | 0 to 40 | ~2.1 to ~7.5 |
| HF-HFO-1234yf-HFC-245fa | 0 to 40 | ~2.9 to ~7.5 |
| HF-HFO-1234yf-HFO-1225yeZ | 0 to 40 | ~6.3 to ~7.7 |
| HF-HFO-1234yf-HFO-1225zc | 0 to 40 | ~6.4 to ~7.7 |

EXAMPLE 9

Temperature and Pressure Range of Quaternary Mixture

| Quaternary | Boiling point range | |
|---|---|---|
| | Temperature ° C. | Pressure bar abs |
| HF-HCFO-1233xf-HFC-245cb-HFO-1234yf | 0 to 40 | ~1.2 to ~10.0 |
| HF-HFO-1234yf-HFC-245cb-HCFO-1233zdE | 0 to 40 | ~1.1 to ~11.3 |
| HF-HFO-1234yf-HFC-245cb-HFO-1234zeE | 0 to 40 | ~2.5 to ~11.5 |
| HF-HFO-1234yf-HFC-245cb-HFO-1234zeZ | 0 to 40 | ~1.3 to ~11.3 |
| HF-HFO-1234yf-HFC-245cb-HFO-1243zf | 0 to 40 | ~2.5 to ~11.6 |
| HF-HCFO-1233xf-HFO-1234yf-HCFO-1233zdE | 0 to 40 | ~1.0 to ~11.1 |
| HF-HCFO-1233xf-HFO-1234yf-HFO-1234zeE | 0 to 40 | ~1.2 to ~11.3 |
| HF-HCFO-1233xf-HFO-1234yf-HFO-1234zeZ | 0 to 40 | ~1.0 to ~11.0 |
| HF-HCFO-1233xf-HFO-1234yf-HFO-1243zf | 0 to 40 | ~1.3 to ~11.3 |
| HF-HFO-1234yf-HFO-1234zeE-HFO-1234zeZ | 0 to 40 | ~1.3 to ~11.3 |
| HF-HFO-1234yf-HFO-1234zeE-HCFO-1233zdE | 0 to 40 | ~1.1 to ~11.3 |
| HF-HFO-1234yf-HFO-1234zeE-HFO-1243zf | 0 to 40 | ~3.0 to ~11.6 |
| HF-HFO-1234yf-HFO-1234zeZ-HCFO-1233zdE | 0 to 40 | ~1.0 to ~11.0 |
| HF-HFO-1234yf-HFO-1234zeZ-HFO-1243zf | 0 to 40 | ~1.3 to ~11.3 |

-continued

| Quaternary | Boiling point range | |
|---|---|---|
| | Temperature ° C. | Pressure bar abs |
| HF-HFO-1234yf-HCFO-1233zdE-HFO-1243zf | 0 to 40 | ~1.2 to ~11.3 |
| HF-HFO-1234yf-HFC-245cb-Trifluoropropyne | 0 to 40 | ~5.9 to ~12.4 |
| HF-HFO-1234yf-HFC-245cb-HCFC-244bb | 0 to 40 | ~1.8 to ~7.7 |
| HF-HFO-1234yf-HFC-245cb-HFC-245fa | 0 to 40 | ~2.7 to ~7.7 |
| HF-HFO-1234yf-HFC-245cb-HFO-1225yeZ | 0 to 40 | ~5.8 to ~7.7 |
| HF-HFO-1234yf-HFC-245cb-HFO-1225zc | 0 to 40 | ~5.8 to ~7.7 |
| HF-HFO-1234yf-HFO-1234zeE-Trifluoropropyne | 0 to 40 | ~5.9 to ~12.4 |
| HF-HFO-1234yf-HFO-1234zeE-HCFC-244bb | 0 to 40 | ~1.8 to ~7.7 |
| HF-HFO-1234yf-HFO-1234zeE-HFC-245fa | 0 to 40 | ~2.7 to ~7.7 |
| HF-HFO-1234yf-HFO-1234zeE-HFO-1225yeZ | 0 to 40 | ~5.2 to ~7.7 |
| HF-HFO-1234yf-HFO-1234zeE-HFO-1225zc | 0 to 40 | ~5.2 to ~7.7 |
| HF-HFO-1234yf-HFO-1225yeZ-Trifluoropropyne | 0 to 40 | ~6.3 to ~12.4 |
| HF-HFO-1234yf-HCFC-244bb-Trifluoropropyne | 0 to 40 | ~1.9 to ~12.4 |
| HF-HFO-1234yf-HCFC-244bb-HFC-245fa | 0 to 40 | ~1.8 to ~7.7 |
| HF-HFO-1234yf-HCFO-1233xf-HCFC-244bb | 0 to 40 | ~0.8 to ~11.0 |

EXAMPLE 10

Temperature and Pressure Range of Penternary Mixture

| System with 5 compounds | Boiling point range | |
|---|---|---|
| | Temperature ° C. | Pressure bar abs |
| HF-HCFO-1233xf-HFC-245cb-HCFO-1233zdE-HFO-1234yf | 0 to 40 | ~1.0 to ~11.2 |
| HF-HCFO-1233xf-HFC-245cb-HFO-1234zeE-HFO-1234yf | 0 to 40 | ~1.0 to ~11.4 |
| HF-HCFO-1233xf-HFC-245cb-HFO-1234zeZ-HFO-1234yf | 0 to 40 | ~1.1 to ~11.2 |
| HF-HCFO-1233xf-HFC-245cb-HFO-1234yf-HFO-1243zf | 0 to 40 | ~1.2 to ~11.4 |
| HF-HCFO-1233xf-HFO-1234yf-HFO-1234zeE-HFO-1234zeZ | 0 to 40 | ~1.1 to ~11.2 |
| HF-HCFO-1233xf-HFO-1234yf-HFO-1234zeE-HFO-1243zf | 0 to 40 | ~1.2 to ~11.4 |
| HF-HCFO-1233xf-HFO-1234yf-HFO-1234zeE-HCFO-1233zdE | 0 to 40 | ~1.0 to ~11.2 |
| HF-HCFO-1233xf-HFO-1234yf-HFO-1234zeZ-HFO-1243zf | 0 to 40 | ~1.2 to ~11.2 |
| HF-HCFO-1233xf-HFO-1234yf-HFO-1234zeZ-HCFO-1233zdE | 0 to 40 | ~1.0~11.1 |
| HF-HCFO-1233xf-HFO-1234yf-HCFO-1233zdE-HFO-1243zf | 0 to 40 | ~1.0~11.2 |
| HF-HFO-1234yf-HFO-1234zeE-HFO-1234zeZ-HCFO-1233zdE | 0 to 40 | ~1.0 to ~11.2 |
| HF-HFO-1234yf-HFO-1234zeE-HFO-1234zeZ-HFO-1243zf | 0 to 40 | ~1.3 to ~11.4 |
| HF-HFO-1234yf-HFO-1234zeE-HCFO-1233zdE-HFO-1243zf | 0 to 40 | ~1.0 to ~11.4 |
| HF-HFO-1234yf-HFO-1234zeZ-HCFO-1233zdE-HFO-1243zf | 0 to 40 | ~1.1 to ~11.2 |
| HF-HFO-1234yf-HFC-245cb-HFO-1234zeE-HCFO-1233zdE | 0 to 40 | ~1.1 to ~11.4 |
| HF-HFO-1234yf-HFC-245cb-HFO-1234zeE-HFO-1234zeZ | 0 to 40 | ~1.3 to ~9.1 |
| HF-HFO-1234yf-HFC-245cb-HFO-1234zeE-HFO-1243zf | 0 to 40 | ~2.5 to ~11.6 |
| HF-HFO-1234yf-HFC-245cb-HFO-1234zeZ-HCFO-1233zdE | 0 to 40 | ~1.0 to ~11.2 |
| HF-HFO-1234yf-HFC-245cb-HFO-1234zeZ-HFO-1243zf | 0 to 40 | ~1.3 to ~10.3 |
| HF-HFO-1234yf-HFC-245cb-HCFO-1233zdE-HFO-1243zf | 0 to 40 | ~1.1 to ~11.4 |
| HF-HCFO-1233xf-HFO-1234yf-HFC-245cb-HCFC-244bb | 0 to 40 | ~0.7 to ~11.6 |

EXAMPLE 11

Temperature and Pressure Range of System with 6 Compounds

| System with 6 compounds | Boiling point range | |
|---|---|---|
| | Temperature ° C. | Pressure bar abs |
| HF-HCFO-1233xf-HFO-1234yf-HFC-245cb-HFO-1234zeE-HFO-1234zeZ | 0 to 40 | ~1.0~11.6 |
| HF-HCFO-1233xf-HFO-1234yf-HFC-245cb-HFO-1234zeE-HCFO-1233zdE | 0 to 40 | ~0.9 to ~11.6 |
| HF-HCFO-1233xf-HFO-1234yf-HFC-245cb-HFO-1234zeE-HFO-1243zf | 0 to 40 | ~1.0 to ~11.6 |
| HF-HCFO-1233xf-HFO-1234yf-HFC-245cb-HFO-1234zeZ-HCFO-1233zdE | 0 to 40 | ~0.9 to ~11.5 |
| HF-HCFO-1233xf-HFO-1234yf-HFC-245cb-HFO-1234zeZ-HFO-1243zf | 0 to 40 | ~1.0 to ~11.6 |
| HF-HCFO-1233xf-HFO-1234yf-HFC-245cb-HCFO-1233zdE-HFO-1243zf | 0 to 40 | ~0.9 to ~11.6 |
| HF-HCFO-1233xf-HFO-1234yf-HFO-1234zeE-HFO-1234zeZ-HCFO-1233zdE | 0 to 40 | ~0.9 to ~11.5 |
| HF-HCFO-1233xf-HFO-1234yf-HFO-1234zeE-HFO-1234zeZ-HFO-1243zf | 0 to 40 | ~1.0 to ~11.6 |
| HF-HCFO-1233xf-HFO-1234yf-HFO-1234zeE-HCFO-1233zdE-HFO-1243zf | 0 to 40 | ~0.9 to ~11.6 |
| HF-HCFO-1233xf-HFO-1234yf-HFO-1234zeZ-HCFO-1233zdE-HFO-1243zf | 0 to 40 | ~0.9 to ~11.6 |
| HF-HFO-1234yf-HFC-245cb-HFO-1234zeE-HFO-1234zeZ-HCFO-1233zdE | 0 to 40 | ~0.9~11.6 |
| HF-HFO-1234yf-HFC-245cb-HFO-1234zeE-HFO-1234zeZ-HFO-1243zf | 0 to 40 | ~1.2 to ~11.6 |
| HF-HFO-1234yf-HFC-245cb-HFO-1234zeE-HCFO-1233zdE-HFO-1243zf | 0 to 40 | ~1.0 to ~11.7 |
| HF-HFO-1234yf-HFC-245cb-HFO-1234zeZ-HCFO-1233zdE-HFO-1243zf | 0 to 40 | ~0.9 to ~11.6 |
| HF-HFO-1234yf-HFO-1234zeE-HFO-1234zeZ-HCFO-1233zdE-HFO-1243zf | 0 to 40 | ~0.9 to ~11.6 |
| HF-HCFC-244bb-HFC-245fa-Trifluoropropyne-HFO-1225yeZ-HFO-1225zc | 0 to 40 | ~0.7 to ~18.0 |

EXAMPLE 12

Temperature and Pressure Range of System with 7 Compounds

| System with 7 compounds | Boiling point range | |
|---|---|---|
| | Temperature ° C. | Pressure bar abs |
| HF-HCFO-1233xf-HFO-1234yf-HFC-245cb-HCFO-1233zdE-HFO-1234zeE-HFO-1234zeZ | 0 to 40 | ~0.9 ~11.5 |
| HF-HCFO-1233xf-HFO-1234yf-HFC-245cb-HCFO-1233zdE-HFO-1234zeE-HFO-1243zf | 0 to 40 | ~1.0 to 11.6 |
| HF-HCFO-1233xf-HFO-1234yf-HFC-245cb-HCFO-1233zdE-HFO-1234zeZ-HFO-1243zf | 0 to 40 | ~0.9 to ~11.5 |
| HF-HCFO-1233xf-HFO-1234yf-HFC-245cb-HFO-1234zeE-HFO-1234zeZ-HFO-1243zf | 0 to 40 | ~1.1 to ~11.6 |
| HF-HCFO-1233xf-HFO-1234yf-HCFO-1233zdE-HFO-1234zeE-HFO-1234zeZ-HFO-1243zf | 0 to 40 | ~0.9 to ~11.5 |
| HF-HFO-1234yf-HFC-245cb-HCFO-1233zdE-HFO-1234zeE-HFO-1234zeZ-HFO-1243zf | 0 to 40 | ~1.0 to ~11.6 |
| HF-HFO-1234yf-HCFC-244bb-HFC-245fa-Trifluoropropyne-HFO-1225yeZ-HFO-1225zc | 0 to 40 | ~0.7 to ~17.5 |
| HF-HFC-245cb-HCFC-244bb-HFC-245fa-Trifluoropropyne-HFO-1225yeZ-HFO-1225zc | 0 to 40 | ~0.7 to ~17.5 |

EXAMPLE 13

Temperature and Pressure Range of System with 8 Compounds

| System with 8 compounds | Boiling point range | |
|---|---|---|
| | Temperature ° C. | Pressure bar abs |
| HF-HCFO-1233xf-HFO-1234yf-HFC-245cb-HCFO-1233zdE-HFO-1234zeE-HFO-1234zeZ-HFO-1243zf | 0 to 40 | ~1.0 ~11.5 |
| HF-HFO-1234yf-HFC-245cb-HCFO-1233xf-HFO-1234zeE-HFO-1234zeZ-HCFO-1233zdE-HCFC-244bb | 0 to 40 | ~0.7 to ~11.5 |

-continued

| System with 8 compounds | Boiling point range Temperature ° C. | Pressure bar abs |
|---|---|---|
| HF-HFO-1234yf-HFC-245cb-HCFO-1233xf-HFO-1234zeE-HFO-1234zeZ-HCFO-1233zdE-Trifluoropropyne | 0 to 40 | ~1.0 to ~17.4 |
| HF-HFO-1234yf-HFC-245cb-HCFO-1233xf-HFO-1234zeE-HFO-1234zeZ-HCFO-1233zdE-HFC-245fa | 0 to 40 | ~0.9 to ~11.5 |
| HF-HFO-1234yf-HFC-245cb-HCFO-1233xf-HFO-1234zeE-HFO-1234zeZ-HCFO-1233zdE-HFO-1225yeZ | 0 to 40 | ~1.0 to ~11.5 |
| HF-HFO-1234yf-HFC-245cb-HCFO-1233xf-HFO-1234zeE-HFO-1234zeZ-HCFC-1233zdE-HFO-1225zc | 0 to 40 | ~1.0 to ~11.5 |

EXAMPLE 14

Temperature and Pressure Range of System with 13 Compounds

| System with 13 compounds | Boiling point range Temperature ° C. | Pressure bar abs |
|---|---|---|
| HF-HFO-1234yf- HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 0 to 40 | ~0.7 ~18.0 |

EXAMPLE 15

Decantation Ranges of Ternary Mixtures

| Ternary | Decantation ranges Mass percentages of HF Isotherm 0° C. | Isotherm 25° C. | Isotherm 40° C. |
|---|---|---|---|
| HF-HFO-1234yf-HFC-245cb | 5-80 | 10-80 | 30-80 |
| HF-HFO-1234yf-HFO-1234zeE | 5-65 | * | * |
| HF-HFO-1234yf-HFO-1234zeZ | 5-75 | 10-70 | 15-30 |
| HF-HFO-1234yf-HFO-1243zf | 5-70 | * | * |
| HF-HFO-1234yf-HCFO-1233xf | 5-75 | 5-75 | 15-50 |
| HF-HFO-1234yf-HCFO-1233zdE | 5-75 | 5-70 | 15-55 |
| HF-HFO-1234yf-Trifluoropropyne | 10-70 | 40-70 | 40-70 |
| HF-HFO-1234yf-HFC-244bb | 5-80 | 5-80 | 5-75 |
| HF-HFO-1234yf-HFC-245fa | 5-75 | 5-70 | 5-55 |
| HF-HFO-1234yf-HFO-1225yeZ | 5-70 | 15-65 | 60-65 |
| HF-HFO-1234yf-HFO-1225zc | 5-65 | * | * |

EXAMPLE 16

Decantation Ranges of Quaternary Mixtures

| Quaternary | Decantation ranges Mass percentages of HF Isotherm 0° C. | Isotherm 25° C. | Isotherm 40° C. |
|---|---|---|---|
| HF-HCFO-1233xf-HFC-245cb-HFO-1234yf | 5-75 | 5-75 | 15-70 |
| HF-HFO-1234yf-HFC-245cb-HCFO-1233zdE | 5-75 | 5-75 | 15-70 |
| HF-HFO-1234yf-HFC-245cb-HFO-1234zeE | 5-75 | 10-70 | * |
| HF-HFO-1234yf-HFC-245cb-HFO-1234zeZ | 5-75 | 10-75 | 20-70 |
| HF-HFO-1234yf-HFC-245cb-HFO-1243zf | 5-75 | 15-70 | 45-70 |
| HF-HCFO-1233xf-HFO-1234yf-HCFO-1233zdE | 5-75 | 5-70 | 10-60 |
| HF-HCFO-1233xf-HFO-1234yf-HFO-1234zeE | 5-70 | 10-60 | * |
| HF-HCFO-1233xf-HFO-1234yf-HFO-1234zeZ | 5-75 | 5-70 | 10-60 |
| HF-HCFO-1233xf-HFO-1234yf-HFO-1243zf | 5-75 | 10-65 | * |
| HF-HFO-1234yf-HFO-1234zeE-HFO-1234zeZ | 5-70 | 10-60 | * |
| HF-HFO-1234yf-HFO-1234zeE-HCFO-1233zdE | 5-70 | 10-60 | * |
| HF-HFO-1234yf-HFO-1234zeE-HFO-1243zf | 5-65 | * | * |
| HF-HFO-1234yf-HFO-1234zeZ-HCFO-1233zdE | 5-75 | 5-70 | 10-60 |
| HF-HFO-1234yf-HFO-1234zeZ-HFO-1243zf | 5-75 | 10-65 | * |
| HF-HFO-1234yf-HCFO-1233zdE-HFO-1243zf | 5-75 | 10-65 | * |
| HF-HFO-1234yf-HFC-245cb-Trifluoropropyne | 5-75 | 30-75 | 40-75 |
| HF-HFO-1234yf-HFC-245cb-HCFC-244bb | 5-80 | 5-80 | 10-70 |
| HF-HFO-1234yf-HFC-245cb-HFC-245fa | 5-80 | 5-75 | 15-70 |
| HF-HFO-1234yf-HFC-245cb-HFO-1225yeZ | 5-75 | 10-75 | 30-75 |
| HF-HFO-1234yf-HFC-245cb-HFO-1225zc | 5-75 | 10-70 | 40-70 |
| HF-HFO-1234yf-HFO-1234zeE-Trifluoropropyne | 10-65 | * | * |
| HF-HFO-1234yf-HFO-1234zeE-HCFC-244bb | 5-80 | 5-75 | 10-65 |
| HF-HFO-1234yf-HFO-1234zeE-HFC-245fa | 5-70 | 10-65 | * |
| HF-HFO-1234yf-HFO-1234zeE-HFO-1225yeZ | 5-70 | 20-45 | * |
| HF-HFO-1234yf-HFO-1234zeE-HFO-1225zc | 5-65 | * | * |
| HF-HFO-1234yf-HFO-1225yeZ-Trifluoropropyne | 5-70 | * | * |
| HF-HFO-1234yf-HCFC-244bb-Trifluoropropyne | 5-80 | 10-75 | 30-70 |
| HF-HFO-1234yf-HCFC-244bb-HFC-245fa | 5-80 | 5-80 | 5-75 |
| HF-HCFO-1233xf-HFO-1234yf-HCFC-244bb | 5-80 | 5-75 | 5-75 |

EXAMPLE 17

Decantation Ranges of Penternary Mixtures

| System with 5 compounds | Decantation ranges Mass percentages of HF Isotherm 0° C. | Isotherm 25° C. | Isotherm 40° C. |
|---|---|---|---|
| HF-HCFO-1233xf-HFC-245cb-HCFO-1233zdE-HFO-1234yf | 5-75 | 5-75 | 10-65 |

-continued

| System with 5 compounds | Decantation ranges Mass percentages of HF | | |
|---|---|---|---|
| | Isotherm 0° C. | Isotherm 25° C. | Isotherm 40° C. |
| HF-HCFO-1233xf-HFC-245cb-HFO-1234zeE-HFO-1234yf | 5-75 | 10-70 | * |
| HF-HCFO-1233xf-HFC-245cb-HFO-1234zeZ-HFO-1234yf | 5-75 | 5-75 | 10-65 |
| HF-HCFO-1233xf-HFC-245cb-HFO-1234yf-HFO-1243zf | 5-75 | 10-70 | * |
| HF-HCFO-1233xf-HFO-1234yf-HFO-1234zeE-HFO-1234zeZ | 5-75 | 5-65 | 15-45 |
| HF-HCFO-1233xf-HFO-1234yf-HFO-1234zeE-HFO-1243zf | 5-70 | 10-60 | * |
| HF-HCFO-1233xf-HFO-1234yf-HFO--H1234zeECFO-1233zdE | 5-75 | 5-65 | 10-50 |
| HF-HCFO-1233xf-HFO-1234yf-HFO-1234zeZ-HFO-1243zf | 5-75 | 10-65 | 20-40 |
| HF-HCFO-1233xf-HFO-1234yf-HFO-1234zeZ-HCFO-1233zdE | 5-75 | 5-70 | 10-60 |
| HF-HCFO-1233xf-HFO-1234yf-HCFO-1233zdE-HFO-1243zf | 5-75 | 5-65 | 15-45 |
| HF-HFO-1234yf-HFO-1234zeE-HFO-1234zeZ-HCFO-1233zdE | 5-75 | 5-65 | 15-45 |
| HF-HFO-1234yf-HFO-1234zeE-HFO-1234zeZ-HFO-1243zf | 5-70 | 10-60 | * |
| HF-HFO-1234yf-HFO-1234zeE-HCFO-1233zdE-HFO-1243zf | 5-70 | 10-60 | * |
| HF-HFO-1234yf-HFO-1234zeZ-HCFO-1233zdE-HFO-1243zf | 5-75 | 10-65 | 15-45 |
| HF-HFO-1234yf-HFC-245cb-HFO-1234zeE-HCFO-1233zdE | 5-75 | 10-70 | * |
| HF-HFO-1234yf-HFC-245cb-HFO-1234zeE-HFO-1234zeZ | 5-75 | 10-70 | * |
| HF-HFO-1234yf-HFC-245cb-HFO-1234zeE-HFO-1243zf | 5-75 | 15-65 | * |
| HF-HFO-1234yf-HFC-245cb-HFO-1234zeZ-HCFO-1233zdE | 5-75 | 5-75 | 10-65 |
| HF-HFO-1234yf-HFC-245cb-HFO-1234zeZ-HFO-1243zf | 5-75 | 10-70 | * |
| HF-HFO-1234yf-HFC-245cb-HCFO-1233zdE-HFO-1243zf | 5-75 | 10-70 | * |
| HF-HCFO-1233xf-HFO-1234yf-HFC-245cb-HCFC-244bb | 5-80 | 5-80 | 5-75 |

EXAMPLE 18

Decantation Ranges of System with 6 Compounds

| System with 6 compounds | Decantation ranges Mass percentages of HF | | |
|---|---|---|---|
| | Isotherm 0° C. | Isotherm 25° C. | Isotherm 40° C. |
| HF-HCFO-1233xf-HFO-1234yf-HFC-245cb-HFO-1234zeE-HFO-1234zeZ | 5-75 | 5-70 | 15-55 |
| HF-HCFO-1233xf-HFO-1234yf-HFC-245cb-HFO-1234zeE-HCFO-1233zdE | 5-75 | 5-70 | 15-55 |
| HF-HCFO-1233xf-HFO-1234yf-HFC-245cb-HFO-1234zeE-HFO-1243zf | 5-75 | 10-65 | * |
| HF-HCFO-1233xf-HFO-1234yf-HFC-245cb-HFO-1234zeZ-HCFO-1233zdE | 5-75 | 5-75 | 10-65 |
| HF-HCFO-1233xf-HFO-1234yf-HFC-245cb-HFO-1234zeZ-HFO-1243zf | 5-75 | 10-70 | 15-50 |
| HF-HCFO-1233xf-HFO-1234yf-HFC-245cb-HCFO-1233zdE-HFO-1243zf | 5-75 | 5-70 | 15-55 |
| HF-HCFO-1233xf-HFO-1234yf-HFO-1234zeE-HFO-1234zeZ-HCFO-1233zdE | 5-75 | 5-65 | 10-55 |
| HF-HCFO-1233xf-HFO-1234yf-HFO-1234zeE-HFO-1234zeZ-HFO-1243zf | 5-70 | 10-65 | * |
| HF-HCFO-1233xf-HFO-1234yf-HFO-1234zeE-HCFO-1233zdE-HFO-1243zf | 5-70 | 10-75 | * |
| HF-HCFO-1233xf-HFO-1234yf-HFO-1234zeZ-HCFO-1233zdE-HFO-1243zf | 5-75 | 5-70 | 10-55 |
| HF-HFO-1234yf-HFC-245cb-HFO-1234zeE-HFO-1234zeZ-HCFO-1233zdE | 5-75 | 5-70 | 15-55 |
| HF-HFO-1234yf-HFC-245cb-HFO-1234zeE-HFO-1234zeZ-HFO-1243zf | 5-75 | 10-65 | * |
| HF-HFO-1234yf-HFC-245cb-HFO-1234zeE-HCFO-1233zdE-HFO-1243zf | 5-75 | 10-65 | * |
| HF-HFO-1234yf-HFC-245cb-HFO-1234zeZ-HCFO-1233zdE-HFO-1243zf | 5-75 | 10-70 | 15-55 |
| HF-HFO-1234yf-HFO-1234zeE-HFO-1234zeZ-HCFO-1233zdE-HFO-1243zf | 5-70 | 10-65 | * |
| HF-HCFC-244bb-HFC-245fa-Trifluoropropyne-HFO-1225yeZ-HFO-1225zc | 5-75 | 10-70 | 15-60 |

EXAMPLE 19

Decantation Ranges of System with 7 Compounds

| System with 7 compounds | Decantation ranges Mass percentages of HF | | |
|---|---|---|---|
| | Temperature | | |
| | 0° C. | 25° C. | 40° C. |
| HF-HCFO-1233xf-HFO-1234yf-HFC-245cb-HCFO-1233zdE-HFO-1234zeE-HFO-1234zeZ | 5-75 | 5-70 | 10-60 |
| HF-HCFO-1233xf-HFO-1234yf-HFC-245cb-HCFO-1233zdE-HFO-1234zeE-HFO-1243zf | 5-75 | 10-65 | 20 |
| HF-HCFO-1233xf-HFO-1234yf-HFC-245cb-HCFO-1233zdE-HFO-1234zeZ-HFO-1243zf | 5-70 | 5-70 | 10-60 |
| HF-HCFO-1233xf-HFO-1234yf-HFC-245cb-HFO-1234zeE-HFO-1234zeZ-HFO-1243zf | 5-75 | 10-65 | * |
| HF-HCFO-1233xf-HFO-1234yf-HCFO-1233zdE-HFO-1234zeE-HFO-1234zeZ-HFO-1243zf | 5-75 | 10-65 | 15-45 |
| HF-HFO-1234yf-HFC-245cb-HCFO-1233zdE-HFO-1234zeE-HFO-1234zeZ-HFO-1243zf | 5-75 | 10-65 | * |
| HF-HFO-1234yf-HCFC-244bb-HFC-245fa-Trifluoropropyne-HFO-1225yeZ-HFO-1225zc | 5-75 | 5-70 | * |
| HF-HFC-245cb-HCFC-244bb-HFC-245fa-Trifluoropropyne-HFO-1225yeZ-HFO-1225zc | 5-75 | 5-75 | 15-65 |

EXAMPLE 20

Decantation Ranges of System with 8 Compounds

| System with 8 compounds | Decantation ranges Mass percentages of HF Temperature 0° C. | 25° C. | 40° C. |
|---|---|---|---|
| HF-HCFO-1233xf-HFO-1234yf-HFC-245cb-HCFO-1233zdE-HFO-1234zeE-HFO-1234zeZ-HFO-1243zf | 5-75% | 5-70% | 15-50% |
| HF-HFO-1234yf-HFC-245cb-HCFO-1233xf-HFO-1234zeE-HFO-1234zeZ-HCFO-1233zdE-HCFC-244bb | 5-80 | 5-75 | 5-70 |
| HF-HFO-1234yf-HFC-245cb-HCFO-1233xf-HFO-1234zeE-HFO-1234zeZ-HCFO-1233zdE-Trifluoropropyne | 5-75 | 10-65 | * |
| HF-HFO-1234yf-HFC-245cb-HCFO-1233xf-HFO-1234zeE-HFO-1234zeZ-HCFO-1233zdE-HFC-245fa | 5-75 | 5-70 | 10-60 |
| HF-HFO-1234yf-HFC-245cb-HCFO-1233xf-HFO-11234zeE-HFO-234zeZ-HCFO-1233zdE-HFO-1225yeZ | 5-75 | 5-70 | 15-55 |
| HF-HFO-1234yf-HFC-245cb-HCFO-1233xf-HFO-1234zeE-HFO-1234zeZ-HCFC-1233zdE-HFO-1225zc | 5-75 | 5-65 | 15-50 |

EXAMPLE 21

Decantation Ranges of System with 13 Compounds

| System with 13 compounds | Decantation ranges Mass percentages of HF Temperature 0° C. | 25° C. | 40° C. |
|---|---|---|---|
| HF-HFO-1234yf-HFC-245cb-HCFO-1233xf-HCFO-1233zdE-HFO-1234zeE-HFO-1234zeZ-HFC-1243zf-HCFC-244bb-TFP-HFC-245fa-HFO-1225yeZ-HFO-1225zc | 5-75% | 10-70% | 15-60% |

EXAMPLE 22

Binary Mixtures

HF-Trifluoropropyne

| HF Massfrac | Binary HF-Trifluoropropyne Isotherm 0° C. Pressure bar | Isotherm 25° C. Pressure bar | Isotherm 40° C. Pressure bar |
|---|---|---|---|
| 0 | 5.9 | 11.7 | 16.7 |
| 0.05 | 6.2 | 12.4 | 18.0 |
| 0.1 | 6.1 | 12.3 | 17.8 |
| 0.15 | 6.1 | 12.2 | 17.6 |
| 0.2 | 6.1 | 12.1 | 17.3 |
| 0.25 | 6.1 | 12.0 | 17.1 |
| 0.3 | 6.1 | 11.9 | 16.8 |
| 0.35 | 6.1 | 11.8 | 16.6 |
| 0.4 | 6.1 | 11.8 | 16.6 |
| 0.45 | 6.1 | 11.8 | 16.6 |
| 0.5 | 6.1 | 11.8 | 16.6 |
| 0.55 | 6.1 | 11.8 | 16.6 |
| 0.6 | 6.1 | 11.8 | 16.6 |
| 0.65 | 6.1 | 11.8 | 16.6 |
| 0.7 | 6.1 | 11.8 | 16.6 |

-continued

HF-Trifluoropropyne

| HF Massfrac | Binary HF-Trifluoropropyne Isotherm 0° C. Pressure bar | Isotherm 25° C. Pressure bar | Isotherm 40° C. Pressure bar |
|---|---|---|---|
| 0.75 | 6.0 | 11.8 | 16.6 |
| 0.8 | 5.7 | 11.6 | 16.6 |
| 0.85 | 5.3 | 10.8 | 15.7 |
| 0.9 | 4.4 | 9.2 | 13.4 |
| 0.95 | 2.9 | 6.1 | 9.0 |
| 1 | 0.5 | 1.2 | 1.9 |

HF-F244bb

| HF Massfrac | Binary HF-F244bb Isotherm 0° C. Pressure bar | Isotherm 25° C. Pressure bar | Isotherm 40° C. Pressure bar |
|---|---|---|---|
| 0 | 0.2 | 0.6 | 1.1 |
| 0.05 | 0.7 | 1.8 | 3.0 |
| 0.1 | 0.7 | 1.8 | 3.0 |
| 0.15 | 0.7 | 1.8 | 3.0 |
| 0.2 | 0.7 | 1.8 | 3.0 |
| 0.25 | 0.7 | 1.8 | 3.0 |
| 0.3 | 0.7 | 1.8 | 3.0 |
| 0.35 | 0.7 | 1.8 | 3.0 |
| 0.4 | 0.7 | 1.8 | 3.0 |
| 0.45 | 0.7 | 1.8 | 3.0 |
| 0.5 | 0.7 | 1.8 | 3.0 |
| 0.55 | 0.7 | 1.8 | 3.0 |
| 0.6 | 0.7 | 1.8 | 3.0 |
| 0.65 | 0.7 | 1.8 | 3.0 |
| 0.7 | 0.7 | 1.8 | 3.0 |
| 0.75 | 0.7 | 1.8 | 3.0 |
| 0.8 | 0.7 | 1.8 | 3.0 |
| 0.85 | 0.7 | 1.8 | 3.0 |
| 0.9 | 0.7 | 1.7 | 2.9 |
| 0.95 | 0.6 | 1.5 | 2.5 |
| 1 | 0.5 | 1.2 | 1.9 |

| HF - F245fa | | | |
|---|---|---|---|
| | Binary HF-F245fa | | |
| HF Massfrac | Isotherm 0° C. Pressure bar | Isotherm 25° C. Pressure bar | Isotherm 40° C. Pressure bar |
| 0 | 0.5 | 1.5 | 2.5 |
| 0.05 | 1.0 | 2.6 | 4.4 |
| 0.1 | 1.0 | 2.6 | 4.4 |
| 0.15 | 1.0 | 2.6 | 4.4 |
| 0.2 | 1.0 | 2.6 | 4.4 |
| 0.25 | 1.0 | 2.6 | 4.4 |
| 0.3 | 1.0 | 2.6 | 4.4 |
| 0.35 | 1.0 | 2.6 | 4.4 |
| 0.4 | 1.0 | 2.6 | 4.4 |
| 0.45 | 1.0 | 2.6 | 4.4 |
| 0.5 | 1.0 | 2.6 | 4.4 |
| 0.55 | 1.0 | 2.6 | 4.4 |
| 0.6 | 1.0 | 2.6 | 4.4 |
| 0.65 | 1.0 | 2.6 | 4.4 |
| 0.7 | 1.0 | 2.6 | 4.4 |
| 0.75 | 1.0 | 2.6 | 4.4 |
| 0.8 | 1.0 | 2.6 | 4.2 |
| 0.85 | 0.9 | 2.4 | 3.9 |
| 0.9 | 0.8 | 2.1 | 3.5 |
| 0.95 | 0.7 | 1.7 | 2.9 |
| 1 | 0.5 | 1.2 | 1.9 |

EXAMPLE 23

Temperature and Pressure Range of Binary Mixtures

| | Boiling point range | |
|---|---|---|
| Binary | Temperature ° C. | Pressure bar abs |
| HF-Trifluoropropyne | 0 to 40 | ~6.0 to ~18.0 |
| HF-F244bb | 0 to 40 | ~0.7 to ~3.0 |
| HF-F245fa | 0 to 40 | ~1.0 to ~4.4 |

EXAMPLE 24

Decantation Ranges of Binary Mixtures

| | Decantation ranges Mass percentages of HF | | |
|---|---|---|---|
| | Temperature | | |
| Binary | 0 ° C. | 25 ° C. | 40 ° C. |
| HF-Trifluoropropyne | 20-65 | 40-75 | 40-80 |
| HF-F244bb | 5-85 | 5-85 | 5-85 |
| HF-F245fa | 5-80 | 5-75 | 5-70 |

The invention claimed is:

1. An azeotropic or quasi-azeotropic composition comprising hydrogen fluoride, 2,3,3,3-tetrafluoropropene, and one or more organic compounds selected from the group consisting of E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, 1,1,1,3,3-pentafluoropropane, 2-chloro,1,1,1,2-tetrafluoropropane, trifluoropropyne, Z-1,1,1,2,3-pentafluoropropene and 1,1,1,3,3-pentafluoropropene, in which the boiling point of said composition is between −20° C. and 80° C., and at a pressure of between 0.1 and 44 bar absolute.

2. The composition as claimed in claim 1, wherein the composition comprises hydrogen fluoride, 2,3,3,3-tetrafluoropropene and one or more organic compounds chosen from E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, 1,1,1,3,3-pentafluoropropane, 2-chloro,1,1,1,2-tetrafluoropropane, trifluoropropyne, Z-1,1,1,2,3-pentafluoropropene and 1,1,1,3,3-pentafluoropropene.

3. The composition as claimed in claim 1, wherein the composition comprises hydrogen fluoride, 2,3,3,3-tetrafluoropropene, and one or more organic compounds chosen from E-1,3,3,3-tetrafluoropropene, Z-1,3,3,3-tetrafluoropropene, 3,3,3-trifluoropropene, 3,3,3-trifluoro-2-chloropropene and E-3,3,3-trifluoro-1-chloropropene.

4. The composition as claimed in claim 1, wherein the composition is heteroazeotropic or quasi-heteroazeotropic.

5. The composition as claimed in claim 1, wherein the composition comprises hydrogen fluoride, 2,3,3,3-tetrafluoropropene, 1,1,1,2,2-pentafluoropropane and at least one compound chosen from E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, 1,1,1,3,3-pentafluoropropane, 2-chloro,1,1,1,2-tetrafluoropropane, trifluoropropyne, Z-1,1,1,2,3-pentafluoropropene and 1,1,1,3,3-pentafluoropropene.

6. The composition as claimed in claim 1, wherein the composition comprises hydrogen fluoride, 2,3,3,3-tetrafluoropropene, E-1,3,3,3-tetrafluoropropene and optionally at least one compound chosen from Z-1,3,3,3-tetrafluoropropene, 3,3,3-trifluoropropene, 3,3,3-trifluoro-2-chloropropene, E-3,3,3-trifluoro-1-chloropropene, 1,1,1,3,3-pentafluoropropane, 2-chloro,1,1,1,2-tetrafluoropropane, trifluoropropyne, Z-1,1,1,2,3-pentafluoropropene and 1,1,1,3,3-pentafluoropropene.

7. The composition as claimed in claim 1, wherein the composition comprises hydrogen fluoride, 2,3,3,3-tetrafluoropropene, Z-1,3,3,3-tetrafluoropropene and optionally at least one compound chosen from 3,3,3-trifluoropropene, 3,3,3-trifluoro-2-chloropropene, 1,1,1,3,3-pentafluoropropane and E-3,3,3-trifluoro-1-chloropropene.

8. The composition as claimed in claim 1, wherein the composition comprises hydrogen fluoride, 2,3,3,3-tetrafluoropropene, 3,3,3-trifluoropropene and optionally at least one compound chosen from 3,3,3-trifluoro-2-chloropropene and E-3,3,3-trifluoro-1-chloropropene.

9. The composition as claimed in claim 1, wherein the composition comprises hydrogen fluoride, 2,3,3,3-tetrafluoropropene, 3,3,3-trifluoro-2-chloropropene and optionally E-3,3,3-trifluoro-1-chloropropene.

10. The composition as claimed in claim 1, wherein the composition comprises hydrogen fluoride, 2,3,3,3-tetrafluoropropene and E-3,3,3-trifluoro-1-chloropropene.

11. The composition as claimed in claim 1, wherein, in which the composition comprises from 1% to 85% by weight of hydrogen fluoride and from 99% to 15% by weight of the sum of the organic compounds.

12. The composition as claimed in claim 1, wherein, in which the composition comprises from 5% to 80% by weight of hydrogen fluoride and from 95% to 20% by weight of the sum of the organic compounds.

13. The composition as claimed in claim 1, wherein, in which the boiling point of said composition is between 0° C. and 40° C. and at a pressure of between 0.7 and 18 bar absolute.

14. The composition as claimed in claim 1, wherein, in which the boiling point of said composition is between 0° C. and 40° C. and at a pressure of between 0.9 and 12.5 bar absolute.

15. The composition as claimed in claim 1, comprising two or more organic compounds selected from the group consisting of E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, 1,1,1,3,3-pentafluoropropane, 2-chloro,1,1,1,2-tetrafluoropropane, trifluoropropyne, Z-1,1,1,2,3-pentafluoropropene and 1,1,1,3,3-pentafluoropropene.

16. An azeotropic or quasi-azeotropic composition comprising hydrogen fluoride, 2,3,3,3-tetrafluoropropene and three or more organic compounds selected from the group consisting of 1,1,1,2,2-pentafluoropropane, E-1,3,3,3-tetrafluoropropene, Z-1,3,3,3-tetrafluoropropene, 3,3,3-trifluoropropene, 3,3,3-trifluoro-2-chloropropene, E-3,3,3-trifluoro-1-chloropropene, 1,1,1,3,3-pentafluoropropane, 2-chloro,1,1,1,2-tetrafluoropropane, trifluoropropyne, Z-1,1,1,2,3-pentafluoropropene and 1,1,1,3,3-pentafluoropropene.

* * * * *